United States Patent
Zwaagstra et al.

(10) Patent No.: US 12,391,743 B2
(45) Date of Patent: Aug. 19, 2025

(54) TGF-β-RECEPTOR ECTODOMAIN FUSION MOLECULES AND USES THEREOF

(71) Applicant: National Research Council of Canada, Ottawa (CA)

(72) Inventors: John C. Zwaagstra, Laval (CA); Traian Sulea, Kirkland (CA); Maria L. Jaramillo, Beaconsfield (CA); Maureen D. O'Connor, Beaconsfield (CA); Anne E. G. Lenferink, Lorraine (CA)

(73) Assignee: National Research Council of Canada, Ottawa (CA)

( * ) Notice: Subject to any disclaimer, the term of this patent is extended or adjusted under 35 U.S.C. 154(b) by 113 days.

(21) Appl. No.: 17/523,602

(22) Filed: Nov. 10, 2021

(65) Prior Publication Data

US 2022/0169702 A1    Jun. 2, 2022

Related U.S. Application Data

(63) Continuation of application No. 15/755,595, filed as application No. PCT/IB2016/055204 on Aug. 31, 2016, now abandoned.

(60) Provisional application No. 62/212,058, filed on Aug. 31, 2015.

(51) Int. Cl.
| | | |
|---|---|---|
| *C07K 14/71* | (2006.01) | |
| *A61P 35/00* | (2006.01) | |
| *C07K 16/22* | (2006.01) | |
| *A61K 39/00* | (2006.01) | |

(52) U.S. Cl.
CPC .............. *C07K 14/71* (2013.01); *A61P 35/00* (2018.01); *C07K 16/22* (2013.01); *A61K 2039/505* (2013.01); *C07K 2317/94* (2013.01); *C07K 2319/30* (2013.01)

(58) Field of Classification Search
None
See application file for complete search history.

(56) References Cited

U.S. PATENT DOCUMENTS

| | | |
|---|---|---|
| 5,693,607 A | 12/1997 | Segarini et al. |
| 6,277,375 B1 | 8/2001 | Ward |
| 8,318,135 B2 | 11/2012 | O'Connor-McCourt et al. |
| 8,658,135 B2 | 2/2014 | O'Connor-McCourt et al. |
| 8,815,247 B2 | 8/2014 | Govindappa et al. |
| 9,782,452 B2 | 10/2017 | Scandura et al. |
| 9,809,637 B2 | 11/2017 | Kumar et al. |
| 2002/0004037 A1 | 1/2002 | Koteliansky et al. |
| 2005/0203022 A1 | 9/2005 | Gotwals et al. |
| 2007/0244042 A1 | 10/2007 | Sun et al. |
| 2011/0293512 A1 | 12/2011 | Violette et al. |
| 2013/0149304 A1 | 6/2013 | Lin et al. |
| 2015/0056199 A1 | 2/2015 | Kumar et al. |
| 2015/0225483 A1 | 8/2015 | Lo |
| 2018/0327477 A1 | 11/2018 | Kumar et al. |
| 2020/0231652 A1 | 7/2020 | Zwaagstra et al. |
| 2022/0204587 A1 | 6/2022 | Lenferink et al. |

FOREIGN PATENT DOCUMENTS

| | | |
|---|---|---|
| CA | 2330939 A1 | 12/1999 |
| CA | 2791383 A1 | 9/2011 |
| CA | 2902830 A1 | 10/2014 |
| CN | 1257545 A | 6/2000 |
| CN | 105658672 A | 6/2016 |
| EP | 3174550 B1 | 1/2020 |
| EP | 3589663 A1 | 1/2020 |
| JP | 2001-515360 A | 9/2001 |
| JP | 2010-529859 A | 9/2010 |
| JP | 2012-530514 A | 12/2012 |
| JP | 2016-037488 A | 3/2016 |
| JP | 2017-501977 A | 1/2017 |
| KR | 10-2001-0006534 A | 1/2001 |
| RU | 2413769 C1 | 3/2011 |
| WO | WO 1995/004069 A1 | 2/1995 |
| WO | WO 1998/048024 A1 | 10/1998 |
| WO | WO 2001/083525 A2 | 11/2001 |
| WO | WO 2004/076670 A1 | 9/2004 |
| WO | WO 2005/028517 A2 | 3/2005 |
| WO | WO 2005/103263 A1 | 11/2005 |
| WO | WO 2008/113185 A1 | 9/2008 |
| WO | WO 2008/157367 A1 | 12/2008 |
| WO | WO 2010/003118 A1 | 1/2010 |
| WO | WO 2010/031168 A1 | 3/2010 |
| WO | WO 2010/099219 A2 | 9/2010 |
| WO | WO 2011/005481 A1 | 1/2011 |
| WO | WO 2011/109789 A2 | 9/2011 |
| WO | WO 2012/071649 A1 | 6/2012 |

(Continued)

OTHER PUBLICATIONS

Witkowski et al, Biochemistry 38:11643-11650, 1999. (Year: 1999).*
Seffernick et al., Bacteriol. 183(8): 2405-2410, 2001. (Year: 2001).*
[No Author Listed] Aflibercept: AVE 0005, AVE 005, AVE0005, VEGF Trap—Regeneron, VEGF Trap (R1R2), VEGF Trap-Eye. Drugs R&D. 2008;9:261-9.
Akhurst et al., Targeting the TGFβ signalling pathway in disease. Macmillan Publishers Limited, Oct. 2012, vol. 11, 23 pages.
Akilesh et al., Neonatal FcR expression in bone marrow-derived cells functions to protect serum IgG from catabolism. J. Immunol. Oct. 1, 2007;179(7):4580-8.
Arteaga, Inhibition of TGF-beta signaling in cancer therapy. Curr Opin Genet Dev 2006;16:30-7.
Biswas et al. Anti-transforming growth factor-beta antibody treatment rescues bone loss and prevents breast cancer metastasis to bone. PloS one 2011;6:e27090.

(Continued)

*Primary Examiner* — Gary B Nickol
*Assistant Examiner* — Cheom-Gil Cheong
(74) *Attorney, Agent, or Firm* — Wolf, Greenfield & Sacks, P.C.

(57) ABSTRACT

The present invention relates, in general, to polypeptides capable of binding and neutralizing transforming growth factor beta (TGF-beta) ligands, and uses of these polypeptides for treating disorders related to TGF-beta expression or activation (e.g. cancer and fibrotic diseases), and methods of making such molecules.

14 Claims, 30 Drawing Sheets

Specification includes a Sequence Listing.

(56) References Cited

FOREIGN PATENT DOCUMENTS

| WO | WO-2012142515 A2 | * | 10/2012 | ............ C07K 14/47 |
| --- | --- | --- | --- | --- |
| WO | WO 2013/000234 A1 | | 1/2013 | |
| WO | WO-2013043516 A1 | * | 3/2013 | ......... C07K 14/7056 |
| WO | WO 2014/164427 A1 | | 10/2014 | |
| WO | WO 2015/027082 A1 | | 2/2015 | |
| WO | WO 2015/077540 A3 | | 11/2015 | |
| WO | WO 2018/158727 A1 | | 9/2018 | |
| WO | WO 2019/191100 A1 | | 10/2019 | |
| WO | WO 2019/211489 A1 | | 11/2019 | |
| WO | WO 2020/093024 A2 | | 5/2020 | |
| WO | WO 2020/146345 A1 | | 7/2020 | |
| WO | WO 2021/123902 A1 | | 6/2021 | |
| WO | WO 2021/248247 A1 | | 12/2021 | |
| WO | WO 2022/271915 A1 | | 12/2022 | |

OTHER PUBLICATIONS

Bogdahn et al., Targeted therapy for high-grade glioma with the TGF-b2 inhibitor trabedersen: results of a randomized and controlled phase 11b study. Neuro-Oncology 13(1):132-142, 2011.

Corcoran et al., BRAF Gene Amplification Can Promote Acquired Resistance to MEK Inhibitors in Cancer Cells Harboring the BRAF V600E Mutation. www.sciencesignaling.org, Nov. 23, 2010, vol. 3, Issue 149, 12 pages.

De Crescenzo et al., Real-time monitoring of the interactions of transforming growth factor-beta (TGF-beta) isoforms with latency-associated protein and the ectodomains of the TGF-beta type II and III receptors reveals different kinetic models and stoichiometries of binding. J Biol Chem 2001;276:29632-43.

Durocher et al., High-level and high-throughput recombinant protein production by transient transfection of suspension-growing human 293-EBNA1 cells. Nucleic Acids Res. 2002;30: E9.

Economides et al., Cytokine traps: multi-component, high-affinity blockers of cytokine action. Nat Med 2003;9:47-52.

Edwards et al. Inhibition of TGF-beta signaling by 1D11 antibody treatment increases bone mass and quality in vivo. J Bone Miner Res 2010;25:2419-26.

Eisenberg et al., Analysis of membrane and surface protein sequences with the hydrophobic moment plot. J Mol Bio. 1984;179: 125-142.

Engelman et al., Acquired resistance to tyrosine kinase inhibitors during cancer therapy. Current Opinion in Genetics & Development 2008, 18:73-79.

Flavell et al., The polarization of immune cells in the tumour environment by TGF β. www.nature.com/reviews/immunol, Aug. 2010, vol. 10, 14 pages.

Gajewski, The Next Hurdle in Cancer Immunotherapy: Overcoming the Non-T-Cell-Inflamed Tumor Microenvironment. Semin Oncol. 2015;42: 663-671.

Garberg et al., In vitro models for the blood-brain barrier. Toxicol In Vitro. 2005;19: 299-334.

Hahn et al., Targeting transforming growth factor beta to enhance cancer immunotherapy. Curr Onco. 2006;13:141-143.

Haqqani et al., Multiplexed evaluation of serum and CSF pharmacokinetics of brain-targeting single-domain antibodies using a NanoLC-SRM-ILIS method. Mol Pharm. 2013;10:1542-1556.

Hawinkels et al., Exploring anti-TGF-beta therapies in cancer and fibrosis. Growth Factors (Chur, Switzerland) 2011;29:140-52.

Heldin et al., Mechanism of TGF-β signaling to growth arrest, apoptosis, and epithelial-mesenchymal transition. Current Opinion in Cell Biology 2009, 21:166-176.

Holash et al. VEGF-Trap: a VEGF blocker with potent antitumor effects. Proc Natl Acad Sci USA 2002;99:11393-8.

Hsu et al., Complement activation mediates cetuximab inhibition of non-small cell lung cancer tumor growth in vivo. Mol Cancer. Jun. 7, 2010;9:139. doi: 10.1186/1476-4598-9-139.

Huang, Receptor-Fc fusion therapeutics, traps, and MIMETIBODY technology. Curr Opin Biotech 2009;20:692-9.

Isaka et al., Gene therapy by transforming growth factor-β receptor-IgG Fc chimera suppressed extracellular matrix accumulation in experimental glomerulonephritis. Kidney International, 1999, vol. 55, pp. 465-475.

Jin et al. Rational optimization of a bispecific ligand trap targeting EGF receptor family ligands. Molecular medicine (Cambridge, Mass) 2009;15:11-20.

Komesli et al., Chimeric extracellular domain type II transforming growth factor (TGF)-beta receptor fused to the Fc region of human immunoglobulin as a TGF-beta antagonist. Eur J Biochem. Jun. 15, 1998;254(3):505-13.

Li et al., Transforming growth factor-beta regulation of immune responses. Annu Rev Immunol. 2006;24:99-146.

Lin et al., Mechanistic basis and clinical relevance of the role of transforming growth factor-beta in cancer. Cancer Biol Med. 2015;12:385-393. Doi: 10.7497/j.issn.2095-3941.2015.0015.

Massague et al., TGFbeta signaling in growth control, cancer, and heritable disorders. Cell 2000; 103:295-309.

Montoyo et al., Conditional deletion of the MHC class I-related receptor FcRn reveals the sites of IgG homeostasis in mice. Proc Natl Acad Sci U S A. Feb. 24, 2009;106(8):2788-93. doi:; 10.1073/pnas.0810796106. Epub Feb. 2, 2009.

Mourskaia et al., Targeting aberrant TGF-beta signaling in pre-clinical models of cancer. Anti-cancer agents in medicinal chemistry 2007;7:504-14.

Muraoka et al., Blockade of TGF-beta inhibits mammary tumor cell viability, migration, and metastases. J Clin Invest. Jun. 2002; 109(12):1551-9.

Nam et al. An anti-transforming growth factor beta antibody suppresses metastasis via cooperative effects on multiple cell compartments. Cancer Res 2008;68:3835-43.

Nam et al. Transforming growth factor beta subverts the immune system into directly promoting tumor growth through interleukin-17. Cancer Res 2008;68:3915-23.

Padua et al., Roles of TGF β in metastasis. Cell Research (2009) 19:89-102.

Pickup et al., The roles of TGF β in the tumour microenvironment. Nat Rev Cancer. Nov. 2013;13(11):788-99. doi: 10.1038/nrc3603. Epub Oct. 17, 2013.

Qin et al., A novel highly potent trivalent TGF-β receptor trap inhibits early-stage tumorigenesis and tumor cell invasion in murine Pten-deficient prostate glands. Oncotarget. Dec. 27, 2016;7(52):86087-86102. doi: 10.18632/oncotarget.13343. Erratum in: Oncotarget. Aug. 21, 2017;8(34):57905.

Rodgarkia-Dara et al. The activin axis in liver biology and disease. Mutat Res 2006;613:123-37.

Rodon Ahnert et al., First human dose (FHD) study of the oral transforming growth factor-beta receptor I kinase inhibitor LY2157299 in patients with treatment-refractory malignant glioma. Journal of Clinical Oncology 29, No. 15 suppl (May 20, 2011) 3011-3011.

Santarpia et al., Programmed cell death protein-1/programmed cell death ligand-1 pathway inhibition and predictive biomarkers: understanding transforming growth factor-beta role. Transl Lung Cancer Res. 2015;4: 728-742.

Schlingensiepen et al., Targeted tumor therapy with the TGF-b2 antisense compound AP 12009. Cytokine & Growth Factor Reviews 17 (2006) 129-139.

Schlingensiepen et al., Transforming growth factor-beta 2 gene silencing with trabedersen (AP 12009) in pancreatic cancer. Cancer Sci, Jun. 2011, vol. 102, No. 6, 1193-1200.

Suragani et al. Ace-1332 (TGFbeta ligand trap) inhibits elevated TGFB1 signaling and reduces fibrosis in a murine model of myelofibrosis. Poster #P288, EHA 2016. 2 pages.

Suragani, Murine TGFbeta-antagonist (RAP-1332) Inhibits Fibrosis in a Murine Model of Myelofibrosis. Retrieved from Acceleronpharma.com on May 3, 2021. 18 pages.

Suzuki et al., Soluble type II transforming growth factor-beta receptor inhibits established murine malignant mesothelioma tumor growth by augmenting host antitumor immunity. Clin Cancer Res. Sep. 1, 2004;10(17):5907-18.

Thiery et al., Epithelial-mesenchymal transitions in development and disease. Cell. Nov. 25, 2009;139(5):871-90. doi:10.1016/j.cell.2009.11.007.

(56) References Cited

OTHER PUBLICATIONS

Ueda et al. Systemic inhibition of transforming growth factor-beta in glioma-bearing mice improves the therapeutic efficacy of glioma-associated antigen peptide vaccines. Clin Cancer Res 2009;15:6551-9.

Wojtowicz-Praga, Reversal of tumor-induced immunosuppression by TGF-beta inhibitors. Invest New Drugs 2003;21:21-32.

Yang et al., Cetuximab-mediated tumor regression depends on innate and adaptive immune responses. Mol Ther. Jan. 2013;21(1):91-100. doi: 10.1038/mt.2012.184. Epub Sep. 18, 2012.

Yang et al., Enlarging the repertoire of therapeutic monoclonal antibodies platforms: domesticating half molecule exchange to produce stable IgG4 and IgG1 bispecific antibodies. Curr Opin Biotechnol. Dec. 2014;30:225-9. doi: 10.1016/j.copbio.2014.09.001. Epub Sep. 23, 2014.

Yang et al., TGF-beta and immune cells: an important regulatory axis in the tumor microenvironment and progression. Trends Immunol. Jun. 2010;31(6):220-7. doi: 10.1016/j.it.2010.04.002. Epub Jun. 1, 2010.

Zheng et al., Silencing IDO in dendritic cells: a novel approach to enhance cancer immunotherapy in a murine breast cancer model. Int J Cancer. 2013;132: 967-977.

Zwaagstra et al., Engineering and therapeutic application of single-chain bivalent TGF-β family traps. Mol Cancer Ther. Jul. 2012;11(7):1477-87. doi:10.1158/1535-7163.MCT-12-0060. Epub May 4, 2012.

[No Author Listed], IMGT Scientific Chart. Human IGHG. Retrieved from www.imgt.org on Aug. 9, 2017. 4 pages.

Akhurst, Targeting TGF-β Signaling for Therapeutic Gain. Cold Spring Harb Perspect Biol. Oct. 3, 2017;9(10):a022301. doi: 10.1101/cshperspect.a022301.

Allanore et al., Systemic sclerosis. Nat Rev Dis Primers. Apr. 23, 2015;1:15002. doi: 10.1038/nrdp.2015.2. 21 pages.

Baardsnes et al., TbetaR-II discriminates the high- and low-affinity TGF-beta isoforms via two hydrogen-bonded ion pairs. Biochemistry. Mar. 17, 2009;48(10):2146-55. doi: 10.1021/bi8019004.

Boocock et al., Mutations in SBDS are associated with Shwachman-Diamond syndrome. Nat Genet. Jan. 2003;33(1):97-101. doi: 10.1038/ng1062. Epub Dec. 23, 2002.

Bragado et al., TGF-β2 dictates disseminated tumour cell fate in target organs through TGF-β-RIII and p38α/β signalling. Nat Cell Biol. Nov. 2013;15(11):1351-61. doi: 10.1038/ncb2861. Epub Oct. 27, 2013.

De Crescenzo et al., Enhancement of the antagonistic potency of transforming growth factor-beta receptor extracellular domains by coiled coil-induced homo- and heterodimerization. J Biol Chem. Jun. 18, 2004;279(25):26013-8. doi: 10.1074/jbc.M400655200. Epub Mar. 24, 2004.

Desmouliere et al., Transforming growth factor-beta 1 induces alpha-smooth muscle actin expression in granulation tissue myofibroblasts and in quiescent and growing cultured fibroblasts. J Cell Biol. Jul. 1993;122(1):103-11. doi: 10.1083/jcb.122.1.103.

Gabrielli et al., Scleroderma. N Engl J Med. May 7, 2009;360(19):1989-2003. doi: 10.1056/NEJMra0806188.

Gourh et al., Transforming Growth Factor Beta 3 (TGFB3)—a Novel Systemic Sclerosis Susceptibility Locus Involved in Fibrosis and Th17 Cell Development Identified By Genome-Wide Association Study in African Americans from the Genome Research in African American Scleroderma Patients Consortium. Arthritis & Rheumatology. 2017. 69(suppl 10).

Govinden et al., Genealogy, expression, and cellular function of transforming growth factor-beta. Pharmacol Ther. May 2003;98(2):257-65. doi: 10.1016/s0163-7258(03)00035-4.

Grütter et al., A cytokine-neutralizing antibody as a structural mimetic of 2 receptor interactions. Proc Natl Acad Sci U S A. Dec. 23, 2008;105(51):20251-6. Epub Dec. 10, 2008. doi: 10.1073/pnas.0807200106.

Guba et al., A Phase 1b/2 Dose Escalation and Cohort Expansion Study of the Safety, Tolerability and Efficacy of a Transforming Growth Factor-beta (TGF-beta) Receptor I Kinase Inhibitor (galunisertib) in Combination with Anti-PD-1 (nivolumab) in Advanced Refractory Solid Tumors. Annals Oncol. 2016;27(Supplement 6):vi359-vi378. doi: 10.1093/annonc/mdw378.55. 1 page.

Guba et al., A Phase 1b/2 Dose Escalation and Cohort Expansion Study of the Safety, Tolerability and Efficacy of a Transforming Growth Factor-beta (TGF-beta) Receptor I Kinase Inhibitor in Advanced Refractory Solid Tumours. Abstrct No. 1102TiP. Presentated at the 41st European Society for Medical Oncology Congress, ESMO 2016. Copenhagen, Denmark. Oct. 7-11, 2016. 2 pages.

Herbertz et al., Clinical development of galunisertib (LY2157299 monohydrate), a small molecule inhibitor of transforming growth factor-beta signaling pathway. Drug Des Devel Ther. Aug. 10, 2015;9:4479-99. doi: 10.2147/DDDT.S86621.

Hunzelmann et al., Scleroderma: from pathophysiology to novel therapeutic approaches. Exp Dermatol. May 2010;19(5):393-400. doi: 10.1111/j.1600-0625.2010.01082.x.

Kissin et al., Myofibroblasts and hyalinized collagen as markers of skin disease in systemic sclerosis. Arthritis Rheum. Nov. 2006;54(11):3655-60. doi: 10.1002/art.22186.

Komai et al., Reevaluation of Pluripotent Cytokine TGF-β3 in Immunity. Int J Mol Sci. Aug. 1, 2018;19(8):2261. doi: 10.3390/ijms19082261.

Lacouture et al., Cutaneous keratoacanthomas/squamous cell carcinomas associated with neutralization of transforming growth factor β by the monoclonal antibody fresolimumab (GC1008). Cancer Immunol Immunother. Apr. 2015;64(4):437-46. Epub Jan. 13, 2015. doi: 10.1007/s00262-015-1653-0.

Lafyatis, Transforming growth factor β—at the centre of systemic sclerosis. Nat Rev Rheumatol. Dec. 2014;10(12):706-19. Epub Aug. 19, 2014. doi: 10.1038/nrrheum.2014.137.

Lahn et al., TGF-beta inhibitors for the treatment of cancer. Expert Opin Investig Drugs. Jun. 2005;14(6):629-43. doi: 10.1517/13543784.14.6.629.

Langer et al., Quantitative trait analysis reveals transforming growth factor-beta2 as a positive regulator of early hematopoietic progenitor and stem cell function. J Exp Med. Jan. 5, 2004;199(1):5-14. doi: 10.1084/jem.20030980.

Leask, Targeting the TGFbeta, endothelin-1 and CCN2 axis to combat fibrosis in scleroderma. Cell Signal. Aug. 2008;20(8):1409-14. Epub Jan. 19, 2008. doi: 10.1016/j.cellsig.2008.01.006.

Martin et al., Selective inhibition of TGFβ1 activation overcomes primary resistance to checkpoint blockade therapy by altering tumor immune landscape. Sci Transl Med. Mar. 25, 2020;12(536):eaay8456. doi: 10.1126/scitranslmed.aay8456.

Mayes et al., Prevalence, incidence, survival, and disease characteristics of systemic sclerosis in a large US population. Arthritis Rheum. Aug. 2003;48(8):2246-55. doi: 10.1002/art.11073.

Meng et al., TGF-β: the master regulator of fibrosis. Nat Rev Nephrol. Jun. 2016;12(6):325-38. Epub Apr. 25, 2016. doi: 10.1038/nrneph.2016.48.

Midgley et al., Transforming growth factor-β1 (TGF-β1)-stimulated fibroblast to myofibroblast differentiation is mediated by hyaluronan (HA)-facilitated epidermal growth factor receptor (EGFR) and CD44 co-localization in lipid rafts. J Biol Chem. May 24, 2013;288(21):14824-38. Epub Apr. 15, 2013. doi: 10.1074/jbc.M113.451336.

Morris et al., Phase I study of GC1008 (fresolimumab): a human anti-transforming growth factor-beta (TGFβ) monoclonal antibody in patients with advanced malignant melanoma or renal cell carcinoma. PLoS One. Mar. 11, 2014;9(3):e90353. doi: 10.1371/journal.pone.0090353.

Nanthakumar et al., Dissecting fibrosis: therapeutic insights from the small-molecule toolbox. Nat Rev Drug Discov. Oct. 2015;14(10):693-720. Epub Sep. 4, 2015. doi: 10.1038/nrd4592.

Paul, Fundamental Immunology. 1993. 3rd Ed. P. 285. Figure 1.

Prud'Homme et al., Pathobiology of transforming growth factor beta in cancer, fibrosis and immunologic disease, and therapeutic considerations. Lab Invest. Nov. 2007;87(11):1077-91. Epub Aug. 27, 2007. doi: 10.1038/labinvest.3700669.

Rice et al., A longitudinal biomarker for the extent of skin disease in patients with diffuse cutaneous systemic sclerosis. Arthritis Rheumatol. Nov. 2015;67(11):3004-15. doi: 10.1002/art.39287.

(56) References Cited

OTHER PUBLICATIONS

Rio et al., TGF-β: a master regulator of the bone marrow failure puzzle in Fanconi anemia. Stem Cell Investig. Nov. 7, 2016;3:75. doi: 10.21037/sci.2016.09.17.

Roberts et al., Role of transforming growth factor-beta in maintenance of function of cultured neonatal cardiac myocytes. Autocrine action and reversal of damaging effects of interleukin-1. J Clin Invest. Nov. 1992;90(5):2056-62. doi: 10.1172/JCI116087.

Rogers et al., Shwachman-Diamond syndrome. UpToDate. 2018. https://www.uptodate.com/contents/shwachman-diamond-syndrome/print.

Schlingensiepen et al., Antisense therapeutics for tumor treatment: the TGF-beta2 inhibitor AP 12009 in clinical development against malignant tumors. Recent Results Cancer Res. 2008;177:137-50. doi: 10.1007/978-3-540-71279-4_16.

Tatusova et al., BLAST 2 Sequences, a new tool for comparing protein and nucleotide sequences. FEMS Microbiol Lett. May 15, 1999;174(2):247-50. doi: 10.1111/j.1574-6968.1999.tb13575.x.

Todd et al., Permanent alveolar collapse is the predominant mechanism in idiopathic pulmonary fibrosis. Expert Rev Respir Med. Aug. 2015;9(4):411-8. doi: 10.1586/17476348.2015.1067609.

Vannucchi et al., A pathobiologic pathway linking thrombopoietin, GATA-1, and TGF-beta 1 in the development of myelofibrosis. Blood. May 1, 2005;105(9):3493-501. Epub Jan. 21, 2005. doi: 10.1182/blood-2004-04-1320.

Varga et al., Antitransforming growth factor-beta therapy in fibrosis: recent progress and implications for systemic sclerosis. Curr Opin Rheumatol. Nov. 2008;20(6):720-8. doi: 10.1097/BOR.0b013e32830e48e8.

Varga et al., Systemic sclerosis: a prototypic multisystem fibrotic disorder. J Clin Invest. Mar. 2007;117(3):557-67. doi: 10.1172/JCI31139.

Varga et al., Transforming growth factor-beta in systemic sclerosis (scleroderma). Front Biosci (Schol Ed). Jun. 1, 2009;1(1):226-35. doi: 10.2741/s22.

Vincenti et al., A Phase 2, Double-Blind, Placebo-Controlled, Randomized Study of Fresolimumab in Patients With Steroid-Resistant Primary Focal Segmental Glomerulosclerosis. Kidney Int Rep. Apr. 7, 2017;2(5):800-810. doi: 10.1016/j.ekir.2017.03.011.

Wang et al., Exosome-Mediated miR-29 Transfer Reduces Muscle Atrophy and Kidney Fibrosis in Mice. Mol Ther. Mar. 6, 2019;27(3):571-583. Epub Jan. 18, 2019. doi: 10.1016/j.ymthe.2019.01.008.

Wang et al., Quantitative analysis of growth factor production in the mechanism of fibrosis in agnogenic myeloid metaplasia. Exp Hematol. Dec. 2006;34(12):1617-23. doi: 10.1016/j.exphem.2006.07.004.

Zhang et al., TGF-β Inhibition Rescues Hematopoietic Stem Cell Defects and Bone Marrow Failure in Fanconi Anemia. Cell Stem Cell. May 5, 2016;18(5):668-81. Epub Mar. 24, 2016. doi: 10.1016/j.stem.2016.03.002.

Zwaagstra et al., Engineering and therapeutic application of single-chain bivalent TGF-β family traps. Mol Cancer Ther. Jul. 2012;11(7):Supplementary Information. 9 pages.

EP 16840942.3, May 31, 2019, Extended European Search Report.
JP 2019-547490, Jan. 11, 2022, Office Action with English Translation.
JP 2019-547490, Jul. 26, 2022, Office Action with English Translation.
PCT/CA2021/050795, Sep. 7, 2021, International Search Report and Written Opinion.
PCT/US2022/034671, Nov. 22, 2022, International Search Report and Written Opinion.
PCT/US2022/034677, Nov. 1, 2022, International Search Report and Written Opinion.

\* cited by examiner

T2m

IPPHVQKSVNNDMIVTDNNGAVKFPQLCKFCDVRFSTCDNQKSCMSNCSITSICEKP
QEVCVAVWRKNDENITLETVCHDPKLPYHDFILEDAASPKCIMKEKKKPGETFFMC
SCSSDECNDNIIFSEEYNTSNPD

T22d35

IPPHVQKSVNNDMIVTDNNGAVKFPQLCKFCDVRFSTCDNQKSCMSNCSITSICEKP
QEVCVAVWRKNDENITLETVCHDPKLPYHDFILEDAASPKCIMKEKKKPGETFFMC
SCSSDECNDNIIFSEEYNTSNPDIPPHVQKSVNNDMIVTDNNGAVKFPQLCKFCDVR
FSTCDNQKSCMSNCSITSICEKPQEVCVAVWRKNDENITLETVCHDPKLPYHDFILE
DAASPKCIMKEKKKPGETFFMCSCSSDECNDNIIFSEEYNTSNPD

FIG. 1A

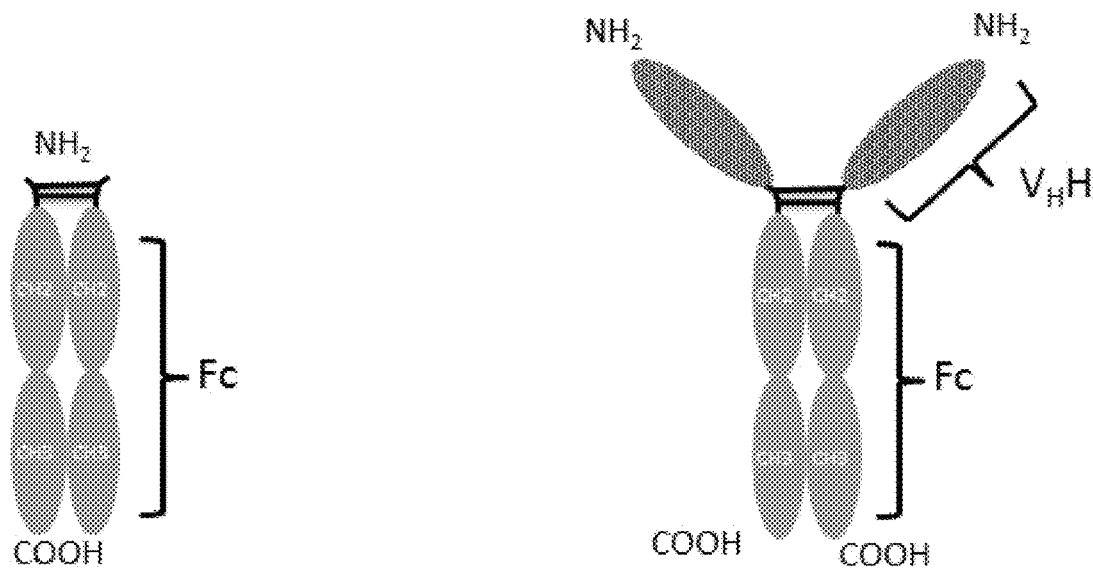

FIG. 1B  FIG. 1C

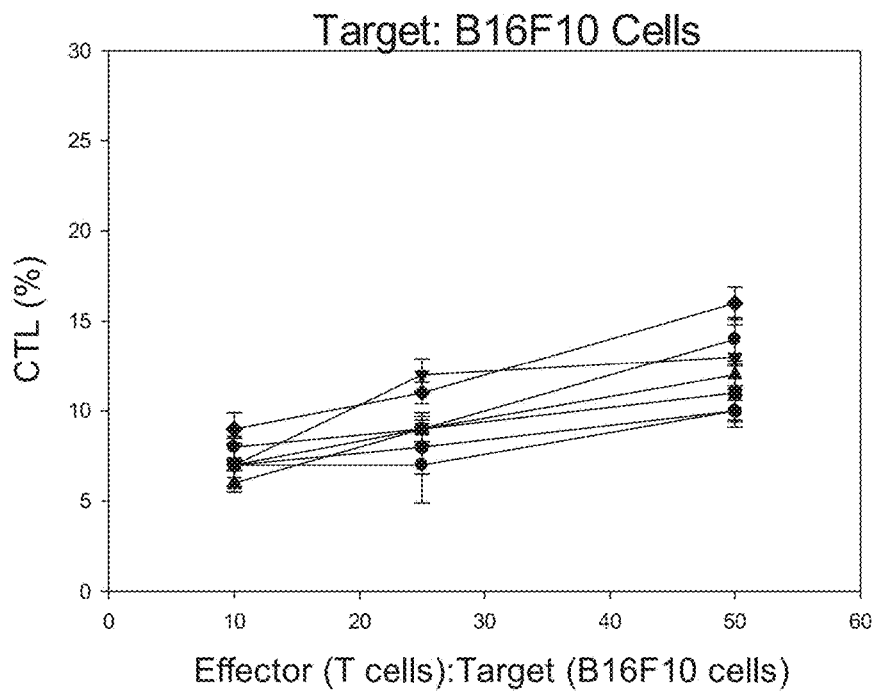

Target: B16F10 Cells

All symbols are as shown for Fig. 9B

| Column | |
|---|---|
| 1 | Effector (T cell):Target (B16F10 cell) ratio |
| 2 | Saline (mean of 3 independent measurements ± SEM) |
| 3 | hIgG1Fc(ΔK)(CC)-T2m (mean of 3 independent measurements ± SEM) |
| 4 | hIgG1Fc(ΔK)(C)-T2m (mean of 3 independent measurements ± SEM) |
| 5 | hIgG2Fc(ΔK)(CC)-T2m (mean of 3 independent measurements ± SEM) |
| 6 | Cet-T2m (mean of 3 independent measurements ± SEM) |
| 7 | T22d35 (mean of 3 independent measurements ± SEM) |
| 8 | ID11 (mean of 3 independent measurements ± SEM) |

| | 1 | 2 | 3 | 4 | 5 | 6 | 7 | 8 |
|---|---|---|---|---|---|---|---|---|
| Effector cell:Target cell Ratio | 10 | 7±0.3 | 7±1.5 | 7±1.2 | 9±0.9 | 6±0.3 | 7±0.3 | 8±0.6 |
| | 25 | 7±2.1 | 12±0.9 | 9±0.3 | 11±0.6 | 9±0.9 | 8±1.5 | 9±0.7 |
| | 50 | 10±0.9 | 13±1.8 | 11±1.5 | 16±0.9 | 12±0.6 | 10±0.6 | 14±1.2 |

FIG. 9C

| | hIgG1FcΔK(CC)-T2m | D10-hIgG1FcΔK(CC)-T2m | D10-GSL-hIgG1FcΔK(CC)-T2m |
|---|---|---|---|
| IC50 | 0.002895 | 0.003794 | 0.004855 |
| | CF770_hIgG1FcΔK(CC)-T2m | CF770_D10-hIgG1FcΔK(CC)-T2m | CF770_D10-GSL-hIgG1FcΔK(CC)-T2m |
| IC50 | 0.01172 | 0.01453 | 0.02093 |

TGF-β-RECEPTOR ECTODOMAIN FUSION MOLECULES AND USES THEREOF

RELATED APPLICATIONS

This application is a continuation of U.S. application Ser. No. 15/755,595, filed Feb. 27, 2018, which is a national stage filing under 35 U.S.C. § 371 of International Application No. PCT/IB2016/055204, filed Aug. 31, 2016, and claims the benefit under 35 U.S.C. § 119(e) of U.S. provisional application Ser. No. 62/212,058, filed Aug. 31, 2015, the entire contents of each of which is incorporated by reference herein in its entirety.

FIELD OF THE INVENTION

The present invention relates to TGF-β superfamily receptor ectodomain fusion molecules and uses thereof. More specifically, the present invention relates to TGF-β superfamily receptor ectodomain fusion molecules and their use in TGF-β superfamily ligand neutralization.

BACKGROUND OF THE INVENTION

TGF-β is part of a superfamily of over 30 ligands that regulate several physiological processes, including cell proliferation, migration and differentiation. Perturbation of their levels and/or signaling gives rise to significant pathological effects. For instance, TGF-β and activin ligands play critical pathogenic roles in many diseases including cancer (Hawinkels & Ten Dijke, 2011; Massague et al, 2000; Rodgarkia-Dara et al, 2006). TGF-β, in particular, is considered as a critical regulator of tumor progression and is overexpressed by most tumor types. It favors tumorigenesis in part by inducing an epithelial-mesenchymal transition (EMT) in the epithelial tumor cells, leading to aggressive metastasis (Thiery et al, 2009). TGF-β also promotes tumorigenesis by acting as a powerful suppressor of the immune response in the tumor microenvironment (Li et al, 2006). In fact, TGF-β is recognized as one of the most potent immunosuppressive factors present in the tumor microenvironment. TGF-β interferes with the differentiation, proliferation and survival of many immune cell types, including dendritic cells, macrophages, NK cells, neutrophils, B-cells and T-cells; thus, it modulates both innate and adaptive immunity (Santarpia et al, 2015; Yang et al, 2010). The importance of TGF-beta in the tumor microenvironment is highlighted by evidence showing that, in several tumor types (including melanoma, lung, pancreatic, colorectal, hepatic and breast), elevated levels of TGF-β ligand are correlated with disease progression and recurrence, metastasis, and mortality. Hence, significant effort has been invested in devising anti-tumor therapeutic approaches that involve TGF-β inhibition (Arteaga, 2006; Mourskaia et al, 2007; Wojtowicz-Praga, 2003).

One approach to developing therapeutic agents that inhibit TGF-β function has been to use antibodies or soluble decoy receptors (also termed receptor ectodomain (ED)-based ligand traps) to bind and sequester ligand, thereby blocking access of ligand to its normal cell surface receptors (Zwaagstra et al, 2012). In general, receptor ED-based traps are a class of therapeutic agents that are able to sequester a wide range of ligands and that can be optimized using protein engineering approaches (Economides et al, 2003; Holash et al, 2002; Jin et al, 2009).

Previously, a novel protein engineering design strategy was used to generate single-chain, bivalent traps that are able to potently neutralize members of the TGF-β superfamily of ligands due to avidity effects (Zwaagstra et al, 2012) [WO 2008/113185; WO 2010/031168]. In this case, bivalency was achieved via covalent linkage of two TβRII ectodomains using portions of the intrinsically disordered regions (IDR) that flank the structured, ligand-binding domain of TβRII-ED. One example of these single-chain bivalent traps, T22d35, exhibited TGF-β neutralization potencies ~100-fold higher than the monovalent non-engineered TβRII ectodomain, though it did not neutralize the TGF-β2 isoform and had a relatively short circulating half-life.

While research to date indicates that single-chain TGF-β traps have promising therapeutic potential, their circulating half-lives and manufacturability present challenges to the commercial application.

SUMMARY OF THE INVENTION

The present invention relates to TGF-β superfamily receptor ectodomain fusion molecules and uses thereof. More specifically, the present invention relates to TGF-β superfamily receptor ectodomain fusion molecules and their use in TGF-β superfamily ligand neutralization.

In some aspects, the invention relates to TGF-β superfamily receptor ectodomain-based polypeptides that are similar to typical Fc fusions in design, in that the ectodomain is fused to a dimeric antibody constant domain. In particular, with respect to the present polypeptides, the Fc portion occupies the N-terminal position. Fc fusions in the prior art typically provide the Fc portion at the C-terminal end of the fusion. As will be evident from the results presented herein, this difference in orientation provides a number of significant advantages.

In other aspects, the present polypeptides incorporate at least two TGF-β superfamily receptor ectodomains that are linked in tandem to the C-terminus of an antibody constant domain.

Thus, there is provided a polypeptide construct comprising: a first portion comprising the second constant domain ($C_{H2}$) and/or third constant domain ($C_{H3}$) of an antibody heavy chain, and a second portion comprising at least two TGF-β superfamily receptor ectodomains (TβSR-ED) linked in tandem; wherein the N-terminus of the second portion is linked to the C-terminus of the first portion.

There is also provided a polypeptide construct comprising: a first portion comprising the second constant domain (CH2) and/or third constant domain (CH3) of an antibody heavy chain, and a second portion comprising at least one TGF-β superfamily receptor ectodomains (TβSR-ED), wherein the N-terminus of the second portion is linked to the C-terminus of the first portion, and further wherein the first portion does not further comprise an antibody that binds to an antigen that is PD-L1, EGFR1, Her-2, CD4, CD6, CD20, CD25, MUC-1, IL-2, IL-6, or CTLA-4.

There is provided a polypeptide construct comprising: a first portion comprising the second constant domain ($C_{H2}$) and/or third constant domain ($C_{H3}$) of an antibody heavy chain, and a second portion comprising at least one TGF-β superfamily receptor ectodomain (TβSR-ED), wherein the N-terminus of the second portion is directly fused to the C-terminus of the first portion.

In an embodiment, there is provided a polypeptide construct comprising a first portion comprising the second constant domain ($C_{H2}$) and/or third constant domain ($C_{H3}$) of an antibody heavy chain, and a second portion comprising at least one TGF-β superfamily receptor ectodomain (TβSR- ED), wherein the N-terminus of the second portion is linked to the C-terminus of the first portion, and wherein the polypeptide construct neutralizes TGF-β with at least 100-fold more potency than the TβSR-ED alone.

In a preferred embodiment, the second portion comprises one, two, or multiple TGF-β superfamily receptor ectodomain (TβSR-ED). In a preferred embodiment, the TβSR-ED is a TGF-β receptor type II ectodomain (TβR-II-ED). In a preferred embodiment, the TβSR-ED comprises a sequence selected from the group consisting of SEQ ID NO:35, SEQ ID NO:69, SEQ ID NO:75, SEQ ID NO:81, and a sequence substantially identical thereto.

The second portion may comprise a sequence selected from the group consisting of SEQ ID NO:43-SEQ ID NO:51, SEQ ID NO:61-SEQ ID NO:68, SEQ ID NO:73, SEQ ID NO:74, SEQ ID NO:79, SEQ ID NO:80, SEQ ID NO:85, SEQ ID NO:86, SEQ ID NO:88, and a sequence substantially identical thereto.

In a preferred embodiment, the first portion of a polypeptide construct of the present invention further comprises a $C_{H1}$, a $C_{H1}$ and $V_H$, or $C_{H1}$ and scFv.

There is provided a polypeptide construct of the present invention wherein the antibody heavy chain is of human origin. In a preferred embodiment, the antibody heavy chain is selected from the group consisting of a human IgG1, IgG2, IgG3, or IgG4 heavy chain. More preferably, the antibody heavy chain is a human IgG1.

In accordance with the present invention, the polypeptide construct shows longer in vivo half-life compared to the half-life of the second portion alone.

There is provided a polypeptide construct of the present invention, wherein the polypeptide construct is a single chain polypeptide.

In an embodiment, the polypeptide construct forms a dimeric polypeptide. In another embodiment, the polypeptide construct is heterodimeric.

There is provided a polypeptide construct selected from the group consisting of any one of SEQ ID NO:91 to SEQ ID NO:120, and a sequence substantially identical thereto.

There is provided a polypeptide construct according to the present invention, wherein the construct comprises an antibody, antigen binding fragment thereof, or a targeting moiety. In a preferred embodiment, the antibody, the antigen binding fragment, or the targeting moiety is at the N-terminus of the first portion.

In a preferred embodiment, the antigen binding fragment may be selected from the group consisting of a Fv, scFv, Fab, or sdAb. In a preferred embodiment, the antigen binding fragment binds to any antigen, provided that it is not PD-L1, EGFR1, Her-2, CD4, CD6, CD20, CD25, MUC-1, IL-2, IL-6, or CTLA-4.

In a preferred embodiment, a polypeptide construct of the present invention comprises an antibody selected from the group consisting of Cetuximab, Avastin, Herceptin, Synagis, and FC5. In a preferred embodiment, the antibody is Cetuximab.

In a preferred embodiment, a polypeptide construct of the present invention comprises a targeting moiety, wherein the targeting moiety comprises a poly-aspartate sequence motif for bone targeting. In a preferred embodiment, the targeting moiety comprises D10.

There is provided a polypeptide construct according to the present invention wherein the construct is a dimeric polypeptide; wherein the dimeric polypeptide comprises: a first single chain polypeptide comprising a first portion comprising the second constant domain ($C_{H2}$) and third constant domain ($C_{H3}$) of an antibody heavy chain, and a heavy chain variable region of a given antibody; a second portion comprising one or more TGF-β superfamily receptor ectodomains (TβSR-ED), wherein the N-terminus of the second portion is linked to the C-terminus of the first portion, and a second single chain polypeptide comprising a first portion comprising the second constant domain ($C_{H2}$) and third constant domain ($C_{H3}$) of an antibody heavy chain, and a light chain variable region of said given antibody; a second portion comprising one or more TGF-β superfamily receptor ectodomain (TβSR-ED) which is the same or different from the ectodomain(s) in the first polypeptide, wherein the N-terminus of the second portion is linked to the C-terminus of the first portion.

There is also provided a nucleic acid molecule encoding the polypeptide construct of the present invention. There is also provided a vector comprising the nucleic acid molecule of claim the present invention.

There is also provided a composition comprising one or more than one independently selected polypeptide construct of the present invention and a pharmaceutically-acceptable carrier, diluent, or excipient.

There is also provided a transgenic cellular host comprising the nucleic acid molecule or a vector of the present invention. The transgenic cellular host further comprising a second nucleic acid molecule or a second vector encoding a second polypeptide construct different from the first polypeptide construct.

There is also provided the use of a polypeptide construct according to the present invention for treatment of a medical condition, disease or disorder; wherein the medical condition, disease or disorder comprises, but is not limited to, cancer, ocular diseases, fibrotic diseases, or genetic disorders of connective tissue.

In a preferred embodiment, there therefore provided a polypeptide construct comprising:
  a first portion comprising the second constant domain (CH2) and/or third constant domain (CH3) of an antibody heavy chain, and
  a second portion comprising at least two TGF-β superfamily receptor ectodomains (TβSR-ED),
    wherein the N-terminus of the second portion is linked to the C-terminus of the first portion.

The antibody constant domain can further comprise, either linked thereto or formed integrally therewith, a binding agent such as a full size antibody, a ligand or any other protein of interest. In the alternative, the antibody constant domain comprises only the CH2 and/or CH3 regions, and not a full size antibody. In these and other types of constructs, the CH2 and/or CH3 region can be altered by deleting or substituting amino acids including one or more of the cysteines that provide cross-linking when the present constructs are provided as dimeric constructs.

In other aspects of the present invention, there is provided a polypeptide construct that incorporates one or more such ectodomains. When the constructs comprise only one ectodomain linked to the antibody constant domain, then the construct is further characterized by at least one of the following: (1) when the constant domain further comprises a full sized antibody, that antibody does not bind effectively to PD-L1 or to an immunoregulatory antigen selected, (2) the constant domain comprises only the CH2 and/or CH3 regions, (3) the constant domain comprises an amino acid alteration relative to a wild type counterpart, such as a cysteine residue alteration; and (4) the first portion is linked to the second portion directly and without intervening amino acids.

In another of its aspects, the present invention provides a polypeptide construct comprising
- a first portion comprising the second constant domain ($C_{H2}$) and/or third constant domain ($C_{H3}$) of an antibody heavy chain, and
- a second portion comprising at least one TGF-β superfamily receptor ectodomain (TβSR-ED), wherein the N-terminus of the second portion is linked to the C-terminus of the first portion. These polypeptide constructs can neutralize TGF-β, and with at least 100-fold more potency than the TβSR-ED alone.

The second portion of the polypeptide construct of the present invention may comprise one or two or more TβSR-ED. In a preferred embodiment the construct comprises two or more independently selected ectodomains linked in tandem and to the C-terminus of the constant domain. The TβSR-ED may be selected from the group consisting of a TGF-β receptor type II ectodomain (TβRII-ED), a bone morphogenetic protein receptor type Ia ectodomain (BMPR-ED), an activin receptor type IIa ectodomain (ActRIIa-ED), and an activin receptor type IIb ectodomain (ActRII-ED). In another preferred embodiment, the ectodomain is a TβR-II ectodomain.

In the polypeptide construct described herein, the first portion further may comprise a $C_{H1}$, a $C_{H1}$ and $V_H$, or a $C_{H1}$ and scFv. It may constitute an Fc region, an antibody, or any ligand binding agent or moiety.

The polypeptide construct of the present invention may comprise a $C_{H2}$ and $C_{H3}$ from an antibody heavy chain that is of human or mouse origin. For example, and without wishing to be limiting, the antibody heavy chain may be selected from the group consisting of a human IgG1, IgG2, IgG3, or IgG4 heavy chain. In embodiments, the constant domain in the constructs is CH2 per se, or CH3 per se or CH2-CH3.

The polypeptide construct described herein may show longer in vivo half-life compared to the half-life of TβSR-ED alone.

In one example, the polypeptide construct of the present invention may be a single chain polypeptide. The polypeptide construct as described herein may also form a dimeric polypeptide. This dimeric polypeptide may be heterodimeric.

The present invention further provides a polypeptide construct comprising
- a first portion comprising the second constant domain ($C_{H2}$) and/or third constant domain ($C_{H3}$) of an antibody heavy chain, and
- a second portion comprising at least one TGF-β superfamily receptor ectodomain (TβSR-ED), wherein the N-terminus of the second portion is linked to the C-terminus of the first portion; additionally, in the construct as just described, the first portion is not derived from certain antibodies discussed infra.

The present invention also provides a polypeptide construct, comprising:
- a first single chain polypeptide comprising a first portion comprising the second constant domain ($C_{H2}$) and/or third constant domain ($C_{H3}$) of an antibody heavy chain, and a heavy chain variable region of a given antibody; and a second portion comprising one or more TGF-β superfamily receptor ectodomains (TβSR-ED), wherein the N-terminus of the second portion is linked to the C-terminus of the first portion, and
- a second single chain polypeptide comprising a first portion comprising the second constant domain ($C_{H2}$) and/or third constant domain ($C_{H3}$) of an antibody heavy chain, and a light chain variable region of said given antibody; and a second portion comprising one or more TGF-β superfamily receptor ectodomain (TβSR-ED) which is the same or different from the ectodomain(s) in the first polypeptide, wherein the N-terminus of the second portion is linked to the C-terminus of the first portion.

In alternative constructs of the present invention, the polypeptide construct comprises an antibody Fc fragment linked at the C-terminus of each heavy chain to at least one TGF-β superfamily receptor ectodomain (TβSR-ED), as described above. In embodiments the receptor ectodomain portion comprises two independently selected ectodomains that are linked in tandem, i.e., in a linear manner. In some embodiments, the ectodomains are the same in sequence, or least the same with respect to their target ligand. The construct may further comprise a binding fragment or moiety at the N-terminus of the Fc; the binding fragment may be selected from the group consisting of a Fv, scFv, Fab, or sdAb, or any other binding moiety such as a motif for bone targeting, also as described above. In the polypeptide constructs as described above, the TGF-β receptor ectodomain does not interfere in the native function or specificity of the binding fragment.

The present invention also provides a nucleic acid molecule encoding the polypeptide constructs as described herein. A vector comprising the nucleic acid molecule just described is also encompassed by the invention. The invention also includes a transgenic cellular host comprising the nucleic acid molecule or a vector as described herein; the cellular host may further include a second nucleic acid molecule or a second vector encoding a second polypeptide construct different from the first polypeptide construct. Systems used to produce the present polypeptides can be secretion systems, particularly in the case where dimerization through disulfide bridges is required, and the expression polynucleotides thus encode secretion signals that are cleaved by the host upon secretion into the culturing medium.

Compositions comprising one or more than one independently selected polypeptide construct described herein and a pharmaceutically-acceptable carrier, diluent, or excipient are also encompassed by the present invention.

Additional aspects and advantages of the present invention will be apparent in view of the following description. The detailed descriptions and examples, while indicating preferred embodiments of the invention, are given by way of illustration only, as various changes and modifications within the scope of the invention will become apparent to those skilled in the art in light of the teachings of this invention.

BRIEF DESCRIPTION OF THE DRAWINGS

These and other features of the invention will now be described by way of example, with reference to the appended drawings, wherein:

FIG. 1A is a schematic diagram showing TGF-β Type II receptor ectodomain (TβRII-ED)-based molecules T2m and T22d35 along with their sequences (SEQ ID NO:43 and 46, respectively). Natural linker sequences (SEQ ID NO:36, 39 and 40) are underlined and depicted as dark grey lines; the sequence of the TβR-II-ED structured domain (SEQ ID NO:35) is shown in bold, and the domain labeled and depicted in dark grey; the site of the fusion of natural linkers is depicted by a slash. FIGS. 1B-1D are schematic diagrams of IgG Fc-based scaffolds: an IgG Fc region (FIG. 1B), a V$_H$H-IgG Fc (comprising a V$_H$H single domain antibody fused to the N-terminus of an Fc region; FIG. 1C), and a full-size antibody (FIG. 1D).

(FIG. 2A) represents constructs in which T22d35 (dark grey) is fused to the C-terminus of IgG Fc regions (IgG isoforms 1, 2, 3 or 4) with no Fab or other functional binding moiety at the N-terminus (Fc-T22d35, FIG. 2A), (FIG. 2D) represents constructs in which T22d35 (dark grey) is fused to the C-terminus of the IgG Fc region of full-size antibodies with heavy and light chain Fabs (FSA-T22d35, FIG. 2D), (FIG. 2E) represents constructs in which T22d35 (dark grey) is fused to the C-terminus of IgG Fc regions that have a non-Fab binding/localization moiety at the N-terminus, such as the variable region of a camelid V$_H$H antibody (V$_H$H-Fc-T22d35) or a deca-aspartate motif for bone targeting (D10-Fc-T22d35). Similarly, (FIG. 2B), (FIG. 2C) and (FIG. 2F) and (FIG. 2G) represent constructs in which T2m (the TGF-β Type II receptor ectodomain, TβRII-ED—dark grey) is fused at the N-terminus of an IgG Fc (T2m-Fc, FIG. 2B) or the C-terminus of IgG Fc regions with no Fab or other functional binding moiety at the N-terminus (Fc-T2m, FIG. 2C), or the C-terminus of full-size antibodies with heavy and light chain Fabs (FSA-T2m, FIG. 2F), or the C-terminus of IgG Fc regions that have a non-Fab binding/localization moiety at the N-terminus, such as the variable region of a camelid V$_H$H antibody (V$_H$H-Fc-T2m, FIG. 2G) or a deca-aspartate motif for bone targeting (D10-Fc-T2m).

FIG. 3A is a (ProtA)-affinity column elution profile for T22d35 fused to the Cetuximab FSA (Cet-T22d35—a representative of construct D (FIG. 2D) in FIGS. 2A-2G). FIG. 3B is the size exclusion (SEC) purification profile of the Cet-T22d35. FIG. 3C show 4-15% SDS-PAGE gels of ProtA-purified Cet-T22d35 under reducing (left panel) and non-reducing (right panel) conditions (CetHC-T22d35, Cetuximab heavy chain fused to T22d35; CetLC, Cetuximab light chain). Lanes 1 are the pooled Prot-A eluted fractions, while lanes 2 are the pooled SEC fractions. FIG. 3D shows the UPLC-SEC profile of ProtA-purified Cet-T22d35. FIG. 3E shows the (ProtA)-affinity column elution profile for hIgG1 FcΔK(C)-T2m (a construct with T2m fused to an Fc region with no functional binding moiety at the N-terminus; a representative of construct D (FIG. 2D) in FIGS. 2A-2G). FIGS. 3F, 3G, and 3H show the UPLC-SEC profile before SEC (FIG. 3F), the UPLC-SEC profile after SEC (FIG. 3G) and the SDS-PAGE (NR & R) (FIG. 3H) of hIgG1FcΔK(C)-T2m. FIGS. 3I, 3K and 3L show the SEC profile before purification and UPLC-SEC profile after SEC purification for Fc-T2m, Fc-T22d35 and hIgG1FcΔK(C)-T22d35, respectively. FIG. 3J shows the UPLC-SEC profile for hIgG2FcΔK(CC)-Tm.

FIG. 7A shows pictures of cultured A549 cells showing their morphologies before treatment (left panel A) and after treatment with EGF+TGF-β1 (right panel B). FIG. 7B shows a western blot of whole cell lysates of A549 cells treated with EGF+TGF-β1 in the presence or absence of various concentrations of Cetuximab (Cetux), Cet-T22d35 or T22d35, probed for the epithelial marker E-Cadherin, while FIG. 7C is the densitometer quantification of the E-cadherin bands in the Western blot. Results show that Cet-T22d35 is much more potent than T22d35 alone or Cetuximab alone in upregulating E-cadherin, i.e. blocking EMT. FIG. 7D shows the inhibition of EGF+TGF-β-induced EMT by Cetuximab (Cetux), Cet-T22d35, T22d35 or Cet-T22d35 plus T22d35 as measured by flow cytometry detection of the epithelial E-Cadherin (top panel) and mesenchymal N-Cadherin (bottom panel) markers.

FIGS. 9A, 9B and 9C present graphs showing the effect of "headless" Fc-T2m constructs (representatives of construct C (FIG. 2C) in FIGS. 2A-2G) and a FSA-T2m construct (a representative of construct F (FIG. 2F) in FIGS. 2A-2G) on tumor growth and T-cell function in an immune-competent syngeneic triple negative breast cancer (4T1) model (for comparison, the effects of the 1D11 antibody and non-Fc-fused T22d35 are also shown). The results demonstrate the improved efficacy on T-cell function of two headless-T2m constructs relative to the FSA-T2m construct, and relative to 1D11 and non-Fc-fused T22d35.

Figure 1D:
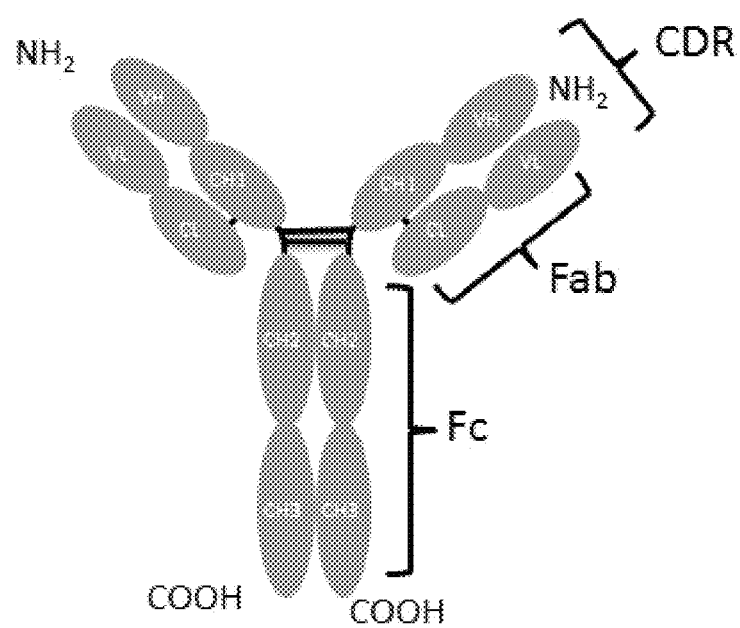
Figure 2A:
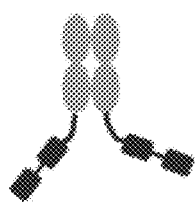
FIGS. 2A-2G are schematic representations of TGF-β superfamily receptor-ectodomain-based fusion constructs of the present invention.
Figure 2B:
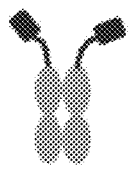
Figure 2C:
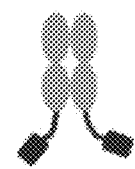
Figure 2D:
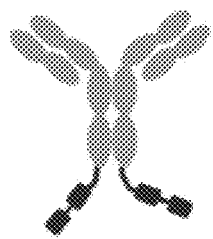
Figure 2E:
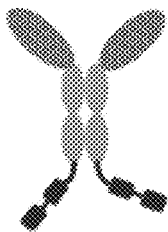
Figure 2F:
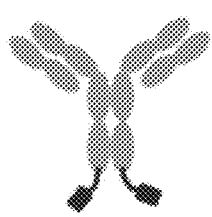
Figure 2G:
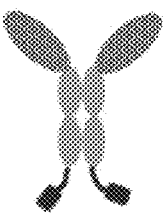

While the light and heavy chain variable regions show significant sequence diversity between antibodies, the constant regions show less sequence diversity and are responsible for binding a number of natural proteins to elicit important biochemical events. Specifically, and without wishing to be limiting, the Fc fragment binds to endogenous Fc receptors on the surface of lymphocytes.

The $C_{H2}$ and $C_{H3}$ domains of the first portion may be of any isotype, including one selected from the group consisting of IgA, IgD, IgE, and IgG. The $C_{H2}$ and $C_{H3}$ domains may also be from any suitable source. For example and without wishing to be limiting, the $C_{H2}$ and $C_{H3}$ domains may originate from a human, mouse and other rodents like rats and degu, rabbit, monkey, or other mammalian source. In one example, the $C_{H2}$ and $C_{H3}$ domains may be of the IgG isotype; in another example, the $C_{H2}$ and $C_{H3}$ domains are from human.

In a specific, non-limiting example, the $C_{H2}$ and $C_{H3}$ domains of the first portion may be of an isotype or comprise a sequence selected from the group consisting of:

```
a human IgG1, for example but not limited to SEQ
ID NO: 1
(APELLGGPSVFLFPPKPKDTLMISRTPEVTCVVVDVSHEDPEVKFNWY

VDGVEVHNAKTKPREEQYNSTYRVVSVLTVLHQDWLNGKEYKCKVSNKA

LPAPIEKTISKAKGQPREPQVYTLPPSRDELTKNQVSLTCLVKGFYPSD

IAVEWESNGQPENNYKTTPPVLDSDGSFFLYSKLTVDKSRWQQGNVFSC

SVMHEALHNHYTQKSLSLSPGK) as comprised in P01857 of the UniProtKB/Swiss-Prot database;

a human IgG2, for example but not limited to SEQ
ID NO: 2
(APPVAGPSVFLFPPKPKDTLMISRTPEVTCVVVDVSHEDPEVQFNWYV

DGVEVHNAKTKPREEEQFNSTFRVVSVLTVVHQDWLNGKEYKCKVSNKGL

PAPIEKTISKTKGQPREPQVYTLPPSREEMTKNQVSLTCLVKGFYPSDI

SVEWESNGQPENNYKTTPPMLDSDGSFFLYSKLTVDKSRWQQGNVFSCS

VMHEALHNHYTQKSLSLSPGK), as comprised in P01859 of the UniProtKB/Swiss-Prot database;

a human IgG3, for example but not limited to SEQ
ID NO: 3
(APELLGGPSVFLFPPKPKDTLMISRTPEVTCVVVDVSHEDPEVQFKWY

VDGVEVHNAKTKPREEQYNSTFRVVSVLTVLHQDWLNGKEYKCKVSNKA

LPAPIEKTISKTKGQPREPQVYTLPPSREEMTKNQVSLTCLVKGFYPSD

IAVEWESSGQPENNYNTTPPMLDSDGSFFLYSKLTVDKSRWQQGNIFSC

SVMHEALHNRFTQKSLSLSPGK), as comprised in P01860 of the UniProtKB/Swiss-Prot database;

a human IgG4, for example but not limited to SEQ
ID NO: 4
(APEFLGGPSVFLFPPKPKDTLMISRTPEVTCVVVDVSQEDPEVQFNWY

VDGVEVHNAKTKPREEQFNSTYRVVSVLTVLHQDWLNGKEYKCKVSNKG

LPSSIEKTISKAKGQPREPQVYTLPPSQEEMTKNQVSLTCLVKGFYPSD
```

```
-continued
IAVEWESNGQPENNYKTTPPVLDSDGSFFLYSRLTVDKSRWQEGNVFSC

SVMHEALHNHYTQKSLSLSLGK), as comprised in P01861 of the UniProtKB/Swiss-Prot database;
``` and
a sequence substantially identical to any of the sequences listed above.

In the protein constructs of the present invention, the first portion may further comprise a sequence corresponding to the hinge region at the N-terminus of the $C_{H2}$ domain. For example, the first portion may further comprise a sequence selected from the group consisting of:

```
                                        (SEQ ID NO: 5)
EPKSCDKTHTCPPCP for human IgG1;

(SEQ ID NO: 6)
ERKCCVECPPCP for human IgG2;

(SEQ ID NO: 7)
ELKTPLGDTTHTCPRCPEPKSCDTPPPCPRCPEPKSCDTPPPCPRCPEP
KSCDTPPPCPRCP for human IgG3;

(SEQ ID NO: 8)
ESKYGPPCPSCP for human IgG4;
``` and a sequence substantially identical to any of the sequences listed above.

Thus, the first portion of the polypeptide construct of the present invention consists of naturally fused Fc and hinge regions for the various IgG isoforms and in embodiments is selected from the group consisting of SEQ ID NO:1-4 for the Fc region and SEQ ID NO:5-8 for the hinge region.

In specific embodiments, the first portion of the polypeptide construct of the present invention is selected from a group of sequences displaying variation in the N-terminal sequence as exemplified by SEQ ID NO:9-34. These differ in the number of cysteine residues retained from the hinge region as a means to modulating the degree of Fc-region dimerization and hence impacting on both efficacy and manufacturability. Thus, in embodiments, the polypeptide construct comprises a variation in the constant domain, wherein at least one cysteine residue involved in cross-linking is deleted or substituted. Suitable substitutions include serine or alanine, and preferably by serine. A substantially identical sequence may comprise one or more conservative amino acid mutations that still provide for proper folding upon secretion into the culturing medium. It is known in the art that one or more conservative amino acid mutations to a reference sequence may yield a mutant peptide with no substantial change in physiological, chemical, physico-chemical or functional properties compared to the reference sequence; in such a case, the reference and mutant sequences would be considered "substantially identical" polypeptides. A conservative amino acid substitution is defined herein as the substitution of an amino acid residue for another amino acid residue with similar chemical properties (e.g. size, charge, or polarity). These conservative amino acid mutations may be made to the framework regions while maintaining the overall structure of the constant domains; thus the function of the Fc is maintained.

In a non-limiting example, a conservative mutation may be an amino acid substitution. Such a conservative amino acid substitution may substitute a basic, neutral, hydrophobic, or acidic amino acid for another of the same group. By the term "basic amino acid" it is meant hydrophilic amino acids having a side chain pK value of greater than 7, which are typically positively charged at physiological pH. Basic amino acids include histidine (His or H), arginine (Arg or R), and lysine (Lys or K). By the term "neutral amino acid" (also "polar amino acid"), it is meant hydrophilic amino acids having a side chain that is uncharged at physiological pH, but which has at least one bond in which the pair of electrons shared in common by two atoms is held more closely by one of the atoms. Polar amino acids include serine (Ser or S), threonine (Thr or T), cysteine (Cys or C), tyrosine (Tyr or Y), asparagine (Asn or N), and glutamine (Gln or Q). The term "hydrophobic amino acid" (also "non-polar amino acid") is meant to include amino acids exhibiting a hydrophobicity of greater than zero according to the normalized consensus hydrophobicity scale of (Eisenberg et al, 1984). Hydrophobic amino acids include proline (Pro or P), isoleucine (Ile or I), phenylalanine (Phe or F), valine (Val or V), leucine (Leu or L), tryptophan (Trp or W), methionine (Met or M), alanine (Ala or A), and glycine (Gly or G).

"Acidic amino acid" refers to hydrophilic amino acids having a side chain pK value of less than 7, which are typically negatively charged at physiological pH. Acidic amino acids include glutamate (Glu or E), and aspartate (Asp or D).

In another non-limiting example, a conservative mutation in the $C_{H2}$ and/or $C_{H3}$ domain may be a substitution that enhances a property selected from the group consisting of the stability, half-life, or Fc properties of $C_{H2}$ and/or $C_{H3}$ domains or alter glycosylation of the $C_{H2}$ and/or $C_{H3}$ domain. For example, and without wishing to be limiting in any manner, the mutation may be an alteration at position 228 (EU numbering, 241 according to Kabat) where the serine is substituted by a proline (S228P), which stabilizes the disulfide linkage within the Fc dimer. Another alteration is the mutation at position 409 (EU numbering, 440 according to Kabat) where an arginine is substituted to a lysine for further stabilization of the Fc homodimer at the $C_{H3}$-domain level (Yang & Ambrogelly, 2014). Yet another alteration within the $C_{H2}$ and/or $C_{H3}$ domain may be a substitution of Asn297 (EU numbering, 314 according to Kabat) by glycine or alanine to alter glycosylation of the constant domain. In yet another example, the $C_{H2}$ and/or $C_{H3}$ domain may be altered by substitution of one or more threonine (T252L, T253S, and/or T256F; see [U.S. Pat. No. 62,777,375]) to increase half-life. Particularly useful are those alterations that enhance Fc properties while remaining silent with respect to conformation, e.g., retaining Fc receptor binding.

In yet another non-limiting example, the conservative mutations in the $C_{H2}$ and/or $C_{H3}$ domain may be a substitution that is naturally-occurring. Such mutations may occur in nature as minor sequence differences between species or race.

Sequence identity is used to evaluate the similarity of two sequences; it is determined by calculating the percent of residues that are the same when the two sequences are aligned for maximum correspondence between residue positions. Any known method may be used to calculate sequence identity; for example, computer software is available to calculate sequence identity. Without wishing to be limiting, sequence identity can be calculated by software such as NCBI BLAST2 service maintained by the Swiss Institute of Bioinformatics (and as found at ca.expasy.org/tools/blast/), or any other appropriate software that is known in the art.

The substantially identical sequences of the present invention may be at least 90% identical; in another example, the substantially identical sequences may have an identity selected from the group consisting of at least 90, 91, 92, 93, 94, 95, 96, 97, 98, 99, or 100% identical, or any percentage there between, at the amino acid level to sequences described herein. Importantly, the substantially identical sequences retain the activity, specificity, and functionality of the reference sequence. In a non-limiting embodiment, the difference in sequence identity may be due to conservative amino acid mutation(s). In a non-limiting example, the first portion of the polypeptide construct of the present invention may comprise a Fc comprising a sequence selected from the group consisting of a sequence at least 95%, 98% or 99% identical to that of the Fc described herein.

Accordingly, it will be appreciated that the first portion of a construct will include at least an antibody region that preferably provides for cross-linking of the polypeptide constructs, thereby to provide a dimeric protein. This first portion comprises at least the minimal CH2 and/or CH3 domain. That portion can be altered (i) by substituting or deleting cysteine residues from the hinge regions (SEQ ID NO:5-8) involved in crosslinking between the antibody heavy chains or between the heavy and light chains in order to potentially improve preparation homogeneity and efficacy, and/or (ii) by deleting or suitably replacing (e.g., by mutation to alanine) the terminal lysine residue 447 (EU numbering, 478 according to Kabat) of an IgG heavy chain in order to improve chemical stability of C-terminal fusions to enzymatic proteolysis (e.g., by several serine proteases and typically by trypsin). These changes have a positive impact on potency and/or manufacturability, as revealed herein. The first portion can also be extended to become a full Fc region, by including the CH1 domain. As a full Fc, this portion will provide normal Fc effector functions that include involvement in immune cell recruitment, ADCC, CDC and other antibody functions. Moreover, and in embodiments of the present invention, the first portion can include a complete antibody or any equivalent thereof. In certain embodiments, such as when a construct comprises just one ectodomain that is a TGF-β receptor II ectodomain, there is the proviso that the second portion is not an antibody that binds to an immune checkpoint protein such as PD-L1 (programmed death ligand 1) and is not an antibody that binds to an immunomodulating agent that counteracts immune tolerance of cancer cells, the nature and identity of which is as described in [U.S. Pat. No. 8,815,247], and is not an antibody that binds one of EGFR1, her-2, CD4, CD6, CD20, CD25, MUC-1, IL-2, IL-6, and CTLA-4.

The second portion of the polypeptide construct of the present invention comprises at least one and preferably two TGF-β superfamily receptor ectodomain/s (TβSR-ED); for example, the second portion may comprise one or two TβSR-ED. The ectodomain of the Transforming Growth Factor-β superfamily receptor (TβSR) is the N-terminal extracellular, ligand-binding portion of the receptor. Without wishing to be limiting in any manner, the TβSR ectodomain may bind a molecule selected from the group consisting of TGF-β, bone morphogenetic protein (BMP) including BMP2, BMP3, BMP4, BMPS, BMP, BMP6, BMP7, BMP8, BMP9, BMP10, BMP11, BMP12, BMP13, BMP14, an BMP15, activin including activins βA, βB and βC, growth differentiation factor (GDF-1) including GDF-3, GDF-8, GDF-9, and GDF-15, nodal, inhibin-α, anti-Mullerian hormone, Lefty-1, Lefty-2, arteman, persephin, neurturin, myostatin, or other known TGF-β superfamily ligands. For example, the TβR ectodomain may be selected from the group consisting of the human TGF-β receptor type II ectodomain (TβR-II-ED), the human TGF-β receptor type IIb (TβR-IIb) ectodomain, the human activin receptor type IIa (ActR-IIa) ectodomain, the human activin receptor type IIb (ActR-IIb) ectodomain, or the BMP type Ia (BMPR-Ia) ectodomain.

In a preferred embodiment the ectodomain binds TGF-β1 and/or TGF-β3. In another preferred embodiment, the ectodomain itself is a human TGF-β receptor type II ectodomain including particularly the TGF-β receptor type IIa (TβRIIa). In one specific, non-limiting example, the TβSR-ED is the TGF-β receptor type II ectodomain (TβRII-ED; SEQ ID NO:35).

In the second portion as described above, the TβSR ectodomain-based portion may further comprise natural linkers. Appropriate, naturally-derived linkers that can be used to fuse two ectodomains head-to-tail are known to those of skill in the art; for example, and without wishing to be limiting, suitable natural linkers are described in [WO2008/113185].

In this embodiment, the natural linker, if present, may be selected from the group consisting of

```
                                            (SEQ ID NO: 36)
IPPHVQKSVNNDMIVTDNNGAVKFP;

(SEQ ID NO: 37)
IPPHVQKSDVEMEAQKDEIICPSCNRTAHPLRHINNDMIVTDNNGAVKF
P;

(SEQ ID NO: 39)
SEEYNTSNPD;

(SEQ ID NO: 40)
SEEYNTSNPDIPPHVQKSVNNDMIVTDNNGAVKFP;

(SEQ ID NO: 41)
SEEYNTSNPDIPPHVQKSDVEMEAQKDEIICPSCNRTAHPLRHINNDMI
VTDNNGAVKFP;
``` and
a combination thereof.

In a specific, non-limiting example, the second portion of the polypeptide construct of the present invention may comprise the sequence selected from the group consisting of:

A single TGF-β Type II receptor ectodomain, such as:

```
IPPHVQKSVNNDMIVTDNNGAVKFPQLCKFCDVRFSTCDNQKSCMSNCS

ITSICEKPQEVCVAVWRKNDENITLETVCHDPKLPYHDFILEDAASPKC

IMKEKKKPGETFFMCSCSSDECNDNIIFSEEYNTSNPD (SEQ ID

NO: 43, also referred to herein as T2m);

(SEQ ID NO: 44)
IPPHVQKSDVEMEAQKDEIICPSCNRTAHPLRHINNDMIVTDNNGAVKF

PQLCKFCDVRFSTCDNQKSCMSNCSITSICEKPQEVCVAVWRKNDENIT

LETVCHDPKLPYHDFILEDAASPKCIMKEKKKPGETFFMCSCSSDECND

NIIFSEEYNTSNPD;
```

A TGF-β Type II receptor ectodomain "doublet", in which a TGF-β Type II receptor ectodomain is linked with another TGF-β Type II receptor ectodomain, which ectodomains can be the same or different TGF-β superfamily receptor ectodomains, such as:

```
IPPHVQKSVNNDMIVTDNNGAVKFPQLCKFCDVRFSTCDNQKSCMSNCS

ITSICEKPQEVCVAVWRKNDENITLETVCHDPKLPYHDFILEDAASPKC

IMKEKKKPGETFFMCSCSSDECNDNIIFSEEYNTSNPDIPPHVQKSVNN

DMIVTDNNGAVKFPQLCKFCDVRFSTCDNQKSCMSNCSITSICEKPQEV

CVAVWRKNDENITLETVCHDPKLPYHDFILEDAASPKCIMKEKKKPGET

FFMCSCSSDECNDNIIFSEEYNTSNPD (SEQ ID NO: 46, also referred to herein as T22d35);

(SEQ ID NO: 47)
IPPHVQKSDVEMEAQKDEIICPSCNRTAHPLRHINNDMIVTDNNGAVKF

PQLCKFCDVRFSTCDNQKSCMSNCSITSICEKPQEVCVAVWRKNDENIT

LETVCHDPKLPYHDFILEDAASPKCIMKEKKKPGETFFMCSCSSDECND

NIIFSEEYNTSNPDIPPHVQKSDVEMEAQKDEIICPSCNRTAHPLRHIN

NDMIVTDNNGAVKFPQLCKFCDVRFSTCDNQKSCMSNCSITSICEKPQE

VCVAVWRKNDENITLETVCHDPKLPYHDFILEDAASPKCIMKEKKKPGE

TFFMCSCSSDECNDNIIFSEEYNTSNPD;
``` and
a sequence substantially identical thereto. "Substantially identical" is as defined above.

In another specific, non-limiting example, the TGF-β receptor ectodomain is the bone morphogenetic protein receptor Ia (BMPRIa; SEQ ID NO:69). In this embodiment, the natural linker, if present, may be selected from the group consisting of

```
                                            (SEQ ID NO: 70)
QNLDSMLHGTGMKSDSDQKKSENGVTLAPED;

(SEQ ID NO: 71)
PVVIGPFFDGSIR;

(SEQ ID NO: 72)
PVVIGPFFDGSIRQNLDSMLHGTGMKSDSDQKKSENGVTLAPED;
``` and
a combination thereof.

Thus, in a specific, non-limiting example, the second portion of the polypeptide construct of the present invention may comprise the sequence selected from the group consisting of:

```
                                            (SEQ ID NO: 74)
QNLDSMLHGTGMKSDSDQKKSENGVTLAPEDTLPFLKCYCSGHCPDDAI

NNTCITNGHCFAIIEEDDQGETTLASGCMKYEGSDFQCKDSPKAQLRRT

IECCRTNLCNQYLQPTLPPVVIGPFFDGSIRQNLDSMLHGTGMKSDSDQ

KKSENGVTLAPEDTLPFLKCYCSGHCPDDAINNTCITNGHCFAIIEEDD

QGETTLASGCMKYEGSDFQCKDSPKAQLRRTIECCRTNLCNQYLQPTLP

PVVIGPFFDGSIR;
``` and
a sequence substantially identical thereto. "Substantially identical" is as defined above.

In another specific, non-limiting example, the TβSR ectodomain is the activin receptor IIa (ActRIIa; SEQ ID NO:75). In this embodiment, the natural linker, if present, may be selected from the group consisting of

AILGRSE; (SEQ ID NO: 76)

EMEVTQPTSNPVTPKPPYYNI; (SEQ ID NO: 77)

EMEVTQPTSNPVTPKPPYYNIAILGRSE; (SEQ ID NO: 78)

and
- a combination thereof.

Thus, another specific non-limiting example of the second portion of the polypeptide construct of the present invention comprises the sequence selected from the group consisting of:

(SEQ ID NO: 80)
AILGRSETQECLFFNANWEKDRTNQTGVEPCYGDKDKRRHCFATWKNIS

GSIEIVKQGCWLDDINCYDRTDCVEKKDSPEVYFCCCEGNMCNEKFSYF

PEMEVTQPTSNPVTPKPPYYNIAILGRSETQECLFFNANWEKDRTNQTG

VEPCYGDKDKRRHCFATWKNISGSIEIVKQGCWLDDINCYDRTDCVEKK

DSPEVYFCCCEGNMCNEKFSYFPEMEVTQPTSNPVTPKPPYYNI;

and
- a sequence substantially identical thereto. "Substantially identical" is as defined above.

In another specific, non-limiting example, the TGF-β receptor ectodomain is the activin receptor IIb (ActRIIb; SEQ ID NO:81). In this embodiment, the natural linker, if present, may be selected from the group consisting of

SGRGEAET; (SEQ ID NO: 82)

EAGGPEVTYEPPPTAPT; (SEQ ID NO: 83)

EAGGPEVTYEPPPTAPTSGRGEAET; (SEQ ID NO: 84)

and
- a combination thereof.

Thus, another specific non-limiting example of the second portion of the polypeptide construct of the present invention comprises the sequence selected from the group consisting of:

(SEQ ID NO: 86)
SGRGEAETRECIYYNANWELERTNQSGLERCEGEQDKRLHCYASWRNSS

GTIELVKKGCWLDDFNCYDRQECVATEENPQVYFCCCEGNFCNERFTHL

PEAGGPEVTYEPPPTAPTSGRGEAETRECIYYNANWELERTNQSGLERC

EGEQDKRLHCYASWRNSSGTIELVKKGCWLDDFNCYDRQECVATEENPQ

VYFCCCEGNFCNERFTHLPEAGGPEVTYEPPPTAPT;

and
- a sequence substantially identical thereto. "Substantially identical" is as defined above.

Thus, in various embodiments of the present invention, the present constructs have an ectodomain comprising an amino acid sequence selected from the group consisting of SEQ ID NO:35, SEQ ID NO:69, SEQ ID NO:75, SEQ ID NO:81, and a sequence substantially identical thereto. In other embodiments, the second portion comprises the entire extracellular portion of a TβSR-ED consisting of a sequence selected from the group consisting of SEQ ID NO:43, SEQ ID NO:44, SEQ ID NO:73, SEQ ID NO:79, SEQ ID NO:85, and a sequence substantially identical thereto.

The at least two ectodomain portion can have the same or different ectodomains, all belonging to the superfamily. In embodiments, the ectodomains bind the same target. In other embodiments, the ectodomains originate from the same receptor species. In other embodiments, the ectodomains are identical and thus are homomeric. In other embodiments the ectodomains are different and thus are heteromeric. In these embodiments, the ectodomain can be for instance a TβRII-ED that is type a, and another ectodomain can be a TβRII-ED that is type b. A third ectodomain could be the same as either one of these, or different still. For example, when there is more than one ectodomain in the second portion of the polypeptide construct of the present invention, the ectodomains may be all the same (homomers) or all different (heteromers), or any combination of superfamily ectodomains.

Thus, in embodiments, the second portion of the polypeptide construct of the present invention comprises a repeat of a given TβSR-ED selected from the group consisting of SEQ ID NO:46, 47, 48, 74, 80, 86, and a sequence substantially identical thereto.

In specific embodiments, the second portion of the polypeptide construct of the present invention comprises heteromeric repeats of two distinct TβSR-EDs genetically fused and selected from the group consisting of SEQ ID NO:61, 62, 63, 88, and a sequence substantially identical thereto.

In yet other embodiments, the second portion of the polypeptide construct of the present invention comprises homo-multimeric and hetero-multimeric repeats of one or more TβSR-EDs selected for instance from the group consisting of SEQ ID NO:49, 50, 51, 64, 65, 66, 67, 68, and a sequence substantially identical thereto.

In the protein construct of the present invention, the first and second portions of the polypeptide construct of the present invention are linked. By the term "linked", it is meant that the two portions are covalently bonded. The chemical bond may be achieved by chemical reaction, or may be the product of recombinant expression of the two portions in a single polypeptide chain. In one specific, non-limiting example, the C-terminus of the first portion is linked directly to the N-terminus of the second portion, that is, no additional "linker" amino acids are present between the two portions. In the case where no linker is present, that is to say direct fusion of the two portions, there will be a direct link between the N-terminus of the full ectodomain and the C-terminus of the antibody constant regions $C_{H2}$-$C_{H3}$. For example, in fusing the Fc variant SEQ ID NO:9 to the SEQ ID NO:43 via the intrinsically disordered linker with SEQ ID NO:36, which is part of the TβRII-ED (i.e., no additional "linker" amino acids added), one connects the glycine at the last position of SEQ ID NO:9 to the isoleucine at the first position of SEQ ID NO:43.

A common practice when producing fusion constructs is to introduce glycine or glycine-serine linkers (such as GGGGS, or $[G_4S]_n$) between the fused components. As taught in the above paragraph, the polypeptide fusions of the present invention can be produced by direct linkage without use of any additional amino-acid sequence except those present in the Fc portion and in the receptor ectodomain portion. One thus can refrain from utilizing foreign sequences as linkers, providing an advantage due to their potential for undesired immunogenicity and their added molecular weight. Entropic factors are also a potential liability for glycine and glycine-serine linkers, which are highly flexible and may become partially restricted upon target binding, hence causing a loss of entropy unfavourable to binding affinity. Therefore, only the flexible, intrinsically disordered N-terminal regions of the TβSR receptor ectodomains were employed as natural linkers in embodiments of the present invention. However, the particular amino acid compositions and lengths of these intrinsically disordered linkers (e.g., SEQ ID NO:36, 37, 70, 76, 82) precluded accurate prediction of whether the resulting direct-fusion constructs will have the required geometry and favourable molecular interactions for correct binding to their intended dimeric ligands.

The first and second portions of the polypeptide construct are, in embodiments, connected by natural intrinsically disordered polypeptide linkers selected from the group consisting of SEQ ID NO:36, 37, 38, 53, 70, 76, 82, and a sequence substantially identical thereto.

In embodiments, when multiple TβSR-ED structured regions are present, these can be fused directly or they can be connected by natural intrinsically disordered polypeptide linkers between the ectodomains, such as SEQ ID NO:40, 41, 42, 55, 58, 59, 60, 72, 78, 84, 87, and a sequence substantially identical thereto.

Non-limiting examples of full-length polypeptide constructs of the present invention that comprise the two aforementioned portions are selected from the group consisting of SEQ ID NO: 91-120, and a sequence substantially identical thereto.

It is particularly important to note that, in the polypeptide constructs of the present invention, the N-terminus of the second portion is linked to the C-terminus of the first portion (see for example FIGS. 2A, C, D, E, F, and G).

Some of the polypeptide constructs of the present invention display significantly greater potency of TGF-β neutralization compared to that of the TGF-β superfamily receptor ectodomain alone; for example, the polypeptide construct may be between at least 50-fold and $1\times10^6$-fold more potent. For example, the polypeptide constructs of the present invention may have a TGF-β neutralization potency selected from the group consisting of at least 50-, 75-, 100-, 150-, 200 -300-, 400-, 500-, 600, 1000 -1500-, 2000-, 3000-, 4000-, 5000-, 6000-, 7000-, 8000-, 9000, 10000-, 20000-, 30000-, 40000-, 50000-, 60000-, 70000-, 80000-, 90000-, 100000-, 150000-, 200000-, 250000-, 300000-, 350000-, 400000-, 450000-, 500000-, 550000-600000-, 650000-, 700000-, 750000-, 800000-, 850000-, 900000-, 950000, or 1000000-fold, more potent than the TβSR-ED alone, or any amount there between. In one example, the potency of the construct is at least 100-fold greater than the receptor ectodomain alone.

Additionally, when the polypeptide constructs of the present invention include a TβSR-ED that binds TGF-β, the polypeptide construct may neutralize, to varying extents, all three isotypes of TGF-β (that is, TGF-β1, TGF-β2, and TGF-β).

The polypeptide constructs of the present invention have, as assessed in cell-based assays, TGF-β neutralizing potencies that are significantly higher (100-fold or more) than those of bivalent comparator polypeptides, i.e. non-Fc-fused T22d35 and T2m-Fc. Within the series of polypeptide constructs of the present invention, those that contain two or more copies of the TβRII ectodomain fused to the C-terminus of the Fc constant region have potencies that are higher than those constructs that contain only one copy, as assessed in cell based assays. Additionally, within the series of polypeptide constructs of the present invention, if the first portion within the construct is "headless", i.e. does not contain a Fab region, the potencies of the constructs are increased by engineering (optimizing) the number of cysteines in the hinge region at the "revealed" N-terminus. Engineering of the cysteine residues at the N-termini of "headless" constructs also markedly reduces the aggregation propensity of the constructs. Lastly, within the series of polypeptide constructs of the present invention, in vivo in tumor models, cysteine optimized "headless" constructs exhibit higher anti-tumor immuno-modulatory potencies than constructs in which the first portion is a full-sized antibody.

The polypeptide construct of the present invention is expressed as a single polypeptide chain. Once expressed, the polypeptide construct of the present invention forms a dimer wherein the $C_{H2}$ and $C_{H3}$ domains of the respective polypeptide constructs interact to form a properly assembled Fc region such as occurs when the expressed products are secreted into the culturing medium. For example, and without wishing to be limiting, examples of dimerized polypeptide constructs of the present invention are shown in FIGS. 2A and C-G. In one example, homodimers may be formed by identical polypeptide constructs. Alternatively, heterodimers may be formed by two different polypeptide constructs; thus, a heterodimer may be formed by two Fc region polypeptide constructs that have been engineered to induce heterodimerization and inhibit homodimerization.

The first portion of the polypeptide construct described above may further comprise, at its N-terminus, any suitable antigen-binding antibody fragment known in the art. For example, and without wishing to be limiting in any manner, the first portion of the polypeptide construct may comprise $C_{H2}$ and $C_{H3}$ domains and one selected from the group consisting of a single-chain Fv (scFv; a molecule consisting of $V_L$ and $V_H$ connected with a peptide linker) and a single-domain antibody (sdAb, a fragment composed of a single $V_L$ or a single $V_H$; see for example FIG. 1C). In other instances, the antigen-binding fragment may be formed by combining the polypeptide construct with a second polypeptide chain. For example, the first portion of the polypeptide construct may comprise $C_{H2}$ and $C_{H3}$ domains along with a $C_{H1}$ and $V_H$ domains, which when combined with a second polypeptide comprising $C_L$ and $V_L$ form a full-size antibody (i.e., Fc and Fab; see for example FIG. 1D). In another example, the first portion of the polypeptide may comprise $C_{H2}$ and $C_{H3}$ domains along with $V_H$, which when combined with a second polypeptide comprising a $V_L$ forms an Fc fused to a Fv.

The combination of constant domains and antigen-binding fragment may be naturally-occurring, or may be obtained by manipulation of a naturally-occurring antibody or by using recombinant methods. The polypeptide constructs such as those just described may require a sequence selected from the group consisting of linker sequences, disulfide bonds, hinge region sequences, and other type of covalent bond to link them to the $C_{H2}$ and $C_{H3}$ domains; those of skill in the art will be familiar with various suitable approaches.

In alternative constructs of the present invention, the polypeptide construct comprises an antibody Fc fragment linked at the C-terminus of each heavy chain to at least one TGF-β superfamily receptor ectodomain (TβSR-ED), as described above and as illustrated in FIG. 2(A,D,E). The construct may further comprise an antigen-binding fragment at the N-terminus of the Fc; the antigen-binding fragment may be selected from the group consisting of a Fv, scFv, Fab, or sdAb, also as described above. In the polypeptide constructs as described above, the TGF-β receptor ectodomain does not interfere in the native function or specificity of the antigen-binding fragment.

The antigen-binding antibody fragment described above, when present, may be directed to any suitable antigen. In certain limited embodiments, the antigen-binding antibody or fragment does not bind to an antigen that is PD-L1, EGFR1, her-2, CD4, CD6, CD20, CD25, MUC-1, IL-2, IL-6, or CTLA-4.

The present constructs can further comprise antibody or antibody fragments that target any antigen of interest. They can also comprise the antigen itself, or any other moiety of interest that is genetically encoded. Particular embodiments herein include the EGFR antibody cetuximab and its active fragments, Avastin, Herceptin, Synagis, FC5, or a poly-aspartate bone-localization motif, such a D10, or sequence substantially identical or equivalent thereto.

The present constructs can comprise a binding protein e.g., antibody and binding fragments thereof, that inhibits a checkpoint protein which may be CTLA-4, PD1, PDL1, PDL2, PDL3, PD1, B7-H3, B7-H4, BTLA, HVEM, TIM3, GALS, LAGS, VISTA, KIR, 2B4, CD160, CGEN-15049, CHK 1, CHK2, A2aR, CD28, CD86, or one of the B-7 family ligands or a combination thereof.

Illustrative immune checkpoint inhibitors include Tremelimumab (CTLA-4 blocking antibody), anti-OX40, PD-LI monoclonal Antibody (Anti-B7-HI; MED14736), MK-3475 (PD-1 blocker), Nivolumab (anti-PDI antibody), CT-011 (anti-PDI antibody), BY55 monoclonal antibody, AMP224 (anti-PDLI antibody), BMS-936559 (anti-PDLI antibody), MPLDL3280A (anti-PDLI antibody), MSB0010718C (anti-PDLI antibody) and Yervoy/ipilimumab (anti-CTLA-4 checkpoint inhibitor).

Other antibodies provided by the present constructs can include rituximab, muromonab-CD3, abciximab, daclizumab, basiliximab, palivizumab, infliximab, trastuzumab, gemtuzumab ozogamicin, alemtuzumab, ibritumomab tiuxetan, adalimumab, omalizumab, tositumomab, I-131 tositumomab, efalizumab, bevacizumab, panitumumab, pertuzumab, natalizumab, etanercept, IGN101, volocixmab, Anti-CD80 mAb, Anti-CD23 mAb, CAT-3888, CDP-791, eraptuzumab, MDX-010, MDX-060, MDX-070, matuzumab, CP-675,206, CAL, SGN-30, zanolimumab, adecatumumab, oregovomab, EGFR-binding antibodies cetuximab, nimotuzumab, necitumumab, panitumumab, matuzumab, and zalutumumab, as well as ABT-874, denosumab, AM 108, AMG 714, fontolizumab, daclizumab, golimumab, CNTO 1275, ocrelizumab, HuMax-CD20, belimumab, epratuzumab, MLN1202, visilizumab, tocilizumab, ocrerlizumab, certolizumab, eculizumab, pexelizumab, abciximab, ranibizimumab, mepolizumab, TNX-355, or MYO-029.

Still other antibodies that can be included in the present constructs are rituximab, zanolimumab, hA20, AME-133, HumaLYM, trastuzumab, pertuzumab, IMC-3G3, ch806, KSB-102, MR1-1, SC100, SC101, SC103, alemtuzumab, muromonab-CD3, OKT4A, ibritumomab, gemtuzumab, alefacept, abciximab, basiliximab, palivizumab, motavizumab, infliximab, adalimumab, CDP-571, etanercept, ABX-CBL, ABX-IL8, ABX-MA1 pemtumomab, Therex, AS1405, natalizumab, HuBC-1, natalizumab, IDEC-131, VLA-1; CAT-152; J695, CAT-192, CAT-213, BR3-Fc, LymphoStat-B, TRAIL-R1mAb, bevacizumab, ranibizumab, omalizumab, efalizumab, MLN-02, zanolimumab, HuMax-IL 15, HuMax-Inflam, HuMax-Cancer, HuMax-Lymphoma, HuMax-TAC, cleneliximab, lumiliximab, BEC2, IMC-1C11, DC101, labetuzumab, arcitumomab, epratuzumab, tacatuzumab, MyelomaCide, LkoCide, ProstaCide, ipilimumab, MDX-060, MDX-070, MDX-018, MDX-1106, MDX-1103, MDX-1333, MDX-214, MDX-1100, MDX-CD4, MDX-1388, MDX-066, MDX-1307, HGS-TR2J, FG-3019, BMS-66513, SGN-30, SGN-40, tocilizumab, CS-1008, IDM-1, golimumab, ONTO 1275, ONTO 95, ONTO 328, mepolizumab, MOR101, MOR102, MOR201, visilizumab, HuZAF, volocixmab, ING-1, MLN2201, daclizumab, HCD122, CDP860, PRO542, C14, oregovomab, edrecolomab, etaracizumab, siplizumab, lintuzumab, Hu1D10, Lym-1, efalizumab, ICM3, galiximab, eculizumab, pexelizumab, LDP-01, huA33, WX-G250, sibrotuzumab, Chimeric KW-2871, hu3S193, huLK26; bivatuzumab, ch14.18, 3F8, BC8, huHMFG1, MORAb-003, MORAb-004, MORAb-009, denosumab, PRO-140, 1D09C3, huMikbeta-1, NI-0401, NI-501, cantuzumab, HuN901, 8H9, chTNT-1/B, bavituximab, huJ591, HeFi-1, Pentacea, abagovomab, tositumomab, 105AD7, GMA161 and GMA321.

In other embodiments, the constant domain/first portion of the constructs can comprise a polypeptide having medicinal properties, such as agents that stimulate the immune system, in particular in relation to the ability of the immune system to attack tumor cells. These polypeptides can include cytokines (such as interleukin-2) or growth factors that stimulate immune cells directly or indirectly (i.e. act by providing gas to the immune system), as well as ectodomains or other binding agents that neutralize ligands which inhibit immune cells, either directly or indirectly (i.e. act by releasing a brake on the immune system).

In other embodiments, the constant domain/first portion of the constructs can comprise a polypeptide that does not have active medicinal properties pe se, but rather provides a localization signal. This localization motif will serve to focus the intrinsic TGF-β neutralization activity of the second portion of the construct to a particular region of the body. In one example, the first portion comprised a long poly-aspartate bone-localization motif, preferably D10 or an equivalent bone-localization moiety, which acts to enhance localisation of the construct to bone. By increasing the TGF-β neutralization activity of the construct within bone, more favourable dosing levels and schedules may be required for the treatment of bone-related diseases, such as osteogenesis imperfecta, relative to that required for a similar construct without the D10 motif.

Embodiments exemplifying polypeptide constructs of the present invention that include antigen-binding fragments at the N-terminus of the Fc region (first portion) are selected from the group consisting of SEQ ID NO: 121-131, and a sequence substantially identical thereto.

In other embodiments, polypeptide constructs of the present invention that include other targeting agents, e.g., a poly-aspartate bone-localization motif, at the N-terminus of the Fc region (first portion), are exemplified by SEQ ID NO: 136-150.

The polypeptide construct of the present invention may also comprise additional sequences to aid in expression, detection or purification of a recombinant antibody or fragment thereof. Any such sequences or tags known to those of skill in the art may be used. For example, and without wishing to be limiting, the antibody or fragment thereof may comprise a targeting or signal sequence (for example, but not limited to ompA), a detection/purification tag (for example, but not limited to c-Myc, $His_5$, $His_6$, or $His_8G$), or a combination thereof. In another example, the signal peptide may be MVLQTQVFISLLLWISGAYG (SEQ ID NO:89) or MDWTWRILFLVAAATGTHA (SEQ ID NO:90). In a further example, the additional sequence may be a biotin recognition site such as that described in [WO/1995/04069] or in [WO/2004/076670]. As is also known to those of skill in the art, linker sequences may be used in conjunction with the additional sequences or tags, or may serve as a detection/purification tag.

The present invention also encompasses nucleic acid sequences encoding the molecules as described herein. Given the degeneracy of the genetic code, a number of nucleotide sequences would have the effect of encoding the desired polypeptide, as would be readily understood by a skilled artisan. The nucleic acid sequence may be codon-optimized for expression in various micro-organisms. The present invention also encompasses vectors comprising the nucleic acids as just described, wherein the vectors typically comprise a promoter and signal sequence that are operably linked to the construct-encoding polynucleotide for driving expression thereof in the selected cellular production host. The vectors can be the same or different provided both result in secretion of the dimeric polypeptide construct.

Furthermore, the invention encompasses cells, also referred to herein as transgenic cellular host, comprising the nucleic acid and/or vector as described, encoding a first polypeptide construct. The host cells may comprise a second nucleic acid and/or vector encoding a second polypeptide construct different from the first polypeptide construct. The co-expression of the first and second polypeptide constructs may lead to the formation of heterodimers.

The present invention also encompasses a composition comprising one or more than one polypeptide construct as described herein. The composition may comprise a single polypeptide construct as described above, or may be a mixture of polypeptide constructs. The composition may also comprise one or more than one polypeptide construct of the present invention linked to one or more than one cargo molecule. For example, and without wishing to be limiting in any manner, the composition may comprise one or more than one polypeptide construct of the present invention linked to a cytotoxic drug in order to generate an antibody-drug conjugate (ADC) in accordance with the present invention.

The composition may also comprise a pharmaceutically acceptable diluent, excipient, or carrier. The diluent, excipient, or carrier may be any suitable diluent, excipient, or carrier known in the art, and must be compatible with other ingredients in the composition, with the method of delivery of the composition, and is not deleterious to the recipient of the composition. The composition may be in any suitable form; for example, the composition may be provided in suspension form, powder form (for example, but limited to lyophilised or encapsulated), capsule or tablet form. For example, and without wishing to be limiting, when the composition is provided in suspension form, the carrier may comprise water, saline, a suitable buffer, or additives to improve solubility and/or stability; reconstitution to produce the suspension is effected in a buffer at a suitable pH to ensure the viability of the antibody or fragment thereof. Dry powders may also include additives to improve stability and/or carriers to increase bulk/volume; for example, and without wishing to be limiting, the dry powder composition may comprise sucrose or trehalose. In a specific, non-limiting example, the composition may be so formulated as to deliver the antibody or fragment thereof to the gastro-intestinal tract of the subject. Thus, the composition may comprise encapsulation, time-release, or other suitable technologies for delivery of the antibody or fragment thereof. It would be within the competency of a person of skill in the art to prepare suitable compositions comprising the present compounds.

The constructs of the present invention may be used to treat diseases or disorders associated with over-expression or over-activation of ligands of the TGF-β superfamily. The disease or disorder can be selected from, but not limited to, cancer, ocular diseases, fibrotic diseases, or genetic disorders of connective tissue.

In the field of cancer therapy, it has recently been demonstrated that TGF-β is a key factor inhibiting the antitumor response elicited by immunotherapies, such as immune checkpoint inhibitors (ICI's) (Hahn & Akporiaye, 2006). Specifically, therapeutic response to ICI antibodies results primarily from the re-activation of tumor-localized T-cells. Resistance to ICI antibodies is attributed to the presence of immunosuppressive mechanisms that result in a dearth of T-cells in the tumor microenvironment. Thus, it is now recognized that in order to elicit responses in resistant patients, ICI antibodies need to be combined with agents that can activate T-cells and induce their recruitment into the tumor, i.e. reversing of the "non-T-cell-inflamed" tumor phenotype. One publication noted that overcoming the non-T-cell-inflamed tumor microenvironment is the most significant next hurdle in immuno-oncology (Gajewski, 2015).

We have shown using a proof-of-principle TGF-β trap, T22d35, that blocking of TGF-β effectively reverses the "non-T cell inflamed" tumor phenotype (Zwaagstra et al, 2012). This positions anti-TGF-β molecules as potential synergistic combinations with ICI's and other immunotherapeutics. In support of this, a 2014 study (Holtzhausen et al., ASCO poster presentation) examined effects of a TGF-β blocker when combined an anti-CTLA-4 antibody in a physiologically-relevant transgenic melanoma model. The study demonstrated that while anti-CTLA-4 antibody monotherapy failed to suppress melanoma progression, the combination of the TGF-β antagonist and anti-CTLA-4 antibody significantly and synergistically suppressed both primary melanoma tumor growth as well as melanoma metastasis. These observations correlated with significant increases in effector T-cells in melanoma tissues.

Fibrotic diseases include those that affect any organ of the body, including, but not limited to kidney, lung, liver, heart, skin and eye. These diseases include, but are not limited to, chronic obstructive pulmonary disease (COPD), glomerulonephritis, liver fibrosis, post-infarction cardiac fibrosis, restenosis, systemic sclerosis, ocular surgery-induced fibrosis, and scarring.

Genetic disorders of connective tissue include, but are not limited to, Marfan syndrome (MFS) and Osteogenesis imperfecta (OI).

The present invention will be further illustrated in the following examples. However, it is to be understood that these examples are for illustrative purposes only and should not be used to limit the scope of the present invention in any manner.

Example 1: Production and Purification of Fusion Molecules

Several fusion molecules comprising full-size antibody (FSA), $V_HH$-IgG Fc, D10-Fc or "headless" Fc C-terminally-fused to the T22d35 or T2m ectodomains were constructed (Table 1). All constructs comprising a heavy chain included the signal sequence MDWTWRILFLVAAATGTHA (SEQ ID NO:89) at the N-terminus, while constructs comprising a light chain included the signal sequence MVLQTQVFIS- LLLWISGAYG (SEQ ID NO:90) at the N-terminus. The DNA coding for constructs were prepared synthetically (Biobasic Inc. or Genescript USA Inc.). Constructs comprising FSA, D10-Fc and "headless" Fc were cloned into the EcoR1 (5' end) and BamH1 (3' end) sites and those comprising V$_H$H-IgG Fc were cloned into the HindIII (5' end) and BamH1 (3' end) sites of the pTT5 mammalian expression plasmid vector (Durocher et al, 2002).

TABLE 1

FSA-, V$_H$H-IgG Fc-, D10-Fc- and Fc-fusion constructs produced. The letter in brackets in the construct column refers to the type of construct as illustrated in FIG. 2.

| Construct | ED | Fusion Scaffold | Antibody source | Construct SEQ ID NO: |
|---|---|---|---|---|
| Cet-T2m (F) | T2m | FSA (hIgG1) | Cetuximab | 121, 123 |
| Cet-T22d35 (D) | T22d35 | FSA (hIgG1) | Cetuximab | 121, 122 |
| Her-T22d35 (D) | T22d35 | FSA (hIgG1) | Herceptin | 124, 125 |
| Ava-T22d35 (D) | T22d35 | FSA (hIgG1) | Avastin | 126, 127 |
| Syn-T22d35 (D) | T22d35 | FSA (hIgG1) | Synagis | 128, 129 |
| FC5-Fc-T22d35 (E) | T22d35 | VHH-Fc (mIgG2) | FC5-Fc | 130 |
| FC5-Fc-T2m (G) | T2m | VHH-Fc (mIgG2) | FC5-Fc | 131 |
| D10-Fc-T2m (G) (several variants with differing D10 linkage and IgG isotype) | T2m | Fc | huIgG | 136-139 |
| Fc-T22d35 (A) (several variants with differing N-termini and IgG isotype) | T22d35 | Fc | huIgG | 100, 105 |
| Fc-T2m (C) (several variants with differing N-termini and IgG isotype) | T2m | Fc | huIgG | 91-97 |
| T2m-Fc (R&D) (B) | T2m | Fc | huIgG1 | 132 |
| T2m-Fc (B) | T2m | Fc | huIgG2 | 133 |

Figure 3A:
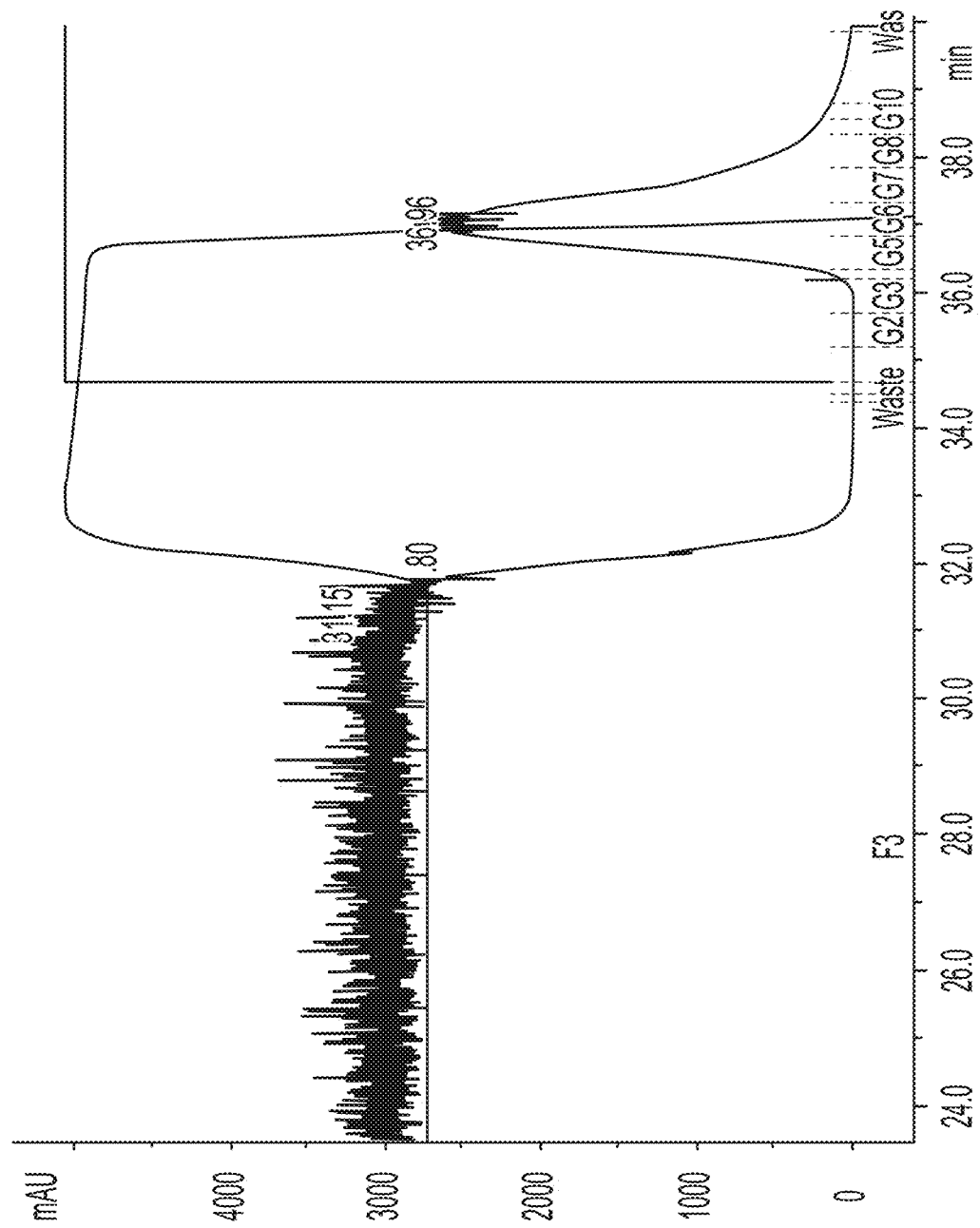
FIGS. 3A-3L presents (ProtA)-affinity column elution profiles, size exclusion (SEC) purification profiles, SDS-PAGE gels, and UPLC-SEC profiles of representatives of constructs type C (FIG. 2C) and D (FIG. 2D) in FIGS. 2A-2G.
Figure 3B:
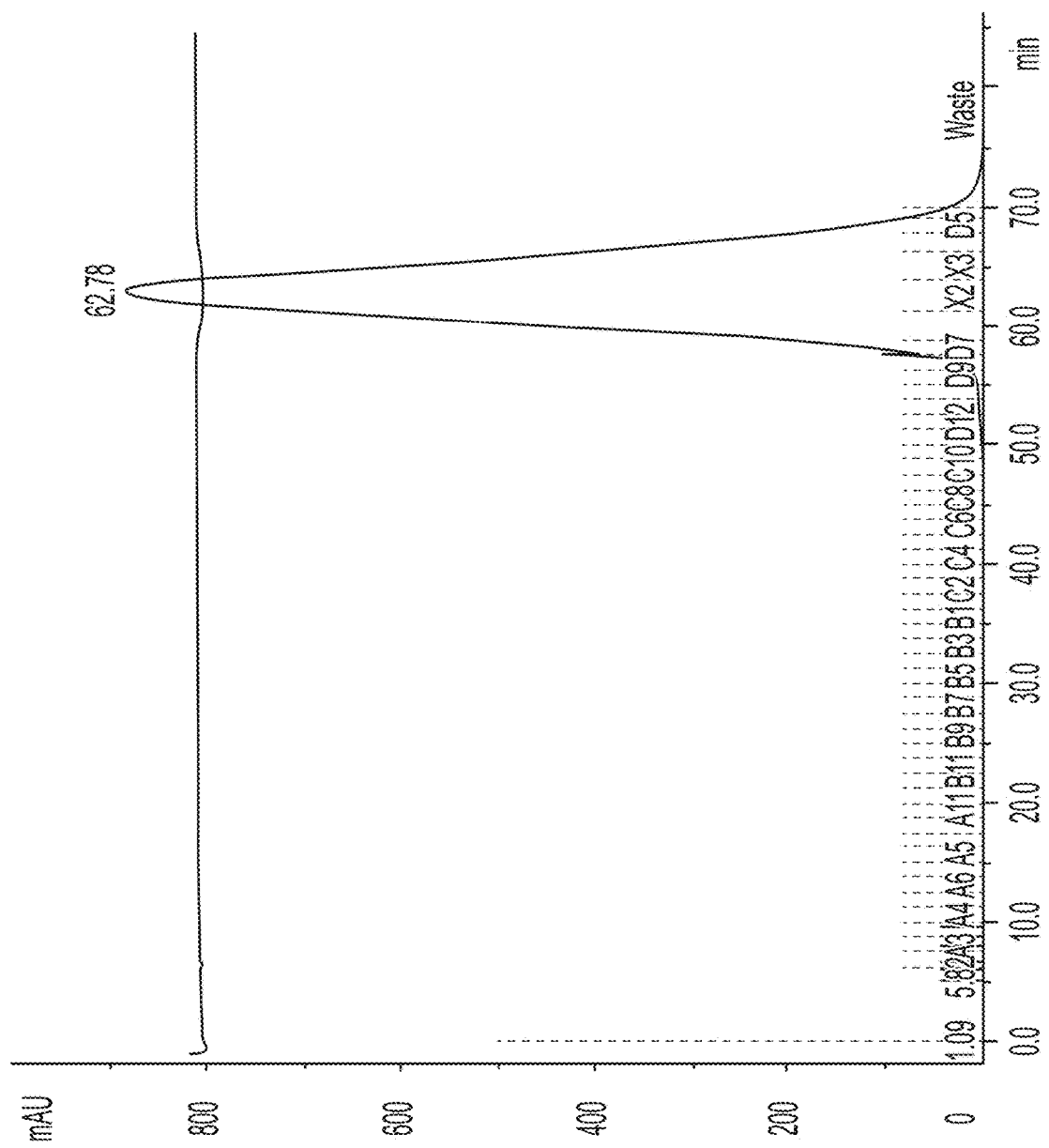

The Cet-T2m and Cet-T22d35 constructs were produced by transient co-transfection of Chinese Hamster Ovary (CHO) cells with the heavy chain (HC)-T2m or (HC)-T22d35 construct combined with the Cetuximab light chain (LC) construct which then assembled as the Cetuximab-T22d35 (Cet-T22d35) or Cetuximab-T2m (Cet-T2m) fusion molecules. Briefly, CetHC-T22d35 (SEQ ID NO:122) and CetLC (SEQ ID NO:121) plasmid DNAs (ratio=3:2) were co-transfected into a 10 L Wavebag culture of CHO-3E7 cells in FreeStyle F17 medium (Invitrogen) containing 4 mM glutamine and 0.1% Kolliphor p-188 (Sigma) in a Wavebag maintained at 37° C. Transfection conditions were: DNA (50% HC+LC plasmids, 30% ssDNA, 15% AKT plasmid, 5% GFP plasmid): PEI(polyethylenimine)pro (Polyplus) (ratio=1:2.5). At 24 hours post-transfection, 10% Tryptone N1feed (TekniScience Inc.) and 0.5 mM Vaporic acid (VPA, Sigma) were added and the temperature was shifted to 32° C. to promote the production and secretion of the fusion proteins and maintained for 15 days post transfection after which the cells were harvested. At final harvest the cell viability was 89.6%. The harvest supernatant (10.8 L) was filtered (0.2 µm) and loaded onto a 55 mL Protein A MabSelect Sure 55 mL column (GE Healthcare). The column was washed with 2 column volumes of PBS and protein was eluted with 3 column volumes of 0.1 M sodium citrate pH 3.6. To maximize the yield, the flow through was reloaded onto the Protein A column and eluted as described above. Eluted fractions were neutralized with 1 M Tris, evaluated by SDS-PAGE and those containing Cet-T22d35 were pooled (FIG. 3A) and subsequently loaded onto a Hi-load Superdex S200 26/60 size exclusion chromatography (SEC) column (GE Healthcare) equilibrated in formulation buffer (DPBS without Ca$^{2+}$, without Mg$^{2+}$). Protein was eluted using 1 column volume formulation buffer, collected into successive fractions and detected by UV absorbance at 280 nM (FIG. 3B). The main peak SEC fractions containing Cet-T22d35 protein were then pooled and concentrated to a concentration of 7.8 mg/mL. The final yield was 533 mg.

Similar transfection, production and purification methods were performed for the other FSA-trap examples listed in Table 1. In the case of the V$_H$H-Fc IgG-, D10 and "headless" Fc-fusion molecules the composition of the transfection mixture was modified as follows: DNA (80% plasmid construct, 15% AKT plasmid, 5% GFP plasmid): PEIpro (ratio 1:2.5).

Figure 3D:
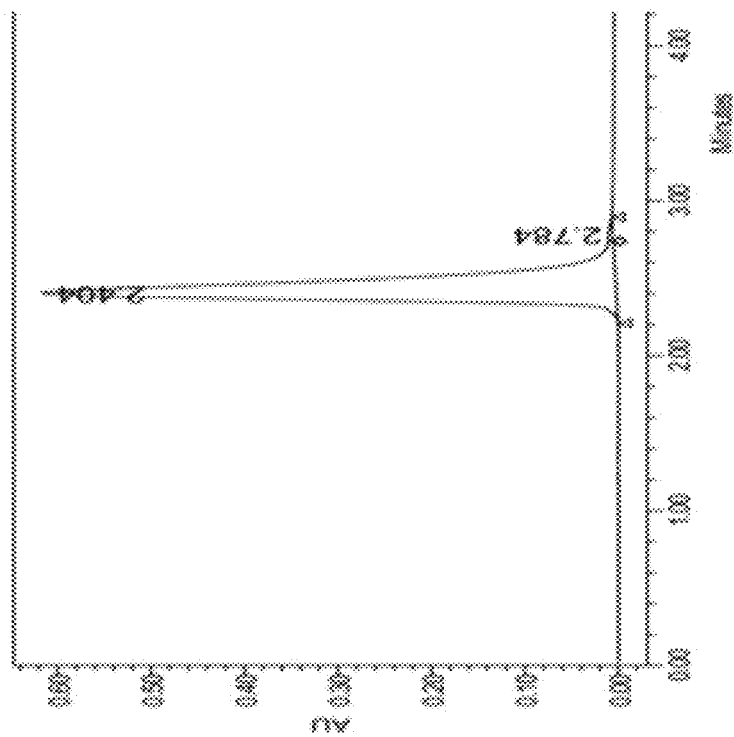
Figure 3C:
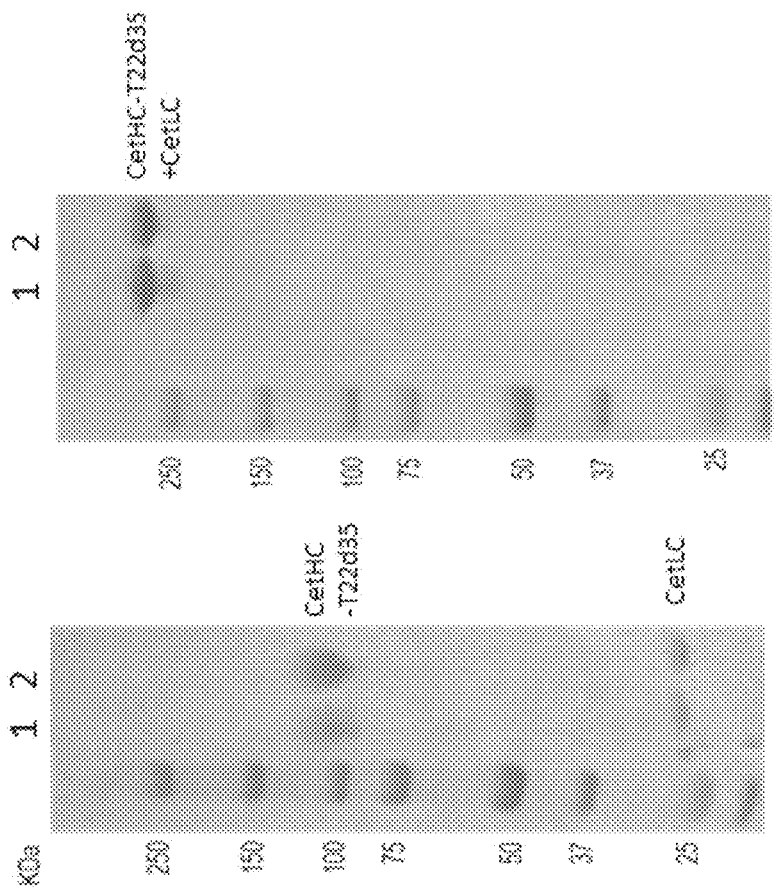

The integrity of the pooled Prot-A and SEC fractions of Cet-T22d35 protein was analyzed by SDS-PAGE (4-15% polyacrylamide) under reducing and non-reducing conditions (FIG. 3C) and by UPLC-SEC (FIG. 3D). For UPLC-SEC, 2-10 µg of protein in DPBS (Hyclone, minus Ca2+, minus Mg2+) was injected onto a Waters BEH200 SEC column (1.7 µm, 4.6×150 mm, SN:01773430816818) and resolved under a flow rate of 0.4 mL/min for 8.5 min at room temperature, using the Waters Acquity UPLC H-Class Bio-System. Protein peaks were detected at 280 nM (Acquity PDA detector). Coomassie brilliant blue (CBB) staining of the gels shows the CetHC-T22d35 (~110 Kd) and CetLC bands (~30 Kd) under reducing conditions while under non-reducing conditions a 250 Kd band is detected which represents the fully assembled and highly pure Cet-T22d35 fusion protein. Additional UPLC-SEC analysis of the SEC purified, pooled ProtA sample confirmed the high degree of purity (99.42%) of the Cet-T22d35 protein and the absence of aggregates. Together, these results demonstrate the manufacturability of the Cet-T22d35 fusion protein.

Similar methods were used to analyse expression levels, purifiability, aggregation levels, and dimeric assembly of several other Fc-ectodomain constructs. The results from these studies are shown in FIG. 3 E to L.

Figure 3E:
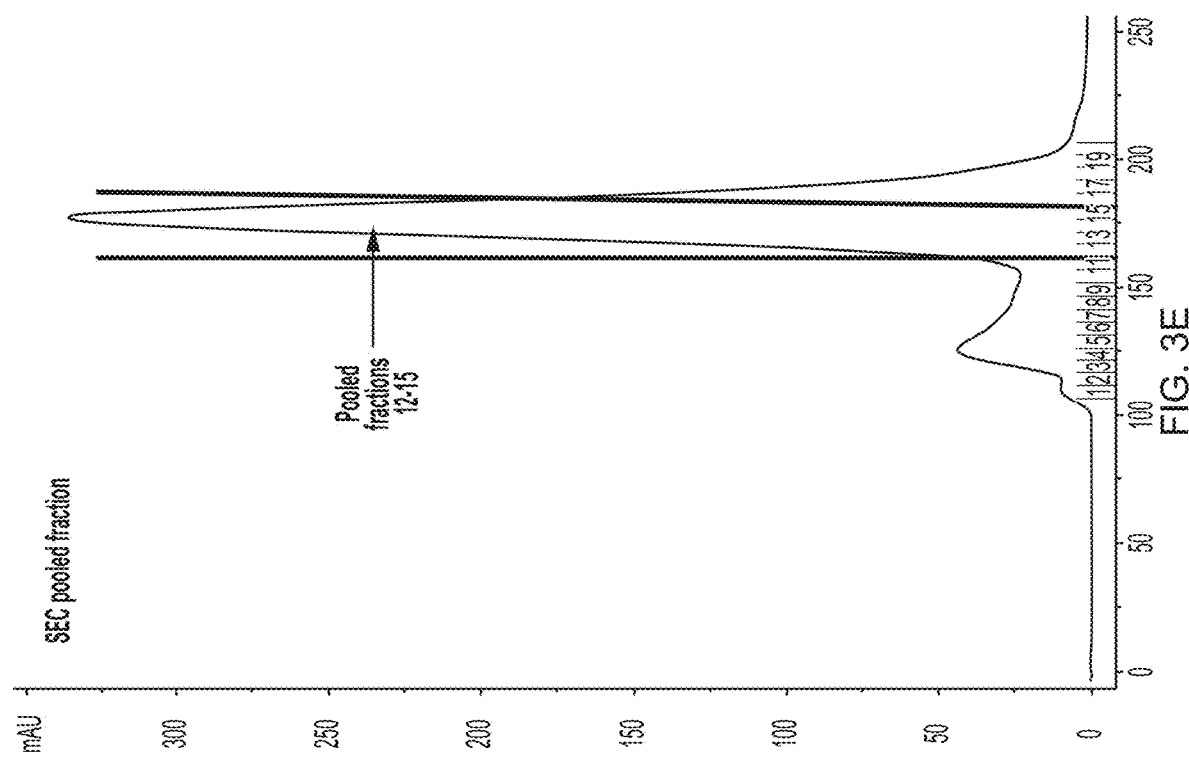
Figures 3F, 3G:
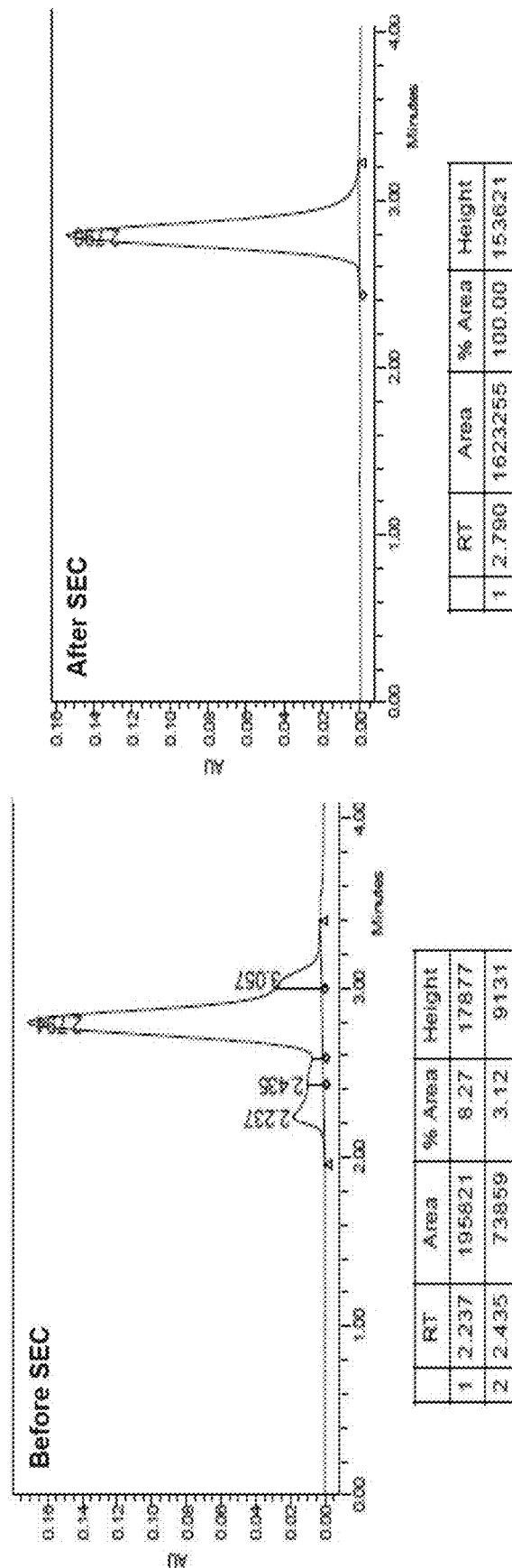
Figure 3H:
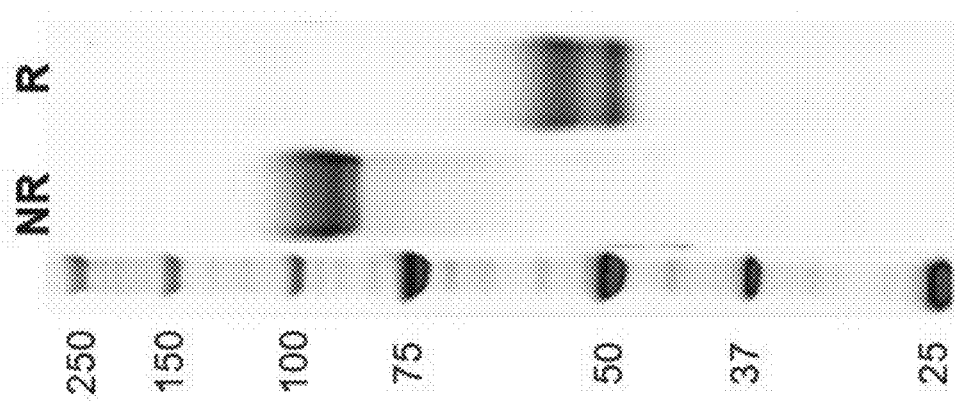

FIG. 3E to 3H show the results from the analysis of the hIgG1FcΔK(C)-T2m construct (an example of Type C construct from FIG. 2). FIG. 3E shows the (ProtA)-affinity column elution profile. Fraction 12-15 were pooled, subjected to a UPLC-SEC evaluation (FIG. 3F), further SEC purified to remove aggregates and re-evaluated by UPLC-SEC (FIG. 3G). This confirmed the high degree of purity of the hIgG1FcΔK(C)-T2m construct and the absence of aggregates. SDS-PAGE (FIG. 3H) under non-reducing (NR) and reducing (R) conditions shows bands of expected molecular weights, demonstrating the expected assembly of hIgG1FcΔK(C)-T2m as a disulphide linked dimer.

Figure 3I:
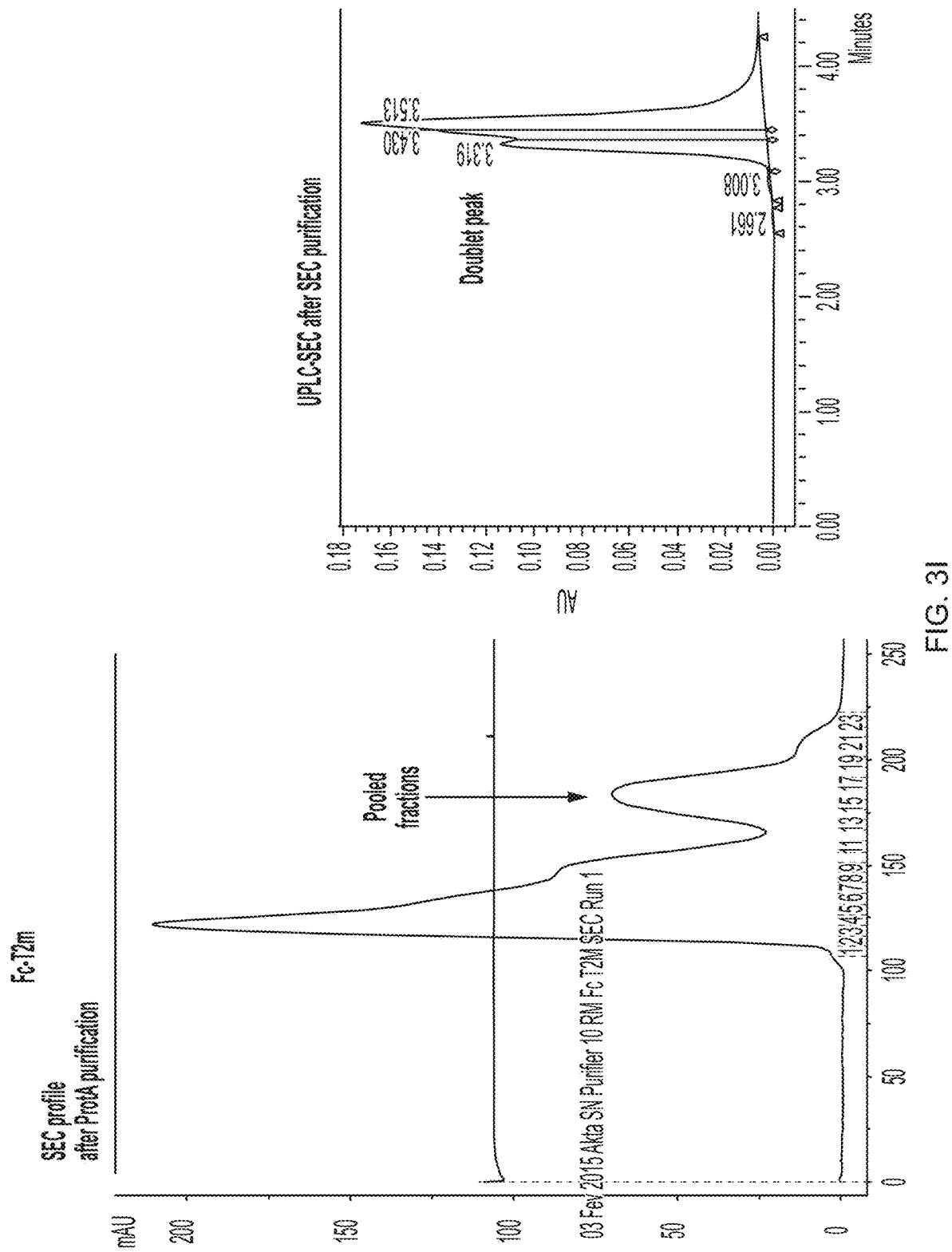
Figure 3J:
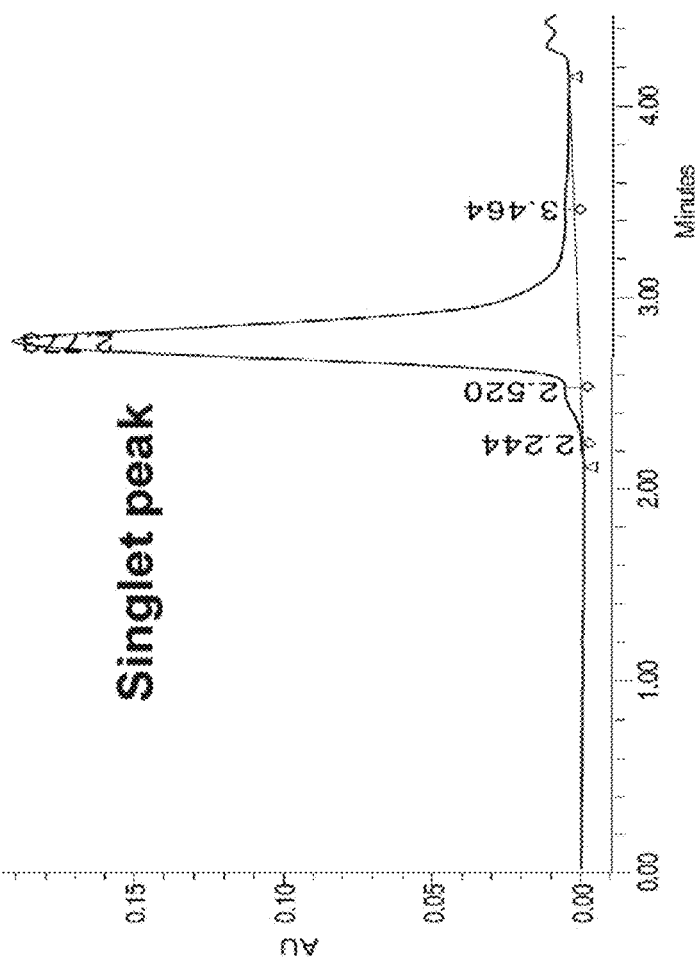

FIGS. 3I and 3J compare the level of aggregation of two "headless" Fc-T2m constructs (examples of Type C in FIG. 2). The Fc-T2m construct is an IgG2-based construct without engineering of the hinge region, thus it contains four cysteine residues, whereas the hIgG2FcΔK(CC)-T2m has been engineered by N-terminal truncation of the hinge region to have only two cysteines in the hinge region. It can be seen that the Fc-T2m construct contains a high level of aggregates after Protein A purification, with a doublet peak remaining even after further SEC purification. In contrast, hIgG2FcΔK(CC)-T2m, which has an engineered N-terminus, exhibited low levels of aggregates after only Protein A purification. These results demonstrate the advantage of carrying out N-terminal engineering of headless Fc-T2m constructs to reduce aggregation.

Figure 3K:
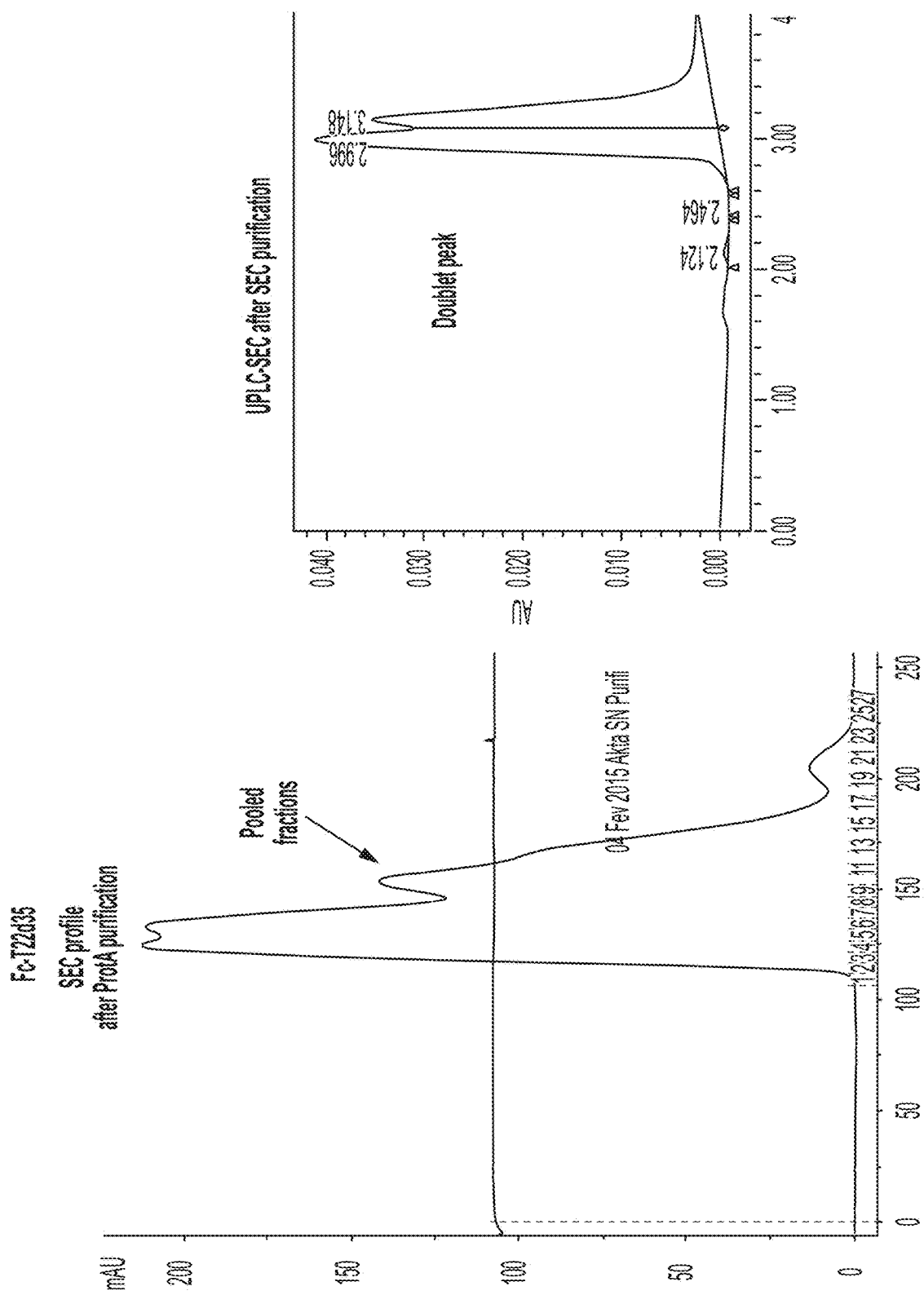
Figure 3L:
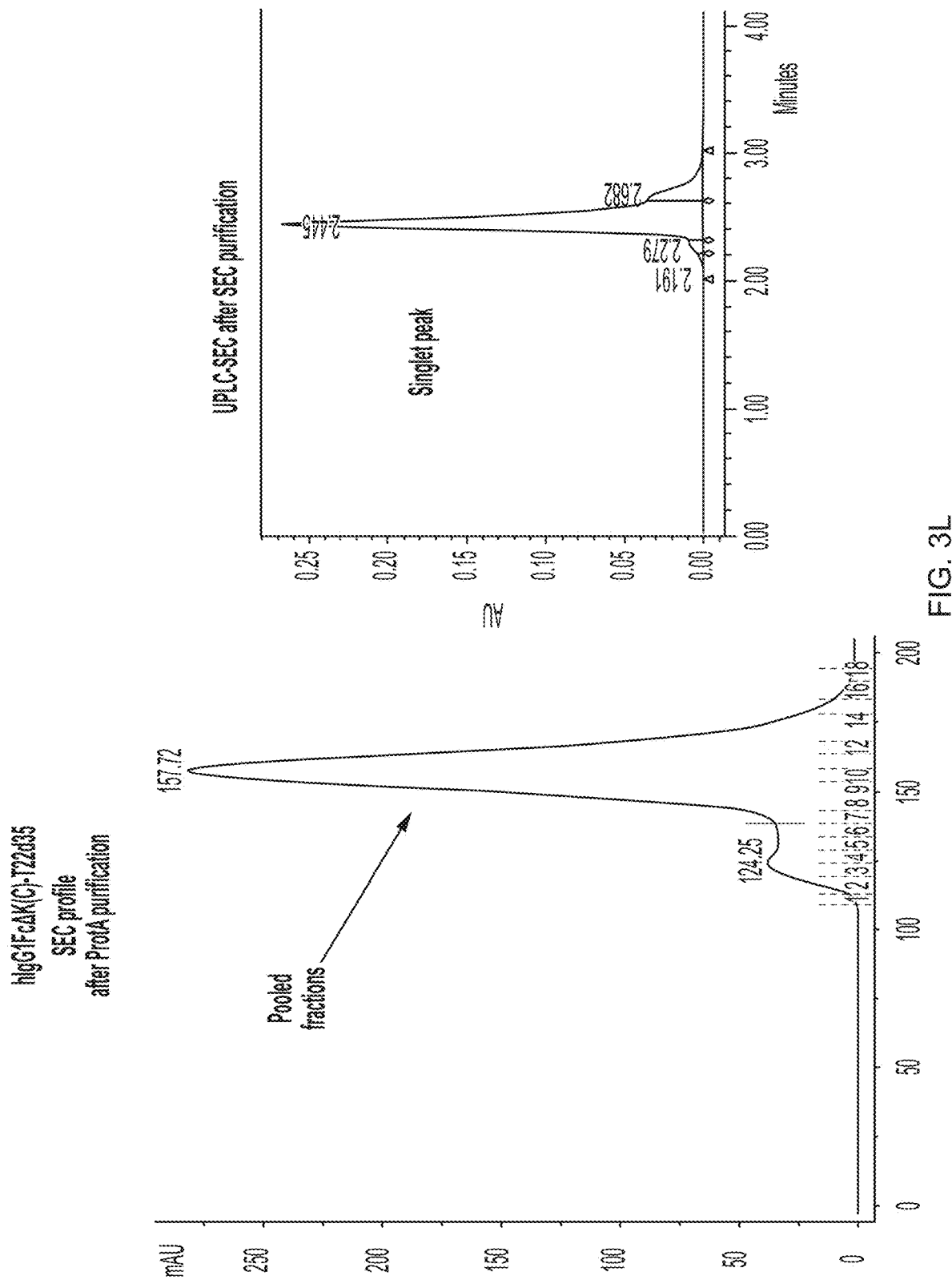

FIGS. 3K and 3L compare the level of aggregation of two "headless" Fc-T22d35 constructs (examples of Type A in FIG. 2). The Fc-T22d35 construct is without engineering of the hinge-region cysteine residues whereas the hIgG1 FcΔK(C)-T22d35 construct has been engineered by N-terminal truncation of the hinge to have only one cysteine in the hinge region. It can be seen that, similarly to Fc-T2m, the Fc-T22d35 construct contains a high level of aggregates after Protein A purification, with a doublet peak remaining as detected by UPLC-SEC even after further SEC purification. In contrast, hIgG1FcΔK(C)-T22d35, which has an engineered N-terminus, exhibited lower levels of aggregates after Protein A purification. Further SEC purification yielded a singlet peak as detected by UPLC-SEC, confirming the absence of aggregates. These results demonstrate the advantage of carrying out N-terminal engineering of headless Fc-T22d35 constructs to reduce aggregation.

Example 2: Neutralization and Binding of TGF-β by Fusion Constructs

The TGF-β neutralization potencies of purified Fc-ectodomain fusion constructs were determined and compared to those of non-Fc-fused T22d35. It should be noted that non-Fc-fused T2m does not neutralize any of TGF-β1, -β2, or -β3 (De Crescenzo et al, 2001).

TGF-β neutralization potencies for TGF-β1, -β2 and -β3 were determined for purified fusion constructs using two cell-based signaling assays: 1) the Mv1 Lu cell luciferase reporter assay with Mv1 Lu cells having a PAI-1-luciferase reporter (as described in (Zwaagstra et al, 2012)) and an A549 cell/IL-11 release assay adapted to the MSD (Meso Scale Discovery) platform.

Mv1Lu cell luciferase reporter assay: Briefly, cells were seeded onto 96-well plates (20,000 cells/well) and then treated with T2m, T22d35, or a fusion construct+25 pM TGF-β at 37° C. for 16 h in DM EM, 1% FBS, 0.1% BSA. Cells were then lysed and luciferase activity was measured (Promega Corp.) using a Synergy 2 plate reader (BioTek Instruments Inc.).

A549 cell IL-11 release assay: Human A549 lung cancer cells (ATCC-CCL-185, Cedarlane Burlington ON) were seeded in 96-well plates ($5 \times 10^3$ cells/well). The following day 10 pM TGF-β in complete media in the absence or presence of a serial dilution of fusion protein was incubated for 30 min at RT prior to adding to the cells. After 21 h of incubation (37° C., 5% CO2, humidified atmosphere) conditioned medium was harvested and added to MSD Streptavidin Gold plates (Meso Scale Diagnostics, Gaithersburg, MD) that were coated with 2 µg/mL biotinylated mouse anti-human IL-11 antibody (MAB618, R&D Systems, Minneapolis, MN). After 18 h (4° C.) plates were washed with PBS containing 0.02% Tween 20, a 2 µg/mL SULFO-tagged goat anti-human IL-11 antibody (AF-218-NA, R&D Systems Minneapolis, MN) was added and plates were incubated for 1 h at RT. After a final wash, plates were read in a MESO QuickPlex SQ120 machine (Meso Scale Diagnostics, Gaithersburg, MD). IL-11 readouts were expressed as percent IL-11 release compared to control cells treated with TGF-β alone.

Figure 4A:
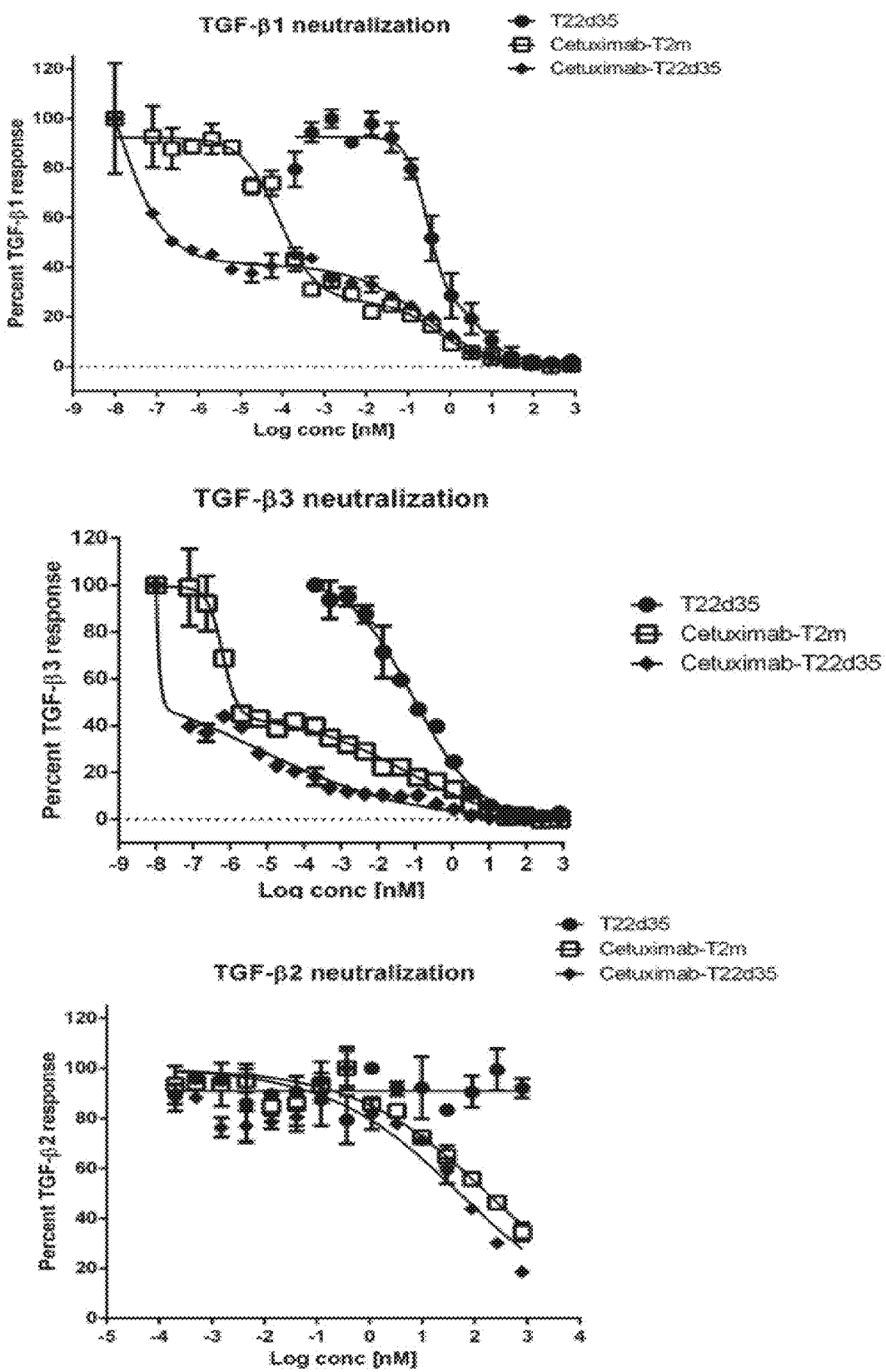
FIG. 4A shows graphs depicting the efficient inhibition of TGF-β1 (top panel), TGF-β3 (middle panel) and TGF-β2 (bottom panel) signaling in Mv1Lu luciferase reporter cells by Cet-T2m (a representative of construct F (FIG. 2F) in FIGS. 2A-2G) and Cet-T22d35 (a representative of construct D (FIG. 2D) in FIGS. 2A-2G), compared to the significantly lower inhibition potency of non-Fc-fused T22d35.

In one set of experiments, using the Mv1Lu cell reporter assay, the neutralization potency of Cet-T2m (construct Type F in FIG. 2), Cet-T22d35 (construct Type D in FIG. 2) and T22d35 (non-Fc-fused) were compared. FIG. 4A shows representative TGF-β1 (top panel), TGF-β3 (middle panel) and TGF-β2 (bottom panel) neutralization curves for Cet-T2m, Cet-T22d35 and T22d35 while Table 2 summarizes TGF-β1, -β2 and -β3 neutralization $IC_{50}$ values. Unexpectedly, the TGF-β1 and TGF-β3 neutralization curves for the Cetuximab fusion constructs indicated extremely high potencies that lie in the picomolar range (determining a single $IC_{50}$ value in these experiments is difficult due to the biphasic nature of the curves). The observed TGF-β1 $IC_{50}$ value for Cet-T22d35 was in the picomolar range. In contrast, the TGF-β1 $IC_{50}$ for non-Fc-fused T22d35 was approximately 1 nM. This illustrates that there is a large increase in T22d35 potency upon fusion to the C-terminus of the Fc region of Cetuximab (due to the biphasic nature of the Cet-T22d35 curve, the fold difference is difficult to determine in these experiments). The TGF-β1 IC50 value for Cet-T2m was also subpicomolar (but less potent than Cet-T22d35), whereas unfused T2m is not able to detectably neutralize TGF-β1, even at concentrations above 500 nM (De Crescenzo et al, 2001). This demonstrates that, similar to T22d35, a very significant increase in T2m potency occurs upon fusion to the C-terminus of the Fc region of Cetuximab. Both Cet-T22d35 and Cet-T2m neutralized TGF-β2 ($IC_{50}$~nM range), whereas T22d35 and T2m (De Crescenzo et al, 2001) alone did not, even at a concentration of 800 nM, again showing the remarkable increase in neutralization potency that occurs upon fusion of T22d35 or T2m to the C-terminus of an Fc region.

In another set of experiments using the Mv1 Lu cell reporter assay, similar extremely high potencies of TGF-β neutralization were observed for other C-terminus Fc fusion constructs (Table 2), e.g. for constructs in which T22d35 or T2m were fused with FSAs such as Herceptin (Her-T22d35), Avastin (Ava-T22d35) or Synagis (Syn-T22d35) [Type F and D constructs in FIG. 2], or with the blood-brain barrier crossing Fc-fused FC5 $V_HH$ antibody (FCS-Fc-T22d35 and FC5-Fc-T2m) [Type E and G constructs in FIG. 2]. In addition, fusion of T22d35 or T2m to the C-terminus of an IgG2-Fc region alone, i.e. an antibody with no Fab region present (Fc-T22d35 and Fc-T2m) [Type A and C constructs in FIG. 2] resulted in fusion proteins with similarly high neutralization potencies. However, fusing T2m to the N-terminus of an IgG2-Fc (T2m-Fc) generates a fusion protein that does not neutralize TGF-β1 and -β3 in the picomolar range, but rather in the range of 1 nanomolar (0.3 to 15 nM in Table 2) and lacks any activity towards TGF-β2. These results are similar to those obtained with commercially available N-terminally IgG1 Fc-fused TGF-β Type II receptor ectodomain (T2m-Fc (R&D Systems)) (0.3 to 0.5 nM in Table 2). Together, these results thus demonstrate that fusion of TGF-β superfamily receptor ectodomains to the C-terminus of an Fc domain in the context of full-size antibodies, a $V_HH$-Fc, or an Fc region alone, give rise to unexpectedly high TGF-β neutralization potencies.

TABLE 2

TGF-β neutralization $IC_{50}$ of fusion constructs. It should be noted that T2m does not neutralize any of TGF-β1, -β2, or -β3 (De Crescenzo et al, 2001). It should also be noted that the $IC_{50}$ values in the table below are estimates due to the biphasic nature of the curves.

| | TGF-β1 Av $IC_{50}$ (nM) | TGF-β3 Av $IC_{50}$ (nM) | TGF-β2 Av $IC_{50}$ (nM) |
|---|---|---|---|
| Cet-T22d35 | 0.000, 001 | 0.000, 002 | 13.6 |
| Cet-T2m | 0.000, 1 | 0.000, 0015 | 129.2 |
| T22d35 | 1.232 | 0.033 | No neutralization |
| Her-T22d35 | 0.000, 13 | 0.000, 05 | 7.89 |
| Ava-T22d35 | 0.000, 000, 72 | 0.000, 00038 | 8.60 |
| Syn-T22d35 | 0.000, 042 | 0.000, 0001 | 35.2 |
| FC5-Fc-T22d35 | 0.000, 001 | 0.000, 001 | 96.2 |
| FC5-Fc-T2m | 0.000, 017 | 0.000, 015 | 432.9 |
| Fc-T22d35 | 0.001, 445 | 0.000, 026 | 108.4 |
| T2m-Fc (R&D) | 0.506 | 0.323 | No neutralization |
| T2m-Fc | 14.523 | 0.276 | No neutralization |
| Fc-T2m | 0.009, 923 | 0.000, 766 | 460.5 |

Figure 4B:
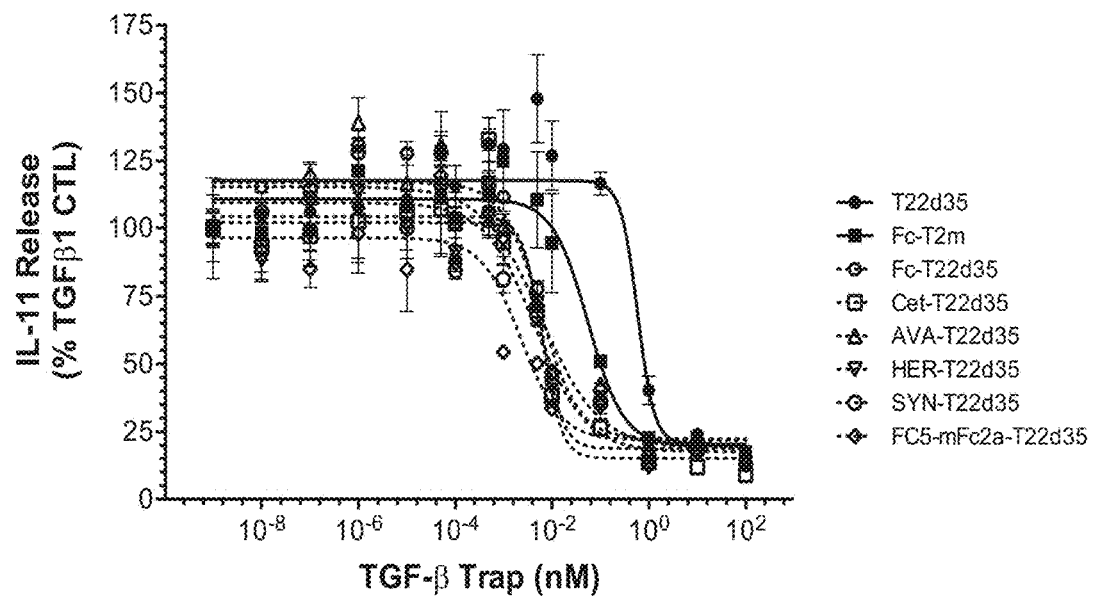
FIG. 4B shows graphs and a summary table depicting the efficient inhibition of TGF-β1 signaling in an A549/IL-11 cell-based assay by several representatives of FSA-T22d35 constructs (Type D construct (FIG. 2D) from FIGS. 2A-2G), compared to the lower inhibition potency of Fc-T2m (Type C construct (FIG. 2C)) and non-Fc-fused T22d35.

In order to confirm the relative potencies of Fc-ectodomain constructs, a second cell-based assay, an A549 cell IL-11 release assay, was used. This IL-11 release assay acts as a model of TGF-β-mediated biological responses that contribute to both tumor metastasis and fibrosis. In the set of experiments shown in FIG. 4B, the neutralization potencies of T22d35, Fc-T2m, Fc-T22d35, Cet-T22d35, Her-T22d35, Ava-T22d35, Syn-T22d35 and FCS-Fc-T22d35 were compared. It can be seen that the neutralization curves in this assay are not biphasic, making it less challenging than the Mv1Lu assay to determine and compare $IC_{50}$ values. All of the constructs in which T22d35 was fused to the C-terminus of an Fc region exhibited $IC_{50}$ values in the range of 5 pM, corroborating the extremely high potency observed for these constructs in the Mv1Lu assay. It can also be seen in FIG. 4B that the $IC_{50}$ value for non-Fc-fused T22d35 was ~0.5 nM. This indicates that a ~100-fold increase in potency occurs upon fusion of T22d35 to the C-terminus of an Fc region. The $IC_{50}$ value for Fc-T2m was 0.05 nM. This indicates that constructs with two ectodomains in the C-terminal portion may be more potent than a construct with one ectodomain in the C-terminal portion (as was observed in the Mv1Lu assay, FIG. 4A), however, it should be noted that Fc-T2m does not have an optimized N-terminus.

Figure 4C:
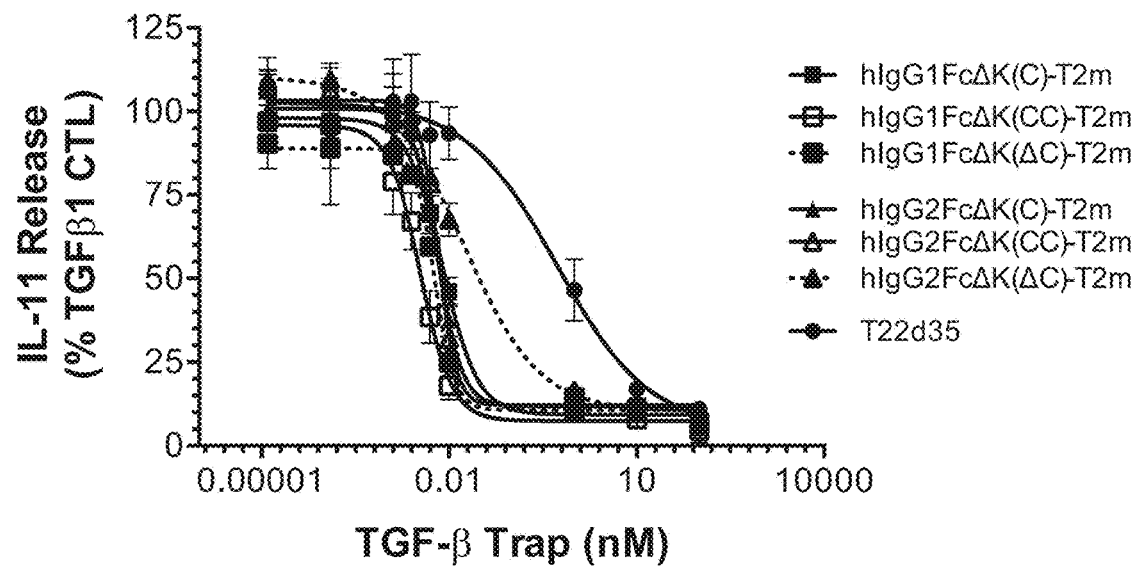
FIG. 4C shows graphs and a summary table depicting the efficient inhibition of TGF-β1 signaling in an A549/IL-11 release cell-based assay by several representatives of "headless"-T2m constructs (Type C construct (FIG. 2C) from FIGS. 2A-2G), compared to the lower inhibition potency of non-Fc-fused T22d35.

An additional set of experiments in which the A549 cell IL-11 release assay was used to compare TGF-β neutralization potencies is shown in FIG. 4C. Here, the potencies of several "headless"-T2m constructs were assessed along with that of non-Fc-fused T22d35. The potency of T22d35 was determined to be ~0.5 nM, consistent with the data shown in FIG. 4B. This is illustrative of the robustness of the A549 cell IL-11 release assay. It can also be seen in FIG. 4C that all of the "headless"-T2m constructs exhibited high potencies with $IC_{50}$s in the range of 5 pM (3 to 17 pM). These values are in the same range as those of the T22d35-containing constructs shown in FIG. 4B, and are 10-fold higher potency than that of the "headless"-T2m containing construct also shown in FIG. 4B (Fc-T2m). Since all of the T2m-containing constructs in FIG. 4C have engineered N-termini, whereas Fc-T2m does not, these results indicate that engineering of the cysteine residues of the hinge region of "headless" constructs is able to increase their potency by approximately 10-fold.

We have also compared the potencies of constructs that include three TβRII structured ectodomains with constructs carrying two ectodomains using the A549 cell IL-11 release assay. We observed that the triple-repeat based constructs (SEQ ID NO:111 and SEQ ID NO:116) are potent in neutralizing TGF-β1 in this assay, and typically have improved IC50 values relative to the corresponding double-repeat based constructs (SEQ ID NO:100 and SEQ ID NO:106, respectively). All constructs involved in this comparative study had the same engineered N-terminus of the Fc portion, hIgG1FcΔK(C).

Figure 4D:
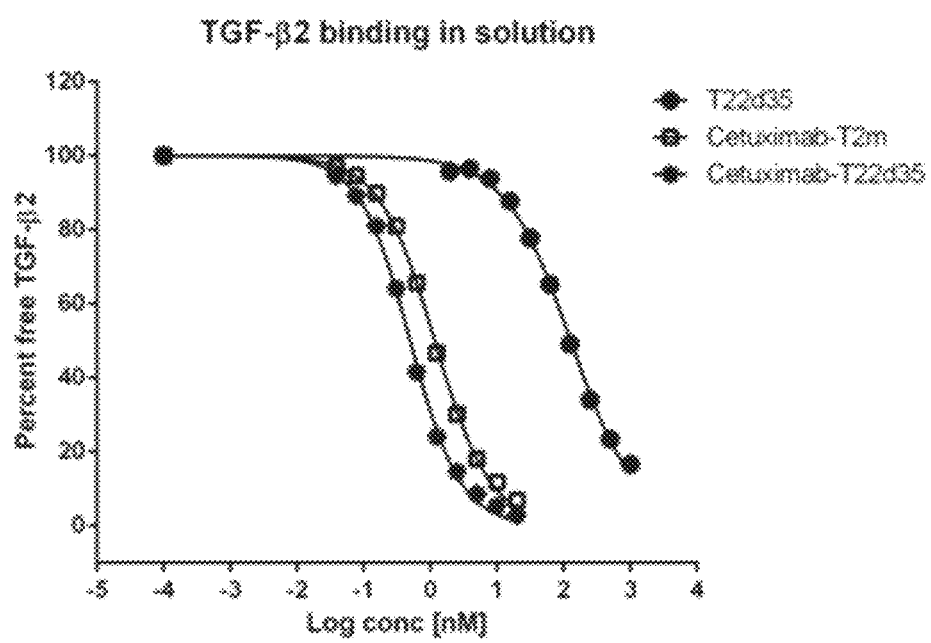
FIG. 4D is a graph showing competitive SPR analysis of binding of Cetuximab-fusion constructs to TGF-β isoforms in solution, compared to T22d35.
Figure 5A:
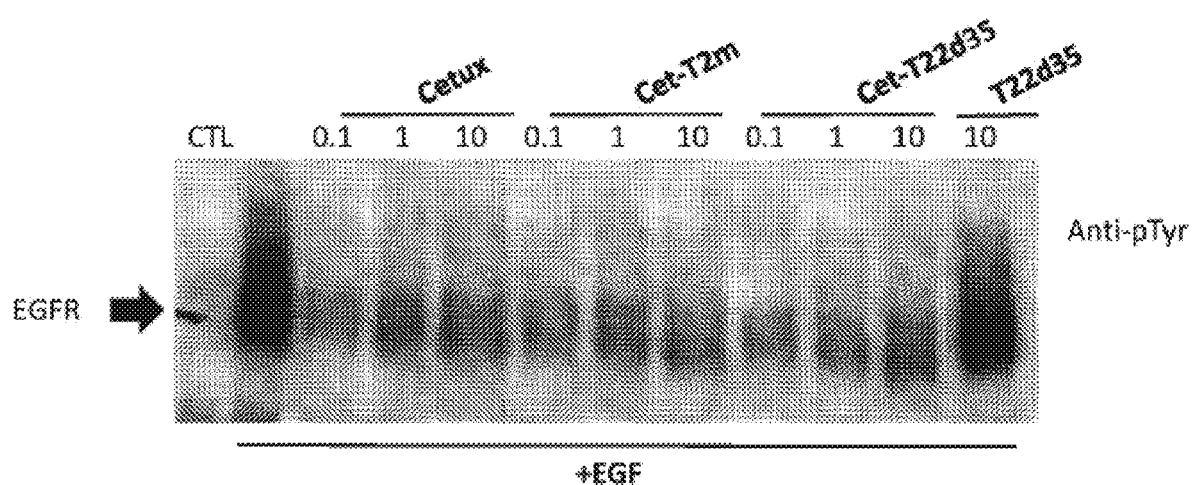
FIG. 5A is a SDS-PAGE gel showing the inhibition of EGFR phosphorylation in A549 cells by Cetuximab-fusion constructs.
Figure 5B:
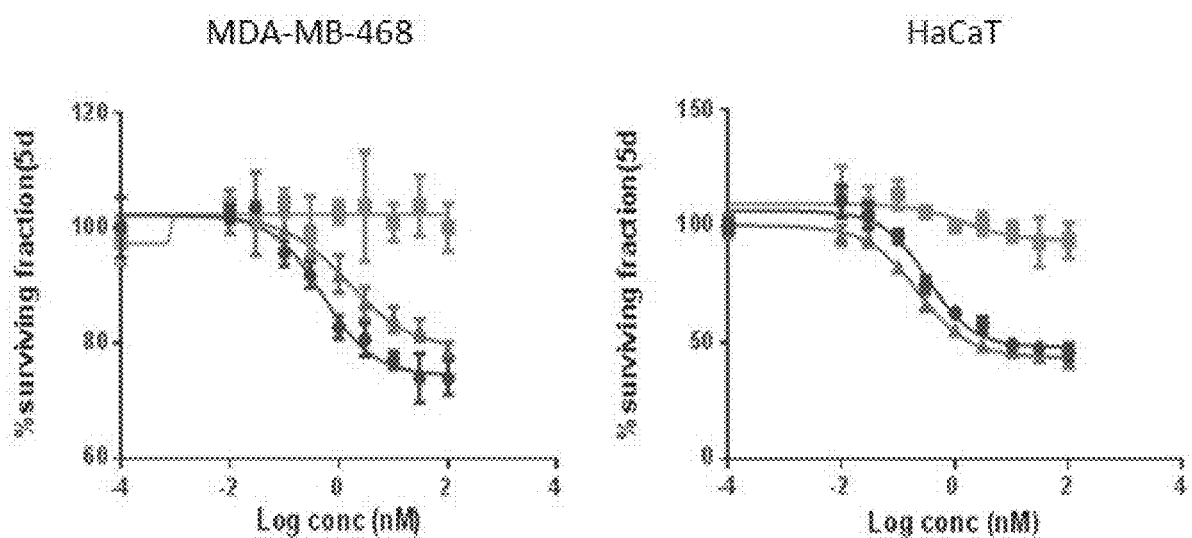
FIG. 5B is a graph showing Cet-T22d35 (triangles) cytotoxicity in MDA-MB-468 and HaCat cells compared to Cetuximab (circles) and T22d35 (squares).

Binding to TGF-β: Binding of T22d35, Cet-T22d35, and Cet-T2m to TGF-β2 was measured using a competitive SPR binding experiment. In this assay, the molecule of interest was first allowed to bind to a fixed amount of TGF-β in solution. A 2-fold dilution series was prepared in PBS-0.05% Tween, starting with 1000 nM T22d35 trap or 20 nM Cet-T22d35 or Cet-T2m. Each diluted sample was pre-incubated with 1 nM TGF-β2 for 30 min at room temperature to allow binding. The mixture was then flowed over immobilized, pan-specific anti-TGF-β antibody 1D11 (2000 RU 1D11) in order to quantify the amount of ligand left unbound (TβRII ectodomain and 1D11 bind to a similar epitope on TGF-β) using a Biacore T200 instrument. The TGF-β2 binding $EC_{50}$ values were determined by plotting the percent free TGF-β versus the protein concentration of the molecule of interest. Binding curves and $EC_{50}$ values are shown in FIG. 4D and Table 3. In the case of TGF-β2 binding, a 100-fold increase in binding was observed between Cet-T22d35 and unfused T22d35 ($EC_{50}$~1 nM versus>100 nM, respectively), indicating that C-terminal fusion of the T22d35 trap to antibody provides a gain in affinity for the TGF-β2 isoform. This correlates with the ability of Cet-T22d35 to neutralize TGF-β2 in the 10 nM range, and the inability of unfused T22d35 to neutralize TGF-β2, as observed in the Mv1 Lu-Luc cell reporter assay.

TABLE 3

$EC_{50}$ of Cetuximab-trap binding to TGF-β in solution. $EC_{50}$ is the Effective Concentration at which 50% of TGF-β is bound and is given in nM. Note: T2m alone shows an IC50 of greater than 1000 nM (Zwaagstra et al, 2012), and thus is not considered neutralizing.

| Trap variant | $EC_{50}$ for TGF-β2 |
|---|---|
| T22d35 | >100 |
| Cetuximab-T2m | 1.17 |
| Cetuximab-T22d35 | 0.50 |

Example 3A: Validation of Antibody Binding

The ability of an antibody alone or in a fusion construct of Example 1 to bind to its intended target antigen was evaluated using surface plasmon resonance (SPR).

Direct binding of Cet-T22d35 or Cetuximab to the EGF receptor extracellular domain (EGFR-ED) was quantified by SPR using a BIAcore T200 instrument, performed in the standard manner. Briefly, Cet-T22d35 or Cetuximab alone were captured on the SPR CM5 chip using immobilized anti-human IgG Fc-specific antibody (2000 RU). Variable concentrations of EGFR-ED in PBS-0.05% Tween were then flowed over the capture surface at 100 μl/min and 25° C. The resulting sensorgrams (data not shown) were analyzed using the Biacore T200 evaluation software. The $K_D$ values of Cet-T22d35 and Cetuximab were very similar (847 and 708 pM, respectively), indicating that fusion of T22d35 to the Fc portion of Cetuximab does not appreciably alter binding to EGFR-ED, compared to the non-fused FSA. Similar SPR methods and analyses were performed for other antibody-trap fusion examples, compared with their corresponding target antigens (see Table 4).

From Table 4 it is evident for each exemplified construct that fusion of a TGF-β superfamily receptor ectodomain(s) to the C-terminus of the Fc region of an antibody did not significantly alter antigen-binding affinities and $K_D$ values of the antibody. This indicates that the ectodomain(s) can be readily fused to any antibody without compromising the ability the antibody to bind its target antigen.

TABLE 4

SPR determination of antigen-binding affinity of T22d35 fusion constructs or antibodies alone. NOTE: FC-5-Fc, FC5-Fc-T2m, and FC-5-Fc-T22d35 binding affinity was assessed via the transwell functional assay (see Example 3C).

| | Antigen | $K_a$ (1/Ms) | $K_d$ (1/s) | $K_D$ (M) |
|---|---|---|---|---|
| Cetuximab-T22d35 | EGFR | $1.22 \times 10^{6}$ | $8.65 \times 10^{-4}$ | $7.08 \times 10^{-10}$ |
| Cetuximab | EGFR | $1.03 \times 10^{6}$ | $8.45 \times 10^{-4}$ | $8.47 \times 10^{-10}$ |
| Her-T22d35 | Her2 | $8.30 \times 10^{4}$ | $5.30 \times 10^{-5}$ | $6.37 \times 10^{-10}$ |
| Herceptin | Her2 | $6.88 \times 10^{4}$ | $5.03 \times 10^{-5}$ | $7.33 \times 10^{-10}$ |
| Syn-T22d35 | RSV-F | $3.55 \times 10^{4}$ | $1.42 \times 10^{-3}$ | $4.10 \times 10^{-9}$ |
| Synagis | RSV-F | $2.57 \times 10^{4}$ | $1.68 \times 10^{-3}$ | $6.60 \times 10^{-9}$ |

Example 3B: Validation of Cetuximab Function

The ability of Cetuximab to maintain its therapeutic function (i.e. inhibition of EGF-induced EGFR phosphorylation and signaling) when fused to either T2m or T22d35 (Example 1) was evaluated.

Phosphorylation of EGFR: The ability of Cetuximab-comprising constructs to inhibit EGF-induced phosphorylation of EGFR in human lung cancer A549 cells was evaluated. A549 cells were seeded in 24-well plates (100,000 cells/well) and either mock treated (−) or pre-treated with Cetuximab, Cet-T2m, or Cet-T22d35 (all at 10, 1 or 0.1 nM) or T22d35 (10 nM) at 37° C. for 3 h, then treated with 50 ng/mL EGF at 37° C. for 10 min. Whole cell lysates were prepared and resolved by SDS-PAGE, western blotted and probed with anti-phosphoTyrosine antibody (Clone 4G10, Millipore 05-321). As shown in FIG. 5A, Cetuximab and Cet-T2m and Cet-T22d35 inhibited EGFR phosphorylation to similar extents, whereas T22d35 had no effect, relative to the +EGF control. These results thus confirm that the TGF-β superfamily receptor ectodomain moieties in Cetuximab-T2m and Cetuximab-T22d35 fusion proteins do not interfere with the function of the Cetuximab antibody (i.e. inhibition of EGF induced EGFR signaling).

Inhibition of EGFR signaling: Inhibition of autocrine EGFR signaling results in varying degrees of cytotoxicity in EGFR-expressing cells treated with Cetuximab. Cytotoxicity of Cet-T22d35 was compared to Cetuximab and T22d35 in human breast cancer cells (MDA-MB-468) and immortalized keratinocyte cells (HaCaT). These cells exhibited significant Cetuximab cytotoxicity, due to their intrinsic dependence on the EGF signaling pathway for basal growth.

The cells were seeded onto 96-well plates (MDA-MB-468, 2300 cells/well; HaCaT, 1500 cells/well) and then treated with different doses of inhibitor at 37° C. for 5 days. Cell viability was measured using sulforhodamine reagent to determine the percentage of viable cells relative to mock-treated controls. Results are shown in FIG. 5B and Table 5. The $IC_{50}$ values for Cet-T22d35 and Cetuximab were similar in both cell lines (0.2-1.4 nM range), while T22d35 resulted in no cytotoxicity. These results further confirm that the TGF-β superfamily receptor ectodomain moiety in Cetuximab-T22d35 does not interfere with the function of the Cetuximab antibody.

TABLE 5

Cetuximab-T22d35 cytotoxicity in MDA-MB-468 and HaCat cells. The cytotoxic potency $IC_{50}$ values are given in nM.

| | MDA-MB-468 $IC_{50}$ | HaCaT $IC_{50}$ |
|---|---|---|
| Cetuximab | 0.50 | 0.33 |
| Cetuximab-T22d35 | 1.42 | 0.22 |
| T22d35 | 0 | 0 |

Example 3C: Validation of FC5 Function

The ability of FC5 $V_HH$ to maintain its function (i.e. transmigrate the blood-brain barrier) when fused with the T2m or T22d35 moieties (see description in Example 2 and activities in Table 2) was evaluated.

Briefly, SV40-immortalized Adult Rat Brain Endothelial Cells (Sv-ARBEC) were used to generate an in vitro blood-brain barrier (BBB) model as described (Garberg et al, 2005; Haqqani et al, 2013). Sv-ARBEC cells (80,000 cells/membrane) were seeded on 0.1 mg/mL rat tail collagen type I-coated tissue culture inserts (pore size-1 μm; surface area 0.9 $cm^2$, Falcon) in 1 ml of growth medium. The bottom chamber of the insert assembly contained 2 ml of growth medium supplemented with the immortalized neonatal rat astrocytes-conditioned medium in a 1:1 (v/v) ratio. Equimolar amounts (5.6 μM) of positive (FC5-Fc) control; negative controls (A20.1); and T22d35, T2m, FC5-Fc-T22d35 or FC5-Fc-T2m were tested for their ability to cross the Sv-ARBEC cell monolayer. Following exposure of equimolar amounts of the proteins to the luminal side of the BBB, samples were taken after 15, 30, and 60 min from the abluminal side. The protein content of each sample was then quantified by mass spectrometry (multiple reaction monitoring-isotype labeled internal standards; MRM-ILIS) as described by (Haqqani et al, 2013) (see method description below).

Quantified values can be directly plotted or the $P_{app}$ (apparent permeability coefficient) values can be determined using the following formula $$Papp = \frac{dQr/dt}{A \times C_0}$$

The $P_{app}$ value is commonly used to determine the specific permeability of a molecule, and is a measure of transport across the brain endothelial monolayer. [Qr/dt=cumulative amount in the receiver (bottom) compartment versus time; A=area of the cell monolayer; C0=initial concentration of the dosing solution (top chamber)].

Figure 6:
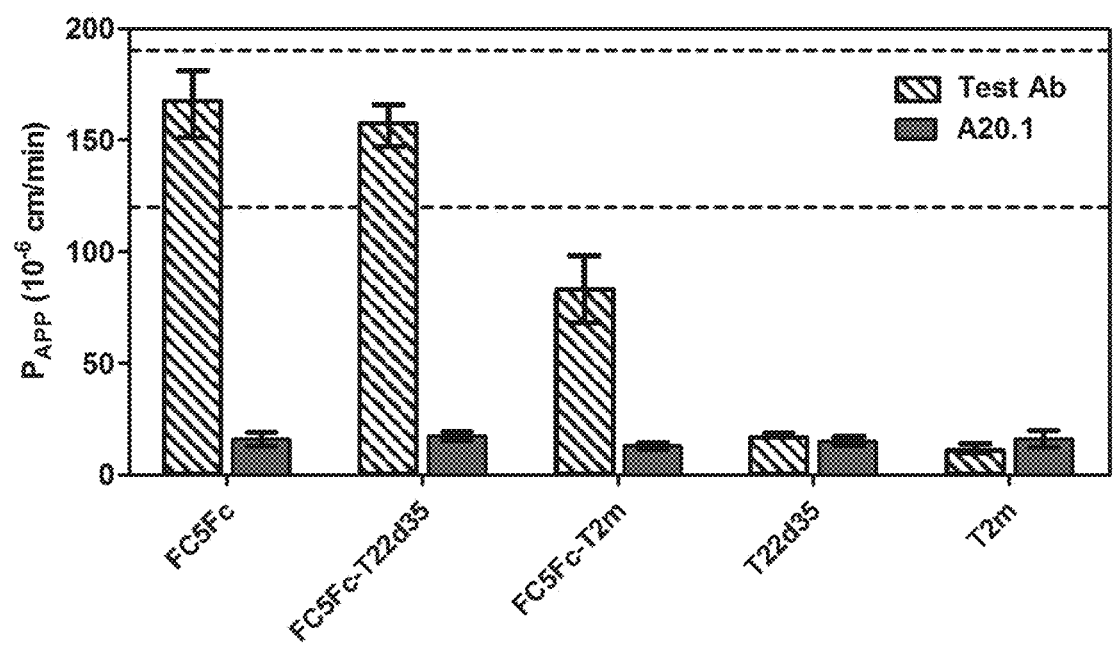
FIG. 6 is a bar graph showing the apparent permeability coefficient (P$_{app}$) values, as a measure of transport of FC5-Fc, FCS-Fc-fusion constructs, T22d35, and T2m across a human brain endothelial cell barrier in vitro, relative to a non-transporting V$_H$H control (A20.1).

FIG. 6 shows the results of the experiment. The $P_{app}$ value of FC5-Fc-T22d35 was similar to the control FC5-Fc, indicating it was transported efficiently and that the fused T22d35 did not interfere with transport. The $P_{app}$ value for FC5-Fc-T2m was approximately 50% less, compared to FC5-Fc-T22d35 and FC5-Fc, indicating somewhat reduced permeability. Nevertheless, the level of transport of FC5-Fc-T2m was about 4-fold greater than the negative controls (T2m, T22d35, and antibody A20.1).

Example 4: Inhibition of Epithelial to Mesenchymal Transition

Figure 7A:
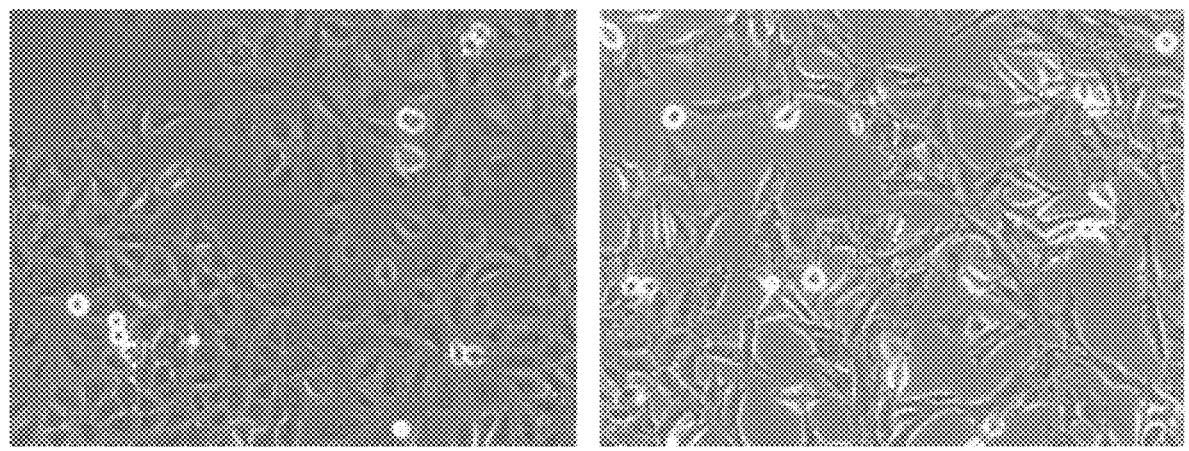
FIGS. 7A-7D demonstrate the Cet-T22d35 inhibition of EGF+TGF-β1 induced EMT in A549 cells.

Treatment of A549 cells with EGF plus TGF-β results in a strong epithelial to mesenchymal transition (EMT). The EMT is phenotypically characterized by changes in cell morphology (tight cellular junctions with "cobble-stone" appearance converts to elongated cells, see FIG. 7A) and changes in the adherin junction proteins E-cadherin and N-cadherin. The ability of the fusion constructs to block EMT was assessed in A549 cells by western blotting (E-cadherin) and flow cytometry (E-cadherin and N-cadherin).

Figure 7B:
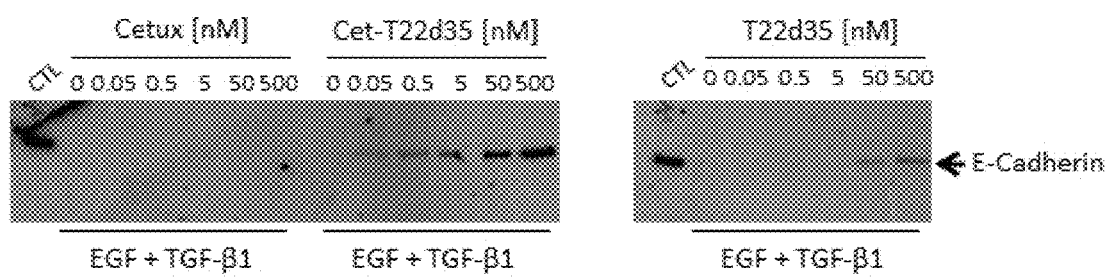
Figure 7C:
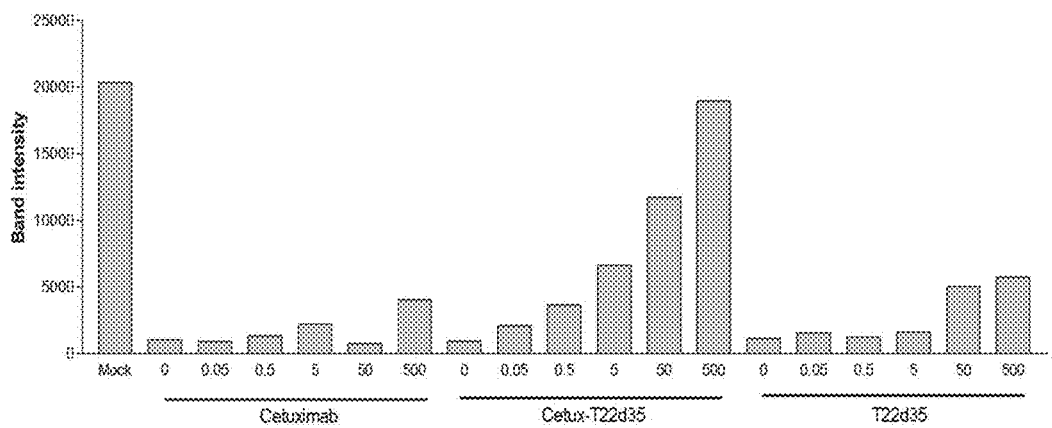

Briefly, for the western blot analysis, A549 cells were seeded in 24-well plates (8000 cells/well) and then treated with EGF (50 ng/mL)+TGF-β1 (50 pM) at 37° C. for 3 days in the presence of Cet-T22d35, Cetuximab, or T22d35 (0, 0.05, 0.5, 5, 50, or 500 nM). Whole cell lysates were prepared and resolved by SDS-PAGE. The proteins were transferred to nitrocellulose and then probed with an E-cadherin antibody (BD Transduction laboratories Biosciences) (FIG. 7B). The E-Cadherin positive bands in the Western blot were quantified by densitometer detection and ImageJ analysis (FIG. 7C). EGF+TGF-β treatment resulted in an EMT, as indicated by the disappearance of E-cadherin (compare non-treated and EGF+TGF-β lanes in the absence of inhibitors). Cet-T22d35 blocked the EMT (E-cadherin disappearance) in a dose-dependent manner whereas 500 nM Cetuximab or T22d35 treatments only modestly blocked the EMT (E-cadherin levels ~20-25% of the non-treated control level).

Figure 7D:
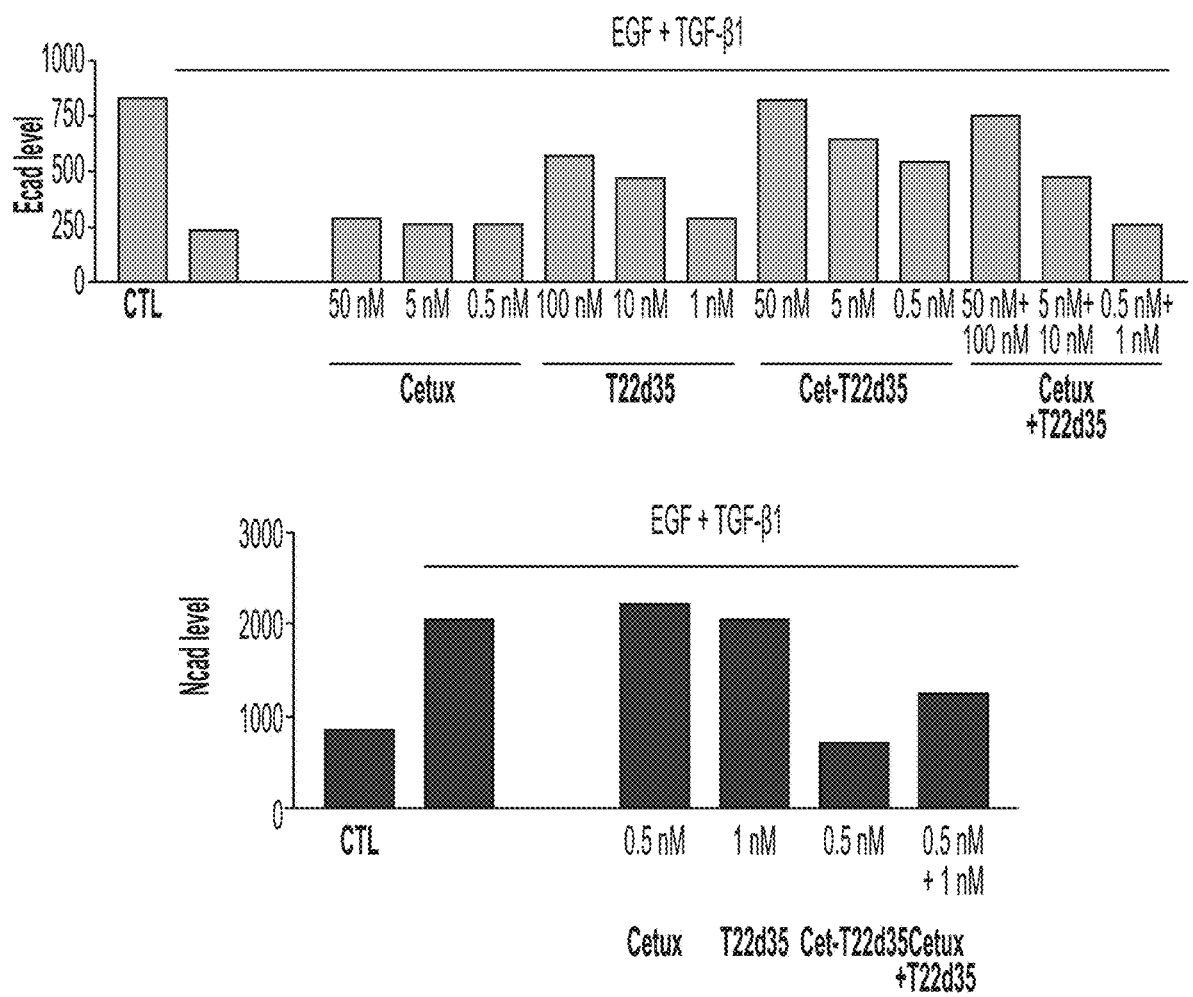

The ability of Cet-T22d35, Cetuximab and T22d35 to block the EGF+TGF-β EMT response was further examined by flow cytometry using A549 cells treated with Cet-T22d35 or Cetuximab, (all at 50, 5, 0.5 nM) or the Cetuximab+T22d35 combination (50 nM+100 nM, 5 nM+10 nM, or 0.5 nM+1 nM, respectively) and evaluating the EMT associated changes in E-cadherin and N-cadherin cell surface expression levels (FIG. 7D). In this experiment the molar amounts of the molecules of interest used in 'T22d35 alone' and 'Cetuximab+T22d35' groups were two-fold higher than for Cet-T22d35 in order to correspond with a 2:1 trap/antibody ratio in the Cet-T22d35 fusion molecule. A549 cells were seeded in 6-well plates (30,000 cells/well) and pre-treated with the inhibitors at 37° C. for 1 h, followed by added treatment with EGF (10 ng/mL)+TGF-β (10 pM) and incubation at 37° C. for 3 days. Cells were then dissociated from the plate using 1 mL Dissociation Buffer (Sigma)/well, centrifuged at 2000 rpm for 2 min and re-suspended in 100 µl RPMI-5 media at 4° C. AlexaFluor488-E-cadherin (Santa Cruz, SC21791) and AlexaFluor647-N-cadherin (BD Biosciences, 563434) antibodies (1/25 v/v dilutions) were added and samples were incubated at 4° C. for 1 h. Cells were then centrifuged, washed once in RPMI-5, and re-suspended in 400 µl RPMI-5 containing 15 µg/mL propidium iodide (Life Technologies) at 4° C. Mean fluorescent intensities (MFI) were measured by flow cytometry (BD LS RII flow cytometer, BD Biosciences) to quantify E-cadherin and N-cadherin levels. The results show that Cet-T22d35 was more effective in preventing down-regulation of E-cadherin (FIG. 7D, top panel) and up-regulation of N-cadherin (FIG. 7D, bottom panel), as a measure of blocking EMT, compared to Cetuximab, T22d34 or the Cetuximab+T22d35 combination at each respective dose, and is most notable at the lowest dose used (0.5 nM).

Example 5: Pharmacokinetic (PK) Studies on Constructs with and without a Lysine Residue at the Fusion Site Between the C-Terminus of the Fc Region and the N-Terminus of the Ectodomain PK studies were carried out in normal, healthy mice to determine whether fusion of T22d35 to an antibody increased its half-life in vivo, and whether removal of a lysine at the fusion site within constructs reduced the amount of cleavage occurring in vivo.

Results from Cet-T22d35 (construct Type D in FIG. 2—containing a lysine at the fusion site): A single bolus of Cet-T22d35 protein (10 mgs/Kg) formulated in DPBS was intravenously injected (IV) into the tail vein of normal Balb/c mice and serum samples were collected from the submandibular vein at selected time points (0.5, 1, 2, 4, 8, 14, 24, 48, 96 h). Blood samples were centrifuged at 2000 g at 4° C. for 10 min and the serum supernatant was removed and stored frozen at −80° C., prior to analyses. The samples were thawed at 4° C. and analyzed via mass spectrometry (multiple reaction monitoring-isotype labeled internal standards; MRM-LIS) in order to measure the levels of both the Cetuximab and T22d35 trap moieties. Briefly, 20 µl of sample was thawed and treated with mild detergents (0.1% RapiGest SF, Waters; 5.5 mM TCEP) at 95° C. for 10 min. The sample was cooled to room temperature and Iodoacetamide (IAA) in 50 mM Ammonium Bicarbonate was added to a final concentration of 10 mM IAA, followed by incubation for 40 min in the dark. DTT (10 mM final) was then added and the sample was incubated at room temperature for 15 min, followed by trypsin digestion (Sigma, 0.8 mg/mL final) at 37° C. for 18 h. A mixture of 5 µM each of isotope-labeled trap and cetuximab peptides (formulated in 30% acetonitrile, 0.1% formic acid) were added to final concentrations of 1 µM, as internal standards for quantification. The isotope-labeled peptides were 13C/15N-(H2N-

Figure 8A:
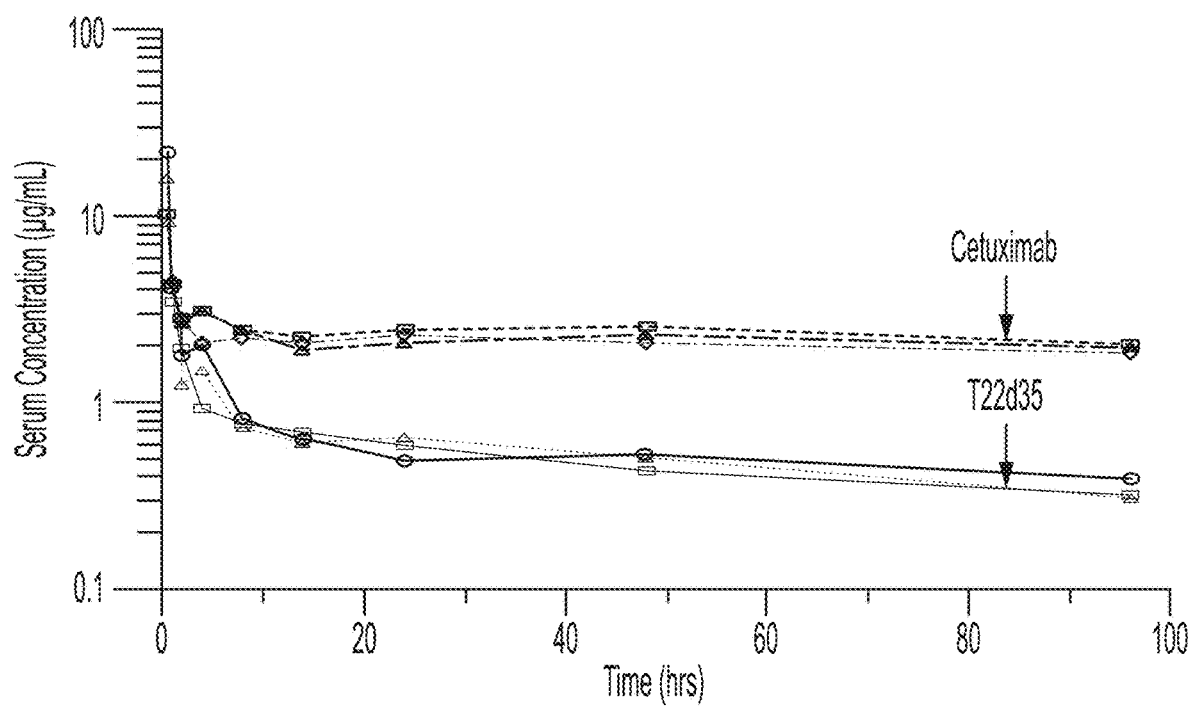
FIG. 8A represents the pharmacokinetic (PK) profile of Cet-T22d35 in the serum collected from BALB/C mice that were injected with a single dose of Cet-T22d35. The fusion construct appears to be cleaved in vivo; the terminal half-life of the T22d35 portion of the construct was determined to be 45.8 hours, while the terminal half-life of the Cetuximab portion of the construct was determined to be 262.5 hours.

LPYHDFILEDAASPK-OH; SEQ ID NO:134) and 13C/15N-(H2N-ALPAPIEK-OH; SEQ ID NO:135) for T22d35 and Cetuximab, respectively (NewEngland Peptide). Trifluoroacetic acid was then added (0.5% final), followed by incubation at 37° C. for 30 min. The samples were centrifuged at 13000 rpm for 20 min and the supernatant was used analyzed via MRM-ILIS using an Agilent 1260 HPLC system coupled with Agilent QQQ6410B at 55° C. The PK profiles seen in FIG. 8A show that the levels of the Cetuximab and T22d35 moieties diverge at early time points (<10 h) after injection, indicating different kinetics and suggesting possible cleavage of T22d35 from the Cet-T22d35 protein in vivo. Nevertheless, analysis of these curves using a two compartmental model (Phoenix WinNonlin Software-Version 6.3) indicated that the average terminal half-life (T½β) of the T22d35 component was 45.8 h. This represents a 7.6-fold increase compared to the previously determined half-life for unfused T22d35 (T½β~6 h). As well, the PK profile shows that the Cetuximab moiety was maintained in the blood, with a T½β=262.5 h, indicating that the Cetuximab moiety has a long circulating half-life.

Figure 8B:
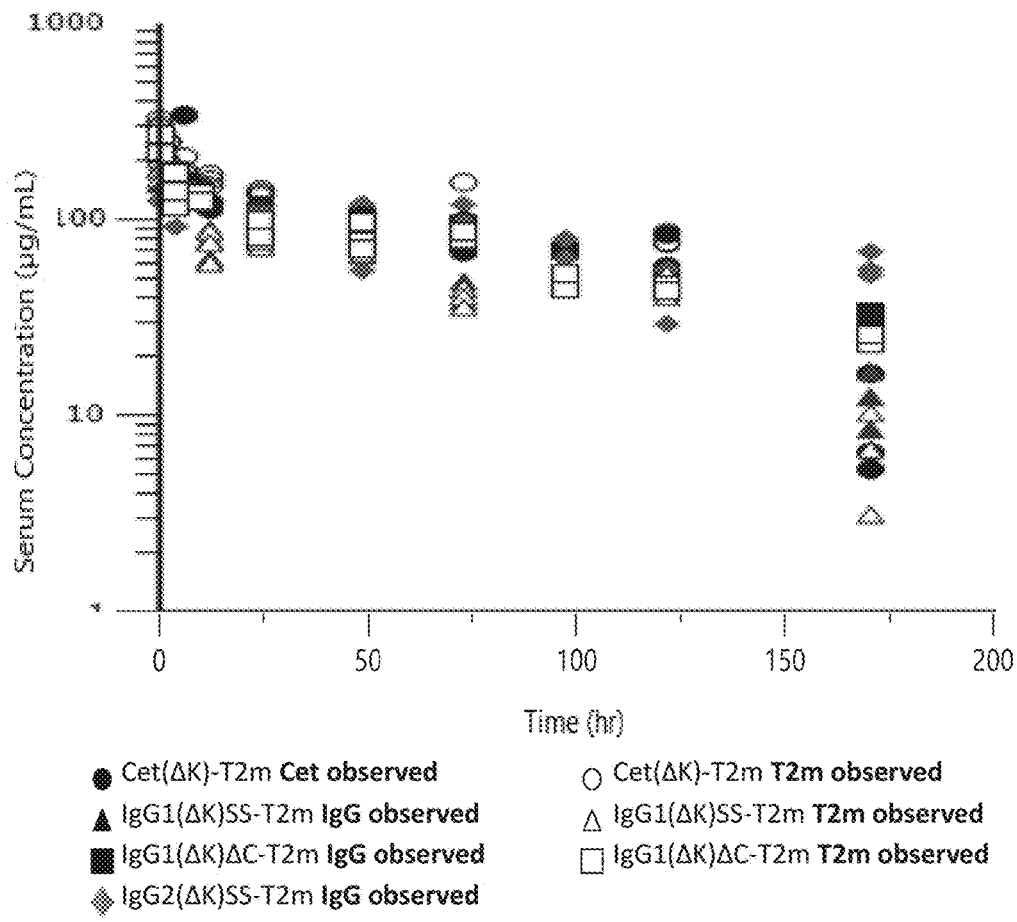
FIG. 8B represents the PK profiles and data table (serum half-lives in bold) for constructs in which the lysine at the C-terminus of the Fc region was removed, i.e. is not present at the fusion joint between the Fc region and T2m (CetΔK-T2m, hIgG1 FcΔK(SS)-T2m, hIgG1FcΔK(AC)-T2m, and hIg2GFcΔK(SS)-T2m). The data demonstrate that the removal of the lysine prevents cleavage of the constructs in vivo.

Results from several constructs with lysine deleted at the fusion site:

The same methods that were used in the PK study of Cet-T22d35 (FIG. 8A) were applied to assess the PK of CetΔK-T2m (Type F in FIG. 2) as well as several "headless" T2m constructs (Type C in FIG. 2; hIgG1FcΔK(SS)-T2m, hIgG1FcΔK(ΔC)-T2m, and hIgG2FcΔK(SS)-T2m), all of which have the lysine deleted at the fusion site. The data shown in FIG. 8B indicate that no detectable cleavage of these constructs is occurring in vivo since the levels of the Fc moieties (closed symbols) and ectodomain moieties (open symbols) do not diverge over time. Additionally, all of the constructs exhibit similar long circulating half-lives with T½ βs of approximately 100 h. This represents an improvement to the half-life of the ectodomain moiety of the construct which has a lysine at the fusion site, presented in FIG. 8A (45.8 h).

Example 6: Efficacy Studies Comparing the Effect of "Headless" Fc-T2m and FSA-T2M Constructs on Tumor Growth (A) and T-Cell Function (B and C) in an Immune-Competent Syngeneic Triple Negative Breast Cancer (4T1) Model A FSA-T2m construct (Cet-T2m—Type F in FIG. 2) and three headless constructs, all with engineered N-termini, (hIgG1FcΔK(CC)-T2m, hIgG1 FcΔK(C)-T2m, and hIgG2FcΔK(CC)-T2m—Type C in FIG. 2) were evaluated for their ability to inhibit tumor growth and to affect T-cell function in a syngeneic tumor model derived from 4T1 triple negative breast cancer cells. The results presented in FIG. 9 show the effect on tumor growth (A) and T-cell function (B, C). The effects of these Fc-fused ectodomain constructs were compared to those of a pan-specific neutralizing anti-TGF-β antibody, 1 D11 and a non-Fc-fused ectodomain construct, T22d35.

The protocols used for these syngeneic mouse model studies are described in (Zheng et al, 2013). Briefly, female BALB/c (H-2Kd) mice 6 weeks of age were purchased from The Jackson Laboratories and kept in filter-top cages. The 4T1 breast cancer cells and B16F10 cells were purchased from American type culture collection and cultured in RPMI-1640 supplemented with 2 mmol/L L-glutamine, 100 U/mL penicillin, 100 microgm/L streptomycin, 50 micromol/L 2-mercaptoethanol, and 10% fetal calf serum. Mice were inoculated subcutaneously in the left flank with 100 uL sterile saline containing $5 \times 10^4$ 4T1 cells. Tumors were grown to ~100 mm$^3$, as measured by caliper, then mice were randomized and divided into the six treatment groups (8 animals/group) (Day 0). Treatments commenced on Day 1 and continued for 15 days with the animals being dosed at 5 mg/kg twice per week such that they received a total of 4 doses. Tumor growth was monitored by caliper measurements 3× per week. Animals were euthanized by exsanguination under anaesthesia on Day 15; T cells were isolated from draining lymph nodes and assessed for their capacity to kill mouse 4T1 and B16F10 tumour cells ex vivo. The capacity of T cells from mice treated with or without test agents to lyse target 4T1 tumor cells was measured using a CytoTox 96 nonradioactive cytotoxicity assay kit (Promega) according to the manufacturer's instructions. Briefly, naïve target 4T1 cells or melanoma cell line B16F10 cells are plated and incubated for 4 hr with CD8+ effector T cells isolated from 4T1 tumor-bearing mice using CD8 magnetic MicroBeads (BD Bioscience). The isolated CD8+ cells are confirmed, by flow cytometry, to be over 85% CD8+. A range of ratios of effectors to target cells is tested (100:1, 50:1, 25:1). Lactate dehydrogenase (LDH) release in response to effector T cells is measured in the buffer bathing target cells. Target cells incubated in the absence of effector cells are used as a comparator to control for spontaneous LDH release. Released LDH in culture supernatants is detected after a 30-min incubation using a coupled enzymatic assay. The intensity of the color formed is proportional to the number of lysed cells. Cytotoxic activity of CTL is calculated using the following formula:

Cytotoxic activity %=[(absorbance)−(spontaneous effector cell LDH release)−(spontaneous target cell LDH release)]/[(maximal LDH release)−(spontaneous target cell LDH release)]×100

Figure 9A:
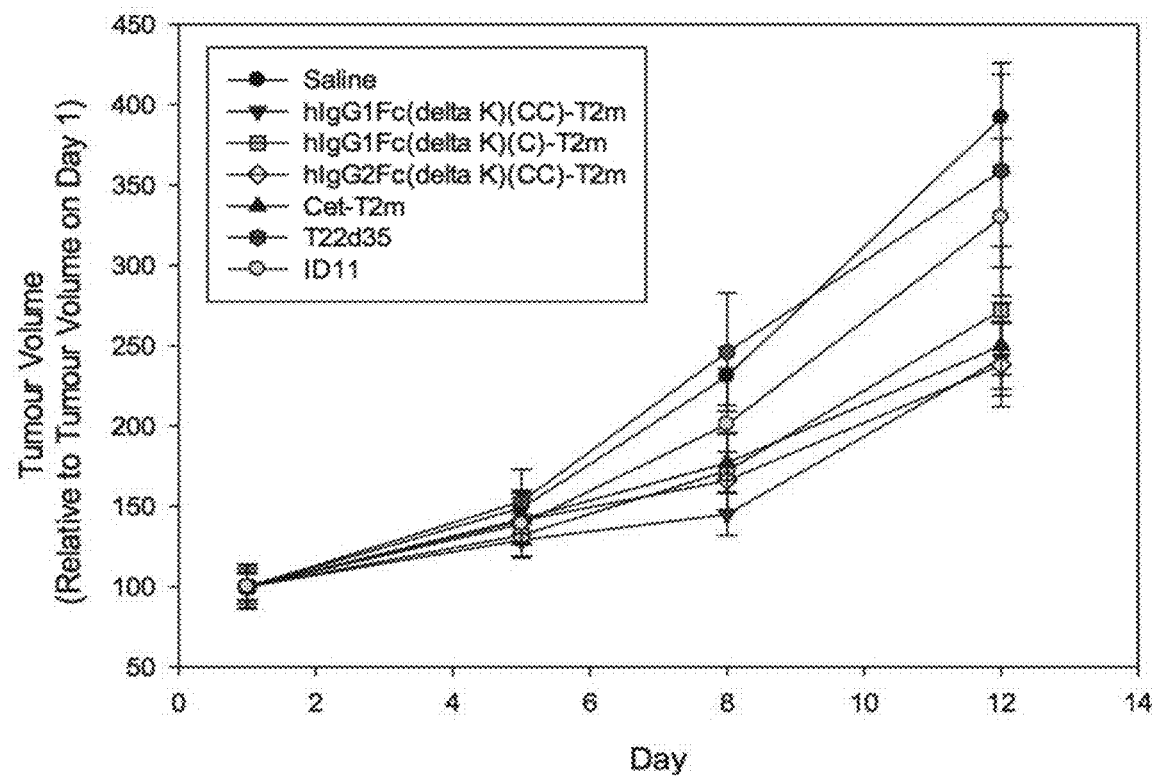

The results presented in FIG. 9A show the effect of the Fc-fused ectodomain constructs listed above on 4T1 tumor growth (the pan-specific neutralizing anti-TGF-β antibody, 1D11, and a non-Fc-fused ectodomain construct, T22d35, being tested as comparators). As can be seen in FIG. 9A, all of the Fc-fused ectodomain constructs reduced tumor growth relative to the saline treatment when tested for significance by t-test. The 1D11 and T22d35 comparator treatments were observed to be less effective relative to the Fc-fused ectodomain treatments, and not significantly different from the saline control. These results demonstrate that constructs with an ectodomain fused to the C-terminus of an Fc region have significant anti-tumor potency, with the efficacy being higher than the 1D11 and T22d35 comparators. There was no significant difference between the FSA-T2m construct (Cet-T2m) and the constructs that have no Fab, i.e. are "headless" (hIgG1 FcΔK(CC)-T2m, hIgG1 FcΔK(C)-T2m, and hIgG2FcΔK(CC)-T2m) with respect to their effect on tumor growth. The high anti-tumor potency of these Fc-ectodomain fusions relative to comparators likely results from high potency neutralization of TGF-β combined with a favourable circulating half-life.

To investigate whether these Fc-ectodomain fusions exhibit an immuno-modulatory effect in vivo on cytotoxic T lymphocyte cells (CTLs) present in tumor draining lymph nodes, lymph nodes were removed from mice treated with or without test agents; T-cells were then isolated and tested for their capacity to lyse target 4T1 tumor cells (and B16F10 cells as a test of tumor specificity) using the methods described above.

Figure 9B:
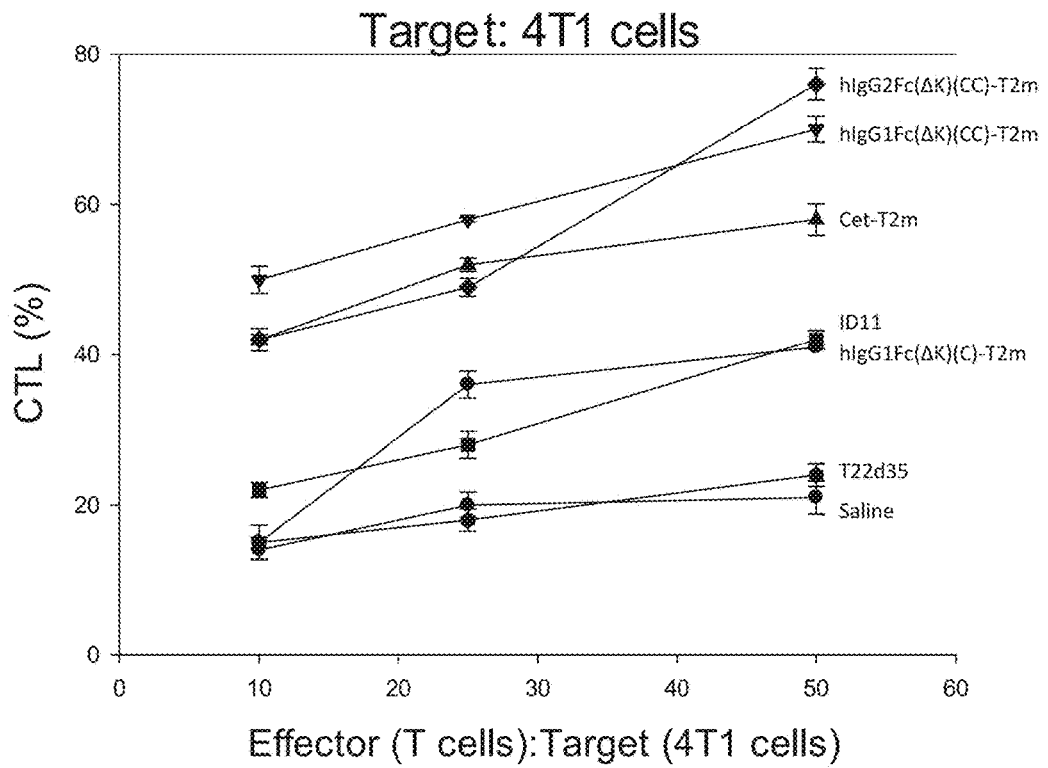

As shown in FIG. 9B, treatment of the animals with Fc-ectodomain fusions significantly increased the ability of draining lymph node T-cells to lyse target 4T1 tumor cells ex vivo. It can be seen that this immuno-stimulatory effect is specific to 4T1 cells since the T-cells were not able to effectively lyse B16F10 melanoma cells (FIG. 9C; maximal lysis of ~15% for B16F10 cells and ~80% for 4T1 cells). When administered at the same 5 mg/kg dose as the Fc-ectodomain fusions, the non-Fc-fused comparator molecule, T22d35, had no effect above saline. This is consistent with its lack of effect on tumor volume. Although the 1D11 antibody had no statistically significant effect on tumor volume (FIG. 9A), it did increase the ability of lymph node T-cells to lyse 4T1 tumor cells.

Interestingly, with respect to the Fc-ectodomain fusions of this invention, the most potent constructs were the hIgG1FcΔK(CC)-T2m and hIgG2FcΔK(CC)-T2m constructs; both of these constructs containing two cysteines in the engineered hinge region. These constructs were more potent than the construct with one cysteine in the engineered hinge region, hIgG1FcΔK(C)-T2m, as well as being more potent than the full-size antibody-T2m construct, Cet-T2m. The difference in potency between constructs with one versus two hinge region cysteines may result from the construct with one cysteine having a lower relative stability. The lower potency of the full size antibody construct relative to the headless constructs with two hinge region cysteines may result from a difference in molecular weight, with the smaller constructs being able to penetrate the tumor microenvironment more effectively.

Example 7: In Vitro and In Vivo Studies Illustrating Enhanced Bone Localization of Constructs Containing a Deca-Aspartate Motif for Bone Targeting at the N-Terminus of the Fc Region In vivo studies were carried out to investigate whether the addition of a 10 amino acid long poly-aspartate bone-localization motif (D10) to the N-terminus of the Fc region of constructs will promote their localization to bone. Optical imaging of D10-hIgG1 Fc-T2m fusions: Upon arrival, male Balb/c mice were housed 3 mice/cage. On the day of the experiment, animals were shaved dorsal and ventral and treated with the hair removal cream, NAIR®. Mice were injected with a single intravenous bolus of 10 mg/kg of two CF770 labeled constructs with a deca-aspartate motif for bone targeting (D10) at their N-termini (D10-hIgG1FcΔK(CC)-T2m, D10-GSL-hIgG1FcΔK(CC)-T2m) or with a control construct without the D10 motif (hIgG1FcΔK(CC)-T2m) and whole body bio-distribution followed using both in vivo and ex-vivo near infrared imaging. Imaging was conducted with a small-animal time-domain eXplore Optix pre-clinical imager MX3 (Advanced Research Technologies, ART) at various time points (prescan, 5 mins, 3 hr, 6 hr, 24 h, 48 h, 72 h, 96 h and 120 h).

The small animal time-domain eXplore Optix preclinical imagers consists of a 785-nm pulsed laser diode with a repetition frequency of 80 MHz and a time resolution of 12.5 ps light pulse was used for excitation. The fluorescence emission beyond 813 nm was collected by a highly sensitive time-correlated single photon counting system and detected through a fast photomultiplier tube. The data were recorded as temporal point-spread functions (TPSF) and the images were presented as fluorescence intensity maps using ART Optix Optiview analysis software 3.02.

For in vivo optical imaging, mice were first anesthetized using isofluorane (1.5-2%), positioned on the animal stage within a chamber which allows for gaseous anesthesia and maintenance of animal temperature at 36° C. The scanning of the mouse at each time point lasted up to 20 mins using a 2.5 mm step size and the mouse is placed back in its home cage between imaging time points.

At the end of the imaging protocol (120 hrs) animals were sacrificed by intracardiac perfusion using heparnized saline with deep anesthesia. The organs (brain, heart, lungs, liver, kidney, spleen and right and left leg bones) were imaged ex-vivo using a 1.0 mm step size using the eXplore Optix pre-clincal imager MX3.

Data analysis was done using eXplore Optix Optiview analysis software 3.02 (Advanced Research Technologies, Montreal, QC) to estimate the fluorescence total and average fluorescence intensity in region of interest containing the ex-vivo organs.

Figures 10A, 10B:
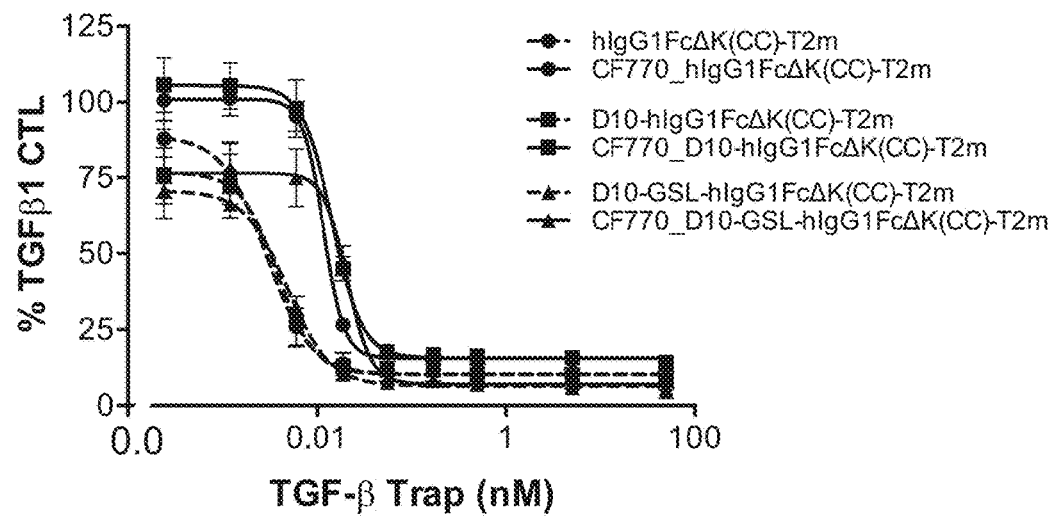
FIGS. 10A-10D show data illustrating enhanced bone localization of two constructs containing a deca-aspartate motif for bone targeting at the N-terminus of the Fc region (D10-hIgG1FcΔK(CC)-T2m (SEQ ID NO:136) and D10-GSL-hIgG1FcΔK(CC)-T2m (SEQ (Fragment, crystallisable). Characteristics described herein for the $C_{H2}$ and $C_{H3}$ domains also apply to the Fc.

The results shown in FIGS. 10A and B demonstrate that the fusion of the deca-aspartate D10 motif on the N-termini of the fusion constructs had no impact on their ability to neutralize TGF-β, i.e. the $IC_{50}$ of the construct lacking the D10 motif (hIgG1FcΔK(CC)-T2m) was 3 nM, which is the same as the value determined in FIG. 4C, while the $IC_{50}$s of the D10 containing constructs, D10-hIgG1FcΔK(CC)-T2m and D10-GSL-hIgG1FcΔK(CC)-T2m, were very similar at 4-5 nM. The results in FIGS. 10A and B also indicate that labeling with the CF770 dye reduced the ability of the constructs to neutralize TGF-β by approximately 4-fold. Since dye conjugation occurs at lysine residues, and since it is know that lysines are at the binding interface between the Type II ectodomain and TGF-β, it is not entirely surprising that labeling reduced neutralization potency. In any case, since this is a comparative study of differences in in vivo localization promoted by the D10 peptide, it was felt that partially active constructs would be informative.

Figure 10C:
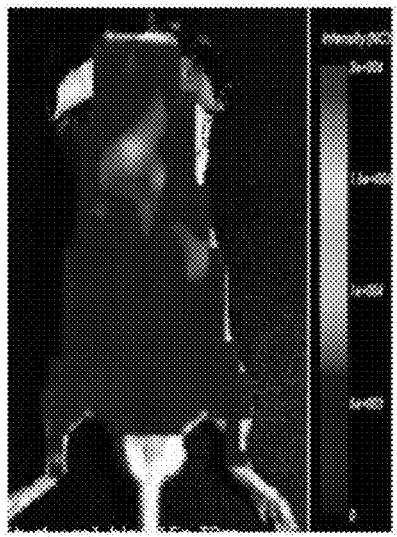
Figure 10C:
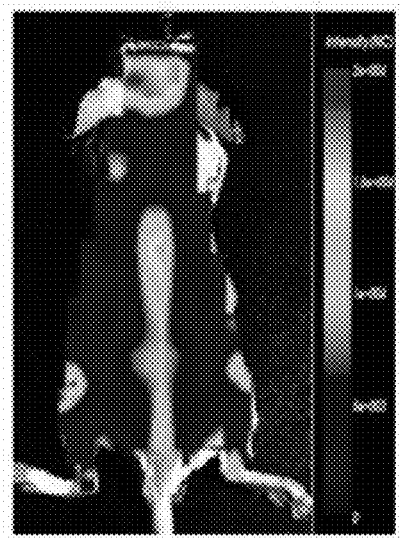
Figure 10C:
Figure 10D:
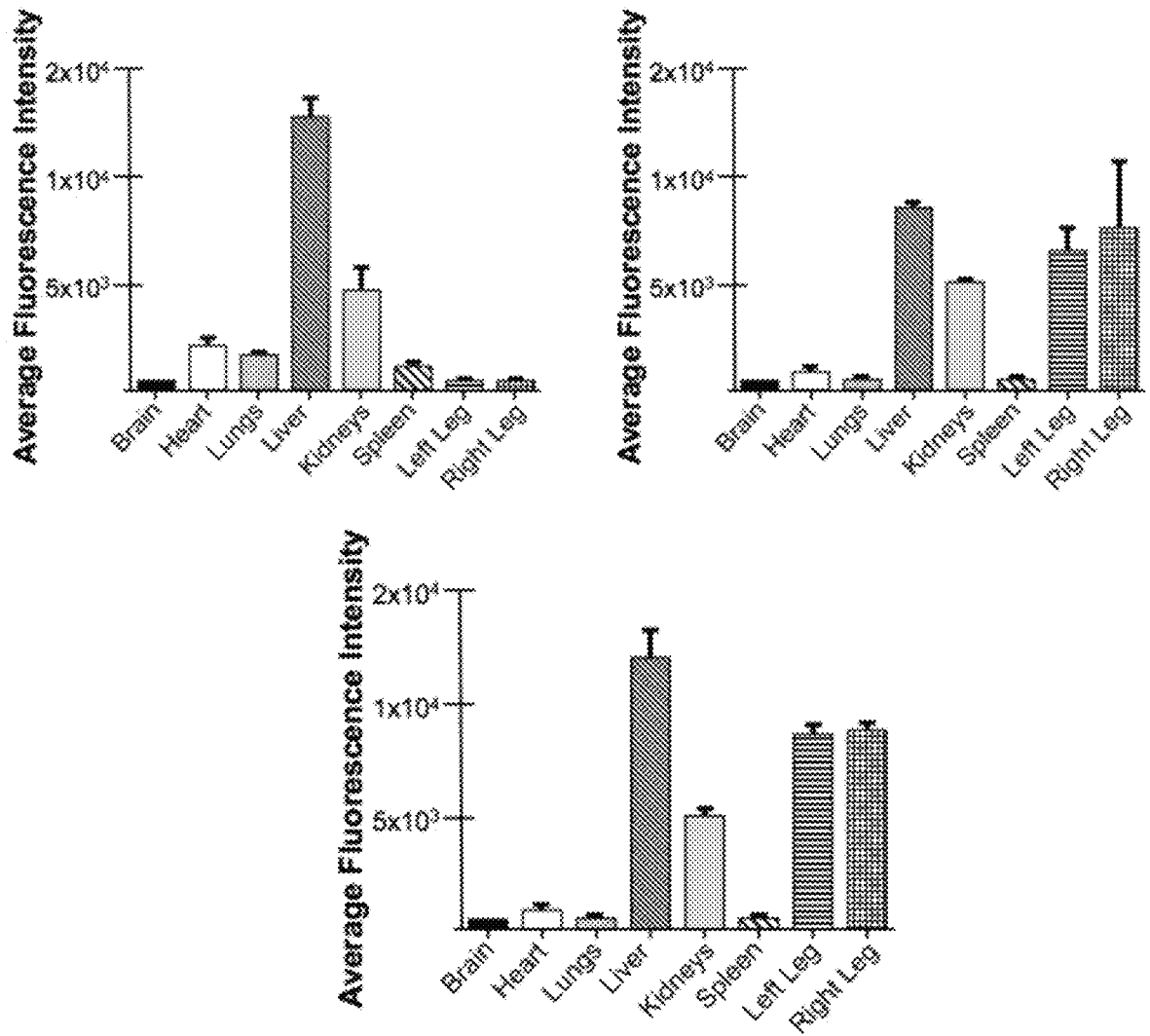

The results shown in FIGS. 10C and D demonstrate that the addition of the D10 peptide to the N-termini of the constructs greatly enhanced bone localization. Images taken 120 h post-injection of the CF770 labeled fusions show a clear accumulation of the D10-fusions in the vertebrae. Further ex vivo imaging of the brain, heart, lungs, liver, kidneys, spleen, and the left and right legs 120 h post-injection confirmed the specific accumulation of the D10-fusions in the bones. The fluorescent signals observed in the kidneys and liver were similar for all fusions indicating that accumulation in these organs was not affected by the presence of the D10 sequence. These results indicate that the TGF-β neutralization activity of constructs may be increased within bone through the addition of the D10 peptide. This could result in more favourable dosing levels and schedules for the treatment of bone-related diseases, such as osteogenesis imperfecta, relative to that required for a similar construct without the D10 motif.

The embodiments and examples described herein are illustrative and are not meant to limit the scope of the invention as claimed. Variations of the foregoing embodiments, including alternatives, modifications and equivalents, are intended by the inventors to be encompassed by the claims. Furthermore, the discussed combination of features might not be necessary for the inventive solution.

| LISTING OF SEQUENCES | | |
|---|---|---|
| SEQ ID NO: | Sequence | Description |
| 1 | APELLGGPSVFLFPPKPKDTLMISR TPEVTCVVVDVSHEDPEVKFNWYVD GVEVHNAKTKPREEQYNSTYRVVSV LTVLHQDWLNGKEYKCKVSNKALPA | Human IgG1 Fc region |

| SEQ ID NO: | Sequence | Description |
|---|---|---|
| | PIEKTISKAKGQPREPQVYTLPPSR DELTKNQVSLTCLVKGFYPSDIAVE WESNGQPENNYKTTPPVLDSDGSFF LYSKLTVDKSRWQQGNVFSCSVKHE ALHNHYTQKSLSLSPGK | |
| 2 | APPVAGPSVFLFPPKPKDTLMISRT PEVTCVVVDVSHEDPEVQFNWYVDG VEVHNAKTKPREEQFNSTFRVVSVL TVVHQDWLNGKEYKCKVSNKGLPAP IEKTISKTKGQPREPQVYTLPPSRE EKTKNQVSLTCLVKGFYPSDISVEW ESNGQPENNYKTTPPMLDSDGSFFL YSKLTVDKSRWQQGNVFSCSVKHEA LHNHYTQKSLSLSPGK | Human IgG2 Fc region |
| 3 | APELLGGPSVFLFPPKPKDTLMISR TPEVTCVVVDVSHEDPEVQFKWYVD GVEVHNAKTKPREEQYNSTFRVVSV LTVLHQDWLNGKEYKCKVSNKALPA PIEKTISKTKGQPREPQVYTLPPSR EEMTKNQVSLTCLVKGFYPSDIAVE WESSGQPENNYNTTPPMLDSDGSFF LYSKLTVDKSRWQQGNIFSCSVMHE ALHNRFTQKSLSLSPGK | Human IgG3 Fc region |
| 4 | APEFLGGPSVFLFPPKPKDTLMISR TPEVTCVVVDVSQEDPEVQFNWYVD GVEVHNAKTKPREEQFNSTYRVVSV LTVLHQDWLNGKEYKCKVSNKGLPS SIEKTISKAKGQPREPQVYTLPPSQ EEMTKNQVSLTCLVKGFYPSDIAVE WESNGQPENNYKTTPPVLDSDGSFF LYSRLTVDKSRWQEGNVFSCSVKHE ALHNHYTQKSLSLSLGK | Human IgG4 Fc region |
| 5 | EPKSCDKTHTCPPCP | Human IgG1 hinge region |
| 6 | ERKCCVECPPCP | Human IgG2 hinge region |
| 7 | ELKTPLCDTTHTCPRCPEPKSCDTP PPCPRCPEPKSCDTPPPCPRCPEPK SCDTPPPCPRCP | Human IgG3 hinge region |
| 8 | ESKYGPPCPSCP | Human IgG4 hinge region |
| 9 | APELLGGPSVFLFPPKPKDTLMISR TPEVTCVVVDVSHEDPEVKFNWYVD GVEVHNAKTKPREEQYNSTYRVVSV LTVLHQDWLNGKEYKCKVSNKALPA PIEKTISKAKGQPREPQVYTLPPSR DELTKNQVSLTCLVKGFYPSDIAVE WESNGQPENNYKTTPPVLDSDGSFF LYSKLTVDKSRWQQGNVFSCSVKHE ALHNHYTQKSLSLSPG | hIgG1FcΔK-AC Fc variant |
| 10 | PPCPAPELLGGPSVFLFPPKPKDTL MISRTPEVTCVVVDVSHEDPEVKFN WYVDGVEVHNAKTKPREEQYNSTYR VVSVLTVLHQDWLNGKEYKCKVSNK ALPAPIEKTISKAKGQPREPQVYTL PPSRDELTKNQVSLTCLVKGFYPSD IAVEWESNGQPENNYKTTPPVLDSD GSFFLYSKLTVDKSRWQQGNVFSCS VKHEALHNHYTQKSLSLSPG | hIgG1FcΔK-C Fc variant |
| 11 | DKTHTCPPCPAPELLGGPSVFLFPP KPKDTLMISRTPEVTCVVVDVSHED PEVKFNWYVDGVEVHNAKTKPREEQ YNSTYRVVSVLTVLHQDWLNGKEYK | hIgG1FcΔK-CC Fc variant |
| | CKVSNKALPAPIEKTISKAKGQPRE PQVYTLPPSRDELTKNQVSLTCLVK GFYPSDIAVEWESNGQPENNYKTTP PVLDSDGSFFLYSKLTVDKSRWQQG NVFSCSVMHEALHNHYTQKSLSLSP G | |
| 12 | EPKSSDKTHTCPPCPAPELLGGPSV FLFPPKPKDTLMISRTPEVTCVVVD VSHEDPEVKFNWYVDGVEVHNAKTK PREEQYNSTYRVVSVLTVLHQDWLN GKEYKCKVSNKALPAPIEKTISKAK GQPREPQVYTLPPSRDELTKNQVSL TCLVKGFYPSDIAVEWESNGQPENN YKTTPPVLDSDGSFFLYSKLTVDKS RWQQGNVFSCSVMHEALHNHYTQKS LSLSPG | hIgG1FcΔK-S Fc variant |
| 13 | EPKSSDKTHTCPPCPAPELLGGPSV FLFPPKPKDTLMISRTPEVTCVVVD VSHEDPEVKFNWYVDGVEVHNAKTK PREEQYNSTYRVVSVLTVLHQDWLN GKEYKCKVSNKALPAPIEKTISKAK GQPREPQVYTLPPSRDELTKNQVSL TCLVKGFYPSDIAVEWESNGQPENN YKTTPPVLDSDGSFFLYSKLTVDKS RWQQGNVFSCSVMHEALHNHYTQKS LSLSPG | hIgG1ΔK-SS Fc variant |
| 14 | EPKSSDKTHTSPPSPAPELLCGPSV FLFPPKPKDTLMISRTPEVTCVVVD VSHEDPEVKFNWYVDCVEVHNAKTK PREEQYNSTYRVVSVLTVLHQDWLN GKEYKCKVSNKALPAPIEKTISKAK GQPREPQVYTLPPSRDELTKNQVSL TCLVKGFYPSDIAVEWESNGQPENN YKTTPPVLDSDGSFFLYSKLTVDKS RWQQCNVFSCSVMHEALHNHYTQKS LSLSPC | hIgG1FcΔK-SSS Fc variant |
| 15 | APPVAGPSVFLFPPKPKDTLMISRT PEVTCVVVDVSHEDPEVQFNWYVDG VEVHNAKTKPREEQFNSTFRVVSVL TVVHQDWLNGKEYKCKVSNKGLPAP IEKTISKTKGQPREPQVYTLPPSRE EMTKNQVSLTCLVKGFYPSDISVEW ESNGQPENNYKTTPPMLDSDGSFFL YSKLTVDKSRWQQGNVFSCSVMHEA LHNHYTQKSLSLSPG | hIgG2FcΔK-AC Fc variant |
| 16 | PPCPAPPVACPSVFLFPPKPKDTLM ISRTPEVTCVVVDVSHEDPEVQFNW YVDGVEVHNAKTKPREEQFNSTFRV VSVLTVVHQDWLNGKEYKCKVSNKG LPAPIEKTISKTKGQPREPQVYTLP PSREEMTKNQVSLTCLVKGFYPSDI SVEWESNGQPENNYKTTPPMLDSDG SFFLYSKLTVDKSRWQQGNVFSCSV MHEALHNHYTQKSLSLSPG | hIgG2FcΔK-C Fc variant |
| 17 | VECPPCPAPPVAGPSVFLFPPKPKD TLMISRTPEVTCVVVDVSHEDPEVQ FNWYVDGVEVHNAKTKPREEQFNST FRVVSVLTVVHQDWLNGKEYKCKVS NKGLPAPIEKTISKTKGQPREPQVY TLPPSREEMTKNQVSLTCLVKGFYP SDISVEWESNGQPENNYKTTPPMLD SDGSFFLYSKLTVDKSRWQQGNVFS CSVMHEALHNHYTQKSLSLSPG | hIgG2FcΔK-CC Fc variant |
| 18 | ERKCCVECPPCPAPPVAGPSVFLFP PKPKDTLMISRTPEVTCVVVDVSHE DPEVQFNWYVDGVEVHNAKTKPREE | hIgG2Fc-CCCC Fc variant |

| SEQ ID NO: | Sequence | Description |
|---|---|---|
|  | QFNSTFRVVSVLTVVHQDWLNGKEY KCKVSNKGLPAPIEKTISKTKGQPR EPQVYTLPPSREEKTKNQVSLTCLV KGFYPSDISVEWESNGQPENNYKTT PPMLDSDGSFFLYSKLTVDKSRWQQ GNVFSCSVKHEALHNHYTQKSLSLS PGK |  |
| 19 | ERKSSVECPPCPAPPVAGPSVFLFP PKPKDTLMISRTPEVTCVVVDVSHE DPEVQFNWYVDGVEVHNAKTKPREE QFNSTFRVVSVLTVVHQDWLNGKEY KCKVSNKGLPAPIEKTISKTKGQPR EPQVYTLPPSREEKTKNQVSLTCLV KGFYPSDISVEWESNGQPENNYKTT PPMLDSDGSFFLYSKLTVDKSRWQQ GNVFSCSVMHEALHNHYTQKSLSLS PG | hIgG2FcΔK-SS Fc variant |
| 20 | ERKSSVESPPCPAPPVAGPSVFLFP PKPKDTLMISRTPEVTCVVVDVSHE DPEVQFNWYVDGVEVHNAKTKPREE QFNSTFRVVSVLTVVHQDWLNGKEY KCKVSNKGLPAPIEKTISKTKGQPR EPQVYTLPPSREEMTKNQVSLTCLV KGFYPSDISVEWESNGQPENNYKTT PPMLDSDGSFFLYSKLTVDKSRWQQ GNVFSCSVMHEALHNHYTQKSLSLS PG | hIgG2FcΔK-SSS Fc variant |
| 21 | ERKSSVESPPSPAPPVAGPSVFLFP PKPKDTLMISRTPEVTCVVVDVSHE DPEVQFNWYVDGVEVHNAKTKPREE QFNSTFRVVSVLTVVHQDWLNGKEY KCKVSNKGLPAPIEKTISKTKGQPR EPQVYTLPPSREEMTKNQVSLTCLV KGFYPSDISVEWESNGQPENNYKTT PPMLDSDGSFFLYSKLTVDKSRWQQ GNVFSCSVMHEALHNHYTQKSLSLS PG | hIgG2FcΔK-SSSS Fc variant |
| 22 | APELLGGPSVFLFPPKPKDTLMISR TPEVTCVVVDVSHEDPEVQFKWYVD GVEVHNAKTKPREEQYNSTFRVVSV LTVLHQDWLNGKEYKCKVSNKALPA PIEKTISKTKGQPREPQVYTLPPSR EEMTKNQVSLTCLVKGFYPSDIAVE WESSGQPENNYNTTPPMLDSDGSFF LYSKLTVDKSRWQQGNIFSCSVMHE ALHNRFTQKSLSLSPG | hIgG3FcΔK-AC Fc variant |
| 23 | PRCPAPELLGGPSVFLFPPKPKDTL MISRTPEVTCVVVDVSHEDPEVQFK WYVDGVEVHNAKTKPREEQYNSTFR VVSVLTVLHQDWLNGKEYKCKVSNK ALPAPIEKTISKTKGQPREPQVYTL PPSREEMTKNQVSLTCLVKGFYPSD IAVEWESSGQPENNYNTTPPMLDSD GSFFLYSKLTVDKSRWQQGNIFSCS VKHEALHNRFTQKSLSLSPG | hIgG3FcΔK-C Fc variant |
| 24 | DTPPPCPRCPAPELLGGPSVFLFPP KPKDTLMISRTPEVTCVVVDVSHED PEVQFKWYVDGVEVHNAKTKPREEQ YNSTFRVVSVLTVLHQDWLNGKEYK CKVSNKALPAPIEKTISKTKCQPRE PQVYTLPPSREEMTKNQVSLTCLVK CFYPSDIAVEWESSGQPENNYNTTP PMLDSDCSFFLYSKLTVDKSRWQQG NIFSCSVMHEALHNRFTQKSLSLSP G | hIgG3FcΔK-CC Fc variant |
| 25 | EPKSSDTPPPCPRCPAPELLGGPSV FLFPPKPKDTLMISRTPEVTCVVVD VSHEDPEVQFKWYVDGVEVHNAKTK PREEQYNSTFRVVSVLTVLHQDWLN GKEYKCKVSNKALPAPIEKTISKTK GQPREPQVYTLPPSREEMTKNQVSL TCLVKGFYPSDIAVEWESSGQPENN YNTTPPMLDSDGSFFLYSKLTVDKS RWQQGNIFSCSVMHEALHNRFTQKS LSLSPG | hIgG3FcΔK-S Fc variant |
| 26 | EPKSSDTPPPSPRCPAPELLGGPSV FLFPPKPKDTLMISRTPEVTCVVVD VSHEDPEVQFKWYVDCVEVHNAKTK PREEQYNSTFRVVSVLTVLHQDWLN GKEYKCKVSNKALPAPIEKTISKTK GQPREPQVYTLPPSREEMTKNQVSL TCLVKCFYPSDIAVEWESSGQPENN YNTTPPMLDSDGSFFLYSKLTVDKS RWQQGNIFSCSVMHEALHNRFTQKS LSLSPG | hIgG3FcΔK-SS Fc variant |
| 27 | EPKSSDTPPPSPRSPAPELLGGPSV FLFPPKPKDTLMISRTPEVTCVVVD VSHEDPEVQFKWYVDGVEVHNAKTK PREEQYNSTFRVVSVLTVLHQDWLN GKEYKCKVSNKALPAPIEKTISKTK GQPREPQVYTLPPSREEMTKNQVSL TCLVKGFYPSDIAVEWESSGQPENN YNTTPPMLDSDGSFFLYSKLTVDKS RWQQGNIFSCSVMHEALHNRFTQKS LSLSPG | hIgG3FcΔK-SSS Fc variant |
| 28 | APEFLGGPSVFLFPPKPKDTLMISR TPEVTCVVVDVSQEDPEVQFNWYVD GVEVHNAKTKPREEQFNSTYRVVSV LTVLHQDWLNGKEYKCKVSNKGLPS SIEKTISKAKCQPREPQVYTLPPSQ EEMTKNQVSLTCLVKGFYPSDIAVE WESNGQPENNYKTTPPVLDSDGSFF LYSRLTVDKSRWQEGNVFSCSVMHE ALHNHYTQKSLSLSLG | hIgG4FcΔK-AC Fc variant |
| 29 | PSCPAPEFLGGPSVFLFPPKPKDTL MISRTPEVTCVVVDVSQEDPEVQFN WYVDGVEVHNAKTKPREEQFNSTYR VVSVLTVLHQDWLNGKEYKCKVSNK GLPSSIEKTISKAKGQPREPQVYTL PPSQEEMTKNQVSLTCLVKGFYPSD IAVEWESNGQPENNYKTTPPVLDSD GSFFLYSRLTVDKSRWQEGNVFSCS VMHEALHNHYTQKSLSLSLG | hIgG4FcΔK-C Fc variant |
| 30 | ESKYGPPCPSCPAPEFLGGPSVFLF PPKPKDTLMISRTPEVTCVVVDVSQ EDPEVQFNWYVDGVEVHNAKTKPRE EQFNSTYRVVSVLTVLHQDWLNGKE YKCKVSNKGLPSSIEKTISKAKGQP REPQVYTLPPSQEEMTKNQVSLTCL VKGFYPSDIAVEWESNGQPENNYKT TPPVLDSDGSFFLYSRLTVDKSRWQ EGNVFSCSVMHEALHNHYTQKSLSL SLG | hIgG4FcΔK-CC Fc variant |
| 31 | ESKYGPPCPPCPAPEFLGGPSVFLF PPKPKDTLMISRTPEVTCVVVDVSQ EDPEVQFNWYVDGVEVHNAKTKPRE EQFNSTYRVVSVLTVLHQDWLNGKE YKCKVSNKGLPSSIEKTISKAKGQP REPQVYTLPPSQEEMTKNQVSLTCL VKGFYPSDIAVEWESNGQPENNYKT TPPVLDSDGSFFLYSRLTVDKSRWQ | hIgG4FcΔK-CC-228P Fc variant |

| SEQ ID NO: | Sequence | Description |
|---|---|---|
| | EGNVFSCSVMHEALHNHYTQKSLSLSLG | |
| 32 | ESKYGPPCPPCPAPEFLGGPSVFLFPPKPKDTLMISRTPEVTCVVVDVSQEDPEVQFNWYVDGVEVHNAKTKPREEQFNSTYRVVSVLTVLHQDWLNGKEYKCKVSNKGLPSSIEKTISKAKGQPREPQVYTLPPSQEEMTKNQVSLTCLVKGFYPSDIAVEWESNGQPENNYKTTPPVLDSDGSFFLYSKLTVDKSRWQEGNVFSCSVMHEALHNHYTQKSLSLSLG | hIgG4FcΔK-CC-228P-409K Fc variant |
| 33 | ESKYCPPSPSCPAPEFLCCPSVFLFPPKPKDTLMISRTPEVTCVVVDVSQEDPEVQFNWYVDGVEVHNAKTKPREEQFNSTYRVVSVLTVLHQDWLNGKEYKCKVSNKGLPSSIEKTISKAKGQPREPQVYTLPPSQEEMTKNQVSLTCLVKGFYPSDIAVEWESNGQPENNYKTTPPVLDSDGSFFLYSRLTVDKSRWQEGNVFSCSVMHEALHNHYTQKSLSLSLG | hIgG4FcΔK-S Fc variant |
| 34 | ESKYGPPSPSSPAPEFLGGPSVFLFPPKPKDTLMISRTPEVTCVVVDVSQEDPEVQFNWYVDGVEVHNAKTKPREEQFNSTYRVVSVLTVLHQDWLNGKEYKCKVSNKGLPSSIEKTISKAKGQPREPQVYTLPPSQEEMTKNQVSLTCLVKGFYPSDIAVEWESNGQPENNYKTTPPVLDSDGSFFLYSRLTVDKSRWQEGNVFSCSVMHEALHNHYTQKSLSLSLG | hIgG4FcΔK-SS Fc variant |
| 35 | QLCKFCDVRFSTCDNQKSCMSNCSITSICEKPQEVCVAVWRKNDENITLETVCHDPKLPYHDFILEDAASPKCIMKEKKKPCETFFMCSCSSDECNDNIIF | TβRII-ED structured domain |
| 36 | IPPHVQKSVNNDMIVTDNNGAVKFP | TβRII-ED N-term unstructured region and natural linker |
| 37 | IPPHVQKSDVEMEAQKDEIICPSCNRTAHPLRHINNDMIVTDNNCAVKFP | TβRIIb-ED N-term unstructured region and natural linker |
| 38 | IPPHVQKSDVEMEAQKDEIIAPSANRTAHPLRHINNDMIVTDNNGAVKFP | TβRIIb-ED Cys-mutated N-term unstructured region and natural linker |
| 39 | SEEYNTSNPD | TβRII-ED C-term unstructured region and natural linker |
| 40 | SEEYNTSNPDIPPHVQKSVNNDMIVTDNNGAVKFP | TβRII-ED natural linker |
| 41 | SEEYNTSNPDIPPHVQKSDVEMEAQKDEIICPSCNRTAHPLRHINNDMIVTDNNGAVKFP | TβRIIb-ED natural linker |
| 42 | SEEYNTSNPDIPPHVQKSDVEMEAQKDEIIAPSANRTAHPLRHINNDMIVTDNNGAVKFP | TβRIIb-ED Cys-mutated linker |
| 43 | IPPHVQKSVNNDMIVTDNNGAVKFPQLCKFCDVRFSTCDNQKSCMSNCSITSICEKPQEVCVAVWRKNDENITLETVCHDPKLPYHDFILEDAASPKCIMKEKKKPGETFFMCSCSSDECNDNIIFSEEYNTSNPD | TβRII-ED monomer, also termed T2 or T2m |
| 44 | IPPHVQKSDVEMEAQKDEIICPSCNRTAHPLRHINNDMIVTDNNGAVKFPQLCKFCDVRFSTCDNQKSCMSNCSITSICEKPQEVCVAVWRKNDENITLETVCHDPKLPYHDFILEDAASPKCIMKEKKKPGETFFMCSCSSDECNDNIIFSEEYNTSNPD | TβbRIIb-ED monomer, also termed T2b |
| 45 | IPPHVQKSDVEMEAQKDEIIAPSANRTAHPLRHINNDMIVTDNNGAVKFPQLCKFCDVRFSTCDNQKSCMSNCSITSICEKPQEVCVAVWRKNDENITLETVCHDPKLPYHDFILEDAASPKCIMKEKKKPGETFFMCSCSSDECNDNIIFSEEYNTSNPD | TβRIIb-ED monomer Cys-mutated in the linker region, also termed T2b$^{\Delta 4}$ |
| 46 | IPPHVQKSVNNDMIVTDNNGAVKFPQLCKFCDVRFSTCDNQKSCMSNCSITSICEKPQEVCVAVWRKNDENITLETVCHDPKLPYHDFILEDAASPKCIMKEKKKPGETFFMCSCSSDECNDNIIFSEEYNTSNPDIPPHVQKSVNNDMIVTDNNGAVKFPQLCKFCDVRFSTCDNQKSCMSNCSITSICEKPQEVCVAVWRKNDENITLETVCHDPKLPYHDFILEDAASPKCIMKEKKKPGETFFMCSCSSDECNDNIIFSEEYNTSNPD | TβRII-ED dimer, also termed T2-T2 or T22d35 |
| 47 | IPPHVQKSDVEMEAQKDEIICPSCNRTAHPLRHINNDMIVTDNNGAVKFPQLCKFCDVRFSTCDNQKSCMSNCSITSICEKPQEVCVAVWRKNDENITLETVCHDPKLPYHDFILEDAASPKCIMKEKKKPGETFFMCSCSSDECNDNIIFSEEYNTSNPDIPPHVQKSDVEMEAQKDEIICPSCNRTAHPLRHINNDMIVTDNNGAVKFPQLCKFCDVRFSTCDNQKSCMSNCSITSICEKPQEVCVAVWRKNDENITLETVCHDPKLPYHDFILEDAASPKCIMKEKKKPGETFFMCSCSSDECNDNIIFSEEYNTSNPD | TβRIIb-ED dimer, also termed T2-T2b |
| 48 | IPPHVQKSDVEMEAQKDEIICPSCNRTAHPLRHINNDMIVTDNNGAVKFPQLCKFCDVRFSTCDNQKSCMSNCSITSICEKPQEVCVAVWRKNDENITLETVCHDPKLPYHDFILEDAASPKCIMKEKKKPGETFFMCSCSSDECNDNIIFSEEYNTSNPDIPPHVQKSDVEMEAQKDEIIAPSANRTAHPLRHINNDMIVTDNNGAVKFPQLCKFCDVRFSTCDNQKSCMSNCSITSICEKPQEVCVAVWRKNDENITLETVCHDPKLPYHDFILEDAASPKCIMKEKKKPGETFFMCSCSSDECNDNIIFSEEYNTSNPD | TβRIIb-ED dimer Cys-mutated in the linker region, also termed T2-T2b$^{\Delta 4}$ |
| 49 | IPPHVQKSVNNDMIVTDNNGAVKFPQLCKFCDVRFSTCDNQKSCMSNCSITSICEKPQEVCVAVWRKNDENITLETVCHDPKLPYHDFILEDAASPKCIMKEKKKPGETFFMCSCSSDECNDNIIFSEEYNTSNPDIPPHVQKSVNNDMIVTDNNGAVKFPQLCKFCDVRFSTCDNQKSCMSNCSITSICEKPQEVCVAVWRKNDENITLETVCHDPKLPYHDFI | TβRII-ED trimer, also termed T2-T2-T2 |

| SEQ ID NO: | Sequence | Description |
| --- | --- | --- |
|  | LEDAASPKCIMKEKKKPGETFFMCS CSSDECCNDNIIFSEEYNTSNPDIPP HVQKSVNNDMIVTDNNGAVKFPQLC KFCDVRFSTCDNQKSCMSNCSITSI CEKPQEVCVAVWRKNDENITLETVC HDPKLPYHDFILEDAASPKCIMKEK KKPGETFFMCSCSSDECNDNIIFSE EYNTSNPD | |
| 50 | IPPHVQKSVNNDMIVTDNNGAVKFP QLCKFCDVRFSTCDNQKSCMSNCSI TSICEKPQEVCVAVWRKNDENITLE TVCHDPKLPYHDFILEDAASPKCIM KEKKKPGETFFMCSCSSDECNDNII FSEEYNTSNPDIPPHVQKSDVEMEA QKDEIICPSCNRTAHPLRHINNDMI VTDNNGAVKFPQLCKFCDVRFSTCD NQKSCMSNCSITSICEKPQEVCVAV WRKNDENITLETVCHDPKLPYHDFI LEDAASPKCIMKEKKKPGETFFMCS CSSDECNDNIIFSEEYNTSNPDIPP HVQKSDVEMEAQKDEIICPSCNRTA HPLRHINNDMIVTDNNGAVKFPQLC KFCDVRFSTCDNQKSCMSNCSITSI CEKPQEVCVAVWRKNDENITLETVC HDPKLPYHDFILEDAASPKCIMKEK KKPGETFFMCSCSSDECNDNIIFSE EYNTSNPD | TβRIIb-ED trimer, also termed T2-T2b-T2b |
| 51 | IPPHVQKSVNNDMIVTDNNGAVKFP QLCKFCDVRFSTCDNQKSCMSNCSI TSICEKPQEVCVAVWRKNDENITLE TVCHDPKLPYHDFILEDAASPKCIM KEKKKPGETFFMCSCSSDECNDNII FSEEYNTSNPDIPPHVQKSDVEMEA QKDEIIAPSANRTAHPLRHINNDMI VTDNNGAVKFPQLCKFCDVRFSTCD NQKSCMSNCSITSICEKPQEVCVAV WRKNDENITLETVCHDPKLPYHDFI LEDAASPKCIMKEKKKPGETFFMCS CSSDECNDNIIFSEEYNTSNPDIPP HVQKSDVEMEAQKDEIIAPSANRTA HPLRHINNDMIVTDNNGAVKFPQLC KFCDVRFSTCDNQKSCMSNCSITSI CEKPQEVCVAVWRKNDENITLETVC HDPKLPYHDFILEDAASPKCIMKEK KKPGETFFMCSCSSDECNDNIIFSE EYNTSNPD | TβRIIb-ED trimer Cys-mutated in the linker regions, also termed T2-T2b$^{44}$-T2b$^{44}$ |
| 52 | ALQCFCHLCTKDNFTCVTDGLCFVS VTETTDKVIHNSMCIAEIDLIPRDR PFVCAPSSKTGSVTTTYCCNQDHCN KIEL | TβRI-ED structured domain |
| 53 | AALLPGAT | TβRI-ED N-term unstructured region and natural linker |
| 54 | PTTVKSSPGLGPVE | TβRI-ED C-term unstructured region and natural linker |
| 55 | PTTVKSSPGLGPVEAALLPGAT | TβRI-ED natural linker |
| 56 | AALLPGATALQCFCHLCTKDNFTCV TDGLCFVSVTETTDKVIHNSMCIAE IDLIPRDRPFVCAPSSKTGSVTTTY CCNQDHCNKIELPTTVKSSPGLGPV E | TβRI-ED monomer, also termed T1 or T1m |
| 57 | AALLPGATALQCFCHLCTKDNFTCV TDGLCFVSVTETTDKVIHNSMCIAE IDLIPRDRPFVCAPSSKTGSVTTTY CCNQDHCNKIELPTTVKSSPGLGPV EEAALLPGATALQCFCHLCTKDNFT CVTDGLCFVSVTETTDKVIHNSMCIA EIDLIPRDRPFVCAPSSKTGSVTTT YCCNQDHCNKIELPTTVKSSPGLGP VE | TβRI-ED dimer, also termed T1-T1 |
| 58 | PTTVKSSPGLGPVEIPPHVQKSVNN DMIVTDNNGAVKFP | TβRI-TβRII-ED natural linker |
| 59 | PTTVKSSPGLGPVEIPPHVQKSDVE MEAQKDEIICPSCNRTAHPLRHINN DMIVTDNNGAVKFP | TβRI-TβRIIb-ED natural linker |
| 60 | SEEYNTSNPDAALLPGAT | TβRII-TβRI-ED natural linker |
| 61 | AALLPGATALQCFCHLCTKDNFTCV TDGLCFVSVTETTDKVIHNSMCIAE IDLIPRDRPFVCAPSSKTGSVTTTY CCNQDHCNKIELPTTVKSSPGLGPV EIPPHVQKSVNNDMIVTDNNGAVKF PQLCKFCDVRFSTCDNQKSCMSNCS ITSICEKPQEVCVAVWRKNDENITL ETVCHDPKLPYHDFILEDAASPKCI MKEKKKPGETFFMCSCSSDECNDNI IFSEEYNTSNPD | TβRI-TβRII-ED dimer T1-T2 |
| 62 | AALLPGATALQCFCHLCTKDNFTCV TDGLCFVSVTETTDKVIHNSMCIAE IDLIPRDRPFVCAPSSKTGSVTTTY CCNQDHCNKIELPTTVKSSPGLCPV EIPPHVQKSDVEMEAQKDEIICPSC NRTAHPLRHINNDMIVTDNNGAVKF PQLCKFCDVRFSTCDNQKSCMSNCS ITSICEKPQEVCVAVWRKNDENITL ETVCHDPKLPYHDFILEDAASPKCI MKEKKKPGETFFMCSCSSDECNDNI IFSEEYNTSNPD | TβRI-TβRII-ED dimer T1-T2b |
| 63 | IPPHVQKSVNNDMIVTDNNGAVKFP QLCKFCDVRFSTCDNQKSCMSNCSI TSICEKPQEVCVAVWRKNDENITLE TVCHDPKLPYHDFILEDAASPKCIM KEKKKPGETFFMCSCSSDECNDNII FSEEYNTSNPDAALLPGATALQCFC HLCTKDNFTCVTDGLCFVSVTETTD KVIHNSMCIAEIDLIPRDRPFVCAP SSKTGSVTTTYCCNQDHCNKIELPT TVKSSPGLGPVE | TβRI-TβRII-ED dimer T2-T1 |
| 64 | AALLPGATALQCFCHLCTKDNFTCV TDGLCFVSVTETTDKVIHNSMCIAE IDLIPRDRPFVCAPSSKTGSVTTTY CCNQDHCNKIELPTTVKSSPGLGPV EIPPHVQKSVNNDMIVTDNNGAVKF PQLCKFCDVRFSTCDNQKSCMSNCS ITSICEKPQEVCVAVWRKNDENITL ETVCHDPKLPYHDFILEDAASPKCI MKEKKKPGETFFMCSCSSDECNDNI IFSEEYNTSNPDIPPHVQKSVNNDM IVTDNNGAVKFPQLCKFCDVRFSTC DNQKSCMSNCSITSICEKPQEVCVA VWRKNDENITLETVCHDPKLPYHDF ILEDAASPKCIMKEKKKPGETFFMC SCSSDECNDNIIFSEEYNTSNPD | TβRI-TβRII-ED trimer T1-T2-T2 |
| 65 | AALLPGATALQCFCHLCTKDNFTCV TDGLCFVSVTETTDKVIHNSMCIAE IDLIPRDRPFVCAPSSKTGSVTTTY | TβRI-TβRII-ED trimer T1-T2-T2b |

| SEQ ID NO: | Sequence | Description |
|---|---|---|
|  | CCNQDHCNKIELPTTVKSSPGLGPV EIPPHVQKSVNNDMIVTDNNGAVKF PQLCKFCDVRFSTCDNQKSCMSNCS ITSICEKPQEVCVAVWRKNDENITL ETVCHDPKLPYHDFILEDAASPKCI MKEKKKPGETFFMCSCSSDECNDNI IFSEEYNTSNPDIPPHVQKSDVEME AQKDEIICPSCNRTAHPLRHINNDM IVTDNNGAVKFPQLCKFCDVRFSTC DNQKSCMSNCSITSICEKPQEVCVA VWRKNDENITLETVCHDPKLPYHDF ILEDAASPKCIMKEKKKPGETFFMC SCSSDECNDNIIFSEEYNTSNPD |  |
| 66 | AALLPGATALQCFCHLCTKDNFTCV TDGLCFVSVTETTDKVIHNSMCIAE IDLIPRDRPFVCAPSSKTGSVTTTY CCNQDHCNKIELPTTVKSSPGLGPV EIPPHVQKSDVEMEAQKDEIICPSC NRTAHPLRHINNDMIVTDNNGAVKF PQLCKFCDVRFSTCDNQKSCMSNCS ITSICEKPQEVCVAVWRKNDENITL ETVCHDPKLPYHDFILEDAASPKCI MKEKKKPGETFFMCSCSSDECNDNI IFSEEYNTSNPDIPPHVQKSDVEME AQKDEIIAPSANRTAHPLRHINNDM IVTDNNGAVKFPQLCKFCDVRFSTC DNQKSCMSNCSITSICEKPQEVCVA VWRKNDENITLETVCHDPKLPYHDF ILEDAASPKCIMKEKKKPGETFFMC SCSSDECNDNIIFSEEYNTSNPD | TβRI-TβRII-ED trimer T1-T2-T2b$^{AA}$ |
| 67 | IPPHVQKSVNNDMIVTDNNGAVKFP QLCKFCDVRFSTCDNQKSCMSNCSI TSICEKPQEVCVAVWRKNDENITLE TVCHDPKLPYHDFILEDAASPKCIM KEKKKPGETFFMCSCSSDECNDNII FSEEYNTSNPDIPPHVQKSVNNDMI VTDNNGAVKFPQLCKFCDVRFSTCD NQKSCMSNCSITSICEKPQEVCVAV WRKNDENITLETVCHDPKLPYHDFI LEDAASPKCIMKEKKKPGETFFMCS CSSDECNDNIIFSEEYNTSNPDAAL LPGATALQCFCHLCTKDNFTCVTDG LCFVSVTETTDKVIHNSMCIAEIDL IPRDRPFVCAPSSKTGSVTTTYCCN QDHCNKIELPTTVKSSPGLPVE | TβRI-TβRII-ED trimer T2-T2-T1 |
| 68 | IPPHVQKSVNNDMIVTDNNGAVKFP QLCKFCDVRFSTCDNQKSCMSNCSI TSICEKPQEVCVAVWRKNDENITLE TVCHDPKLPYHDFILEDAASPKCIM KEKKKPGETFFMCSCSSDECNDNII FSEEYNTSNPDIPPHVQKSDVEMEA QKDEIIAPSANRTAHPLRHINNDMI VTDNNGAVKFPQLCKFCDVRFSTCD NQKSCMSNCSITSICEKPQEVCVAV WRKNDENITLETVCHDPKLPYHDFI LEDAASPKCIMKEKKKPGETFFMCS CSSDECNDNIIFSEEYNTSNPDAAL LPGATALQCFCHLCTKDNFTCVTDG LCFVSVTETTDKVIHNSMCIAEIDL IPRDRPFVCAPSSKTCSVTTTYCCN QDHCNKIELPTTVKSSPGLPVE | TβRI-TβRII-ED trimer T2-T2b$^{AA}$-T1 |
| 69 | TLPFLKCYCSGHCPDDAINNTCITN GHCFAIIEEDDQGETTLASGCMKYE GSDFQCKDSPKAQLRRTIECCRTNL CNQYLQPTLP | BMPRIa-ED structured domain |
| 70 | QNLDSMLHGTGMKSDSDQKKSENGV TLAPED | BMPRIa-ED N-term unstructured region and natural linker |
| 71 | PWIGPFFDGSIR | BMPRIa-ED C-term unst

| SEQ ID NO: | Sequence | Description |
|---|---|---|
| 82 | SGRGEAET | ActRIIb-ED N-term unstructured region and natural linker |
| 83 | EAGGPEVTYEPPPTAPT | ActRIIb-ED C-term unstructured region and natural linker |
| 84 | EAGGPEVTYEPPPTAPTSGRGEAET | ActRIIb-ED natural linker |
| 85 | SGRGEAETRECIYYNANWELERTNQ SGLERCEGEQDKRLHCYASWRNSSG TIELVKKGCWLDDFNCYDRQECVAT EENPQVYFCCCECNFCNERFTHLPE AGGPEVTYEPPPTAPT | ActRIIb-ED monomer |
| 86 | SGRGEAETRECIYYNANWELERTNQ SGLERCEGEQDKRLHCYASWRNSSG TIELVKKGCWLDDFNCYDRQECVAT EENPQVYFCCCEGNFCNERFTHLPE AGGPEVTYEPPPTAPTSGRGEAETR ECIYYNANWELERTNQSGLERCEGE QDKRLHCYASWRNSSGTIELVKKGC WLDDFNCYDRQECVATEENPQVYFC CCEGNFCNERFTHLPEAGGPEVTYE PPPTAPT | ActRIIb-ED dimer |
| 87 | EMEVTQPTSNPVTPKPPYYNIQNLD SMLHGTCMKSDSDQKKSENCVTLAP ED | ActRIIa-BMPRIa-ED natural linker |
| 88 | AILGRSETQECLFFNANWEKDRTNQ TGVEPCYGDKDKRRHCFATWKNISG SIEIVKQGCWLDDINCYDRTDCVEK KDSPEVYFCCCEGNMCNEKFSYFPE MEVTQPTSNPVTPKPPYYNIQNLDS MLHGTGMKSDSDQKKSENGVTLAPE DTLPFLKCYCSGHCPDDAINNTCIT NGHCFAIIEEDDQGETTLASGCMKY EGSDFQCKDSPKAQLRRTIECCRTN LCNQYLQPTLPPWIGPFFDGSIR | ActRIIa-BMPRIa-ED dimer |
| 89 | MDWTWRILFLVAAATCTHA | Signal peptide |
| 90 | MVLQTQVFISLLLWISGAYG | Signal peptide |
| 91 | APELLGGPSVFLFPPKPKDTLMISR TPEVTCVVVDVSHEDPEVKFNWYVD GVEVHNAKTKPREEQYNSTYRVVSV LTVLHQDWLNGKEYKCKVSNKALPA PIEKTISKAKGQPREPQVYTLPPSR DELTKNQVSLTCLVKGFYPSDIAVE WESNGQPENNYKTTPPVLDSDGSFF LYSKLTVDKSRWQQGNVFSCSVMHE ALHNHYTQKSLSLSPGIPPHVQKSV NNDKIVTDNNGAVKFPQLCKFCDVR FSTCDNQKSCKSNCSITSICEKPQE VCVAVWRKNDENITLETVCHDPKLP YHDFILEDAASPKCIMKEKKKPGET FFMCSCSSDECNDNIIFSEEYNTSN PD | hIgG1FcΔK-AC-T2m fusion |
| 92 | PPCPAPELLGGPSVFLFPPKPKDTL MISRTPEVTCVVVDVSHEDPEVKFN WYVDGVEVHNAKTKPREEQYNSTYR VVSVLTVLHQDWLNGKEYKCKVSNK ALPAPIEKTISKAKGQPREPQVYTL PPSRDELTKNQVSLTCLVKGFYPSD IAVEWESNGQPENNYKTTPPVLDSD GSFFLYSKLTVDKSRWQQGNVFSCS | hIgG1FcΔK-C-T2m fusion |
| | VKHEALHNHYTQKSLSLSPGIPPHV QKSVNNDMIVTDNNGAVKFPQLCKF CDVRFSTCDNQKSCMSNCSITSICE KPQEVCVAVWRKNDENITLETVCHD PKLPYHDFILEDAASPKCIMKEKKK PGETFFMCSCSSDECNDNIIFSEEY NTSNPD | |
| 93 | DKTHTCPPCPAPELLGGPSVFLFPP KPKDTLMISRTPEVTCVVVDVSHED PEVKFNWYVDGVEVHNAKTKPREEQ YNSTYRVVSVLTVLHQDWLNGKEYK CKVSNKALPAPIEKTISKAKGQPRE PQVYTLPPSRDELTKNQVSLTCLVK GFYPSDIAVEWESNGQPENNYKTTP PVLDSDGSFFLYSKLTVDKSRWQQG NVFSCSVMHEALHNHYTQKSLSLSP GIPPHVQKSVNNDMIVTDNNGAVKF PQLCKFCDVRFSTCDNQKSCMSNCS ITSICEKPQEVCVAVWRKNDENITL ETVCHDPKLPYHDFILEDAASPKCI MKEKKKPGETFFMCSCSSDECNDNI IFSEEYNTSNPD | hIgG1FcΔK-CC-T2m fusion |
| 94 | APPVAGPSVFLFPPKPKDTLMISRT PEVTCVVVDVSHEDPEVQFNWYVDG VEVHNAKTKPREEQFNSTFRVVSVL TVVHQDWLNGKEYKCKVSNKGLPAP IEKTISKTKGQPREPQVYTLPPSRE EMTKNQVSLTCLVKGFYPSDISVEW ESNGQPENNYKTTPPMLDSDGSFFL YSKLTVDKSRWQQGNVFSCSVKHEA LHNHYTQKSLSLSPGIPPHVQKSVN NDMIVTDNNGAVKFPQLCKFCDVRF STCDNQKSCMSNCSITSICEKPQEV CVAVWRKNDENITLETVCHDPKLPY HDFILEDAASPKCIMKEKKKPGETF FMCSCSSDECNDNIIFSEEYNTSNP D | hIgG2FcΔK-AC-T2m fusion |
| 95 | PPCPAPPVAGPSVFLFPPKPKDTLM ISRTPEVTCVVVDVSHEDPEVQFNWY VDGVEVHNAKTKPREEQFNSTFRVV SVLTVVHQDWLNGKEYKCKVSNKGL PAPIEKTISKTKGQPREPQVYTLPP SREEMTKNQVSLTCLVKGFYPSDIS VEWESNGQPENNYKTTPPMLDSDGS FFLYSKLTVDKSRWQQGNVFSCSVM HEALHNHYTQKSLSLSPGIPPHVQK SVNNDMIVTDNNGAVKFPQLCKFCD VRFSTCDNQKSCMSNCSITSICEKP QEVCVAVWRKNDENITLETVCHDPK LPYHDFILEDAASPKCIMKEKKKPG ETFFMCSCSSDECNDNIIFSEEYNT SNPD | hIgG2FcΔK-C-T2m fusion |
| 96 | APPVAGPSVFLFPPKPKDTLMISRT PEVTCVVVDVSHEDPEVQFNWYVDG VEVHNAKTKPREEQFNSTFRVVSVL TVVHQDWLNGKEYKCKVSNKGLPAP IEKTISKTKGQPREPQVYTLPPSRE EMTKNQVSLTCLVKGFYPSDISVEW ESNGQPENNYKTTPPMLDSDGSFFL YSKLTVDKSRWQQGNVFSCSVMHEA LHNHYTQKSLSLSPGIPPHVQKSVN NDMIVTDNNGAVKFPQLCKFCDVRF STCDNQKSCMSNCSITSICEKPQEV CVAVWRKNDENITLETVCHDPKLPY HDFILEDAASPKCIMKEKKKPGETF FMCSCSSDECNDNIIFSEEYNTSNP D | hIgG2FcΔK-CC-T2m fusion |

| SEQ ID NO: | Sequence | Description |
|---|---|---|
| 97 | MDWTWRILFLVAAATGTHAERKCCV ECPPCPAPPVAGPSVFLFPPKPKDT LMISRTPEVTCVVVDVSHEDPEVQF NWYVDGVEVHNAKTKPREEQFNSTF RVVSVLTVVHQDWLNGKEYKCKVSN KGLPAPIEKTISKTKGQPREPQVYT LPPSREEMTKNQVSLTCLVKCFYPS DISVEWESNCQPENNYKTTPPMLDS DCSFFLYSKLTVDKSRWQQGNVFSC SVKHEALHNHYTQKSLSLSPGKIPP HVQKSVNNDMIVTDNNGAVKFPQLC KFCDVRFSTCDNQKSCKSNCSITSI CEKPQEVCVAVWRKNDENITLETVC HDPKLPYHDFILEDAASPKCIMKEK KKPGETFFMCSCSSDECNDNIIFSE EYNTSNPD | hIgG2Fc-CCCC-T2 fusion, also termed Fc-T2m |
| 98 | ESKYGPPCPPCPAPEFLGGPSVFLF PPKPKDTLMISRTPEVTCVVVDVSQ EDPEVQFNWYVDGVEVHNAKTKPRE EQFNSTYRVVSVLTVLHQDWLNGKE YKCKVSNKGLPSSIEKTISKAKGQP REPQVYTLPPSQEEMTKNQVSLTCL VKGFYPSDIAVEWESNGQPENNYKT TPPVLDSDGSFFLYSRLTVDKSRWQ EGNVFSCSVMHEALHNHYTQKSLSL SLGIPPHVQKSVNNDMIVTDNNCAV KFPQLCKFCDVRFSTCDNQKSCMSN CSITSICEKPQEVCVAVWRKNDENI TLETVCHDPKLPYHDFILEDAASPK CIMKEKKKPGETFFMCSCSSDECND NIIFSEEYNTSNPD | hIgG4FcΔK-CC-228P-T2m fusion |
| 99 | ESKYGPPCPPCPAPEFLGGPSVFLF PPKPKDTLMISRTPEVTCVVVDVSQ EDPEVQFNWYVDGVEVHNAKTKPRE EQFNSTYRVVSVLTVLHQDWLNGKE YKCKVSNKGLPSSIEKTISKAKGQP REPQVYTLPPSQEEMTKNQVSLTCL VKGFYPSDIAVEWESNGQPENNYKT TPPVLDSDGSFFLYSKLTVDKSRWQ EGNVFSCSVMHEALHNHYTQKSLSL SLGIPPHVQKSVNNDMIVTDNNGAV KFPQLCKFCDVRFSTCDNQKSCKSN CSITSICEKPQEVCVAVWRKNDENI TLETVCHDPKLPYHDFILEDAASPK CIMKEKKKPGETFFMCSCSSDECND NIIFSEEYNTSNPD | hIgG4FcΔK-CC-228P-409K-T2m fusion |
| 100 | PPCPAPELLGGPSVFLFPPKPKDTL MISRTPEVTCVVVDVSHEDPEVKFN WYVDGVEVHNAKTKPREEQYNSTYR VVSVLTVLHQDWLNGKEYKCKVSNK ALPAPIEKTISKAKGQPREPQVYTL PPSRDELTKNQVSLTCLVKGFYPSD IAVEWESNGQPENNYKTTPPVLDSD GSFFLYSKLTVDKSRWQQGNVFSCS VKHEALHNHYTQKSLSLSPGIPPHV QKSVNNDMIVTDNNGAVKFPQLCKF CDVRFSTCDNQKSCMSNCSITSICE KPQEVCVAVWRKNDENITLETVCHD PKLPYHDFILEDAASPKCIMKEKKK PGETFFMCSCSSDECNDNIIFSEEY NTSNPDIPPHVQKSVNNDMIVTDNN GAVKFPQLCKFCDVRFSTCDNQKSC MSNCSITSICEKPQEVCVAVWRKND ENITLETVCHDPKLPYHDFILEDAA SPKCIMKEKKKPGETFFMCSCSSDE CNDNIIFSEEYNTSNPD | hIgG1FcΔK-C-T22d35 fusion |
| 101 | DKTHTCPPCPAPELLGGPSVFLFPP KPKPKDTLMISRTPEVTCVVVDVSHED PEVKFNWYVDCVEVHNAKTKPREEQ YNSTYRVVSVLTVLHQDWLNCKEYK CKVSNKALPAPIEKTISKAKGQPRE PQVYTLPPSRDELTKNQVSLTCLVK GFYPSDIAVEWESNGQPENNYKTTP PVLDSDGSFFLYSKLTVDKSRWQQG NVFSCSVMHEALHNHYTQKSLSLSP GIPPHVQKSVNNDMIVTDNNGAVKF PQLCKFCDVRFSTCDNQKSCMSNCS ITSICEKPQEVCVAVWRKNDENITL ETVCHDPKLPYHDFILEDAASPKCI MKEKKKPGETFFMCSCSSDECNDNI IFSEEYNTSNPDIPPHVQKSVNNDM IVTDNNGAVKFPQLCKFCDVRFSTC DNQKSCMSNCSITSICEKPQEVCVA VWRKNDENITLETVCHDPKLPYHDF ILEDAASPKCIMKEKKKPGETFFMC SCSSDECNDNIIFSEEYNTSNPD | hIgG1FcΔK-CC-T22d35 fusion |
| 102 | VECPPCPAPPVAGPSVFLFPPKPKD TLMISRTPEVTCVVVDVSHEDPEVQ FNWYVDGVEVHNAKTKPREEQFNST FRVVSVLTVVHQDWLNGKEYKCKVS NKGLPAPIEKTISKTKGQPREPQVY TLPPSREEMTKNQVSLTCLVKGFYP SDISVEWESNGQPENNYKTTPPMLD SDGSFFLYSKLTVDKSRWQQGNVFS CSVMHEALHNHYTQKSLSLSPGIPP HVQKSVNNDMIVTDNNGAVKFPQLC KFCDVRFSTCDNQKSCMSNCSITSI CEKPQEVCVAVWRKNDENITLETVC HDPKLPYHDFILEDAASPKCIMKEK KKPGETFFMCSCSSDECNDNIIFSE EYNTSNPDIPPHVQKSVNNDMIVTD NNGAVKFPQLCKFCDVRFSTCDNQK SCMSNCSITSICEKPQEVCVAVWRK NDENITLETVCHDPKLPYHDFILED AASPKCIMKEKKKPGETFFMCSCSS DECNDNIIFSEEYNTSNPD | hIgG2FcΔK-CC-T22d35 fusion |
| 103 | ESKYGPPCPPCPAPEFLGGPSVFLF PPKPKDTLMISRTPEVTCVVVDVSQ EDPEVQFNWYVDGVEVHNAKTKPRE EQFNSTYRVVSVLTVLHQDWLNGKE YKCKVSNKGLPSSIEKTISKAKGQP REPQVYTLPPSQEEMTKNQVSLTCL VKGFYPSDIAVEWESNGQPENNYKT TPPVLDSDGSFFLYSRLTVDKSRWQ EGNVFSCSVMHEALHNHYTQKSLSL SLGIPPHVQKSVNNDMIVTDNNGAV KFPQLCKFCDVRFSTCDNQKSCMSN CSITSICEKPQEVCVAVWRKNDENI TLETVCHDPKLPYHDFILEDAASPK CIMKEKKKPGETFFMCSCSSDECND NIIFSEEYNTSNPDIPPHVQKSVNN DMIVTDNNGAVKFPQLCKFCDVRFS TCDNQKSCMSNCSITSICEKPQEVC VAVWRKNDENITLETVCHDPKLPYH DFILEDAASPKCIMKEKKKPGETFF MCSCSSDECNDNIIFSEEYNTSNPD | hIgG4FcΔK-CC-228P-T22d35 fusion |
| 104 | ESKYGPPCPPCPAPEFLGGPSVFLF PPKPKDTLMISRTPEVTCVVVDVSQ EDPEVQFNWYVDGVEVHNAKTKPRE EQFNSTYRVVSVLTVLHQDWLNGKE YKCKVSNKGLPSSIEKTISKAKGQP REPQVYTLPPSQEEMTKNQVSLTCL VKGFYPSDIAVEWESNGQPENNYKT TPPVLDSDGSFFLYSKLTVDKSRWQ EGNVFSCSVMHEALHNHYTQKSLSL SLGIPPHVQKSVNNDMIVTDNNGAV KFPQLCKFCDVRFSTCDNQKSCMSN CSITSICEKPQEVCVAVWRKNDENI TLETVCHDPKLPYHDFILEDAASPK | hIgG4FcΔK-CC-228P-409K-T22d35 fusion |

| SEQ ID NO: | Sequence | Description |
|---|---|---|
| | CIMKEKKKPGETFFMCSCSSDECND NIIFSEEYNTSNPDIPPHVQKSVNN DMIVTDNNGAVKFPQLCKFCDVRFS TCDNQKSCMSNCSITSICEKPQEVC VAVWRKNDENITLETVCHDPKLPYH DFILEDAASPKCIMKEKKKPGETFF MCSCSSDECNDIIFSEEYNTSNPD | |
| 105 | MDWTWRILFLVAAATGTHAERKCCV ECPPCPAPPVAGPSVFLFPPKPKDT LMISRTPEVTCVVVDVSHEDPEVQF NWYVDGVEVHNAKTKPREEQFNSTF RVVSVLTVVHQDWLNGKEYKCKVSN KGLPAPIEKTISKTKGQPREPQVYT LPPSREEMTKNQVSLTCLVKGFYPS DISVEWESNGQPENNYKTTPPMLDS DGSFFLYSKLTVDKSRWQQGNVFSC SVMHEALHNHYTQKSLSLSPGKIPP HVQKSVNNDMIVTDNNGAVKFPQLC KFCDVRFSTCDNQKSCMSNCSITSI CEKPQEVCVAVWRKNDENITLETVC HDPKLPYHDFILEDAASPKCIMKEK KKPGETFFMCSCSSDECNDIIFSE EYNTSNPDIPPHVQKSVNNDMIVTD NNGAVKFPQLCKFCDVRFSTCDNQK SCMSNCSITSICEKPQEVCVAVWRK NDENITLETVCHDPKLPYHDFILED AASPKCIMKEKKKPGETFFMCSCSS DECNDIIFSEEYNTSNPD | hIgG2Fc-CCCC-T22d35 fusion, also termed Fc-T22d35 |
| 106 | PPCPAPELLGGPSVFLFPPKPKDTL MISRTPEVTCVVDVSHEDPEVKFNW YVDGVEVHNAKTKPREEQYNSTYRV VSVLTVLHQDWLNGKEYKCKVSNKA LPAPIEKTISKAKGQPREPQVYTLP PSRDELTKNQVSLTCLVKGFYPSDI AVEWESNGQPENNYKTTPPVLDSDG SFFLYSKLTVDKSRWQQGNVFSCSV MHEALHNHYTQKSLSLSPGIPPHVQ KSVNNDMIVTDNNGAVKFPQLCKFC DVRFSTCDNQKSCMSNCSITSICEK PQEVCVAVWRKNDENITLETVCHDP KLPYHDFILEDAASPKCIMKEKKKP GETFFMCSCSSDECNDIIFSEEYN TSNPDIPPHVQKSDVEMEAQKDEII APSANRTAHPLRHINNDMIVTDNNC AVKFPQLCKFCDVRFSTCDNQKSCM SNCSITSICEKPQEVCVAVWRKNDE NITLETVCHDPKLPYHDFILEDAAS PKCIMKEKKKPGETFFMCSCSSDEC NDIIFSEEYNTSNPD | hIgG1FcΔK-C-T2-T2b[44] fusion |
| 107 | DKTHTCPPCPAPELLGGPSVFLFPP KPKDTLMISRTPEVTCVVVDVSHED PEVKFNWYVDGVEVHNAKTKPREEQ YNSTYRVVSVLTVLHQDWLNGKEYK CKVSNKALPAPIEKTISKAKGQPRE PQVYTLPPSRDELTKNQVSLTCLVK GFYPSDIAVEWESNGQPENNYKTTP PVLDSDGSFFLYSKLTVDKSRWQQG NVFSCSVMHEALHNHYTQKSLSLSP GIPPHVQKSVNNDMIVTDNNGAVKF PQLCKFCDVRFSTCDNQKSCMSNCS ITSICEKPQEVCVAVWRKNDENITL ETVCHDPKLPYHDFILEDAASPKCI MKEKKKPGETFFMCSCSSDECNDI IFSEEYNTSNPDIPPHVQKSDVEME AQKDEIIAPSANRTAHPLRHINNDM IVTDNNGAVKFPQLCKFCDVRFSTC DNQKSCMSNCSITSICEKPQEVCVA VWRKNDENITLETVCHDPKLPYHDF ILEDAASPKCIMKEKKKPGETFFMC SCSSDECNDIIFSEEYNTSNPD | hIgG1FcΔK-CC-TP-TPb+ fusion |
| 108 | VECPPCPAPPVAGPSVFLFPPKPKD TLMISRTPEVTCVVVDVSHEDPEVQ FNWYVDGVEVHNAKTKPREEQFNST FRVVSVLTVVHQDWLNGKEYKCKVS NKGLPAPIEKTISKTKGQPREPQVY TLPPSREEMTKNQVSLTCLVKGFYP SDISVEWESNGQPENNYKTTPPMLD SDGSFFLYSKLTVDKSRWQQGNVFS CSVMHEALHNHYTQKSLSLSPGIPP HVQKSVNNDMIVTDNNGAVKFPQLC KFCDVRFSTCDNQKSCMSNCSITSI CEKPQEVCVAVWRKNDENITLETVC HDPKLPYHDFILEDAASPKCIMKEK KKPGETFFMCSCSSDECNDIIFSE EYNTSNPDIPPHVQKSDVEMEAQKD EIIAPSANRTAHPLRHINNDMIVTD NNGAVKFPQLCKFCDVRFSTCDNQK SCMSNCSITSICEKPQEVCVAVWRK NDENITLETVCHDPKLPYHDFILED AASPKCIMKEKKKPGETFFMCSCSS DECNDIIFSEEYNTSNPD | hIgG2FcΔK-CC-T2-T2b[44] fusion |
| 109 | ESKYGPPCPPCPAPEFLGGPSVFLF PPKPKDTLMISRTPEVTCVVVDVSQ EDPEVQFNWYVDGVEVHNAKTKPRE EQFNSTYRVVSVLTVLHQDWLNGKE YKCKVSNKGLPSSIEKTISKAKGQP REPQVYTLPPSQEEMTKNQVSLTCL VKGFYPSDIAVEWESNGQPENNYKT TPPVLDSDGSFFLYSRLTVDKSRWQ EGNVFSCSVMHEALHNHYTQKSLSL SLGIPPHVQKSVNNDMIVTDNNGAV KFPQLCKFCDVRFSTCDNQKSCMSN CSITSICEKPQEVCVAVWRKNDENI TLETVCHDPKLPYHDFILEDAASPK CIMKEKKKPGETFFMCSCSSDECND NIIFSEEYNTSNPDIPPHVQKSDVE MEAQKDEIIAPSANRTAHPLRHINN DMIVTDNNGAVKFPQLCKFCDVRFS TCDNQKSCMSNCSITSICEKPQEVC VAVWRKNDENITLETVCHDPKLPYH DFILEDAASPKCIMKEKKKPGETFF MCSCSSDECNDIIFSEEYNTSNPD | hIgG4FcΔK-CC-228P-T2-T2b[44] fusion |
| 110 | ESKYGPPCPPCPAPEFLGGPSVFLF PPKPKDTLMISRTPEVTCVVVDVSQ EDPEVQFNWYVDGVEVHNAKTKPRE EQFNSTYRVVSVLTVLHQDWLNGKE YKCKVSNKGLPSSIEKTISKAKGQP REPQVYTLPPSQEEMTKNQVSLTCL VKGFYPSDIAVEWESNGQPENNYKT TPPVLDSDGSFFLYSKLTVDKSRWQ EGNVFSCSVMHEALHNHYTQKSLSL SLGIPPHVQKSVNNDMIVTDNNGAV KFPQLCKFCDVRFSTCDNQKSCMSN CSITSICEKPQEVCVAVWRKNDENI TLETVCHDPKLPYHDFILEDAASPK CIMKEKKKPGETFFMCSCSSDECND NIIFSEEYNTSNPDIPPHVQKSDVE MEAQKDEIIAPSANRTAHPLRHINN DMIVTDNNGAVKFPQLCKFCDVRFS TCDNQKSCMSNCSITSICEKPQEVC VAVWRKNDENITLETVCHDPKLPYH DFILEDAASPKCIMKEKKKPGETFF MCSCSSDECNDIIFSEEYNTSNPD | hIgG4FcΔK-CC-228P-409K-T2-T2b[44] fusion |
| 111 | PPCPAPELLGGPSVFLFPPKPKDTL MISRTPEVTCVVVDVSHEDPEVKFN WYVDGVEVHNAKTKPREEQYNSTYR VVSVLTVLHQDWLNGKEYKCKVSNK ALPAPIEKTISKAKGQPREPQVYTL PPSRDELTKNQVSLTCLVKGFYPSD | hIgG1FcΔK-C-T2-T2-T2 fusion |

| SEQ ID NO: | Sequence | Description |
|---|---|---|
| | IAVEWESNGQPENNYKTTPPVLDSD GSFFLYSKLTVDKSRWQQGNVFSCS VMHEALHNHYTQKSLSLSPGIPPHV QKSVNNDMIVTDNNGAVKFPQLCKF CDVRFSTCDNQKSCMSNCSITSICE KPQEVCVAVWRKNDENITLETVCHD PKLPYHDFILEDAASPKCIMKEKKK PGETFFMCSCSSDECNDNIIFSEEY NTSNPDIPPHVQKSVNNDMIVTDNN GAVKFPQLCKFCDVRFSTCDNQKSC MSNCSITSICEKPQEVCVAVWRKND ENITLETVCHDPKLPYHDFILEDAA SPKCIMKEKKKPGETFFMCSCSSDE CNDNIIFSEEYNTSNPDIPPHVQKS VNNDMIVTDNNGAVKFPQLCKFCDV RFSTCDNQKSCMSNCSITSICEKPQ EVCVAVWRKNDENITLETVCHDPKL PYHDFILEDAASPKCIMKEKKKPGE TFFMCSCSSDECNDNIIFSEEYNTS NPD | |
| 112 | DKTHTCPPCPAPELLGGPSVFLFPP KPKDTLKISRTPEVTCVVVDVSHED PEVKFNWYVDGVEVHNAKTKPREEQ YNSTYRVVSVLTVLHQDWLNGKEYK CKVSNKALPAPIEKTISKAKGQPRE PQVYTLPPSRDELTKNQVSLTCLVK GFYPSDIAVEWESNGQPENNYKTTP PVLDSDGSFFLYSKLTVDKSRWQQG NVFSCSVMHEALHNHYTQKSLSLSP GIPPHVQKSVNNDMIVTDNNGAVKF PQLCKFCDVRFSTCDNQKSCMSNCS ITSICEKPQEVCVAVWRKNDENITL ETVCHDPKLPYHDFILEDAASPKCI MKEKKKPGETFFMCSCSSDECNDNI IFSEEYNTSNPDIPPHVQKSVNNDM IVTDNNGAVKFPQLCKFCDVRFSTC DNQKSCMSNCSITSICEKPQEVCVA VWRKNDENITLETVCHDPKLPYHDF ILEDAASPKCIMKEKKKPGETFFMC SCSSDECNDNIIFSEEYNTSNPDIP PHVQKSVNNDMIVTDNNGAVKFPQL CKFCDVRFSTCDNQKSCMSNCSITS ICEKPQEVCVAVWRKNDENITLETV CHDPKLPYHDFILEDAASPKCIMKE KKKPGETFFMCSCSSDECNDNIIFS EEYNTSNPD | hIgG1FcΔK-CC-T2-T2-T2 fusion |
| 113 | VECPPCPAPPVAGPSVFLFPPKPKD TLMISRTPEVTCVVVDVSHEDPEVQ FNWYVDGVEVHNAKTKPREEQFNST FRVVSVLTVVHQDWLNGKEYKCKVS NKGLPAPIEKTISKTKGQPREPQVY TLPPSREEMTKNQVSLTCLVKGFYP SDISVEWESNGQPENNYKTTPPMLD SDGSFFLYSKLTVDKSRWQQGNVFS CSVMHEALHNHYTQKSLSLSPGIPP HVQKSVNNDMIVTDNNGAVKFPQLC KFCDVRFSTCDNQKSCMSNCSITSI CEKPQEVCVAVWRKNDENITLETVC HDPKLPYHDFILEDAASPKCIMKEK KKPGETFFMCSCSSDECNDNIIFSE EYNTSNPDIPPHVQKSVNNDMIVTD NNGAVKFPQLCKFCDVRFSTCDNQK SCMSNCSITSICEKPQEVCVAVWRK NDENITLETVCHDPKLPYHDFILED AASPKCIMKEKKKPGETFFMCSCSS DECNDNIIFSEEYNTSNPDIPPHVQ KSVNNDMIVTDNNGAVKFPQLCKFC DVRFSTCDNQKSCMSNCSITSICEK PQEVCVAVWRKNDENITLETVCHDP | hIgG2FcΔK-CC-T2-T2-T2 fusion |
| | KLPYHDFILEDAASPKCIMKEKKKP GETFFMCSCSSDECNDNIIFSEEYN TSNPD | |
| 114 | ESKYGPPCPPCPAPEFLGGPSVFLF PPKPKDTLMISRTPEVTCVVVDVSQ EDPEVQFNWYVDGVEVHNAKTKPRE EQFNSTYRVVSVLTVLHQDWLNGKE YKCKVSNKGLPSSIEKTISKAKGQP REPQVYTLPPSQEEMTKNQVSLTCL VKGFYPSDIAVEWESNGQPENNYKT TPPVLDSDGSFFLYSKLTVDKSRWQ EGNVFSCSVMHEALHNHYTQKSLSL SLGIPPHVQKSVNNDMIVTDNNGAV KFPQLCKFCDVRFSTCDNQKSCMSN CSITSICEKPQEVCVAVWRKNDENI TLETVCHDPKLPYHDFILEDAASPK CIMKEKKKPGETFFMCSCSSDECND NIIFSEEYNTSNPDIPPHVQKSVNN DMIVTDNNGAVKFPQLCKFCDVRFS TCDNQKSCMSNCSITSICEKPQEVC VAVWRKNDENITLETVCHDPKLPYH DFILEDAASPKCIMKEKKKPGETFF MCSCSSDECNDNIIFSEEYNTSNPD IPPHVQKSVNNDMIVTDNNGAVKFP QLCKFCDVRFSTCDNQKSCMSNCSI TSICEKPQEVCVAVWRKNDENITLE TVCHDPKLPYHDFILEDAASPKCIM KEKKKPGETFFMCSCSSDECNDNII FSEEYNTSNPD | hIgG4FcΔK-CC-228P-T2-T2-T2 fusion |
| 115 | ESKYGPPCPPCPAPEFLGGPSVFLF PPKPKDTLMISRTPEVTCVVVDVSQ EDPEVQFNWYVDGVEVHNAKTKPRE EQFNSTYRVVSVLTVLHQDWLNGKE YKCKVSNKGLPSSIEKTISKAKGQP REPQVYTLPPSQEEMTKNQVSLTCL VKGFYPSDIAVEWESNGQPENNYKT TPPVLDSDGSFFLYSKLTVDKSRWQ EGNVFSCSVMHEALHNHYTQKSLSL SLGIPPHVQKSVNNDMIVTDNNGAV KFPQLCKFCDVRFSTCDNQKSCMSN CSITSICEKPQEVCVAVWRKNDENI TLETVCHDPKLPYHDFILEDAASPK CIMKEKKKPGETFFMCSCSSDECND NIIFSEEYNTSNPDIPPHVQKSVNN DMIVTDNNGAVKFPQLCKFCDVRFS TCDNQKSCMSNCSITSICEKPQEVC VAVWRKNDENITLETVCHDPKLPYH DFILEDAASPKCIMKEKKKPGETFF MCSCSSDECNDNIIFSEEYNTSNPD IPPHVQKSVNNDMIVTDNNGAVKFP QLCKFCDVRFSTCDNQKSCMSNCSI TSICEKPQEVCVAVWRKNDENITLE TVCHDPKLPYHDFILEDAASPKCIM KEKKKPGETFFMCSCSSDECNDNII FSEEYNTSNPD | hIgG4FcΔK-CC-228P-409K-T2-T2-T2 fusion |
| 116 | PPCPAPELLGGPSVFLFPPKPKDTL MISRTPEVTCVVVDVSHEDPEVKFN WYVDGVEVHNAKTKPREEQYNSTYR VVSVLTVLHQDWLNGKEYKCKVSNK ALPAPIEKTISKAKGQPREPQVYTL PPSRDELTKNQVSLTCLVKGFYPSD IAVEWESNGQPENNYKTTPPVLDSD GSFFLYSKLTVDKSRWQQGNVFSCS VMHEALHNHYTQKSLSLSPGIPPHV QKSVNNDMIVTDNNGAVKFPQLCKF CDVRFSTCDNQKSCMSNCSITSICE KPQEVCVAVWRKNDENITLETVCHD PKLPYHDFILEDAASPKCIMKEKKK PGETFFMCSCSSDECNDNIIFSEEY NTSNPDIPPHVQKSDVEMEAQKDEI | hIgG1FcΔK-C-T2-T2b$^{AA}$-T2b$^{AA}$ fusion |

| SEQ ID NO: | Sequence | Description |
|---|---|---|
| | IAPSANRTAHPLRHINNDMIVTDNN GAVKFPQLCKFCDVRFSTCDNQKSC MSNCSITSICEKPQEVCVAVWRKND ENITLETVCHDPKLPYHDFILEDAA SPKCIMKEKKKPGETFFMCSCSSDE CNDNIIFSEEYNTSNPDIPPHVQKS DVEMEAQKDEIIAPSANRTAHPLRH INNDMIVTDNNGAVKFPQLCKFCDV RFSTCDNQKSCMSNCSITSICEKPQ EVCVAVWRKNDENITLETVCHDPKL PYHDFILEDAASPKCIMKEKKKPGE TFFMCSCSSDECNDNIIFSEEYNTS NPD | |
| 117 | DKTHTCPPCPAPELLGGPSVFLFPP KPKDTLMISRTPEVTCVVVDVSHED PEVKFNWYVDGVEVHNAKTKPREEQ YNSTYRVVSVLTVLHQDWLNGKEYK CKVSNKALPAPIEKTISKAKGQPRE PQVYTLPPSRDELTKNQVSLTCLVK GFYPSDIAVEWESNGQPENNYKTTP PVLDSDGSFFLYSKLTVDKSRWQQG NVFSCSVMHEALHNHYTQKSLSLSP GIPPHVQKSVNNDMIVTDNNGAVKF PQLCKFCDVRFSTCDNQKSCMSNCS ITSICEKPQEVCVAVWRKNDENITL ETVCHDPKLPYHDFILEDAASPKCI MKEKKKPGETFFMCSCSSDECNDNI IFSEEYNTSNPDIPPHVQKSDVEME AQKDEIIAPSANRTAHPLRHINNDM IVTDNNGAVKFPQLCKFCDVRFSTC DNQKSCMSNCSITSICEKPQEVCVA VWRKNDENITLETVCHDPKLPYHDF ILEDAASPKCIMKEKKKPGETFFMC SCSSDECNDNIIFSEEYNTSNPDIP PHVQKSDVEMEAQKDEIIAPSANRT AHPLRHINNDMIVTDNNGAVKFPQL CKFCDVRFSTCDNQKSCMSNCSITS ICEKPQEVCVAVWRKNDENITLETV CHDPKLPYHDFILEDAASPKCIMKE KKKPGETFFMCSCSSDECNDNIIFS EEYNTSNPD | hIgG1FcΔK-CC-T2-T2b$^{AA}$-T2b$^{AA}$ fusion |
| 118 | VECPPCPAPPVAGPSVFLFPPKPKD TLMISRTPEVTCVVVDVSHEDPEVQ FNWYVDGVEVHNAKTKPREEQFNST FRVVSVLTVVHQDWLNGKEYKCKVS NKGLPAPIEKTISKTKGQPREPQVY TLPPSREEMTKNQVSLTCLVKGFYP SDISVEWESNGQPENNYKTTPPMLD SDGSFFLYSKLTVDKSRWQQGNVFS CSVMHEALHNHYTQKSLSLSPGIPP HVQKSVNNDMIVTDNNGAVKFPQLC KFCDVRFSTCDNQKSCMSNCSITSI CEKPQEVCVAVWRKNDENITLETVC HDPKLPYHDFILEDAASPKCIMKEK KKPGETFFMCSCSSDECNDNIIFSE EYNTSNPDIPPHVQKSDVEMEAQKD EIIAPSANRTAHPLRHINNDMIVTD NNGAVKFPQLCKFCDVRFSTCDNQK SCMSNCSITSICEKPQEVCVAVWRK NDENITLETVCHDPKLPYHDFILED AASPKCIMKEKKKPGETFFMCSCSS DECNDNIIFSEEYNTSNPDIPPHVQ KSDVEMEAQKDEIIAPSANRTAHPL RHINNDMIVTDNNGAVKFPQLCKFC DVRFSTCDNQKSCMSNCSITSICEK PQEVCVAVWRKNDENITLETVCHDP KLPYHDFILEDAASPKCIMKEKKKP GETFFMCSCSSDECNDNIIFSEEYN TSNPD | hIgG2FcΔK-CC-T2-T2b$^{AA}$-T2b$^{AA}$ fusion |
| 119 | ESKYGPPCPPCPAPEFLGGPSVFLF PPKPKDTLMISRTPEVTCVVVDVSQ EDPEVQFNWYVDGVEVHNAKTKPRE EQFNSTYRVVSVLTVLHQDWLNGKE YKCKVSNKGLPSSIEKTISKAKGQP REPQVYTLPPSQEEMTKNQVSLTCL VKGFYPSDIAVEWESNGQPENNYKT TPPVLDSDGSFFLYSRLTVDKSRWQ EGNVFSCSVMHEALHNHYTQKSLSL SLGIPPHVQKSVNNDMIVTDNNGAV KFPQLCKFCDVRFSTCDNQKSCMSN CSITSICEKPQEVCVAVWRKNDENI TLETVCHDPKLPYHDFILEDAASPK CIMKEKKKPGETFFMCSCSSDECND NIIFSEEYNTSNPDIPPHVQKSDVE MEAQKDEIIAPSANRTAHPLRHINN DMIVTDNNGAVKFPQLCKFCDVRFS TCDNQKSCMSNCSITSICEKPQEVC VAVWRKNDENITLETVCHDPKLPYH DFILEDAASPKCIMKEKKKPGETFF MCSCSSDECNDNIIFSEEYNTSNPD IPPHVQKSDVEMEAQKDEIIAPSAN RTAHPLRHINNDMIVTDNNGAVKFP QLCKFCDVRFSTCDNQKSCMSNCSI TSICEKPQEVCVAVWRKNDENITLE TVCHDPKLPYHDFILEDAASPKCIM KEKKKPGETFFMCSCSSDECNDNII FSEEYNTSNPD | hIgG4FcΔK-CC-228P-T2-T2b$^{AA}$-T2b$^{AA}$ fusion |
| 120 | ESKYGPPCPPCPAPEFLGGPSVFLF PPKPKDTLMISRTPEVTCVVVDVSQ EDPEVQFNWYVDGVEVHNAKTKPRE EQFNSTYRVVSVLTVLHQDWLNGKE YKCKVSNKGLPSSIEKTISKAKGQP REPQVYTLPPSQEEMTKNQVSLTCL VKGFYPSDIAVEWESNGQPENNYKT TPPVLDSDGSFFLYSKLTVDKSRWQ EGNVFSCSVMHEALHNHYTQKSLSL SLGIPPHVQKSVNNDMIVTDNNGAV KFPQLCKFCDVRFSTCDNQKSCMSN CSITSICEKPQEVCVAVWRKNDENI TLETVCHDPKLPYHDFILEDAASPK CIMKEKKKPGETFFMCSCSSDECND NIIFSEEYNTSNPDIPPHVQKSDVE MEAQKDEIIAPSANRTAHPLRHINN DMIVTDNNGAVKFPQLCKFCDVRFS TCDNQKSCMSNCSITSICEKPQEVC VAVWRKNDENITLETVCHDPKLPYH DFILEDAASPKCIMKEKKKPGETFF MCSCSSDECNDNIIFSEEYNTSNPD IPPHVQKSDVEMEAQKDEIIAPSAN RTAHPLRHINNDMIVTDNNGAVKFP QLCKFCDVRFSTCDNQKSCMSNCSI TSICEKPQEVCVAVWRKNDENITLE TVCHDPKLPYHDFILEDAASPKCIM KEKKKPGETFFMCSCSSDECNDNII FSEEYNTSNPD | hIgG4FcΔK-CC-228P-409K-T2-T2b$^{AA}$-T2b$^{AA}$ fusion |
| 121 | DILLTQSPVILSVPGERVSFSCRA SQSIGTNIHWYQQRTNGSPRLLIKY ASESISGIPSRFSGSGSGTDFTLSI NSVESEDIADYYCQQNNNWPTTFGA GTKLELKRTVAAPSVFIFPPSDEQL KSGTASVVCLLNNFYPREAKVQWKV DNALQSGNSQESVTEQDSKDSTYSL SSTLTLSKADYEKHKVYACEVTHQG LSSPVTKSFNRGEC | Cetuximab LC |
| 122 | QVQLKQSGPGLVQPSQSLSITCTVS GFSLTNYGVHWVRQSPGKGLEWLGV IWSGGNTDYNTPFTSRLSINKDNSK SQVFFKMNSLQSNDTAIYYCARALT YYDYEFAYWGQGTLVTVSAASTKGP | Cetuximab HC-T22d35 |

| SEQ ID NO: | Sequence | Description |
|---|---|---|
| | SVFPLAPSSKSTSGGTAALGCLVKD YFPEPVTVSWNSGALTSGVHTFPAV LQSSGLYSLSSVVTVPSSSLGTQTY ICNVNHKPSNTKVDKRVEPKSCDKT HTCPPCPAPELLGGPSVFLFPPKPK DTLMISRTPEVTCVVVDVSHEDPEV KFNWYVDGVEVHNAKTKPREEQYNS TYRVVSVLTVLHQDWLNGKEYKCKV SNKALPAPIEKTISKAKGQPREPQV YTLPPSRDELTKNQVSLTCLVKGFY PSDIAVEWESNGQPENNYKTTPPVL DSDGSFFLYSKLTVDKSRWQQGNVF SCSVMHEALHNHYTQKSLSLSPGKI PPHVQKSVNNDMIVTDNNGAVKFPQ LCKFCDVRFSTCDNQKSCMSNCSIT SICEKPQEVCVAVWRKNDENITLET VCHDPKLPYHDFILEDAASPKCIMK EKKKPGETFFMCSCSSDECNDNIIF SEEYNTSNPDIPPHVQKSVNNDMIV TDNNGAVKFPQLCKFCDVRFSTCDN QKSCMSNCSITSICEKPQEVCVAVW RKNDENITLETVCHDPKLPYHDFIL EDAASPKCIMKEKKKPGETFFMCSC SSDECNDNIIFSEEYNTSNPD | |
| 123 | QVQLKQSGPGLVQPSQSLSITCTVS GFSLTNYGVHWVRQSPGKGLEWLGV IWSGGNTDYNTPFTSRLSINKDNSK SQVFFKMNSLQSNDTAIYYCARALT YYDYEFAYWGQGTLVTVSAASTKGP SVFPLAPSSKSTSGGTAALGCLVKD YFPEPVTVSWNSGALTSGVHTFPAV LQSSGLYSLSSVVTVPSSSLGTQTY ICNVNHKPSNTKVDKRVEPKSCDKT HTCPPCPAPELLGGPSVFLFPPKPK DTLMISRTPEVTCVVVDVSHEDPEV KFNWYVDGVEVHNAKTKPREEQYNS TYRVVSVLTVLHQDWLNGKEYKCKV SNKALPAPIEKTISKAKGQPREPQV YTLPPSRDELTKNQVSLTCLVKGFY PSDIAVEWESNGQPENNYKTTPPVL DSDGSFFLYSKLTVDKSRWQQGNVF SCSVMHEALHNHYTQKSLSLSPGKI PPHVQKSVNNDMIVTDNNGAVKFPQ LCKFCDVRFSTCDNQKSCMSNCSIT SICEKPQEVCVAVWRKNDENITLET VCHDPKLPYHDFILEDAASPKCIMK EKKKPGETFFMCSCSSDECNDNIIF SEEYNTSNPD | Cetuximab HC-T2m |
| 124 | DIQMTQSPSSLSASVGDRVTITCRA SQDVNTAVAWYQQKPGKAPKLLIYS ASFLYSGVPSRFSGSRSGTDFTLTI SSLQPEDFATYYCQQHYTTPPTFGQ GTKVEIKRTVAAPSVFIFPPSDEQL KSGTASVVCLLNNFYPREAKVQWKV DNALQSGNSQESVTEQDSKDSTYSL SSTLTLSKADYEKHKVYACEVTHQG LSSPVTKSFNRGEC | Herceptin LC |
| 125 | EVQLVESGGGLVQPGGSLRLSCAAS GFNIKDTYIHWVRQAPGKGLEWVAR IYPTNGYTRYADSVKGRFTISADTS KNTAYLQMNSLRAEDTAVYYCSRWGG DGFYAMDYWGQGTLVTVSSASTKGPS VFPLAPSSKSTSGGTAALGCLVKDY FPEPVTVSWNSGALTSGVHTFPAVL QSSGLYSLSSVVTVPSSSLGTQTYI CNVNHKPSNTKVDKKVEPKSCDKTH TCPPCPAPELLGGPSVFLFPPKPKD TLMISRTPEVTCVVVDVSHEDPEV KFNWYVDGVEVHNAKTKPREEQYNST YRVVSVLTVLHQDWLNGKEYKCKVS | Herceptin HC-T22d35 |
| | NKALPAPIEKTISKAKGQPREPQVY TLPPSRDELTKNQVSLTCLVKGFYP SDIAVEWESNGQPENNYKTTPPVLD SDGSFFLYSKLTVDKSRWQQGNVFS CSVMHEALHNHYTQKSLSLSPGKIP PHVQKSVNNDMIVTDNNGAVKFPQL CKFCDVRFSTCDNQKSCMSNCSITS ICEKPQEVCVAVWRKNDENITLETV CHDPKLPYHDFILEDAASPKCIMKE KKKPGETFFMCSCSSDECNDNIIFS EEYNTSNPDIPPHVQKSVNNDMIVT DNNGAVKFPQLCKFCDVRFSTCDNQ KSCMSNCSITSICEKPQEVCVAVWR KNDENITLETVCHDPKLPYHDFILE DAASPKCIMKEKKKPGETFFMCSCS SDECNDNIIFSEEYNTSNPD | |
| 126 | DIQMTQSPSSLSASVGDRVTITCSA SQDISNYLNWYQQKPGKAPKVLIYF TSSLHSGVPSRFSGSGSGTDFTLTI SSLQPEDFATYYCQQYSTVPWTFGQ GTKVEIKRTVAAPSVFIFPPSDEQL KSGTASVVCLLNNFYPREAKVQWKV DNALQSGNSQESVTEQDSKDSTYSL SSTLTLSKADYEKHKVYACEVTHQG LSSPVTKSFNRGEC | Avastin LC |
| 127 | EVQLVESGGGLVQPGGSLRLSCAAS GYTFTNYGMNWVRQAPGKGLEWVGW INTYTGEPTYAADFKRRFTFSLDTS KSTAYLQMNSLRAEDTAVYYCAKYP HYYGSSHWYFDVWGQGTLVTVSSAS TKGPSVFPLAPSSKSTSGGTAALGC LVKDYFPEPVTVSWNSGALTSGVHT FPAVLQSSGLYSLSSVVTVPSSSLG TQTYICNVNHKPSNTKVDKKVEPKS CDKTHTCPPCPAPELLGGPSVFLFP PKPKDTLMISRTPEVTCVVVDVSHE DPEVKFNWYVDGVEVHNAKTKPREE QYNSTYRVVSVLTVLHQDWLNGKEY KCKVSNKALPAPIEKTISKAKGQPR EPQVYTLPPSRDELTKNQVSLTCLV KGFYPSDIAVEWESNGQPENNYKTT PPVLDSDGSFFLYSKLTVDKSRWQQ GNVFSCSVMHEALHNHYTQKSLSLS PGKIPPHVQKSVNNDMIVTDNNGAV KFPQLCKFCDVRFSTCDNQKSCMSN CSITSICEKPQEVCVAVWRKNDENI TLETVCHDPKLPYHDFILEDAASPK CIMKEKKKPGETFFMCSCSSDECND NIIFSEEYNTSNPDIPPHVQKSVNN DMIVTDNNGAVKFPQLCKFCDVRFS TCDNQKSCMSNCSITSICEKPQEVC VAVWRKNDENITLETVCHDPKLPYH DFILEDAASPKCIMKEKKKPGETFF MCSCSSDECNDNIIFSEEYNTSNPD | Avastin HC-T22d35 |
| 128 | DIQMTQSPSTLSASVGDRVTITCKC QLSVGYMHWYQQKPGKAPKLLIYDT SKLASGVPSRFSGSGSGTEFTLTIS SLQPDDFATYYCFQGSGYPFTFGGG TKLEIKRTVAAPSVFIFPPSDEQLK SGTASVVCLLNNFYPREAKVQWKVD NALQSGNSQESVTEQDSKDSTYSLS STLTLSKADYEKHKVYACEVTHQGL SSPVTKSFNRGEC | Synagis LC |
| 129 | QVTLRESGPALVKPTQTLTLTCTFS GFSLSTSGMSVGWIRQPPGKALEWL ADIWWDDKKDYNPSLKSRLTISKDT SKNQVVLKVTNMDPADTATYYCARS MITNWYFDVWGAGTTVTVSSASTKG PSVFPLAPSSAAAAGGTAALGCLVK | Synagis HC-T22d35 |

| SEQ ID NO: | Sequence | Description |
|---|---|---|
| | DYFPEPVTVSWNSGALTSGVHTFPA VLQSSGLYSLSSVVTVPSSSLGTQT YICNVNHKPSNTKVDKRVEPKSCDK THTCPPCPAPELLGGPSVFLFPPKP KDTLMISRTPEVTCVVVDVSHEDPE VKFNWYVDGVEVHNAKTKPREEQYN STYRVVSVLTVLHQDWLNGKEYKCK VSNKALPAPIEKTISKAKGQPREPQ VYTLPPSRDELTKNQVSLTCLVKGF YPSDIAVEWESNGQPENNYKTTPPV LDSDGSFFLYSKLTVDKSRWQQGNV FSCSVMHEALHNHYTQKSLSLSPGI PPHVQKSVNNDMIVTDNNGAVKFPQ LCKFCDVRFSTCDNQKSCMSNCSIT SICEKPQEVCVAVWRKNDENITLET VCHDPKLPYHDFILEDAASPKCIMK EKKKPGETFFMCSCSSDECNDNIIF SEEYNTSNPDIPPHVQKSVNNDMIV TDNNGAVKFPQLCKFCDVRFSTCDN QKSCMSNCSITSICEKPQEVCVAVW RKNDENITLETVCHDPKLPYHDFIL EDAASPKCIMKEKKKPGETFFMCSC SSDECNDNIIFSEEYNTSNPD | |
| 130 | EVQLQASGGGLVQAGGSLRLSCAAS GFKITHYTMGWFRQAPGKEREFVSR ITWGGDNTFYSNSVKGRFTISRDNA KNTVYLQMNSLKPEDTADYYCAAGST STATPLRVDYWGKGTQVTVSSASEPR GPTIKPCPPCKCPAPNLLGGPSVFI FPPKIKDVLMISLSPIVTCVVVDVS EDDPDVQISWFVNNVEVHTAQTQTH REDYNSTLRVVSALPIQHQDWMSGK EFKCKVNNKDLPAPIERTISKPKGS VRAPQVYVLPPPEEEMTKKQVTLTC MVTDFMPEDIYVEWTNNGKTELNYK NTEPVLDSDCSYFMYSKLRVEKKNW VERNSYSCSVVHEGLHNHHTTKSFS RTPGTGIPPHVQKSVNNDMIVTDNN CAVKFPQLCKFCDVRFSTCDNQKSC MSNCSITSICEKPQEVCVAVWRKND ENITLETVCHDPKLPYHDFILEDAA SPKCIMKEKKKPGETFFMCSCSSDE CNDNIIFSEEYNTSNPDIPPHVQKS VNNDMIVTDNNGAVKFPQLCKFCDV RFSTCDNQKSCMSNCSITSICEKPQ EVCVAVWRKNDENITLETVCHDPKL PYHDFILEDAASPKCIMKEKKKPGE TFFMCSCSSDECNDNIIFSEEYNTS NPD | FC5-Fc-T22d35 |
| 131 | EVQLQASGGGLVQAGGSLRLSCAAS GFKITHYTMGWFRQAPGKEREFVSR ITWGGDNTFYSNSVKGRFTISRDNA KNTVYLQMNSLKPEDTADYYCAAGS TSTATPLRVDYWGKGTQVTVSSASE PRGPTIKPCPPCKCPAPNLLGGPSV FIFPPKIKDVLMISLSPIVTCVVVD VSEDDPDVQISWFVNNVEVHTAQTQ THREDYNSTLRVVSALPIQHQDWMS GKEFKCKVNNKDLPAPIERTISKPK GSVRAPQVYVLPPPEEEMTKKQVTL TCMVTDFMPEDIYVEWTNNGKTELN YKNTEPVLDSDGSYFMYSKLRVEKK NWVERNSYSCSVVHEGLHNHHTTKS FSRTPGTGIPPHVQKSVNNDMIVTD NNGAVKFPQLCKFCDVRFSTCDNQK SCMSNCSITSICEKPQEVCVAVWRK NDENITLETVCHDPKLPYHDFILED AASPKCIMKEKKKPGETFFMCSCSS DECNDNIIFSEEYNTSNPD | FC5-Fc-T2m |
| 132 | MGRGLLRGLWPLHIVLWTRIASTIP PHVQKSVNNDMIVTDNNGAVKFPQL CKFCDVRFSTCDNQKSCMSNCSITS ICEKPQEVCVAVWRKNDENITLETV CHDPKLPYHDFILEDAASPKCIMKE KKKPCETFFMCSCSSDECNDNIIFS EEYNTSNPDMDPKSCDKTHTCPPCP APELLGGPSVFLFPPKPKDTLMISR TPEVTCVVVDVSHEDPEVKFNWYVD GVEVHNAKTKPREEQYNSTYRVVSV LTVLHQDWLNGKEYKCKVSNKALPA PIEKTISKAKGQPREPQVYTLPPSR DELTKNQVSLTCLVKGFYPSDIAVE WESNGQPENNYKTTPPVLDSDGSFF LYSKLTVDKSRWQQGNVFSCSVMHE ALHNHYTQKSLSLSPGK | T2-hIgG1Fc fusion from R&D, also termed T2m-Fc (R&D) |
| 133 | MDWTWRILFLVAAATGTHAIPPHVQ KSVNNDMIVTDNNGAVKFPQLCKFC DVRFSTCDNQKSCMSNCSITSICEK PQEVCVAVWRKNDENITLETVCHDP KLPYHDFILEDAASPKCIMKEKKKP GETFFMCSCSSDECNDNIIFSEEYN TSNPDERKCCVECPPCPAPPVACPS VFLFPPKPKDTLMISRTPEVTCVVV DVSHEDPEVQFNWYVDGVEVHNAKT KPREEQFNSTFRVVSVLTVVHQDWL NGKEYKCKVSNKGLPAPIEKTISKT KGQPREPQVYTLPPSREEMTKNQVS LTCLVKGFYPSDISVEWESNGQPEN NYKTTPPMLDSDGSFFLYSKLTVDK SRWQQGNVFSCSVMHEALHNHYTQK SLSLSPG | T2-hIgG2Fc-CCCC fusion, also termed T2m-Fc |
| 134 | LPYHDFILEDAASPK | Isotope-labelled peptide for T22d35 |
| 135 | ALPAPIEK | Isotope-labelled peptide for Cetuximab |
| 136 | DDDDDDDDDDKTHTCPPCPAPELL GGPSVFLFPPKPKDTLMISRTPEVT CVVVDVSHEDPEVKFNWYVDGVEVH NAKTKPREEQYNSTYRVVSVLTVLH QDWLNGKEYKCKVSNKALPAPIEKT ISKAKGQPREPQVYTLPPSRDELTK NQVSLTCLVKGFYPSDIAVEWESNG QPENNYKTTPPVLDSDGSFFLYSKL TVDKSRWQQGNVFSCSVMHEALHNH YTQKSLSLSPGIPPHVQKSVNNDMI VTDNNGAVKFPQLCKFCDVRFSTCD NQKSCMSNCSITSICEKPQEVCVAV WRKNDENITLETVCHDPKLPYHDFI LEDAASPKCIMKEKKKPGETFFMCS CSSDECNDNIIFSEEYNTSNPD | D10-hIgG1FcΔK-CC-T2m fusion |
| 137 | DDDDDDDDDDGGGSDKTHTCPPCPA PELLGGPSVFLFPPKPKDTLMISRT PEVTCVVVDVSHEDPEVKFNWYVDG VEVHNAKTKPREEQYNSTYRVVSVL TVLHQDWLNGKEYKCKVSNKALPAP IEKTISKAKGQPREPQVYTLPPSRD ELTKNQVSLTCLVKGFYPSDIAVEW ESNGQPENNYKTTPPVLDSDGSFFL YSKLTVDKSRWQQGNVFSCSVMHEA LHNHYTQKSLSLSPGIPPHVQKSVN NDMIVTDNNGAVKFPQLCKFCDVRF STCDNQKSCMSNCSITSICEKPQEV CVAVWRKNDENITLETVCHDPKLPY | D10-GsS-hIgG1FcΔK-CC-T2m fusion |

| SEQ ID NO: | Sequence | Description |
|---|---|---|
| | HDFILEDAASPKCIMKEKKKPGETF FMCSCSSDECNDNIIFSEEYNTSNP D | |
| 138 | DDDDDDDDDDPPCPAPELLGGPSVF LFPPKPKDTLMISRTPEVTCVVVDV SHEDPEVKFNWYVDGVEVHNAKTKP REEQYNSTYRVVSVLTVLHQDWLNG KEYKCKVSNKALPAPIEKTISKAKG QPREPQVYTLPPSRDELTKNQVSLT CLVKGFYPSDIAVEWESNGQPENNY KTTPPVLDSDGSFFLYSKLTVDKSR WQQGNVFSCSVMHEALHNHYTQKSL SLSPGIPPHVQKSVNNDMIVTDNNG AVKFPQLCKFCDVRFSTCDNQKSCM SNCSITSICEKPQEVCVAVWRKNDE NITLETVCHDPKLPYHDFILEDAAS PKCIMKEKKKPGETFFMCSCSSDEC NDNIIFSEEYNTSNPD | D10-hIgG1FcΔK-C-T2m fusion |
| 139 | DDDDDDDDDDGGGSGGGSPPCPAPE LLGGPSVFLFPPKPKDTLMISRTPE VTCVVVDVSHEDPEVKFNWYVDGVE VHNAKTKPREEQYNSTYRVVSVLTV LHQDWLNGKEYKCKVSNKALPAPIE KTISKAKGQPREPQVYTLPPSRDEL TKNQVSLTCLVKGFYPSDIAVEWES NGQPENNYKTTPPVLDSDGSFFLYS KLTVDKSRWQQGNVFSCSVMHEALH NHYTQKSLSLSPGIPPHVQKSVNND MIVTDNNGAVKFPQLCKFCDVRFST CDNQKSCMSNCSITSICEKPQEVCV AVWRKNDENITLETVCHDPKLPYHD FILEDAASPKCIMKEKKKPGETFFM CSCSSDECNDNIIFSEEYNTSNPD | D10-(G3S)2-hIgG1FcΔK-C-T2m fusion |
| 140 | DDDDDDDDDDVECPPCPAPPVAGPS VFLFPPKPKDTLMISRTPEVTCVVV DVSHEDPEVQFNWYVDGVEVHNAKT KPREEQFNSTFRVVSVLTVVHQDWL NGKEYKCKVSNKGLPAPIEKTISKT KGQPREPQVYTLPPSREEMTKNQVS LTCLVKGFYPSDISVEWESNGQPEN NYKTTPPMLDSDGSFFLYSKLTVDK SRWQQGNVFSCSVMHEALHNHYTQK SLSLSPGIPPHVQKSVNNDMIVTDN NGAVKFPQLCKFCDVRFSTCDNQKS CMSNCSITSICEKPQEVCVAVWRKN DENITLETVCHDPKLPYHDFILEDA ASPKCIMKEKKKPGETFFMCSCSSD ECNDNIIFSEEYNTSNPD | D10-hIgG2FcΔK-CC-T2m fusion |
| 141 | DDDDDDDDDDESKYGPPCPPCPAPE FLCCPSVFLFPPKPKDTLMISRTPE VTCVVVDVSQEDPEVQFNWYVDGVE VHNAKTKPREEQFNSTYRVVSVLTV LHQDWLNGKEYKCKVSNKGLPSSIE KTISKAKGQPREPQVYTLPPSQEEM TKNQVSLTCLVKGFYPSDIAVEWES NGQPENNYKTTPPVLDSDGSFFLYS RLTVDKSRWQEGNVFSCSVMHEALH NHYTQKSLSLSLGIPPHVQKSVNND MIVTDNNGAVKFPQLCKFCDVRFST CDNQKSCMSNCSITSICEKPQEVCV AVWRKNDENITLETVCHDPKLPYHD FILEDAASPKCIMKEKKKPGETFFM CSCSSDECNDNIIFSEEYNTSNPD | D10-hIgG4FcΔK-CC-228P-T2m fusion |
| 142 | DDDDDDDDDDESKYGPPCPPCPAPE FLGGPSVFLFPPKPKDTLMISRTPE VTCVVVDVSQEDPEVQFNWYVDGVE VHNAKTKPREEQFNSTYRVVSVLTV LHQDWLNCKEYKCKVSNKGLPSSIE KTISKAKGQPREPQVYTLPPSQEEM TKNQVSLTCLVKGFYPSDIAVEWES NGQPENNYKTTPPVLDSDGSFFLYS KLTVDKSRWQEGNVFSCSVMHEALH NHYTQKSLSLSLGIPPHVQKSVNND MIVTDNNGAVKFPQLCKFCDVRFST CDNQKSCMSNCSITSICEKPQEVCV AVWRKNDENITLETVCHDPKLPYHD FILEDAASPKCIMKEKKKPGETFFM CSCSSDECNDNIIFSEEYNTSNPD | D10-hIgG4FcΔK-CC-228P-409K-T2m fusion |
| 143 | DDDDDDDDDDKTHTCPPCPAPELL GGPSVFLFPPKPKDTLMISRTPEVT CVVVDVSHEDPEVKFNWYVDGVEVH NAKTKPREEQYNSTYRVVSVLTVLH QDWLNCKEYKCKVSNKALPAPIEKT ISKAKGQPREPQVYTLPPSRDELTK NQVSLTCLVKGFYPSDIAVEWESNG QPENNYKTTPPVLDSDGSFFLYSKL TVDKSRWQQGNVFSCSVMHEALHNH YTQKSLSLSPGIPPHVQKSVNNDMI VTDNNGAVKFPQLCKFCDVRFSTCD NQKSCMSNCSITSICEKPQEVCVAV WRKNDENITLETVCHDPKLPYHDFI LEDAASPKCIMKEKKKPGETFFMCS CSSDECNDNIIFSEEYNTSNPDIPP HVQKSVNNDMIVTDNNGAVKFPQLC KFCDVRFSTCDNQKSCMSNCSITSI CEKPQEVCVAVWRKNDENITLETVC HDPKLPYHDFILEDAASPKCIMKEK KKPGETFFMCSCSSDECNDNIIFSE EYNTSNPD | D10-hIgG1FcΔK-CC-T22d35 fusion |
| 144 | DDDDDDDDDDVECPPCPAPPVAGPS VFLFPPKPKDTLMISRTPEVTCVVV DVSHEDPEVQFNWYVDGVEVHNAKT KPREEQFNSTFRVVSVLTVVHQDWL NGKEYKCKVSNKGLPAPIEKTISKT KCQPREPQVYTLPPSREEMTKNQVS LTCLVKGFYPSDISVEWESNGQPEN NYKTTPPMLDSDGSFFLYSKLTVDK SRWQQGNVFSCSVMHEALHNHYTQK SLSLSPGIPPHVQKSVNNDMIVTDN NGAVKFPQLCKFCDVRFSTCDNQKS CMSNCSITSICEKPQEVCVAVWRKN DENITLETVCHDPKLPYHDFILEDA ASPKCIMKEKKKPGETFFMCSCSSD ECNDNIIFSEEYNTSNPDIPPHVQK SVNNDMIVTDNNGAVKFPQLCKFCD VRFSTCDNQKSCMSNCSITSICEKP QEVCVAVWRKNDENITLETVCHDPK LPYHDFILEDAASPKCIMKEKKKPG ETFFMCSCSSDECNDNIIFSEEYNT SNPD | D10-hIgG2FcΔK-CC-T22d35 fusion |
| 145 | DDDDDDDDDDESKYGPPCPPCPAPE FLGGPSVFLFPPKPKDTLMISRTPE VTCVVVDVSQEDPEVQFNWYVDGVE VHNAKTKPREEQFNSTYRVVSVLTV LHQDWLNCKEYKCKVSNKGLPSSIE KTISKAKGQPREPQVYTLPPSQEEM TKNQVSLTCLVKGFYPSDIAVEWES NGQPENNYKTTPPVLDSDGSFFLYS RLTVDKSRWQEGNVFSCSVMHEALH NHYTQKSLSLSLGIPPHVQKSVNND MIVTDNNGAVKFPQLCKFCDVRFST CDNQKSCMSNCSITSICEKPQEVCV AVWRKNDENITLETVCHDPKLPYHD FILEDAASPKCIMKEKKKPGETFFM CSCSSDECNDNIIFSEEYNTSNPDI PPHVQKSVNNDMIVTDNNGAVKFPQ LCKFCDVRFSTCDNQKSCMSNCSIT SICEKPQEVCVAVWRKNDENITLET | D10-hIgG4FcΔK-CC-228P-T22d35 fusion |

LISTING OF SEQUENCES

| SEQ ID NO: | Sequence | Description |
|---|---|---|
| | VCHDPKLPYHDFILEDAASPKCIMK EKKKPGETFFMCSCSSDECNDNIIF SEEYNTSNPD | |
| 146 | DDDDDDDDDDESKYGPPCPPCPAPE FLCCPSVFLFPPKPKDTLMISRTPE VTCVVVDVSQEDPEVQFNWYVDGVE VHNAKTKPREEQFNSTYRVVSVLTV LHQDWLNGKEYKCKVSNKGLPSSIE KTISKAKGQPREPQVYTLPPSQEEM TKNQVSLTCLVKGFYPSDIAVEWES NGQPENNYKTTPPVLDSDGSFFLYS KLTVDKSRWQEGNVFSCSVMHEALH NHYTQKSLSLSLGIPPHVQKSVNND MIVTDNNGAVKFPQLCKFCDVRFST CDNQKSCMSNCSITSICEKPQEVCV AVWRKNDENITLETVCHDPKLPYHD FILEDAASPKCIMKEKKKPGETFFM CSCSSDECNDNIIFSEEYNTSNPDI PPHVQKSVNNDMIVTDNNGAVKFPQ LCKFCDVRFSTCDNQKSCMSNCSIT SICEKPQEVCVAVWRKNDENITLET VCHDPKLPYHDFILEDAASPKCIMK EKKKPGETFFMCSCSSDECNDNIIF SEEYNTSNPD | D10-hIgG4FcΔK-CC-228P-409K-T22d35 fusion |
| 147 | DDDDDDDDDDKTHTCPPCPAPELL GGPSVFLFPPKPKDTLMISRTPEVT CVVVDVSHEDPEVKFNWYVDGVEVH NAKTKPREEQYNSTYRVVSVLTVLH QDWLNGKEYKCKVSNKALPAPIEKT ISKAKGQPREPQVYTLPPSRDELTK NQVSLTCLVKGFYPSDIAVEWESNG QPENNYKTTPPVLDSDGSFFLYSKL TVDKSRWQQGNVFSCSVMHEALHNH YTQKSLSLSPGIPPHVQKSVNNDMI VTDNNGAVKFPQLCKFCDVRFSTCD NQKSCMSNCSITSICEKPQEVCVAV WRKNDENITLETVCHDPKLPYHDFI LEDAASPKCIMKEKKKPGETFFMCS CSSDECNDNIIFSEEYNTSNPDIPP HVQKSVNNDMIVTDNNGAVKFPQLC KFCDVRFSTCDNQKSCMSNCSITSI CEKPQEVCVAVWRKNDENITLETVC HDPKLPYHDFILEDAASPKCIMKEK KKPGETFFMCSCSSDECNDNIIFSE EYNTSNPDIPPHVQKSVNNDMIVTD NNGAVKFPQLCKFCDVRFSTCDNQK SCMSNCSITSICEKPQEVCVAVWRK NDENITLETVCHDPKLPYHDFILED AASPKCIMKEKKKPGETFFMCSCSS DECNDNIIFSEEYNTSNPD | D10-hIgG1FcΔK-CC-T2-T2-T2 fusion |
| 148 | DDDDDDDDDDVECPPCPAPPVAGPS VFLFPPKPKDTLMISRTPEVTCVVV DVSHEDPEVQFNWYVDGVEVHNAKT KPREEQFNSTFRVVSVLTVVHQDWL NGKEYKCKVSNKGLPAPIEKTISKT KGQPREPQVYTLPPSREEMTKNQVS LTCLVKGFYPSDISVEWESNGQPEN NYKTTPPMLDSDGSFFLYSKLTVDK SRWQQGNVFSCSVMHEALHNHYTQK SLSLSPGIPPHVQKSVNNDMIVTDN NCAVKFPQLCKFCDVRFSTCDNQKS CMSNCSITSICEKPQEVCVAVWRKN DENITLETVCHDPKLPYHDFILEDA ASPKCIMKEKKKPGETFFMCSCSSD ECNDNIIFSEEYNTSNPDIPPHVQK SVNNDMIVTDNNGAVKFPQLCKFCD VRFSTCDNQKSCMSNCSITSICEKP QEVCVAVWRKNDENITLETVCHDPK LPYHDFILEDAASPKCIMKEKKKPG ETFFMCSCSSDECNDNIIFSEEYNT SNPDIPPHVQKSVNNDMIVTDNNGA VKFPQLCKFCDVRFSTCDNQKSCMS NCSITSICEKPQEVCVAVWRKNDEN ITLETVCHDPKLPYHDFILEDAASP KCIMKEKKKPGETFFMCSCSSDECN DNIIFSEEYNTSNPD | D10-hIgG2FcΔK-CC-T2-T2-T2 fusion |
| 149 | DDDDDDDDDDESKYGPPCPPCPAPE FLGCPSVFLFPPKPKDTLMISRTPE VTCVVVDVSQEDPEVQFNWYVDCVE VHNAKTKPREEQFNSTYRVVSVLTV LHQDWLNGKEYKCKVSNKGLPSSIE KTISKAKGQPREPQVYTLPPSQEEM TKNQVSLTCLVKGFYPSDIAVEWES NGQPENNYKTTPPVLDSDGSFFLYS RLTVDKSRWQEGNVFSCSVMHEALH NHYTQKSLSLSLGIPPHVQKSVNND MIVTDNNGAVKFPQLCKFCDVRFST CDNQKSCMSNCSITSICEKPQEVCV AVWRKNDENITLETVCHDPKLPYHD FILEDAASPKCIMKEKKKPGETFFM CSCSSDECNDNIIFSEEYNTSNPDI PPHVQKSVNNDMIVTDNNGAVKFPQ LCKFCDVRFSTCDNQKSCMSNCSIT SICEKPQEVCVAVWRKNDENITLET VCHDPKLPYHDFILEDAASPKCIMK EKKKPGETFFMCSCSSDECNDNIIF SEEYNTSNPDIPPHVQKSVNNDMIV TDNNGAVKFPQLCKFCDVRFSTCDN QKSCMSNCSITSICEKPQEVCVAVW RKNDENITLETVCHDPKLPYHDFIL EDAASPKCIMKEKKKPGETFFMCSC SSDECNDNIIFSEEYNTSNPD | D10-hIgG4FcΔK-CC-228P-T2-T2-T2 fusion |
| 150 | DDDDDDDDDDESKYGPPCPPCPAPE FLGGPSVFLFPPKPKDTLMISRTPE VTCVVVDVSQEDPEVQFNWYVDGVE VHNAKTKPREEQFNSTYRVVSVLTV LHQDWLNGKEYKCKVSNKGLPSSIE KTISKAKGQPREPQVYTLPPSQEEM TKNQVSLTCLVKGFYPSDIAVEWES NGQPENNYKTTPPVLDSDGSFFLYS KLTVDKSRWQEGNVFSCSVMHEALH NHYTQKSLSLSLGIPPHVQKSVNND MIVTDNNGAVKFPQLCKFCDVRFST CDNQKSCMSNCSITSICEKPQEVCV AVWRKNDENITLETVCHDPKLPYHD FILEDAASPKCIMKEKKKPGETFFM CSCSSDECNDNIIFSEEYNTSNPDI PPHVQKSVNNDMIVTDNNGAVKFPQ LCKFCDVRFSTCDNQKSCMSNCSIT SICEKPQEVCVAVWRKNDENITLET VCHDPKLPYHDFILEDAASPKCIMK EKKKPGETFFMCSCSSDECNDNIIF SEEYNTSNPDIPPHVQKSVNNDMIV TDNNGAVKFPQLCKFCDVRFSTCDN QKSCMSNCSITSICEKPQEVCVAVW RKNDENITLETVCHDPKLPYHDFIL EDAASPKCIMKEKKKPGETFFMCSC SSDECNDNIIFSEEYNTSNPD | D10-hIgG4FcΔK-CC-228P-409K-T2-T2-T2 fusion |

REFERENCES

All patents, patent applications and publications referred to throughout the application are listed below.

Arteaga C L (2006) Inhibition of TGFbeta signaling in cancer therapy. *Curr Opin Genet Dev* 16: 30-37

De Crescenzo G, Grothe S, Zwaagstra J, Tsang M, O'Connor-McCourt MD (2001) Real-time monitoring of the interactions of transforming growth factor-beta (TGF-beta) isoforms with latency-associated protein and the ectodomains of the TGF-beta type II and III receptors reveals different kinetic models and stoichiometries of binding. *J Biol Chem* 276: 29632-29643

Durocher Y, Perret S, Kamen A (2002) High-level and high-throughput recombinant protein production by transient transfection of suspension-growing human 293-EBNA1 cells. *Nucleic Acids Res* 30: E9

Economides A N, Carpenter L R, Rudge J S, Wong V, Koehler-Stec E M, Hartnett C, Pyles E A, Xu X, Daly T J, Young M R, Fandl J P, Lee F, Carver S, McNay J, Bailey K, Ramakanth S, Hutabarat R, Huang T T, Radziejewski C, Yancopoulos G D, Stahl N (2003) Cytokine traps: multi-component, high-affinity blockers of cytokine action. *Nat Med* 9: 47-52

Eisenberg D, Schwarz E, Komaromy M, Wall R (1984) Analysis of membrane and surface protein sequences with the hydrophobic moment plot. *J Mol Biol* 179: 125-142

Gajewski T F (2015) The Next Hurdle in Cancer Immunotherapy: Overcoming the Non-T-Cell-Inflamed Tumor Microenvironment. *Semin Oncol* 42: 663-671

Garberg P, Ball M, Borg N, Cecchelli R, Fenart L, Hurst R D, Lindmark T, Mabondzo A, Nilsson J E, Raub T J, Stanimirovic D, Terasaki T, Oberg J O, Osterberg T (2005) In vitro models for the blood-brain barrier. *Toxicol In Vitro* 19: 299-334

Hahn T, Akporiaye E T (2006) Targeting transforming growth factor beta to enhance cancer immunotherapy. *Curr Oncol* 13: 141-143

Haqqani A S, Caram-Salas N, Ding W, Brunette E, Delaney C E, Baumann E, Boileau E, Stanimirovic D (2013) Multiplexed evaluation of serum and CSF pharmacokinetics of brain-targeting single-domain antibodies using a NanoLC-SRM-ILIS method. *Mol Pharm* 10: 1542-1556

Hawinkels L J, Ten Dijke P (2011) Exploring anti-TGF-beta therapies in cancer and fibrosis. *Growth Factors* 29: 140-152

Holash J, Davis S, Papadopoulos N, Croll S D, Ho L, Russell M, Boland P, Leidich R, Hylton D, Burova E, Ioffe E, Huang T, Radziejewski C, Bailey K, Fandl J P, Daly T, Wiegand S J, Yancopoulos G D, Rudge J S (2002) VEGF-Trap: a VEGF blocker with potent antitumor effects. *Proc Natl Acad Sci USA* 99: 11393-11398

Jin P, Zhang J, Beryt M, Turin L, Brdlik C, Feng Y, Bai X, Liu J, Jorgensen B, Shepard H M (2009) Rational optimization of a bispecific ligand trap targeting EGF receptor family ligands. *Mol Med* 15: 11-20

Li M O, Wan Y Y, Sanjabi S, Robertson A K, Flavell R A (2006) Transforming growth factor-beta regulation of immune responses. *Annu Rev Immunol* 24: 99-146

Massague J, Blain S W, Lo R S (2000) TGFbeta signaling in growth control, cancer, and heritable disorders. *Cell* 103: 295-309

Mourskaia A A, Northey J J, Siegel P M (2007) Targeting aberrant TGF-beta signaling in pre-clinical models of cancer. *Anticancer Agents Med Chem* 7: 504-514

Rodgarkia-Dara C, Vejda S, Erlach N, Losert A, Bursch W, Berger W, Schulte-Hermann R, Grusch M (2006) The activin axis in liver biology and disease. *Mutat Res* 613: 123-137

Santarpia M, Gonzalez-Cao M, Viteri S, Karachaliou N, Altavilla G, Rosell R (2015) Programmed cell death protein-1/programmed cell death ligand-1 pathway inhibition and predictive biomarkers: understanding transforming growth factor-beta role. *Transl Lung Cancer Res* 4: 728-742

Thiery J P, Acloque H, Huang R Y, Nieto M A (2009) Epithelial-mesenchymal transitions in development and disease. *Cell* 139: 871-890

Wojtowicz-Praga S (2003) Reversal of tumor-induced immunosuppression by TGF-beta inhibitors. *Invest New Drugs* 21: 21-32

Yang L, Pang Y, Moses H L (2010) TGF-beta and immune cells: an important regulatory axis in the tumor microenvironment and progression. *Trends Immunol* 31: 220-227

Yang X, Ambrogelly A (2014) Enlarging the repertoire of therapeutic monoclonal antibodies platforms: domesticating half molecule exchange to produce stable IgG4 and IgG1 bispecific antibodies. *Curr Opin Biotechnol* 30: 225-229

Zheng X, Koropatnick J, Chen D, Velenosi T, Ling H, Zhang X, Jiang N, Navarro B, Ichim T E, Urquhart B, Min W (2013) Silencing IDO in dendritic cells: a novel approach to enhance cancer immunotherapy in a murine breast cancer model. *Int J Cancer* 132: 967-977

Zwaagstra J C, Sulea T, Baardsnes J, Lenferink A E, Collins C, Cantin C, Paul-Roc B, Grothe S, Hossain S, Richer LP, L'Abbe D, Tom R, Cass B, Durocher Y, O'Connor-McCourt MD (2012) Engineering and therapeutic application of single-chain bivalent TGF-beta family traps. *Mol Cancer Ther* 11: 1477-1487

WO/1995/04069
WO/2004/076670
WO 2008/113185
WO 2010/031168
U.S. Pat. No. 8,815,247
U.S. 62/777,375
US2015/0225483

The invention claimed is:

1. A polypeptide construct comprising:
a first portion comprising the second constant domain (CH2) and/or third constant domain (CH3) of an antibody heavy chain, and
a second portion comprising at least two TGF-β superfamily receptor ectodomains (TβSR-ED) linked in tandem,
wherein the N-terminus of the second portion is linked to the C-terminus of the first portion,
wherein the at least two TβSR-EDs are TGF-β receptor II ectodomains (TβR-II-EDs), and
wherein the polypeptide construct has neutralization activity against TGF-β2.

2. The polypeptide construct of claim 1, wherein the second portion comprises two TβSR-ED.

3. The polypeptide construct of claim 1, wherein the first portion further comprises a CH1, a CH1 and VH, or CH1 and scFv.

4. The polypeptide construct of claim 1, wherein the polypeptide construct shows longer in vivo half-life compared to the half-life of the second portion alone.

5. The polypeptide construct of claim 1, wherein the polypeptide construct forms a dimeric polypeptide.

6. The polypeptide construct of claim 1, wherein the construct comprises an antibody or an antigen binding fragment thereof, or a targeting moiety.

7. The polypeptide construct of claim 6, wherein the antibody or the antigen binding fragment thereof binds to an antigen that is not PD-L1, CD4, CD6, CD20, CD25, MUC-1, IL-2, IL-6, or CTLA-4.

8. The polypeptide construct according to claim 6, wherein the targeting moiety comprises a poly-aspartate sequence motif for bone targeting.

9. A composition comprising one or more than one independently selected polypeptide construct of claim 1 and a pharmaceutically-acceptable carrier, diluent, or excipient.

10. The polypeptide construct of claim 1, wherein the N-terminus of the second portion is directly linked to the C-terminus of the first portion, and wherein the C-terminal residue of the amino acid sequence of the first portion is not a lysine residue.

11. The polypeptide construct of claim 1, wherein each of the at least two TβSR-EDs comprises the amino acid sequence set forth in SEQ ID NO: 35.

12. The polypeptide construct of claim 11, wherein the at least two TβSR-EDs are joined by a linker.

13. The polypeptide construct of claim 12, wherein the linker comprises the amino acid sequence set forth in SEQ ID NO: 39.

14. The polypeptide construct of claim 1, wherein the second portion comprises the amino acid sequence set forth in SEQ ID NO: 46.

* * * * *

SEQUENCE LISTING

<160> NUMBER OF SEQ ID NOS: 150

<210> SEQ ID NO 1
<211> LENGTH: 217
<212> TYPE: PRT
<213> ORGANISM: Artificial Sequence
<220> FEATURE:
<223> OTHER INFORMATION: Human IgG1 Fc region

<400> SEQUENCE: 1

Ala Pro Glu Leu Leu Gly Gly Pro Ser Val Phe Leu Phe Pro Pro Lys
1               5                   10                  15

```
Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Asp Glu Leu
        115                 120                 125

Thr Lys Asn Gln Val Ser Leu Thr Cys Leu Val Lys Gly Phe Tyr Pro
130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Tyr Ser Lys Leu Thr Val Asp Lys Ser Arg Trp Gln Gln Gly Asn Val
            180                 185                 190

Phe Ser Cys Ser Val Met His Glu Ala Leu His Asn His Tyr Thr Gln
        195                 200                 205

Lys Ser Leu Ser Leu Ser Pro Gly Lys
    210                 215

<210> SEQ ID NO 2
<211> LENGTH: 216
<212> TYPE: PRT
<213> ORGANISM: Artificial Sequence
<220> FEATURE:
<223> OTHER INFORMATION: Human IgG2 Fc region

<400> SEQUENCE: 2

Ala Pro Pro Val Ala Gly Pro Ser Val Phe Leu Phe Pro Pro Lys Pro
1               5                   10                  15

Lys Asp Thr Leu Met Ile Ser Arg Thr Pro Glu Val Thr Cys Val Val
            20                  25                  30

Val Asp Val Ser His Glu Asp Pro Glu Val Gln Phe Asn Trp Tyr Val
        35                  40                  45

Asp Gly Val Glu Val His Asn Ala Lys Thr Lys Pro Arg Glu Glu Gln
    50                  55                  60

Phe Asn Ser Thr Phe Arg Val Val Ser Val Leu Thr Val Val His Gln
65                  70                  75                  80

Asp Trp Leu Asn Gly Lys Glu Tyr Lys Cys Lys Val Ser Asn Lys Gly
                85                  90                  95

Leu Pro Ala Pro Ile Glu Lys Thr Ile Ser Lys Thr Lys Gly Gln Pro
            100                 105                 110

Arg Glu Pro Gln Val Tyr Thr Leu Pro Pro Ser Arg Glu Glu Met Thr
        115                 120                 125

Lys Asn Gln Val Ser Leu Thr Cys Leu Val Lys Gly Phe Tyr Pro Ser
130                 135                 140

Asp Ile Ser Val Glu Trp Glu Ser Asn Gly Gln Pro Glu Asn Asn Tyr
145                 150                 155                 160
```

```
Lys Thr Thr Pro Pro Met Leu Asp Ser Asp Gly Ser Phe Phe Leu Tyr
            165                 170                 175

Ser Lys Leu Thr Val Asp Lys Ser Arg Trp Gln Gln Gly Asn Val Phe
            180                 185                 190

Ser Cys Ser Val Met His Glu Ala Leu His Asn His Tyr Thr Gln Lys
            195                 200                 205

Ser Leu Ser Leu Ser Pro Gly Lys
            210                 215

<210> SEQ ID NO 3
<211> LENGTH: 217
<212> TYPE: PRT
<213> ORGANISM: Artificial Sequence
<220> FEATURE:
<223> OTHER INFORMATION: Human IgG3 Fc region

<400> SEQUENCE: 3

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Gln Phe Lys Trp Tyr
        35                  40                  45

Val Asp Gly Val Glu Val His Asn Ala Lys Thr Lys Pro Arg Glu Glu
    50                  55                  60

Gln Tyr Asn Ser Thr Phe Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Thr Lys Gly Gln
            100                 105                 110

Pro Arg Glu Pro Gln Val Tyr Thr Leu Pro Pro Ser Arg Glu Glu Met
        115                 120                 125

Thr Lys Asn Gln Val Ser Leu Thr Cys Leu Val Lys Gly Phe Tyr Pro
    130                 135                 140

Ser Asp Ile Ala Val Glu Trp Glu Ser Ser Gly Gln Pro Glu Asn Asn
145                 150                 155                 160

Tyr Asn Thr Thr Pro Pro Met Leu Asp Ser Asp Gly Ser Phe Phe Leu
                165                 170                 175

Tyr Ser Lys Leu Thr Val Asp Lys Ser Arg Trp Gln Gln Gly Asn Ile
            180                 185                 190

Phe Ser Cys Ser Val Met His Glu Ala Leu His Asn Arg Phe Thr Gln
        195                 200                 205

Lys Ser Leu Ser Leu Ser Pro Gly Lys
    210                 215

<210> SEQ ID NO 4
<211> LENGTH: 217
<212> TYPE: PRT
<213> ORGANISM: Artificial Sequence
<220> FEATURE:
<223> OTHER INFORMATION: Human IgG4 Fc region

<400> SEQUENCE: 4

Ala Pro Glu Phe Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
```

```
                 20                  25                  30

Val Val Asp Val Ser Gln Glu Asp Pro Glu Val Gln Phe Asn Trp Tyr
             35                  40                  45

Val Asp Gly Val Glu Val His Asn Ala Lys Thr Lys Pro Arg Glu Glu
         50                  55                  60

Gln Phe Asn Ser Thr Tyr Arg Val Val Ser Val Leu Thr Val Leu His
 65                  70                  75                  80

Gln Asp Trp Leu Asn Gly Lys Glu Tyr Lys Cys Lys Val Ser Asn Lys
                 85                  90                  95

Gly Leu Pro Ser Ser Ile Glu Lys Thr Ile Ser Lys Ala Lys Gly Gln
            100                 105                 110

Pro Arg Glu Pro Gln Val Tyr Thr Leu Pro Pro Ser Gln Glu Glu Met
            115                 120                 125

Thr Lys Asn Gln Val Ser Leu Thr Cys Leu Val Lys Gly Phe Tyr Pro
        130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Tyr Ser Arg Leu Thr Val Asp Lys Ser Arg Trp Gln Gln Gly Asn Val
            180                 185                 190

Phe Ser Cys Ser Val Met His Glu Ala Leu His Asn His Tyr Thr Gln
        195                 200                 205

Lys Ser Leu Ser Leu Ser Leu Gly Lys
    210                 215

<210> SEQ ID NO 5
<211> LENGTH: 15
<212> TYPE: PRT
<213> ORGANISM: Artificial Sequence
<220> FEATURE:
<223> OTHER INFORMATION: Human IgG1 hinge region

<400> SEQUENCE: 5

Glu Pro Lys Ser Cys Asp Lys Thr His Thr Cys Pro Pro Cys Pro
1               5                   10                  15

<210> SEQ ID NO 6
<211> LENGTH: 12
<212> TYPE: PRT
<213> ORGANISM: Artificial Sequence
<220> FEATURE:
<223> OTHER INFORMATION: Human IgG2 hinge region

<400> SEQUENCE: 6

Glu Arg Lys Cys Cys Val Glu Cys Pro Pro Cys Pro
1               5                   10

<210> SEQ ID NO 7
<211> LENGTH: 62
<212> TYPE: PRT
<213> ORGANISM: Artificial Sequence
<220> FEATURE:
<223> OTHER INFORMATION: Human IgG3 hinge region

<400> SEQUENCE: 7

Glu Leu Lys Thr Pro Leu Gly Asp Thr Thr His Thr Cys Pro Arg Cys
1               5                   10                  15

Pro Glu Pro Lys Ser Cys Asp Thr Pro Pro Pro Cys Pro Arg Cys Pro
            20                  25                  30
```

```
Glu Pro Lys Ser Cys Asp Thr Pro Pro Cys Pro Arg Cys Pro Glu
            35                  40                  45

Pro Lys Ser Cys Asp Thr Pro Pro Cys Pro Arg Cys Pro
    50                  55                  60

<210> SEQ ID NO 8
<211> LENGTH: 12
<212> TYPE: PRT
<213> ORGANISM: Artificial Sequence
<220> FEATURE:
<223> OTHER INFORMATION: Human IgG4 hinge region

<400> SEQUENCE: 8

Glu Ser Lys Tyr Gly Pro Pro Cys Pro Ser Cys Pro
1               5                   10

<210> SEQ ID NO 9
<211> LENGTH: 216
<212> TYPE: PRT
<213> ORGANISM: Artificial Sequence
<220> FEATURE:
<223> OTHER INFORMATION: hIgG1FcdeltaK-deltaC Fc variant

<400> SEQUENCE: 9

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Asp Glu Leu
        115                 120                 125

Thr Lys Asn Gln Val Ser Leu Thr Cys Leu Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Tyr Ser Lys Leu Thr Val Asp Lys Ser Arg Trp Gln Gln Gly Asn Val
            180                 185                 190

Phe Ser Cys Ser Val Met His Glu Ala Leu His Asn His Tyr Thr Gln
        195                 200                 205

Lys Ser Leu Ser Leu Ser Pro Gly
    210                 215

<210> SEQ ID NO 10
<211> LENGTH: 220
<212> TYPE: PRT
<213> ORGANISM: Artificial Sequence
<220> FEATURE:
<223> OTHER INFORMATION: hIgG1FcdeltaK-C Fc variant
```

```
<400> SEQUENCE: 10

Pro Pro Cys Pro Ala Pro Glu Leu Leu Gly Gly Pro Ser Val Phe Leu
1               5                   10                  15

Phe Pro Pro Lys Pro Lys Asp Thr Leu Met Ile Ser Arg Thr Pro Glu
                20                  25                  30

Val Thr Cys Val Val Val Asp Val Ser His Glu Asp Pro Glu Val Lys
            35                  40                  45

Phe Asn Trp Tyr Val Asp Gly Val Glu Val His Asn Ala Lys Thr Lys
    50                  55                  60

Pro Arg Glu Glu Gln Tyr Asn Ser Thr Tyr Arg Val Val Ser Val Leu
65                  70                  75                  80

Thr Val Leu His Gln Asp Trp Leu Asn Gly Lys Glu Tyr Lys Cys Lys
                85                  90                  95

Val Ser Asn Lys Ala Leu Pro Ala Pro Ile Glu Lys Thr Ile Ser Lys
                100                 105                 110

Ala Lys Gly Gln Pro Arg Glu Pro Gln Val Tyr Thr Leu Pro Pro Ser
            115                 120                 125

Arg Asp Glu Leu Thr Lys Asn Gln Val Ser Leu Thr Cys Leu Val Lys
130                 135                 140

Gly Phe Tyr Pro Ser Asp Ile Ala Val Glu Trp Glu Ser Asn Gly Gln
145                 150                 155                 160

Pro Glu Asn Asn Tyr Lys Thr Thr Pro Pro Val Leu Asp Ser Asp Gly
                165                 170                 175

Ser Phe Phe Leu Tyr Ser Lys Leu Thr Val Asp Lys Ser Arg Trp Gln
                180                 185                 190

Gln Gly Asn Val Phe Ser Cys Ser Val Met His Glu Ala Leu His Asn
            195                 200                 205

His Tyr Thr Gln Lys Ser Leu Ser Leu Ser Pro Gly
            210                 215                 220

<210> SEQ ID NO 11
<211> LENGTH: 226
<212> TYPE: PRT
<213> ORGANISM: Artificial Sequence
<220> FEATURE:
<223> OTHER INFORMATION: hIgG1FcdeltaK-CC Fc variant

<400> SEQUENCE: 11

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
                20                  25                  30

Ile Ser Arg Thr Pro Glu Val Thr Cys Val Val Val Asp Val Ser His
            35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
                100                 105                 110

Glu Lys Thr Ile Ser Lys Ala Lys Gly Gln Pro Arg Glu Pro Gln Val
            115                 120                 125
```

```
Tyr Thr Leu Pro Pro Ser Arg Asp Glu Leu Thr Lys Asn Gln Val Ser
        130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
210                 215                 220

Pro Gly
225

<210> SEQ ID NO 12
<211> LENGTH: 231
<212> TYPE: PRT
<213> ORGANISM: Artificial Sequence
<220> FEATURE:
<223> OTHER INFORMATION: hIgG1FcdeltaK-S Fc variant

<400> SEQUENCE: 12

Glu Pro Lys Ser Ser Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Asp Glu Leu Thr
130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
210                 215                 220

Ser Leu Ser Leu Ser Pro Gly
225                 230

<210> SEQ ID NO 13
<211> LENGTH: 231
```

```
<212> TYPE: PRT
<213> ORGANISM: Artificial Sequence
<220> FEATURE:
<223> OTHER INFORMATION: hIgG1deltaK-SS Fc variant

<400> SEQUENCE: 13

Glu Pro Lys Ser Ser Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
                20                  25                  30

Lys Asp Thr Leu Met Ile Ser Arg Thr Pro Glu Val Thr Cys Val Val
            35                  40                  45

Val Asp Val Ser His Glu Asp Pro Glu Val Lys Phe Asn Trp Tyr Val
50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Asp Glu Leu Thr
130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly
225                 230

<210> SEQ ID NO 14
<211> LENGTH: 231
<212> TYPE: PRT
<213> ORGANISM: Artificial Sequence
<220> FEATURE:
<223> OTHER INFORMATION: hIgG1FcdeltaK-SSS Fc variant

<400> SEQUENCE: 14

Glu Pro Lys Ser Ser Asp Lys Thr His Thr Ser Pro Pro Ser Pro Ala
1               5                   10                  15

Pro Glu Leu Leu Gly Gly Pro Ser Val Phe Leu Phe Pro Pro Lys Pro
                20                  25                  30

Lys Asp Thr Leu Met Ile Ser Arg Thr Pro Glu Val Thr Cys Val Val
            35                  40                  45

Val Asp Val Ser His Glu Asp Pro Glu Val Lys Phe Asn Trp Tyr Val
50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95
```

```
Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
            115                 120                 125

Arg Glu Pro Gln Val Tyr Thr Leu Pro Pro Ser Arg Asp Glu Leu Thr
130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
            195                 200                 205

Ser Cys Ser Val Met His Glu Ala Leu His Asn His Tyr Thr Gln Lys
            210                 215                 220

Ser Leu Ser Leu Ser Pro Gly
225                 230

<210> SEQ ID NO 15
<211> LENGTH: 215
<212> TYPE: PRT
<213> ORGANISM: Artificial Sequence
<220> FEATURE:
<223> OTHER INFORMATION: hIgG2FcdeltaK-deltaC Fc variant

<400> SEQUENCE: 15

Ala Pro Pro Val Ala Gly Pro Ser Val Phe Leu Phe Pro Pro Lys Pro
1               5                   10                  15

Lys Asp Thr Leu Met Ile Ser Arg Thr Pro Glu Val Thr Cys Val Val
            20                  25                  30

Val Asp Val Ser His Glu Asp Pro Glu Val Gln Phe Asn Trp Tyr Val
        35                  40                  45

Asp Gly Val Glu Val His Asn Ala Lys Thr Lys Pro Arg Glu Glu Gln
50                  55                  60

Phe Asn Ser Thr Phe Arg Val Val Ser Val Leu Thr Val Val His Gln
65                  70                  75                  80

Asp Trp Leu Asn Gly Lys Glu Tyr Lys Cys Lys Val Ser Asn Lys Gly
            85                  90                  95

Leu Pro Ala Pro Ile Glu Lys Thr Ile Ser Lys Thr Lys Gly Gln Pro
            100                 105                 110

Arg Glu Pro Gln Val Tyr Thr Leu Pro Pro Ser Arg Glu Glu Met Thr
            115                 120                 125

Lys Asn Gln Val Ser Leu Thr Cys Leu Val Lys Gly Phe Tyr Pro Ser
130                 135                 140

Asp Ile Ser Val Glu Trp Glu Ser Asn Gly Gln Pro Glu Asn Asn Tyr
145                 150                 155                 160

Lys Thr Thr Pro Pro Met Leu Asp Ser Asp Gly Ser Phe Phe Leu Tyr
            165                 170                 175

Ser Lys Leu Thr Val Asp Lys Ser Arg Trp Gln Gln Gly Asn Val Phe
            180                 185                 190

Ser Cys Ser Val Met His Glu Ala Leu His Asn His Tyr Thr Gln Lys
            195                 200                 205

Ser Leu Ser Leu Ser Pro Gly
210                 215
```

<210> SEQ ID NO 16
<211> LENGTH: 219
<212> TYPE: PRT
<213> ORGANISM: Artificial Sequence
<220> FEATURE:
<223> OTHER INFORMATION: hIgG2FcdeltaK-C Fc variant

<400> SEQUENCE: 16

```
Pro Pro Cys Pro Ala Pro Pro Val Ala Gly Pro Ser Val Phe Leu Phe
1               5                   10                  15

Pro Pro Lys Pro Lys Asp Thr Leu Met Ile Ser Arg Thr Pro Glu Val
            20                  25                  30

Thr Cys Val Val Val Asp Val Ser His Glu Asp Pro Glu Val Gln Phe
        35                  40                  45

Asn Trp Tyr Val Asp Gly Val Glu Val His Asn Ala Lys Thr Lys Pro
    50                  55                  60

Arg Glu Glu Gln Phe Asn Ser Thr Phe Arg Val Val Ser Val Leu Thr
65                  70                  75                  80

Val Val His Gln Asp Trp Leu Asn Gly Lys Glu Tyr Lys Cys Lys Val
                85                  90                  95

Ser Asn Lys Gly Leu Pro Ala Pro Ile Glu Lys Thr Ile Ser Lys Thr
            100                 105                 110

Lys Gly Gln Pro Arg Glu Pro Gln Val Tyr Thr Leu Pro Pro Ser Arg
        115                 120                 125

Glu Glu Met Thr Lys Asn Gln Val Ser Leu Thr Cys Leu Val Lys Gly
    130                 135                 140

Phe Tyr Pro Ser Asp Ile Ser Val Glu Trp Glu Ser Asn Gly Gln Pro
145                 150                 155                 160

Glu Asn Asn Tyr Lys Thr Thr Pro Pro Met Leu Asp Ser Asp Gly Ser
                165                 170                 175

Phe Phe Leu Tyr Ser Lys Leu Thr Val Asp Lys Ser Arg Trp Gln Gln
            180                 185                 190

Gly Asn Val Phe Ser Cys Ser Val Met His Glu Ala Leu His Asn His
        195                 200                 205

Tyr Thr Gln Lys Ser Leu Ser Leu Ser Pro Gly
    210                 215
```

<210> SEQ ID NO 17
<211> LENGTH: 222
<212> TYPE: PRT
<213> ORGANISM: Artificial Sequence
<220> FEATURE:
<223> OTHER INFORMATION: hIgG2FcdeltaK-CC Fc variant

<400> SEQUENCE: 17

```
Val Glu Cys Pro Pro Cys Pro Ala Pro Pro Val Ala Gly Pro Ser Val
1               5                   10                  15

Phe Leu Phe Pro Pro Lys Pro Lys Asp Thr Leu Met Ile Ser Arg Thr
            20                  25                  30

Pro Glu Val Thr Cys Val Val Val Asp Val Ser His Glu Asp Pro Glu
        35                  40                  45

Val Gln Phe Asn Trp Tyr Val Asp Gly Val Glu Val His Asn Ala Lys
    50                  55                  60

Thr Lys Pro Arg Glu Glu Gln Phe Asn Ser Thr Phe Arg Val Val Ser
65                  70                  75                  80

Val Leu Thr Val Val His Gln Asp Trp Leu Asn Gly Lys Glu Tyr Lys
```

```
             85                  90                  95
Cys Lys Val Ser Asn Lys Gly Leu Pro Ala Pro Ile Glu Lys Thr Ile
            100                 105                 110

Ser Lys Thr Lys Gly Gln Pro Arg Glu Pro Gln Val Tyr Thr Leu Pro
            115                 120                 125

Pro Ser Arg Glu Glu Met Thr Lys Asn Gln Val Ser Leu Thr Cys Leu
            130                 135                 140

Val Lys Gly Phe Tyr Pro Ser Asp Ile Ser Val Glu Trp Glu Ser Asn
145                 150                 155                 160

Gly Gln Pro Glu Asn Asn Tyr Lys Thr Thr Pro Pro Met Leu Asp Ser
                165                 170                 175

Asp Gly Ser Phe Phe Leu Tyr Ser Lys Leu Thr Val Asp Lys Ser Arg
                180                 185                 190

Trp Gln Gln Gly Asn Val Phe Ser Cys Ser Val Met His Glu Ala Leu
                195                 200                 205

His Asn His Tyr Thr Gln Lys Ser Leu Ser Leu Ser Pro Gly
                210                 215                 220
```

<210> SEQ ID NO 18
<211> LENGTH: 228
<212> TYPE: PRT
<213> ORGANISM: Artificial Sequence
<220> FEATURE:
<223> OTHER INFORMATION: hIgG2Fc-CCCC Fc variant

<400> SEQUENCE: 18

```
Glu Arg Lys Cys Cys Val Glu Cys Pro Cys Pro Ala Pro Pro Val
1               5                   10                  15

Ala Gly Pro Ser Val Phe Leu Phe Pro Pro Lys Pro Lys Asp Thr Leu
                20                  25                  30

Met Ile Ser Arg Thr Pro Glu Val Thr Cys Val Val Val Asp Val Ser
                35                  40                  45

His Glu Asp Pro Glu Val Gln Phe Asn Trp Tyr Val Asp Gly Val Glu
            50                  55                  60

Val His Asn Ala Lys Thr Lys Pro Arg Glu Glu Gln Phe Asn Ser Thr
65                  70                  75                  80

Phe Arg Val Val Ser Val Leu Thr Val Val His Gln Asp Trp Leu Asn
                85                  90                  95

Gly Lys Glu Tyr Lys Cys Lys Val Ser Asn Lys Gly Leu Pro Ala Pro
            100                 105                 110

Ile Glu Lys Thr Ile Ser Lys Thr Lys Gly Gln Pro Arg Glu Pro Gln
            115                 120                 125

Val Tyr Thr Leu Pro Pro Ser Arg Glu Glu Met Thr Lys Asn Gln Val
            130                 135                 140

Ser Leu Thr Cys Leu Val Lys Gly Phe Tyr Pro Ser Asp Ile Ser Val
145                 150                 155                 160

Glu Trp Glu Ser Asn Gly Gln Pro Glu Asn Asn Tyr Lys Thr Thr Pro
                165                 170                 175

Pro Met Leu Asp Ser Asp Gly Ser Phe Phe Leu Tyr Ser Lys Leu Thr
                180                 185                 190

Val Asp Lys Ser Arg Trp Gln Gln Gly Asn Val Phe Ser Cys Ser Val
                195                 200                 205

Met His Glu Ala Leu His Asn His Tyr Thr Gln Lys Ser Leu Ser Leu
            210                 215                 220

Ser Pro Gly Lys
```

<210> SEQ ID NO 19
<211> LENGTH: 227
<212> TYPE: PRT
<213> ORGANISM: Artificial Sequence
<220> FEATURE:
<223> OTHER INFORMATION: hIgG2FcdeltaK-SS Fc variant

<400> SEQUENCE: 19

```
Glu Arg Lys Ser Ser Val Glu Cys Pro Pro Cys Pro Ala Pro Pro Val
1               5                   10                  15
Ala Gly Pro Ser Val Phe Leu Phe Pro Pro Lys Pro Lys Asp Thr Leu
            20                  25                  30
Met Ile Ser Arg Thr Pro Glu Val Thr Cys Val Val Val Asp Val Ser
        35                  40                  45
His Glu Asp Pro Glu Val Gln Phe Asn Trp Tyr Val Asp Gly Val Glu
    50                  55                  60
Val His Asn Ala Lys Thr Lys Pro Arg Glu Glu Gln Phe Asn Ser Thr
65                  70                  75                  80
Phe Arg Val Val Ser Val Leu Thr Val Val His Gln Asp Trp Leu Asn
                85                  90                  95
Gly Lys Glu Tyr Lys Cys Lys Val Ser Asn Lys Gly Leu Pro Ala Pro
            100                 105                 110
Ile Glu Lys Thr Ile Ser Lys Thr Lys Gly Gln Pro Arg Glu Pro Gln
        115                 120                 125
Val Tyr Thr Leu Pro Pro Ser Arg Glu Glu Met Thr Lys Asn Gln Val
    130                 135                 140
Ser Leu Thr Cys Leu Val Lys Gly Phe Tyr Pro Ser Asp Ile Ser Val
145                 150                 155                 160
Glu Trp Glu Ser Asn Gly Gln Pro Glu Asn Asn Tyr Lys Thr Thr Pro
                165                 170                 175
Pro Met Leu Asp Ser Asp Gly Ser Phe Phe Leu Tyr Ser Lys Leu Thr
            180                 185                 190
Val Asp Lys Ser Arg Trp Gln Gln Gly Asn Val Phe Ser Cys Ser Val
        195                 200                 205
Met His Glu Ala Leu His Asn His Tyr Thr Gln Lys Ser Leu Ser Leu
    210                 215                 220
Ser Pro Gly
225
```

<210> SEQ ID NO 20
<211> LENGTH: 227
<212> TYPE: PRT
<213> ORGANISM: Artificial Sequence
<220> FEATURE:
<223> OTHER INFORMATION: hIgG2FcdeltaK-SSS Fc variant

<400> SEQUENCE: 20

```
Glu Arg Lys Ser Ser Val Glu Ser Pro Pro Cys Pro Ala Pro Pro Val
1               5                   10                  15
Ala Gly Pro Ser Val Phe Leu Phe Pro Pro Lys Pro Lys Asp Thr Leu
            20                  25                  30
Met Ile Ser Arg Thr Pro Glu Val Thr Cys Val Val Val Asp Val Ser
        35                  40                  45
His Glu Asp Pro Glu Val Gln Phe Asn Trp Tyr Val Asp Gly Val Glu
    50                  55                  60
```

Val His Asn Ala Lys Thr Lys Pro Arg Glu Glu Gln Phe Asn Ser Thr
 65                  70                  75                  80

Phe Arg Val Val Ser Val Leu Thr Val Val His Gln Asp Trp Leu Asn
                 85                  90                  95

Gly Lys Glu Tyr Lys Cys Lys Val Ser Asn Lys Gly Leu Pro Ala Pro
             100                 105                 110

Ile Glu Lys Thr Ile Ser Lys Thr Lys Gly Gln Pro Arg Glu Pro Gln
         115                 120                 125

Val Tyr Thr Leu Pro Pro Ser Arg Glu Glu Met Thr Lys Asn Gln Val
130                 135                 140

Ser Leu Thr Cys Leu Val Lys Gly Phe Tyr Pro Ser Asp Ile Ser Val
145                 150                 155                 160

Glu Trp Glu Ser Asn Gly Gln Pro Glu Asn Asn Tyr Lys Thr Thr Pro
                165                 170                 175

Pro Met Leu Asp Ser Asp Gly Ser Phe Phe Leu Tyr Ser Lys Leu Thr
             180                 185                 190

Val Asp Lys Ser Arg Trp Gln Gln Gly Asn Val Phe Ser Cys Ser Val
         195                 200                 205

Met His Glu Ala Leu His Asn His Tyr Thr Gln Lys Ser Leu Ser Leu
210                 215                 220

Ser Pro Gly
225

<210> SEQ ID NO 21
<211> LENGTH: 227
<212> TYPE: PRT
<213> ORGANISM: Artificial Sequence
<220> FEATURE:
<223> OTHER INFORMATION: hIgG2FcdeltaK-SSSS Fc variant

<400> SEQUENCE: 21

Glu Arg Lys Ser Ser Val Glu Ser Pro Pro Ser Pro Ala Pro Pro Val
1               5                   10                  15

Ala Gly Pro Ser Val Phe Leu Phe Pro Pro Lys Pro Lys Asp Thr Leu
             20                  25                  30

Met Ile Ser Arg Thr Pro Glu Val Thr Cys Val Val Val Asp Val Ser
         35                  40                  45

His Glu Asp Pro Glu Val Gln Phe Asn Trp Tyr Val Asp Gly Val Glu
 50                  55                  60

Val His Asn Ala Lys Thr Lys Pro Arg Glu Glu Gln Phe Asn Ser Thr
 65                  70                  75                  80

Phe Arg Val Val Ser Val Leu Thr Val Val His Gln Asp Trp Leu Asn
                 85                  90                  95

Gly Lys Glu Tyr Lys Cys Lys Val Ser Asn Lys Gly Leu Pro Ala Pro
             100                 105                 110

Ile Glu Lys Thr Ile Ser Lys Thr Lys Gly Gln Pro Arg Glu Pro Gln
         115                 120                 125

Val Tyr Thr Leu Pro Pro Ser Arg Glu Glu Met Thr Lys Asn Gln Val
130                 135                 140

Ser Leu Thr Cys Leu Val Lys Gly Phe Tyr Pro Ser Asp Ile Ser Val
145                 150                 155                 160

Glu Trp Glu Ser Asn Gly Gln Pro Glu Asn Asn Tyr Lys Thr Thr Pro
                165                 170                 175

Pro Met Leu Asp Ser Asp Gly Ser Phe Phe Leu Tyr Ser Lys Leu Thr
             180                 185                 190

```
Val Asp Lys Ser Arg Trp Gln Gln Gly Asn Val Phe Ser Cys Ser Val
            195                 200                 205

Met His Glu Ala Leu His Asn His Tyr Thr Gln Lys Ser Leu Ser Leu
    210                 215                 220

Ser Pro Gly
225

<210> SEQ ID NO 22
<211> LENGTH: 216
<212> TYPE: PRT
<213> ORGANISM: Artificial Sequence
<220> FEATURE:
<223> OTHER INFORMATION: hIgG3FcdeltaK-deltaC Fc variant

<400> SEQUENCE: 22

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Gln Phe Lys Trp Tyr
        35                  40                  45

Val Asp Gly Val Glu Val His Asn Ala Lys Thr Lys Pro Arg Glu Glu
    50                  55                  60

Gln Tyr Asn Ser Thr Phe Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Thr Lys Gly Gln
            100                 105                 110

Pro Arg Glu Pro Gln Val Tyr Thr Leu Pro Pro Ser Arg Glu Glu Met
        115                 120                 125

Thr Lys Asn Gln Val Ser Leu Thr Cys Leu Val Lys Gly Phe Tyr Pro
    130                 135                 140

Ser Asp Ile Ala Val Glu Trp Glu Ser Ser Gly Gln Pro Glu Asn Asn
145                 150                 155                 160

Tyr Asn Thr Thr Pro Pro Met Leu Asp Ser Asp Gly Ser Phe Phe Leu
                165                 170                 175

Tyr Ser Lys Leu Thr Val Asp Lys Ser Arg Trp Gln Gln Gly Asn Ile
            180                 185                 190

Phe Ser Cys Ser Val Met His Glu Ala Leu His Asn Arg Phe Thr Gln
        195                 200                 205

Lys Ser Leu Ser Leu Ser Pro Gly
    210                 215

<210> SEQ ID NO 23
<211> LENGTH: 220
<212> TYPE: PRT
<213> ORGANISM: Artificial Sequence
<220> FEATURE:
<223> OTHER INFORMATION: hIgG3FcdeltaK-C Fc variant

<400> SEQUENCE: 23

Pro Arg Cys Pro Ala Pro Glu Leu Leu Gly Gly Pro Ser Val Phe Leu
1               5                   10                  15

Phe Pro Pro Lys Pro Lys Asp Thr Leu Met Ile Ser Arg Thr Pro Glu
            20                  25                  30

Val Thr Cys Val Val Val Asp Val Ser His Glu Asp Pro Glu Val Gln
        35                  40                  45
```

```
Phe Lys Trp Tyr Val Asp Gly Val Glu Val His Asn Ala Lys Thr Lys
 50                  55                  60

Pro Arg Glu Glu Gln Tyr Asn Ser Thr Phe Arg Val Val Ser Val Leu
 65                  70                  75                  80

Thr Val Leu His Gln Asp Trp Leu Asn Gly Lys Glu Tyr Lys Cys Lys
                 85                  90                  95

Val Ser Asn Lys Ala Leu Pro Ala Pro Ile Glu Lys Thr Ile Ser Lys
                100                 105                 110

Thr Lys Gly Gln Pro Arg Glu Pro Gln Val Tyr Thr Leu Pro Pro Ser
            115                 120                 125

Arg Glu Glu Met Thr Lys Asn Gln Val Ser Leu Thr Cys Leu Val Lys
130                 135                 140

Gly Phe Tyr Pro Ser Asp Ile Ala Val Glu Trp Glu Ser Ser Gly Gln
145                 150                 155                 160

Pro Glu Asn Asn Tyr Asn Thr Thr Pro Pro Met Leu Asp Ser Asp Gly
                165                 170                 175

Ser Phe Phe Leu Tyr Ser Lys Leu Thr Val Asp Lys Ser Arg Trp Gln
                180                 185                 190

Gln Gly Asn Ile Phe Ser Cys Ser Val Met His Glu Ala Leu His Asn
            195                 200                 205

Arg Phe Thr Gln Lys Ser Leu Ser Leu Ser Pro Gly
210                 215                 220

<210> SEQ ID NO 24
<211> LENGTH: 226
<212> TYPE: PRT
<213> ORGANISM: Artificial Sequence
<220> FEATURE:
<223> OTHER INFORMATION: hIgG3FcdeltaK-CC Fc variant

<400> SEQUENCE: 24

Asp Thr Pro Pro Cys Pro Arg Cys Pro Ala Pro Glu Leu Leu Gly
 1               5                  10                  15

Gly Pro Ser Val Phe Leu Phe Pro Pro Lys Pro Lys Asp Thr Leu Met
                 20                  25                  30

Ile Ser Arg Thr Pro Glu Val Thr Cys Val Val Val Asp Val Ser His
             35                  40                  45

Glu Asp Pro Glu Val Gln Phe Lys Trp Tyr Val Asp Gly Val Glu Val
 50                  55                  60

His Asn Ala Lys Thr Lys Pro Arg Glu Glu Gln Tyr Asn Ser Thr Phe
 65                  70                  75                  80

Arg Val Val Ser Val Leu Thr Val Leu His Gln Asp Trp Leu Asn Gly
                 85                  90                  95

Lys Glu Tyr Lys Cys Lys Val Ser Asn Lys Ala Leu Pro Ala Pro Ile
            100                 105                 110

Glu Lys Thr Ile Ser Lys Thr Lys Gly Gln Pro Arg Glu Pro Gln Val
            115                 120                 125

Tyr Thr Leu Pro Pro Ser Arg Glu Glu Met Thr Lys Asn Gln Val Ser
130                 135                 140

Leu Thr Cys Leu Val Lys Gly Phe Tyr Pro Ser Asp Ile Ala Val Glu
145                 150                 155                 160

Trp Glu Ser Ser Gly Gln Pro Glu Asn Asn Tyr Asn Thr Thr Pro Pro
                165                 170                 175

Met Leu Asp Ser Asp Gly Ser Phe Phe Leu Tyr Ser Lys Leu Thr Val
                180                 185                 190
```

Asp Lys Ser Arg Trp Gln Gln Gly Asn Ile Phe Ser Cys Ser Val Met
        195                 200                 205

His Glu Ala Leu His Asn Arg Phe Thr Gln Lys Ser Leu Ser Leu Ser
    210                 215                 220

Pro Gly
225

<210> SEQ ID NO 25
<211> LENGTH: 231
<212> TYPE: PRT
<213> ORGANISM: Artificial Sequence
<220> FEATURE:
<223> OTHER INFORMATION: hIgG3FcdeltaK-S Fc variant

<400> SEQUENCE: 25

Glu Pro Lys Ser Ser Asp Thr Pro Pro Cys Pro Arg Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Gln Phe Lys Trp Tyr Val
    50                  55                  60

Asp Gly Val Glu Val His Asn Ala Lys Thr Lys Pro Arg Glu Glu Gln
65                  70                  75                  80

Tyr Asn Ser Thr Phe Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Thr Lys Gly Gln Pro
        115                 120                 125

Arg Glu Pro Gln Val Tyr Thr Leu Pro Pro Ser Arg Glu Glu Met Thr
    130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Ser Gly Gln Pro Glu Asn Asn Tyr
                165                 170                 175

Asn Thr Thr Pro Pro Met Leu Asp Ser Asp Gly Ser Phe Phe Leu Tyr
            180                 185                 190

Ser Lys Leu Thr Val Asp Lys Ser Arg Trp Gln Gln Gly Asn Ile Phe
        195                 200                 205

Ser Cys Ser Val Met His Glu Ala Leu His Asn Arg Phe Thr Gln Lys
    210                 215                 220

Ser Leu Ser Leu Ser Pro Gly
225                 230

<210> SEQ ID NO 26
<211> LENGTH: 231
<212> TYPE: PRT
<213> ORGANISM: Artificial Sequence
<220> FEATURE:
<223> OTHER INFORMATION: hIgG3FcdeltaK-SS Fc variant

<400> SEQUENCE: 26

Glu Pro Lys Ser Ser Asp Thr Pro Pro Ser Pro Arg Cys Pro Ala
1               5                   10                  15

Pro Glu Leu Leu Gly Gly Pro Ser Val Phe Leu Phe Pro Pro Lys Pro

```
                    20                  25                  30
Lys Asp Thr Leu Met Ile Ser Arg Thr Pro Glu Val Thr Cys Val Val
             35                  40                  45

Val Asp Val Ser His Glu Asp Pro Glu Val Gln Phe Lys Trp Tyr Val
 50                  55                  60

Asp Gly Val Glu Val His Asn Ala Lys Thr Lys Pro Arg Glu Glu Gln
 65                  70                  75                  80

Tyr Asn Ser Thr Phe Arg Val Val Ser Val Leu Thr Val Leu His Gln
                 85                  90                  95

Asp Trp Leu Asn Gly Lys Glu Tyr Lys Cys Lys Val Ser Asn Lys Ala
                100                 105                 110

Leu Pro Ala Pro Ile Glu Lys Thr Ile Ser Lys Thr Lys Gly Gln Pro
            115                 120                 125

Arg Glu Pro Gln Val Tyr Thr Leu Pro Pro Ser Arg Glu Glu Met Thr
        130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Ser Gly Gln Pro Glu Asn Asn Tyr
                165                 170                 175

Asn Thr Thr Pro Pro Met Leu Asp Ser Asp Gly Ser Phe Phe Leu Tyr
            180                 185                 190

Ser Lys Leu Thr Val Asp Lys Ser Arg Trp Gln Gln Gly Asn Ile Phe
        195                 200                 205

Ser Cys Ser Val Met His Glu Ala Leu His Asn Arg Phe Thr Gln Lys
    210                 215                 220

Ser Leu Ser Leu Ser Pro Gly
225                 230

<210> SEQ ID NO 27
<211> LENGTH: 231
<212> TYPE: PRT
<213> ORGANISM: Artificial Sequence
<220> FEATURE:
<223> OTHER INFORMATION: hIgG3FcdeltaK-SSS Fc variant

<400> SEQUENCE: 27

Glu Pro Lys Ser Ser Asp Thr Pro Pro Ser Pro Arg Ser Pro Ala
1               5                  10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Gln Phe Lys Trp Tyr Val
 50                  55                  60

Asp Gly Val Glu Val His Asn Ala Lys Thr Lys Pro Arg Glu Glu Gln
 65                  70                  75                  80

Tyr Asn Ser Thr Phe Arg Val Val Ser Val Leu Thr Val Leu His Gln
                 85                  90                  95

Asp Trp Leu Asn Gly Lys Glu Tyr Lys Cys Lys Val Ser Asn Lys Ala
                100                 105                 110

Leu Pro Ala Pro Ile Glu Lys Thr Ile Ser Lys Thr Lys Gly Gln Pro
            115                 120                 125

Arg Glu Pro Gln Val Tyr Thr Leu Pro Pro Ser Arg Glu Glu Met Thr
        130                 135                 140

Lys Asn Gln Val Ser Leu Thr Cys Leu Val Lys Gly Phe Tyr Pro Ser
```

```
                145                 150                 155                 160
Asp Ile Ala Val Glu Trp Glu Ser Ser Gly Gln Pro Glu Asn Asn Tyr
                        165                 170                 175

Asn Thr Thr Pro Pro Met Leu Asp Ser Asp Gly Ser Phe Phe Leu Tyr
                    180                 185                 190

Ser Lys Leu Thr Val Asp Lys Ser Arg Trp Gln Gln Gly Asn Ile Phe
                195                 200                 205

Ser Cys Ser Val Met His Glu Ala Leu His Asn Arg Phe Thr Gln Lys
            210                 215                 220

Ser Leu Ser Leu Ser Pro Gly
225                 230

<210> SEQ ID NO 28
<211> LENGTH: 216
<212> TYPE: PRT
<213> ORGANISM: Artificial Sequence
<220> FEATURE:
<223> OTHER INFORMATION: hIgG4FcdeltaK-deltaC Fc variant

<400> SEQUENCE: 28

Ala Pro Glu Phe Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
                20                  25                  30

Val Val Asp Val Ser Gln Glu Asp Pro Glu Val Gln Phe Asn Trp Tyr
            35                  40                  45

Val Asp Gly Val Glu Val His Asn Ala Lys Thr Lys Pro Arg Glu Glu
        50                  55                  60

Gln Phe Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Gly Leu Pro Ser Ser Ile Glu Lys Thr Ile Ser Lys Ala Lys Gly Gln
            100                 105                 110

Pro Arg Glu Pro Gln Val Tyr Thr Leu Pro Pro Ser Gln Glu Glu Met
        115                 120                 125

Thr Lys Asn Gln Val Ser Leu Thr Cys Leu Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Tyr Ser Arg Leu Thr Val Asp Lys Ser Arg Trp Gln Glu Gly Asn Val
            180                 185                 190

Phe Ser Cys Ser Val Met His Glu Ala Leu His Asn His Tyr Thr Gln
        195                 200                 205

Lys Ser Leu Ser Leu Ser Leu Gly
    210                 215

<210> SEQ ID NO 29
<211> LENGTH: 220
<212> TYPE: PRT
<213> ORGANISM: Artificial Sequence
<220> FEATURE:
<223> OTHER INFORMATION: hIgG4FcdeltaK-C Fc variant

<400> SEQUENCE: 29
```

```
Pro Ser Cys Pro Ala Pro Glu Phe Leu Gly Pro Ser Val Phe Leu
1               5                   10                  15

Phe Pro Pro Lys Pro Lys Asp Thr Leu Met Ile Ser Arg Thr Pro Glu
            20                  25                  30

Val Thr Cys Val Val Val Asp Val Ser Gln Glu Asp Pro Glu Val Gln
        35                  40                  45

Phe Asn Trp Tyr Val Asp Gly Val Glu Val His Asn Ala Lys Thr Lys
    50                  55                  60

Pro Arg Glu Glu Gln Phe Asn Ser Thr Tyr Arg Val Val Ser Val Leu
65                  70                  75                  80

Thr Val Leu His Gln Asp Trp Leu Asn Gly Lys Glu Tyr Lys Cys Lys
                85                  90                  95

Val Ser Asn Lys Gly Leu Pro Ser Ser Ile Glu Lys Thr Ile Ser Lys
            100                 105                 110

Ala Lys Gly Gln Pro Arg Glu Pro Gln Val Tyr Thr Leu Pro Pro Ser
        115                 120                 125

Gln Glu Glu Met Thr Lys Asn Gln Val Ser Leu Thr Cys Leu Val Lys
    130                 135                 140

Gly Phe Tyr Pro Ser Asp Ile Ala Val Glu Trp Glu Ser Asn Gly Gln
145                 150                 155                 160

Pro Glu Asn Asn Tyr Lys Thr Thr Pro Pro Val Leu Asp Ser Asp Gly
                165                 170                 175

Ser Phe Phe Leu Tyr Ser Arg Leu Thr Val Asp Lys Ser Arg Trp Gln
            180                 185                 190

Glu Gly Asn Val Phe Ser Cys Ser Val Met His Glu Ala Leu His Asn
        195                 200                 205

His Tyr Thr Gln Lys Ser Leu Ser Leu Ser Leu Gly
    210                 215                 220

<210> SEQ ID NO 30
<211> LENGTH: 228
<212> TYPE: PRT
<213> ORGANISM: Artificial Sequence
<220> FEATURE:
<223> OTHER INFORMATION: hIgG4FcdeltaK-CC Fc variant

<400> SEQUENCE: 30

Glu Ser Lys Tyr Gly Pro Pro Cys Pro Ser Cys Pro Ala Pro Glu Phe
1               5                   10                  15

Leu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
        115                 120                 125

Gln Val Tyr Thr Leu Pro Pro Ser Gln Glu Glu Met Thr Lys Asn Gln
    130                 135                 140
```

```
Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
            165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
            195                 200                 205

Val Met His Glu Ala Leu His Asn His Tyr Thr Gln Lys Ser Leu Ser
            210                 215                 220

Leu Ser Leu Gly
225

<210> SEQ ID NO 31
<211> LENGTH: 228
<212> TYPE: PRT
<213> ORGANISM: Artificial Sequence
<220> FEATURE:
<223> OTHER INFORMATION: hIgG4FcdeltaK-CC-228P Fc variant

<400> SEQUENCE: 31

Glu Ser Lys Tyr Gly Pro Pro Cys Pro Pro Cys Pro Ala Pro Glu Phe
1               5                   10                  15

Leu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
            35                  40                  45

Ser Gln Glu Asp Pro Glu Val Gln Phe Asn Trp Tyr Val Asp Gly Val
50                  55                  60

Glu Val His Asn Ala Lys Thr Lys Pro Arg Glu Glu Gln Phe Asn Ser
65                  70                  75                  80

Thr Tyr Arg Val Val Ser Val Leu Thr Val Leu His Gln Asp Trp Leu
            85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
            115                 120                 125

Gln Val Tyr Thr Leu Pro Pro Ser Gln Glu Glu Met Thr Lys Asn Gln
130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
            165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
            195                 200                 205

Val Met His Glu Ala Leu His Asn His Tyr Thr Gln Lys Ser Leu Ser
            210                 215                 220

Leu Ser Leu Gly
225

<210> SEQ ID NO 32
<211> LENGTH: 228
<212> TYPE: PRT
<213> ORGANISM: Artificial Sequence
<220> FEATURE:
```

<223> OTHER INFORMATION: hIgG4FcdeltaK-CC-228P-409K Fc variant

<400> SEQUENCE: 32

```
Glu Ser Lys Tyr Gly Pro Pro Cys Pro Pro Cys Pro Ala Pro Glu Phe
1               5                   10                  15
Leu Gly Gly Pro Ser Val Phe Leu Phe Pro Pro Lys Pro Lys Asp Thr
            20                  25                  30
Leu Met Ile Ser Arg Thr Pro Glu Val Thr Cys Val Val Val Asp Val
        35                  40                  45
Ser Gln Glu Asp Pro Glu Val Gln Phe Asn Trp Tyr Val Asp Gly Val
    50                  55                  60
Glu Val His Asn Ala Lys Thr Lys Pro Arg Glu Gln Phe Asn Ser
65                  70                  75                  80
Thr Tyr Arg Val Val Ser Val Leu Thr Val Leu His Gln Asp Trp Leu
                85                  90                  95
Asn Gly Lys Glu Tyr Lys Cys Lys Val Ser Asn Lys Gly Leu Pro Ser
            100                 105                 110
Ser Ile Glu Lys Thr Ile Ser Lys Ala Lys Gly Gln Pro Arg Glu Pro
        115                 120                 125
Gln Val Tyr Thr Leu Pro Pro Ser Gln Glu Glu Met Thr Lys Asn Gln
    130                 135                 140
Val Ser Leu Thr Cys Leu Val Lys Gly Phe Tyr Pro Ser Asp Ile Ala
145                 150                 155                 160
Val Glu Trp Glu Ser Asn Gly Gln Pro Glu Asn Asn Tyr Lys Thr Thr
                165                 170                 175
Pro Pro Val Leu Asp Ser Asp Gly Ser Phe Phe Leu Tyr Ser Lys Leu
            180                 185                 190
Thr Val Asp Lys Ser Arg Trp Gln Glu Gly Asn Val Phe Ser Cys Ser
        195                 200                 205
Val Met His Glu Ala Leu His Asn His Tyr Thr Gln Lys Ser Leu Ser
    210                 215                 220
Leu Ser Leu Gly
225
```

<210> SEQ ID NO 33
<211> LENGTH: 228
<212> TYPE: PRT
<213> ORGANISM: Artificial Sequence
<220> FEATURE:
<223> OTHER INFORMATION: hIgG4FcdeltaK-S Fc variant

<400> SEQUENCE: 33

```
Glu Ser Lys Tyr Gly Pro Pro Ser Pro Ser Cys Pro Ala Pro Glu Phe
1               5                   10                  15
Leu Gly Gly Pro Ser Val Phe Leu Phe Pro Pro Lys Pro Lys Asp Thr
            20                  25                  30
Leu Met Ile Ser Arg Thr Pro Glu Val Thr Cys Val Val Val Asp Val
        35                  40                  45
Ser Gln Glu Asp Pro Glu Val Gln Phe Asn Trp Tyr Val Asp Gly Val
    50                  55                  60
Glu Val His Asn Ala Lys Thr Lys Pro Arg Glu Gln Phe Asn Ser
65                  70                  75                  80
Thr Tyr Arg Val Val Ser Val Leu Thr Val Leu His Gln Asp Trp Leu
                85                  90                  95
Asn Gly Lys Glu Tyr Lys Cys Lys Val Ser Asn Lys Gly Leu Pro Ser
            100                 105                 110
```

```
Ser Ile Glu Lys Thr Ile Ser Lys Ala Lys Gly Gln Pro Arg Glu Pro
            115                 120                 125

Gln Val Tyr Thr Leu Pro Pro Ser Gln Glu Glu Met Thr Lys Asn Gln
        130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
210                 215                 220

Leu Ser Leu Gly
225

<210> SEQ ID NO 34
<211> LENGTH: 228
<212> TYPE: PRT
<213> ORGANISM: Artificial Sequence
<220> FEATURE:
<223> OTHER INFORMATION: hIgG4FcdeltaK-SS Fc variant

<400> SEQUENCE: 34

Glu Ser Lys Tyr Gly Pro Pro Ser Pro Ser Ser Pro Ala Pro Glu Phe
1               5                   10                  15

Leu Gly Gly Pro Ser Val Phe Leu Phe Pro Pro Lys Pro Lys Asp Thr
                20                  25                  30

Leu Met Ile Ser Arg Thr Pro Glu Val Thr Cys Val Val Val Asp Val
            35                  40                  45

Ser Gln Glu Asp Pro Glu Val Gln Phe Asn Trp Tyr Val Asp Gly Val
        50                  55                  60

Glu Val His Asn Ala Lys Thr Lys Pro Arg Glu Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
        115                 120                 125

Gln Val Tyr Thr Leu Pro Pro Ser Gln Glu Glu Met Thr Lys Asn Gln
    130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
210                 215                 220

Leu Ser Leu Gly
225
```

<210> SEQ ID NO 35
<211> LENGTH: 101
<212> TYPE: PRT
<213> ORGANISM: Artificial Sequence
<220> FEATURE:
<223> OTHER INFORMATION: TbetaRII-ED structured domain

<400> SEQUENCE: 35

Gln Leu Cys Lys Phe Cys Asp Val Arg Phe Ser Thr Cys Asp Asn Gln
1               5                   10                  15

Lys Ser Cys Met Ser Asn Cys Ser Ile Thr Ser Ile Cys Glu Lys Pro
            20                  25                  30

Gln Glu Val Cys Val Ala Val Trp Arg Lys Asn Asp Glu Asn Ile Thr
        35                  40                  45

Leu Glu Thr Val Cys His Asp Pro Lys Leu Pro Tyr His Asp Phe Ile
    50                  55                  60

Leu Glu Asp Ala Ala Ser Pro Lys Cys Ile Met Lys Glu Lys Lys
65                  70                  75                  80

Pro Gly Glu Thr Phe Phe Met Cys Ser Cys Ser Ser Asp Glu Cys Asn
                85                  90                  95

Asp Asn Ile Ile Phe
            100

<210> SEQ ID NO 36
<211> LENGTH: 25
<212> TYPE: PRT
<213> ORGANISM: Artificial Sequence
<220> FEATURE:
<223> OTHER INFORMATION: TbetaRII-ED N-term unstructured region and
      natural linker

<400> SEQUENCE: 36

Ile Pro Pro His Val Gln Lys Ser Val Asn Asn Asp Met Ile Val Thr
1               5                   10                  15

Asp Asn Asn Gly Ala Val Lys Phe Pro
            20                  25

<210> SEQ ID NO 37
<211> LENGTH: 50
<212> TYPE: PRT
<213> ORGANISM: Artificial Sequence
<220> FEATURE:
<223> OTHER INFORMATION: TbetaRIIb-ED N-term unstructured region and
      natural linker

<400> SEQUENCE: 37

Ile Pro Pro His Val Gln Lys Ser Asp Val Glu Met Glu Ala Gln Lys
1               5                   10                  15

Asp Glu Ile Ile Cys Pro Ser Cys Asn Arg Thr Ala His Pro Leu Arg
            20                  25                  30

His Ile Asn Asn Asp Met Ile Val Thr Asp Asn Asn Gly Ala Val Lys
        35                  40                  45

Phe Pro
    50

<210> SEQ ID NO 38
<211> LENGTH: 50
<212> TYPE: PRT
<213> ORGANISM: Artificial Sequence
<220> FEATURE:
<223> OTHER INFORMATION: TbetaRIIb-ED Cys-mutated N-term unstructured region and natural linker

<400> SEQUENCE: 38

Ile Pro Pro His Val Gln Lys Ser Asp Val Glu Met Glu Ala Gln Lys
1               5                   10                  15

Asp Glu Ile Ile Ala Pro Ser Ala Asn Arg Thr Ala His Pro Leu Arg
            20                  25                  30

His Ile Asn Asn Asp Met Ile Val Thr Asp Asn Asn Gly Ala Val Lys
        35                  40                  45

Phe Pro
    50

<210> SEQ ID NO 39
<211> LENGTH: 10
<212> TYPE: PRT
<213> ORGANISM: Artificial Sequence
<220> FEATURE:
<223> OTHER INFORMATION: TbetaRII-ED C-term unstructured region and
      natural linker

<400> SEQUENCE: 39

Ser Glu Glu Tyr Asn Thr Ser Asn Pro Asp
1               5                   10

<210> SEQ ID NO 40
<211> LENGTH: 35
<212> TYPE: PRT
<213> ORGANISM: Artificial Sequence
<220> FEATURE:
<223> OTHER INFORMATION: TbetaRII-ED natural linker

<400> SEQUENCE: 40

Ser Glu Glu Tyr Asn Thr Ser Asn Pro Asp Ile Pro Pro His Val Gln
1               5                   10                  15

Lys Ser Val Asn Asn Asp Met Ile Val Thr Asp Asn Asn Gly Ala Val
            20                  25                  30

Lys Phe Pro
        35

<210> SEQ ID NO 41
<211> LENGTH: 60
<212> TYPE: PRT
<213> ORGANISM: Artificial Sequence
<220> FEATURE:
<223> OTHER INFORMATION: TbetaRIIb-ED natural linker

<400> SEQUENCE: 41

Ser Glu Glu Tyr Asn Thr Ser Asn Pro Asp Ile Pro Pro His Val Gln
1               5                   10                  15

Lys Ser Asp Val Glu Met Glu Ala Gln Lys Asp Glu Ile Ile Cys Pro
            20                  25                  30

Ser Cys Asn Arg Thr Ala His Pro Leu Arg His Ile Asn Asn Asp Met
        35                  40                  45

Ile Val Thr Asp Asn Asn Gly Ala Val Lys Phe Pro
50                  55                  60

<210> SEQ ID NO 42
<211> LENGTH: 60
<212> TYPE: PRT
<213> ORGANISM: Artificial Sequence
<220> FEATURE:
<223> OTHER INFORMATION: TbetaRIIb-ED Cys-mutated linker

```
<400> SEQUENCE: 42

Ser Glu Glu Tyr Asn Thr Ser Asn Pro Asp Ile Pro Pro His Val Gln
1               5                   10                  15

Lys Ser Asp Val Glu Met Glu Ala Gln Lys Asp Glu Ile Ile Ala Pro
            20                  25                  30

Ser Ala Asn Arg Thr Ala His Pro Leu Arg His Ile Asn Asn Asp Met
        35                  40                  45

Ile Val Thr Asp Asn Asn Gly Ala Val Lys Phe Pro
    50                  55                  60

<210> SEQ ID NO 43
<211> LENGTH: 136
<212> TYPE: PRT
<213> ORGANISM: Artificial Sequence
<220> FEATURE:
<223> OTHER INFORMATION: TbetaRII-ED monomer, also termed T2 or T2m

<400> SEQUENCE: 43

Ile Pro Pro His Val Gln Lys Ser Val Asn Asn Asp Met Ile Val Thr
1               5                   10                  15

Asp Asn Asn Gly Ala Val Lys Phe Pro Gln Leu Cys Lys Phe Cys Asp
            20                  25                  30

Val Arg Phe Ser Thr Cys Asp Asn Gln Lys Ser Cys Met Ser Asn Cys
        35                  40                  45

Ser Ile Thr Ser Ile Cys Glu Lys Pro Gln Glu Val Cys Val Ala Val
    50                  55                  60

Trp Arg Lys Asn Asp Glu Asn Ile Thr Leu Glu Thr Val Cys His Asp
65                  70                  75                  80

Pro Lys Leu Pro Tyr His Asp Phe Ile Leu Glu Asp Ala Ala Ser Pro
                85                  90                  95

Lys Cys Ile Met Lys Glu Lys Lys Lys Pro Gly Glu Thr Phe Phe Met
            100                 105                 110

Cys Ser Cys Ser Ser Asp Glu Cys Asn Asp Asn Ile Ile Phe Ser Glu
        115                 120                 125

Glu Tyr Asn Thr Ser Asn Pro Asp
    130                 135

<210> SEQ ID NO 44
<211> LENGTH: 161
<212> TYPE: PRT
<213> ORGANISM: Artificial Sequence
<220> FEATURE:
<223> OTHER INFORMATION: TbetabRIIb-ED monomer, also termed T2b

<400> SEQUENCE: 44

Ile Pro Pro His Val Gln Lys Ser Asp Val Glu Met Glu Ala Gln Lys
1               5                   10                  15

Asp Glu Ile Ile Cys Pro Ser Cys Asn Arg Thr Ala His Pro Leu Arg
            20                  25                  30

His Ile Asn Asn Asp Met Ile Val Thr Asp Asn Asn Gly Ala Val Lys
        35                  40                  45

Phe Pro Gln Leu Cys Lys Phe Cys Asp Val Arg Phe Ser Thr Cys Asp
    50                  55                  60

Asn Gln Lys Ser Cys Met Ser Asn Cys Ser Ile Thr Ser Ile Cys Glu
65                  70                  75                  80

Lys Pro Gln Glu Val Cys Val Ala Val Trp Arg Lys Asn Asp Glu Asn
                85                  90                  95
```

```
Ile Thr Leu Glu Thr Val Cys His Asp Pro Lys Leu Pro Tyr His Asp
            100                 105                 110

Phe Ile Leu Glu Asp Ala Ala Ser Pro Lys Cys Ile Met Lys Glu Lys
            115                 120                 125

Lys Lys Pro Gly Glu Thr Phe Phe Met Cys Ser Cys Ser Ser Asp Glu
        130                 135                 140

Cys Asn Asp Asn Ile Ile Phe Ser Glu Glu Tyr Asn Thr Ser Asn Pro
145                 150                 155                 160

Asp

<210> SEQ ID NO 45
<211> LENGTH: 161
<212> TYPE: PRT
<213> ORGANISM: Artificial Sequence
<220> FEATURE:
<223> OTHER INFORMATION: TbetaRIIb-ED monomer Cys-mutated in the linker
      region, also termed T2bAA

<400> SEQUENCE: 45

Ile Pro Pro His Val Gln Lys Ser Asp Val Glu Met Glu Ala Gln Lys
1               5                   10                  15

Asp Glu Ile Ile Ala Pro Ser Ala Asn Arg Thr Ala His Pro Leu Arg
            20                  25                  30

His Ile Asn Asn Asp Met Ile Val Thr Asp Asn Asn Gly Ala Val Lys
        35                  40                  45

Phe Pro Gln Leu Cys Lys Phe Cys Asp Val Arg Phe Ser Thr Cys Asp
    50                  55                  60

Asn Gln Lys Ser Cys Met Ser Asn Cys Ser Ile Thr Ser Ile Cys Glu
65                  70                  75                  80

Lys Pro Gln Glu Val Cys Val Ala Val Trp Arg Lys Asn Asp Glu Asn
                85                  90                  95

Ile Thr Leu Glu Thr Val Cys His Asp Pro Lys Leu Pro Tyr His Asp
            100                 105                 110

Phe Ile Leu Glu Asp Ala Ala Ser Pro Lys Cys Ile Met Lys Glu Lys
            115                 120                 125

Lys Lys Pro Gly Glu Thr Phe Phe Met Cys Ser Cys Ser Ser Asp Glu
        130                 135                 140

Cys Asn Asp Asn Ile Ile Phe Ser Glu Glu Tyr Asn Thr Ser Asn Pro
145                 150                 155                 160

Asp

<210> SEQ ID NO 46
<211> LENGTH: 272
<212> TYPE: PRT
<213> ORGANISM: Artificial Sequence
<220> FEATURE:
<223> OTHER INFORMATION: TbetaRII-ED dimer, also termed T2-T2 or T22d35

<400> SEQUENCE: 46

Ile Pro Pro His Val Gln Lys Ser Val Asn Asn Asp Met Ile Val Thr
1               5                   10                  15

Asp Asn Asn Gly Ala Val Lys Phe Pro Gln Leu Cys Lys Phe Cys Asp
            20                  25                  30

Val Arg Phe Ser Thr Cys Asp Asn Gln Lys Ser Cys Met Ser Asn Cys
        35                  40                  45

Ser Ile Thr Ser Ile Cys Glu Lys Pro Gln Glu Val Cys Val Ala Val
    50                  55                  60
```

```
Trp Arg Lys Asn Asp Glu Asn Ile Thr Leu Glu Thr Val Cys His Asp
 65                  70                  75                  80

Pro Lys Leu Pro Tyr His Asp Phe Ile Leu Glu Asp Ala Ala Ser Pro
                 85                  90                  95

Lys Cys Ile Met Lys Glu Lys Lys Pro Gly Glu Thr Phe Phe Met
            100                 105                 110

Cys Ser Cys Ser Ser Asp Glu Cys Asn Asp Asn Ile Ile Phe Ser Glu
            115                 120                 125

Glu Tyr Asn Thr Ser Asn Pro Asp Ile Pro Pro His Val Gln Lys Ser
        130                 135                 140

Val Asn Asn Asp Met Ile Val Thr Asp Asn Asn Gly Ala Val Lys Phe
145                 150                 155                 160

Pro Gln Leu Cys Lys Phe Cys Asp Val Arg Phe Ser Thr Cys Asp Asn
                165                 170                 175

Gln Lys Ser Cys Met Ser Asn Cys Ser Ile Thr Ser Ile Cys Glu Lys
            180                 185                 190

Pro Gln Glu Val Cys Val Ala Val Trp Arg Lys Asn Asp Glu Asn Ile
        195                 200                 205

Thr Leu Glu Thr Val Cys His Asp Pro Lys Leu Pro Tyr His Asp Phe
210                 215                 220

Ile Leu Glu Asp Ala Ala Ser Pro Lys Cys Ile Met Lys Glu Lys Lys
225                 230                 235                 240

Lys Pro Gly Glu Thr Phe Phe Met Cys Ser Cys Ser Ser Asp Glu Cys
                245                 250                 255

Asn Asp Asn Ile Ile Phe Ser Glu Glu Tyr Asn Thr Ser Asn Pro Asp
        260                 265                 270

<210> SEQ ID NO 47
<211> LENGTH: 322
<212> TYPE: PRT
<213> ORGANISM: Artificial Sequence
<220> FEATURE:
<223> OTHER INFORMATION: TbetaRIIb-ED dimer, also termed T2-T2b

<400> SEQUENCE: 47

Ile Pro Pro His Val Gln Lys Ser Asp Val Glu Met Glu Ala Gln Lys
  1               5                  10                  15

Asp Glu Ile Ile Cys Pro Ser Cys Asn Arg Thr Ala His Pro Leu Arg
                 20                  25                  30

His Ile Asn Asn Asp Met Ile Val Thr Asp Asn Asn Gly Ala Val Lys
             35                  40                  45

Phe Pro Gln Leu Cys Lys Phe Cys Asp Val Arg Phe Ser Thr Cys Asp
         50                  55                  60

Asn Gln Lys Ser Cys Met Ser Asn Cys Ser Ile Thr Ser Ile Cys Glu
 65                  70                  75                  80

Lys Pro Gln Glu Val Cys Val Ala Val Trp Arg Lys Asn Asp Glu Asn
                 85                  90                  95

Ile Thr Leu Glu Thr Val Cys His Asp Pro Lys Leu Pro Tyr His Asp
             100                 105                 110

Phe Ile Leu Glu Asp Ala Ala Ser Pro Lys Cys Ile Met Lys Glu Lys
         115                 120                 125

Lys Lys Pro Gly Glu Thr Phe Phe Met Cys Ser Cys Ser Ser Asp Glu
     130                 135                 140

Cys Asn Asp Asn Ile Ile Phe Ser Glu Glu Tyr Asn Thr Ser Asn Pro
145                 150                 155                 160
```

```
Asp Ile Pro Pro His Val Gln Lys Ser Asp Val Glu Met Glu Ala Gln
                165                 170                 175

Lys Asp Glu Ile Ile Cys Pro Ser Cys Asn Arg Thr Ala His Pro Leu
            180                 185                 190

Arg His Ile Asn Asn Asp Met Ile Val Thr Asp Asn Asn Gly Ala Val
            195                 200                 205

Lys Phe Pro Gln Leu Cys Lys Phe Cys Asp Val Arg Phe Ser Thr Cys
210                 215                 220

Asp Asn Gln Lys Ser Cys Met Ser Asn Cys Ser Ile Thr Ser Ile Cys
225                 230                 235                 240

Glu Lys Pro Gln Glu Val Cys Val Ala Val Trp Arg Lys Asn Asp Glu
                245                 250                 255

Asn Ile Thr Leu Glu Thr Val Cys His Asp Pro Lys Leu Pro Tyr His
                260                 265                 270

Asp Phe Ile Leu Glu Asp Ala Ala Ser Pro Lys Cys Ile Met Lys Glu
                275                 280                 285

Lys Lys Lys Pro Gly Glu Thr Phe Phe Met Cys Ser Cys Ser Ser Asp
                290                 295                 300

Glu Cys Asn Asp Asn Ile Ile Phe Ser Glu Glu Tyr Asn Thr Ser Asn
305                 310                 315                 320

Pro Asp

<210> SEQ ID NO 48
<211> LENGTH: 322
<212> TYPE: PRT
<213> ORGANISM: Artificial Sequence
<220> FEATURE:
<223> OTHER INFORMATION: TbetaRIIb-ED dimer Cys-mutated in the linker
      region, also termed T2-T2bAA

<400> SEQUENCE: 48

Ile Pro Pro His Val Gln Lys Ser Asp Val Glu Met Glu Ala Gln Lys
1               5                   10                  15

Asp Glu Ile Ile Cys Pro Ser Cys Asn Arg Thr Ala His Pro Leu Arg
            20                  25                  30

His Ile Asn Asn Asp Met Ile Val Thr Asp Asn Asn Gly Ala Val Lys
        35                  40                  45

Phe Pro Gln Leu Cys Lys Phe Cys Asp Val Arg Phe Ser Thr Cys Asp
    50                  55                  60

Asn Gln Lys Ser Cys Met Ser Asn Cys Ser Ile Thr Ser Ile Cys Glu
65                  70                  75                  80

Lys Pro Gln Glu Val Cys Val Ala Val Trp Arg Lys Asn Asp Glu Asn
                85                  90                  95

Ile Thr Leu Glu Thr Val Cys His Asp Pro Lys Leu Pro Tyr His Asp
            100                 105                 110

Phe Ile Leu Glu Asp Ala Ala Ser Pro Lys Cys Ile Met Lys Glu Lys
        115                 120                 125

Lys Lys Pro Gly Glu Thr Phe Phe Met Cys Ser Cys Ser Ser Asp Glu
    130                 135                 140

Cys Asn Asp Asn Ile Ile Phe Ser Glu Glu Tyr Asn Thr Ser Asn Pro
145                 150                 155                 160

Asp Ile Pro Pro His Val Gln Lys Ser Asp Val Glu Met Glu Ala Gln
                165                 170                 175

Lys Asp Glu Ile Ile Ala Pro Ser Ala Asn Arg Thr Ala His Pro Leu
            180                 185                 190
```

```
Arg His Ile Asn Asn Asp Met Ile Val Thr Asp Asn Gly Ala Val
        195                 200                 205

Lys Phe Pro Gln Leu Cys Lys Phe Cys Asp Val Arg Phe Ser Thr Cys
210                 215                 220

Asp Asn Gln Lys Ser Cys Met Ser Asn Cys Ser Ile Thr Ser Ile Cys
225                 230                 235                 240

Glu Lys Pro Gln Glu Val Cys Val Ala Val Trp Arg Lys Asn Asp Glu
            245                 250                 255

Asn Ile Thr Leu Glu Thr Val Cys His Asp Pro Lys Leu Pro Tyr His
            260                 265                 270

Asp Phe Ile Leu Glu Asp Ala Ala Ser Pro Lys Cys Ile Met Lys Glu
        275                 280                 285

Lys Lys Lys Pro Gly Glu Thr Phe Phe Met Cys Ser Cys Ser Ser Asp
    290                 295                 300

Glu Cys Asn Asp Asn Ile Ile Phe Ser Glu Glu Tyr Asn Thr Ser Asn
305                 310                 315                 320

Pro Asp

<210> SEQ ID NO 49
<211> LENGTH: 408
<212> TYPE: PRT
<213> ORGANISM: Artificial Sequence
<220> FEATURE:
<223> OTHER INFORMATION: TbetaRII-ED trimer, also termed T2-T2-T2

<400> SEQUENCE: 49

Ile Pro Pro His Val Gln Lys Ser Val Asn Asn Asp Met Ile Val Thr
1               5                   10                  15

Asp Asn Asn Gly Ala Val Lys Phe Pro Gln Leu Cys Lys Phe Cys Asp
            20                  25                  30

Val Arg Phe Ser Thr Cys Asp Asn Gln Lys Ser Cys Met Ser Asn Cys
        35                  40                  45

Ser Ile Thr Ser Ile Cys Glu Lys Pro Gln Glu Val Cys Val Ala Val
    50                  55                  60

Trp Arg Lys Asn Asp Glu Asn Ile Thr Leu Glu Thr Val Cys His Asp
65                  70                  75                  80

Pro Lys Leu Pro Tyr His Asp Phe Ile Leu Glu Asp Ala Ala Ser Pro
                85                  90                  95

Lys Cys Ile Met Lys Glu Lys Lys Lys Pro Gly Glu Thr Phe Phe Met
            100                 105                 110

Cys Ser Cys Ser Ser Asp Glu Cys Asn Asp Asn Ile Ile Phe Ser Glu
        115                 120                 125

Glu Tyr Asn Thr Ser Asn Pro Asp Ile Pro Pro His Val Gln Lys Ser
    130                 135                 140

Val Asn Asn Asp Met Ile Val Thr Asp Asn Asn Gly Ala Val Lys Phe
145                 150                 155                 160

Pro Gln Leu Cys Lys Phe Cys Asp Val Arg Phe Ser Thr Cys Asp Asn
                165                 170                 175

Gln Lys Ser Cys Met Ser Asn Cys Ser Ile Thr Ser Ile Cys Glu Lys
            180                 185                 190

Pro Gln Glu Val Cys Val Ala Val Trp Arg Lys Asn Asp Glu Asn Ile
        195                 200                 205

Thr Leu Glu Thr Val Cys His Asp Pro Lys Leu Pro Tyr His Asp Phe
    210                 215                 220

Ile Leu Glu Asp Ala Ala Ser Pro Lys Cys Ile Met Lys Glu Lys Lys
```

```
                225                 230                 235                 240

Lys Pro Gly Glu Thr Phe Phe Met Cys Ser Cys Ser Ser Asp Glu Cys
                245                 250                 255

Asn Asp Asn Ile Ile Phe Ser Glu Glu Tyr Asn Thr Ser Asn Pro Asp
                260                 265                 270

Ile Pro Pro His Val Gln Lys Ser Val Asn Asn Asp Met Ile Val Thr
                275                 280                 285

Asp Asn Asn Gly Ala Val Lys Phe Pro Gln Leu Cys Lys Phe Cys Asp
                290                 295                 300

Val Arg Phe Ser Thr Cys Asp Asn Gln Lys Ser Cys Met Ser Asn Cys
305                 310                 315                 320

Ser Ile Thr Ser Ile Cys Glu Lys Pro Gln Glu Val Cys Val Ala Val
                325                 330                 335

Trp Arg Lys Asn Asp Glu Asn Ile Thr Leu Glu Thr Val Cys His Asp
                340                 345                 350

Pro Lys Leu Pro Tyr His Asp Phe Ile Leu Glu Asp Ala Ala Ser Pro
                355                 360                 365

Lys Cys Ile Met Lys Glu Lys Lys Pro Gly Glu Thr Phe Phe Met
                370                 375                 380

Cys Ser Cys Ser Ser Asp Glu Cys Asn Asp Asn Ile Ile Phe Ser Glu
385                 390                 395                 400

Glu Tyr Asn Thr Ser Asn Pro Asp
                405

<210> SEQ ID NO 50
<211> LENGTH: 458
<212> TYPE: PRT
<213> ORGANISM: Artificial Sequence
<220> FEATURE:
<223> OTHER INFORMATION: TbetaRIIb-ED trimer, also termed T2-T2b-T2b

<400> SEQUENCE: 50

Ile Pro Pro His Val Gln Lys Ser Val Asn Asn Asp Met Ile Val Thr
1               5                   10                  15

Asp Asn Asn Gly Ala Val Lys Phe Pro Gln Leu Cys Lys Phe Cys Asp
                20                  25                  30

Val Arg Phe Ser Thr Cys As

```
                180             185             190
Asp Val Arg Phe Ser Thr Cys Asp Asn Gln Lys Ser Cys Met Ser Asn
            195                 200                 205
Cys Ser Ile Thr Ser Ile Cys Glu Lys Pro Gln Glu Val Cys Val Ala
            210                 215                 220
Val Trp Arg Lys Asn Asp Glu Asn Ile Thr Leu Glu Thr Val Cys His
225                 230                 235                 240
Asp Pro Lys Leu Pro Tyr His Asp Phe Ile Leu Glu Asp Ala Ala Ser
                245                 250                 255
Pro Lys Cys Ile Met Lys Glu Lys Lys Pro Gly Glu Thr Phe Phe
            260                 265                 270
Met Cys Ser Cys Ser Ser Asp Glu Cys Asn Asp Asn Ile Ile Phe Ser
            275                 280                 285
Glu Glu Tyr Asn Thr Ser Asn Pro Asp Ile Pro Pro His Val Gln Lys
            290                 295                 300
Ser Asp Val Glu Met Glu Ala Gln Lys Asp Glu Ile Ile Cys Pro Ser
305                 310                 315                 320
Cys Asn Arg Thr Ala His Pro Leu Arg His Ile Asn Asn Asp Met Ile
                325                 330                 335
Val Thr Asp Asn Asn Gly Ala Val Lys Phe Pro Gln Leu Cys Lys Phe
                340                 345                 350
Cys Asp Val Arg Phe Ser Thr Cys Asp Asn Gln Lys Ser Cys Met Ser
                355                 360                 365
Asn Cys Ser Ile Thr Ser Ile Cys Glu Lys Pro Gln Glu Val Cys Val
            370                 375                 380
Ala Val Trp Arg Lys Asn Asp Glu Asn Ile Thr Leu Glu Thr Val Cys
385                 390                 395                 400
His Asp Pro Lys Leu Pro Tyr His Asp Phe Ile Leu Glu Asp Ala Ala
                405                 410                 415
Ser Pro Lys Cys Ile Met Lys Glu Lys Lys Pro Gly Glu Thr Phe
                420                 425                 430
Phe Met Cys Ser Cys Ser Ser Asp Glu Cys Asn Asp Asn Ile Ile Phe
                435                 440                 445
Ser Glu Glu Tyr Asn Thr Ser Asn Pro Asp
            450                 455

<210> SEQ ID NO 51
<211> LENGTH: 458
<212> TYPE: PRT
<213> ORGANISM: Artificial Sequence
<220> FEATURE:
<223> OTHER INFORMATION: TbetaRIIb-ED trimer Cys-mutated in the linker
      regions, also termed T2-T2bAA-T2bAA

<400> SEQUENCE: 51

Ile Pro Pro His Val Gln Lys Ser Val Asn Asn Asp Met Ile Val Thr
1               5                   10                  15
Asp Asn Asn Gly Ala Val Lys Phe Pro Gln Leu Cys Lys Phe Cys Asp
                20                  25                  30
Val Arg Phe Ser Thr Cys Asp Asn Gln Lys Ser Cys Met Ser Asn Cys
            35                  40                  45
Ser Ile Thr

```
Pro Lys Leu Pro Tyr His Asp Phe Ile Leu Glu Asp Ala Ala Ser Pro
                85                  90                  95
Lys Cys Ile Met Lys Glu Lys Lys Lys Pro Gly Glu Thr Phe Phe Met
            100                 105                 110
Cys Ser Cys Ser Ser Asp Glu Cys Asn Asp Asn Ile Ile Phe Ser Glu
        115                 120                 125
Glu Tyr Asn Thr Ser Asn Pro Asp Ile Pro Pro His Val Gln Lys Ser
    130                 135                 140
Asp Val Glu Met Glu Ala Gln Lys Asp Glu Ile Ile Ala Pro Ser Ala
145                 150                 155                 160
Asn Arg Thr Ala His Pro Leu Arg His Ile Asn Asn Asp Met Ile Val
                165                 170                 175
Thr Asp Asn Asn Gly Ala Val Lys Phe Pro Gln Leu Cys Lys Phe Cys
            180                 185                 190
Asp Val Arg Phe Ser Thr Cys Asp Asn Gln Lys Ser Cys Met Ser Asn
        195                 200                 205
Cys Ser Ile Thr Ser Ile Cys Glu Lys Pro Gln Glu Val Cys Val Ala
    210                 215                 220
Val Trp Arg Lys Asn Asp Glu Asn Ile Thr Leu Glu Thr Val Cys His
225                 230                 235                 240
Asp Pro Lys Leu Pro Tyr His Asp Phe Ile Leu Glu Asp Ala Ala Ser
                245                 250                 255
Pro Lys Cys Ile Met Lys Glu Lys Lys Lys Pro Gly Glu Thr Phe Phe
            260                 265                 270
Met Cys Ser Cys Ser Ser Asp Glu Cys Asn Asp Asn Ile Ile Phe Ser
        275                 280                 285
Glu Glu Tyr Asn Thr Ser Asn Pro Asp Ile Pro Pro His Val Gln Lys
    290                 295                 300
Ser Asp Val Glu Met Glu Ala Gln Lys Asp Glu Ile Ile Ala Pro Ser
305                 310                 315                 320
Ala Asn Arg Thr Ala His Pro Leu Arg His Ile Asn Asn Asp Met Ile
                325                 330                 335
Val Thr Asp Asn Asn Gly Ala Val Lys Phe Pro Gln Leu Cys Lys Phe
            340                 345                 350
Cys Asp Val Arg Phe Ser Thr Cys Asp Asn Gln Lys Ser Cys Met Ser
        355                 360                 365
Asn Cys Ser Ile Thr Ser Ile Cys Glu Lys Pro Gln Glu Val Cys Val
    370                 375                 380
Ala Val Trp Arg Lys Asn Asp Glu Asn Ile Thr Leu Glu Thr Val Cys
385                 390                 395                 400
His Asp Pro Lys Leu Pro Tyr His Asp Phe Ile Leu Glu Asp Ala Ala
                405                 410                 415
Ser Pro Lys Cys Ile Met Lys Glu Lys Lys Lys Pro Gly Glu Thr Phe
            420                 425                 430
Phe Met Cys Ser Cys Ser Ser Asp Glu Cys Asn Asp Asn Ile Ile Phe
        435                 440                 445
Ser Glu Glu Tyr Asn Thr Ser Asn Pro Asp
    450                 455
```

<210> SEQ ID NO 52
<211> LENGTH: 79
<212> TYPE: PRT
<213> ORGANISM: Artificial Sequence
<220> FEATURE:
<223> OTHER INFORMATION: TbetaRI-ED structured domain

<400> SEQUENCE: 52

Ala Leu Gln Cys Phe Cys His Leu Cys Thr Lys Asp Asn Phe Thr Cys
1               5                   10                  15

Val Thr Asp Gly Leu Cys Phe Val Ser Val Thr Glu Thr Thr Asp Lys
            20                  25                  30

Val Ile His Asn Ser Met Cys Ile Ala Glu Ile Asp Leu Ile Pro Arg
        35                  40                  45

Asp Arg Pro Phe Val Cys Ala Pro Ser Ser Lys Thr Gly Ser Val Thr
    50                  55                  60

Thr Thr Tyr Cys Cys Asn Gln Asp His Cys Asn Lys Ile Glu Leu
65                  70                  75

<210> SEQ ID NO 53
<211> LENGTH: 8
<212> TYPE: PRT
<213> ORGANISM: Artificial Sequence
<220> FEATURE:
<223> OTHER INFORMATION: TbetaRI-ED N-term unstructured region and
      natural linker

<400> SEQUENCE: 53

Ala Ala Leu Leu Pro Gly Ala Thr
1               5

<210> SEQ ID NO 54
<211> LENGTH: 14
<212> TYPE: PRT
<213> ORGANISM: Artificial Sequence
<220> FEATURE:
<223> OTHER INFORMATION: TbetaRI-ED C-term unstructured region and
      natural linker

<400> SEQUENCE: 54

Pro Thr Thr Val Lys Ser Ser Pro Gly Leu Gly Pro Val Glu
1               5                   10

<210> SEQ ID NO 55
<211> LENGTH: 22
<212> TYPE: PRT
<213> ORGANISM: Artificial Sequence
<220> FEATURE:
<223> OTHER INFORMATION: TbetaRI-ED natural linker

<400> SEQUENCE: 55

Pro Thr Thr Val Lys Ser Ser Pro Gly Leu Gly Pro Val Glu Ala Ala
1               5                   10                  15

Leu Leu Pro Gly Ala Thr
            20

<210> SEQ ID NO 56
<211> LENGTH: 101
<212> TYPE: PRT
<213> ORGANISM: Artificial Sequence
<220> FEATURE:
<223> OTHER INFORMATION: TbetaRI-ED monomer, also termed T1 or T1m

<400> SEQUENCE: 56

Ala Ala Leu Leu Pro Gly Ala Thr Ala Leu Gln Cys Phe Cys His Leu
1               5                   10                  15

Cys Thr Lys Asp Asn Phe Thr Cys Val Thr Asp Gly Leu Cys Phe Val
            20                  25                  30

Ser Val Thr Glu Thr Thr Asp Lys Val Ile His Asn Ser Met Cys Ile

```
                35                  40                  45

Ala Glu Ile Asp Leu Ile Pro Arg Asp Arg Pro Phe Val Cys Ala Pro
         50                  55                  60

Ser Ser Lys Thr Gly Ser Val Thr Thr Thr Tyr Cys Cys Asn Gln Asp
 65                  70                  75                  80

His Cys Asn Lys Ile Glu Leu Pro Thr Thr Val Lys Ser Ser Pro Gly
                 85                  90                  95

Leu Gly Pro Val Glu
            100

<210> SEQ ID NO 57
<211> LENGTH: 202
<212> TYPE: PRT
<213> ORGANISM: Artificial Sequence
<220> FEATURE:
<223> OTHER INFORMATION: TbetaRI-ED dimer, also termed T1-T1

<400> SEQUENCE: 57

Ala Ala Leu Leu Pro Gly Ala Thr Ala Leu Gln Cys Phe Cys His Leu
 1               5                  10                  15

Cys Thr Lys Asp Asn Phe Thr Cys Val Thr Asp Gly Leu Cys Phe Val
                20                  25                  30

Ser Val Thr Glu Thr Thr Asp Lys Val Ile His Asn Ser Met Cys Ile
            35                  40                  45

Ala Glu Ile Asp Leu Ile Pro Arg Asp Arg Pro Phe Val Cys Ala Pro
         50                  55                  60

Ser Ser Lys Thr Gly Ser Val Thr Thr Thr Tyr Cys Cys Asn Gln Asp
 65                  70                  75                  80

His Cys Asn Lys Ile Glu Leu Pro Thr Thr Val Lys Ser Ser Pro Gly
                 85                  90                  95

Leu Gly Pro Val Glu Ala Ala Leu Leu Pro Gly Ala Thr Ala Leu Gln
            100                 105                 110

Cys Phe Cys His Leu Cys Thr Lys Asp Asn Phe Thr Cys Val Thr Asp
        115                 120                 125

Gly Leu Cys Phe Val Ser Val Thr Glu Thr Thr Asp Lys Val Ile His
    130                 135                 140

Asn Ser Met Cys Ile Ala Glu Ile Asp Leu Ile Pro Arg Asp Arg Pro
145                 150                 155                 160

Phe Val Cys Ala Pro Ser Ser Lys Thr Gly Ser Val Thr Thr Thr Tyr
                165                 170                 175

Cys Cys Asn Gln Asp His Cys Asn Lys Ile Glu Leu Pro Thr Thr Val
            180                 185                 190

Lys Ser Ser Pro Gly Leu Gly Pro Val Glu
        195                 200

<210> SEQ ID NO 58
<211> LENGTH: 39
<212> TYPE: PRT
<213> ORGANISM: Artificial Sequence
<220> FEATURE:
<223> OTHER INFORMATION: TbetaRI-TbetaRII-ED natural linker

<400> SEQUENCE: 58

Pro Thr Thr Val Lys Ser Ser Pro Gly Leu Gly Pro Val Glu Ile Pro
 1               5                  10                  15

Pro His Val Gln Lys Ser Val Asn Asn Asp Met Ile Val Thr Asp Asn
                20                  25                  30
```

```
Asn Gly Ala Val Lys Phe Pro
            35

<210> SEQ ID NO 59
<211> LENGTH: 64
<212> TYPE: PRT
<213> ORGANISM: Artificial Sequence
<220> FEATURE:
<223> OTHER INFORMATION: TbetaRI-TbetaRIIb-ED natural linker

<400> SEQUENCE: 59

Pro Thr Thr Val Lys Ser Ser Pro Gly Leu Gly Pro Val Glu Ile Pro
1               5                   10                  15

Pro His Val Gln Lys Ser Asp Val Glu Met Glu Ala Gln Lys Asp Glu
            20                  25                  30

Ile Ile Cys Pro Ser Cys Asn Arg Thr Ala His Pro Leu Arg His Ile
        35                  40                  45

Asn Asn Asp Met Ile Val Thr Asp Asn Asn Gly Ala Val Lys Phe Pro
    50                  55                  60

<210> SEQ ID NO 60
<211> LENGTH: 18
<212> TYPE: PRT
<213> ORGANISM: Artificial Sequence
<220> FEATURE:
<223> OTHER INFORMATION: TbetaRII-TbetaRI-ED natural linker

<400> SEQUENCE: 60

Ser Glu Glu Tyr Asn Thr Ser Asn Pro Asp Ala Ala Leu Leu Pro Gly
1               5                   10                  15

Ala Thr

<210> SEQ ID NO 61
<211> LENGTH: 237
<212> TYPE: PRT
<213> ORGANISM: Artificial Sequence
<220> FEATURE:
<223> OTHER INFORMATION: TbetaRI-TbetaRII-ED dimer T1-T2

<400> SEQUENCE: 61

Ala Ala Leu Leu Pro Gly Ala Thr Ala Leu Gln Cys Phe Cys His Leu
1               5                   10                  15

Cys Thr Lys Asp Asn Phe Thr Cys Val Thr Asp Gly Leu Cys Phe Val
            20                  25                  30

Ser Val Thr Glu Thr Thr Asp Lys Val Ile His Asn Ser Met Cys Ile
        35                  40                  45

Ala Glu Ile Asp Leu Ile Pro Arg Asp Arg Pro Phe Val Cys Ala Pro
    50                  55                  60

Ser Ser Lys Thr Gly Ser Val Thr Thr Thr Tyr Cys Cys Asn Gln Asp
65                  70                  75                  80

His Cys Asn Lys Ile Glu Leu Pro Thr Thr Val Lys Ser Ser Pro Gly
                85                  90                  95

Leu Gly Pro Val Glu Ile Pro Pro His Val Gln Lys Ser Val Asn Asn
            100                 105                 110

Asp Met Ile Val Thr Asp Asn Asn Gly Ala Val Lys Phe Pro Gln Leu
        115                 120                 125

Cys Lys Phe Cys Asp Val Arg Phe Ser Thr Cys Asp Asn Gln Lys Ser
    130                 135                 140

Cys Met Ser Asn Cys Ser Ile Thr Ser Ile Cys Glu Lys Pro Gln Glu
145                 150                 155                 160
```

```
Val Cys Val Ala Val Trp Arg Lys Asn Asp Glu Asn Ile Thr Leu Glu
            165                 170                 175

Thr Val Cys His Asp Pro Lys Leu Pro Tyr His Asp Phe Ile Leu Glu
            180                 185                 190

Asp Ala Ala Ser Pro Lys Cys Ile Met Lys Glu Lys Lys Pro Gly
            195                 200                 205

Glu Thr Phe Phe Met Cys Ser Cys Ser Ser Asp Glu Cys Asn Asp Asn
            210                 215                 220

Ile Ile Phe Ser Glu Glu Tyr Asn Thr Ser Asn Pro Asp
225                 230                 235

<210> SEQ ID NO 62
<211> LENGTH: 262
<212> TYPE: PRT
<213> ORGANISM: Artificial Sequence
<220> FEATURE:
<223> OTHER INFORMATION: TbetaRI-TbetaRII-ED dimer T1-T2b

<400> SEQUENCE: 62

Ala Ala Leu Leu Pro Gly Ala Thr Ala Leu Gln Cys Phe Cys His Leu
1               5                   10                  15

Cys Thr Lys Asp Asn Phe Thr Cys Val Thr Asp Gly Leu Cys Phe Val
            20                  25                  30

Ser Val Thr Glu Thr Thr Asp Lys Val Ile His Asn Ser Met Cys Ile
            35                  40                  45

Ala Glu Ile Asp Leu Ile Pro Arg Asp Arg Pro Phe Val Cys Ala Pro
        50                  55                  60

Ser Ser Lys Thr Gly Ser Val Thr Thr Thr Tyr Cys Cys Asn Gln Asp
65                  70                  75                  80

His Cys Asn Lys Ile Glu Leu Pro Thr Thr Val Lys Ser Ser Pro Gly
                85                  90                  95

Leu Gly Pro Val Glu Ile Pro Pro His Val Gln Lys Ser Asp Val Glu
            100                 105                 110

Met Glu Ala Gln Lys Asp Glu Ile Ile Cys Pro Ser Cys Asn Arg Thr
        115                 120                 125

Ala His Pro Leu Arg His Ile Asn Asn Asp Met Ile Val Thr Asp Asn
130                 135                 140

Asn Gly Ala Val Lys Phe Pro Gln Leu Cys Lys Phe Cys Asp Val Arg
145                 150                 155                 160

Phe Ser Thr Cys Asp Asn Gln Lys Ser Cys Met Ser Asn Cys Ser Ile
                165                 170                 175

Thr Ser Ile Cys Glu Lys Pro Gln Glu Val Cys Val Ala Val Trp Arg
            180                 185                 190

Lys Asn Asp Glu Asn Ile Thr Leu Glu Thr Val Cys His Asp Pro Lys
        195                 200                 205

Leu Pro Tyr His Asp Phe Ile Leu Glu Asp Ala Ala Ser Pro Lys Cys
210                 215                 220

Ile Met Lys Glu Lys Lys Pro Gly Glu Thr Phe Phe Met Cys Ser
225                 230                 235                 240

Cys Ser Ser Asp Glu Cys Asn Asp Asn Ile Ile Phe Ser Glu Glu Tyr
                245                 250                 255

Asn Thr Ser Asn Pro Asp
            260

<210> SEQ ID NO 63
```

<211> LENGTH: 237
<212> TYPE: PRT
<213> ORGANISM: Artificial Sequence
<220> FEATURE:
<223> OTHER INFORMATION: TbetaRI-TbetaRII-ED dimer T2-T1

<400> SEQUENCE: 63

Ile Pro Pro His Val Gln Lys Ser Val Asn Asp Met Ile Val Thr
1               5                   10                  15

Asp Asn Asn Gly Ala Val Lys Phe Pro Gln Leu Cys Lys Phe Cys
                20                  25                  30

Val Arg Phe Ser Thr Cys Asp Asn Gln Lys Ser Cys Met Ser Asn Cys
            35                  40                  45

Ser Ile Thr Ser Ile Cys Glu Lys Pro Gln Glu Val Cys Val Ala Val
    50                  55                  60

Trp Arg Lys Asn Asp Glu Asn Ile Thr Leu Glu Thr Val Cys His Asp
65                  70                  75                  80

Pro Lys Leu Pro Tyr His Asp Phe Ile Leu Glu Asp Ala Ala Ser Pro
                85                  90                  95

Lys Cys Ile Met Lys Glu Lys Lys Pro Gly Glu Thr Phe Phe Met
            100                 105                 110

Cys Ser Cys Ser Ser Asp Glu Cys Asn Asp Asn Ile Ile Phe Ser Glu
            115                 120                 125

Glu Tyr Asn Thr Ser Asn Pro Asp Ala Ala Leu Leu Pro Gly Ala Thr
    130                 135                 140

Ala Leu Gln Cys Phe Cys His Leu Cys Thr Lys Asp Asn Phe Thr Cys
145                 150                 155                 160

Val Thr Asp Gly Leu Cys Phe Val Ser Val Thr Glu Thr Thr Asp Lys
                165                 170                 175

Val Ile His Asn Ser Met Cys Ile Ala Glu Ile Asp Leu Ile Pro Arg
            180                 185                 190

Asp Arg Pro Phe Val Cys Ala Pro Ser Ser Lys Thr Gly Ser Val Thr
        195                 200                 205

Thr Thr Tyr Cys Cys Asn Gln Asp His Cys Asn Lys Ile Glu Leu Pro
    210                 215                 220

Thr Thr Val Lys Ser Ser Pro Gly Leu Gly Pro Val Glu
225                 230                 235

<210> SEQ ID NO 64
<211> LENGTH: 373
<212> TYPE: PRT
<213> ORGANISM: Artificial Sequence
<220> FEATURE:
<223> OTHER INFORMATION: TbetaRI-TbetaRII-ED trimer T1-T2-T2

<400> SEQUENCE: 64

Ala Ala Leu Leu Pro Gly Ala Thr Ala Leu Gln Cys Phe Cys His Leu
1               5                   10                  15

Cys Thr Lys Asp Asn Phe Thr Cys Val Thr Asp Gly Leu Cys Phe Val
                20                  25                  30

Ser Val Thr Glu Thr Thr Asp Lys Val Ile His Asn Ser Met Cys Ile
            35                  40                  45

Ala Glu Ile Asp Leu Ile Pro Arg Asp Arg Pro Phe Val Cys Ala Pro
    50                  55                  60

Ser Ser Lys Thr Gly Ser Val Thr Thr Thr Tyr Cys Cys Asn Gln Asp
65                  70                  75                  80

His Cys Asn Lys Ile Glu Leu Pro Thr Thr Val Lys Ser Ser Pro Gly

```
                    85                  90                  95

Leu Gly Pro Val Glu Ile Pro Pro His Val Gln Lys Ser Val Asn Asn
                100                 105                 110

Asp Met Ile Val Thr Asp Asn Asn Gly Ala Val Lys Phe Pro Gln Leu
            115                 120                 125

Cys Lys Phe Cys Asp Val Arg Phe Ser Thr Cys Asp Asn Gln Lys Ser
        130                 135                 140

Cys Met Ser Asn Cys Ser Ile Thr Ser Ile Cys Glu Lys Pro Gln Glu
145                 150                 155                 160

Val Cys Val Ala Val Trp Arg Lys Asn Asp Glu Asn Ile Thr Leu Glu
                165                 170                 175

Thr Val Cys His Asp Pro Lys Leu Pro Tyr His Asp Phe Ile Leu Glu
            180                 185                 190

Asp Ala Ala Ser Pro Lys Cys Ile Met Lys Glu Lys Lys Pro Gly
        195                 200                 205

Glu Thr Phe Phe Met Cys Ser Cys Ser Ser Asp Glu Cys Asn Asp Asn
        210                 215                 220

Ile Ile Phe Ser Glu Glu Tyr Asn Thr Ser Asn Pro Asp Ile Pro Pro
225                 230                 235                 240

His Val Gln Lys Ser Val Asn Asn Asp Met Ile Val Thr Asp Asn Asn
                245                 250                 255

Gly Ala Val Lys Phe Pro Gln Leu Cys Lys Phe Cys Asp Val Arg Phe
                260                 265                 270

Ser Thr Cys Asp Asn Gln Lys Ser Cys Met Ser Asn Cys Ser Ile Thr
            275                 280                 285

Ser Ile Cys Glu Lys Pro Gln Glu Val Cys Val Ala Val Trp Arg Lys
        290                 295                 300

Asn Asp Glu Asn Ile Thr Leu Glu Thr Val Cys His Asp Pro Lys Leu
305                 310                 315                 320

Pro Tyr His Asp Phe Ile Leu Glu Asp Ala Ala Ser Pro Lys Cys Ile
                325                 330                 335

Met Lys Glu Lys Lys Pro Gly Glu Thr Phe Phe Met Cys Ser Cys
            340                 345                 350

Ser Ser Asp Glu Cys Asn Asp Asn Ile Ile Phe Ser Glu Glu Tyr Asn
        355                 360                 365

Thr Ser Asn Pro Asp
    370

<210> SEQ ID NO 65
<211> LENGTH: 398
<212> TYPE: PRT
<213> ORGANISM: Artificial Sequence
<220> FEATURE:
<223> OTHER INFORMATION: TbetaRI-TbetaRII-ED trimer T1-T2-T2b

<400> SEQUENCE: 65

Ala Ala Leu Leu Pro Gly Ala Thr Ala Leu Gln Cys Phe Cys His Leu
1               5                   10                  15

Cys Thr Lys Asp Asn Phe Thr Cys Val Thr Asp Gly Leu Cys Phe Val
                20                  25                  30

Ser Val Thr Glu Thr Thr Asp Lys Val Ile His Asn Ser Met Cys Ile
            35                  40                  45

Ala Gl

```
             65                  70                  75                  80
His Cys Asn Lys Ile Glu Leu Pro Thr Thr Val Lys Ser Ser Pro Gly
                 85                  90                  95

Leu Gly Pro Val Glu Ile Pro Pro His Val Gln Lys Ser Val Asn Asn
            100                 105                 110

Asp Met Ile Val Thr Asp Asn Gly Ala Val Lys Phe Pro Gln Leu
            115                 120                 125

Cys Lys Phe Cys Asp Val Arg Phe Ser Thr Cys Asp Asn Gln Lys Ser
            130                 135                 140

Cys Met Ser Asn Cys Ser Ile Thr Ser Ile Cys Glu Lys Pro Gln Glu
145                 150                 155                 160

Val Cys Val Ala Val Trp Arg Lys Asn Asp Glu Asn Ile Thr Leu Glu
                165                 170                 175

Thr Val Cys His Asp Pro Lys Leu Pro Tyr His Asp Phe Ile Leu Glu
            180                 185                 190

Asp Ala Ala Ser Pro Lys Cys Ile Met Lys Glu Lys Lys Pro Gly
            195                 200                 205

Glu Thr Phe Phe Met Cys Ser Cys Ser Ser Asp Glu Cys Asn Asp Asn
            210                 215                 220

Ile Ile Phe Ser Glu Glu Tyr Asn Thr Ser Asn Pro Asp Ile Pro Pro
225                 230                 235                 240

His Val Gln Lys Ser Asp Val Glu Met Glu Ala Gln Lys Asp Glu Ile
                245                 250                 255

Ile Cys Pro Ser Cys Asn Arg Thr Ala His Pro Leu Arg His Ile Asn
                260                 265                 270

Asn Asp Met Ile Val Thr Asp Asn Gly Ala Val Lys Phe Pro Gln
            275                 280                 285

Leu Cys Lys Phe Cys Asp Val Arg Phe Ser Thr Cys Asp Asn Gln Lys
            290                 295                 300

Ser Cys Met Ser Asn Cys Ser Ile Thr Ser Ile Cys Glu Lys Pro Gln
305                 310                 315                 320

Glu Val Cys Val Ala Val Trp Arg Lys Asn Asp Glu Asn Ile Thr Leu
                325                 330                 335

Glu Thr Val Cys His Asp Pro Lys Leu Pro Tyr His Asp Phe Ile Leu
                340                 345                 350

Glu Asp Ala Ala Ser Pro Lys Cys Ile Met Lys Glu Lys Lys Pro
            355                 360                 365

Gly Glu Thr Phe Phe Met Cys Ser Cys Ser Ser Asp Glu Cys Asn Asp
            370                 375                 380

Asn Ile Ile Phe Ser Glu Glu Tyr Asn Thr Ser Asn Pro Asp
385                 390                 395

<210> SEQ ID NO 66
<211> LENGTH: 423
<212> TYPE: PRT
<213> ORGANISM: Artificial Sequence
<220> FEATURE:
<223> OTHER INFORMATION: TbetaRI-TbetaRII-ED trimer T1-T2-T2bAA

<400> SEQUENCE: 66

Ala Ala Leu Leu Pro Gly Ala Thr Ala Leu Gln Cys Phe Cys His Leu
1               5                   10                  15

Cys Thr Lys Asp Asn Phe Thr C

```
            35                  40                  45
Ala Glu Ile Asp Leu Ile Pro Arg Asp Arg Pro Phe Val Cys Ala Pro
 50                  55                  60

Ser Ser Lys Thr Gly Ser Val Thr Thr Thr Tyr Cys Cys Asn Gln Asp
 65                  70                  75                  80

His Cys Asn Lys Ile Glu Leu Pro Thr Thr Val Lys Ser Ser Pro Gly
                 85                  90                  95

Leu Gly Pro Val Glu Ile Pro Pro His Val Gln Lys Ser Asp Val Glu
            100                 105                 110

Met Glu Ala Gln Lys Asp Glu Ile Ile Cys Pro Ser Cys Asn Arg Thr
        115                 120                 125

Ala His Pro Leu Arg His Ile Asn Asn Asp Met Ile Val Thr Asp Asn
    130                 135                 140

Asn Gly Ala Val Lys Phe Pro Gln Leu Cys Lys Phe Cys Asp Val Arg
145                 150                 155                 160

Phe Ser Thr Cys Asp Asn Gln Lys Ser Cys Met Ser Asn Cys Ser Ile
                165                 170                 175

Thr Ser Ile Cys Glu Lys Pro Gln Glu Val Cys Val Ala Val Trp Arg
            180                 185                 190

Lys Asn Asp Glu Asn Ile Thr Leu Glu Thr Val Cys His Asp Pro Lys
        195                 200                 205

Leu Pro Tyr His Asp Phe Ile Leu Glu Asp Ala Ala Ser Pro Lys Cys
    210                 215                 220

Ile Met Lys Glu Lys Lys Pro Gly Glu Thr Phe Phe Met Cys Ser
225                 230                 235                 240

Cys Ser Ser Asp Glu Cys Asn Asp Asn Ile Ile Phe Ser Glu Glu Tyr
                245                 250                 255

Asn Thr Ser Asn Pro Asp Ile Pro Pro His Val Gln Lys Ser Asp Val
            260                 265                 270

Glu Met Glu Ala Gln Lys Asp Glu Ile Ile Ala Pro Ser Ala Asn Arg
        275                 280                 285

Thr Ala His Pro Leu Arg His Ile Asn Asn Asp Met Ile Val Thr Asp
    290                 295                 300

Asn Asn Gly Ala Val Lys Phe Pro Gln Leu Cys Lys Phe Cys Asp Val
305                 310                 315                 320

Arg Phe Ser Thr Cys Asp Asn Gln Lys Ser Cys Met Ser Asn Cys Ser
                325                 330                 335

Ile Thr Ser Ile Cys Glu Lys Pro Gln Glu Val Cys Val Ala Val Trp
            340                 345                 350

Arg Lys Asn Asp Glu Asn Ile Thr Leu Glu Thr Val Cys His Asp Pro
        355                 360                 365

Lys Leu Pro Tyr His Asp Phe Ile Leu Glu Asp Ala Ala Ser Pro Lys
    370                 375                 380

Cys Ile Met Lys Glu Lys Lys Pro Gly Glu Thr Phe Phe Met Cys
385                 390                 395                 400

Ser Cys Ser Ser Asp Glu Cys Asn Asp Asn Ile Ile Phe Ser Glu Glu
                405                 410                 415

Tyr Asn Thr Ser Asn Pro Asp
            420

<210> SEQ ID NO 67
<211> LENGTH: 373
<212> TYPE: PRT
<213> ORGANISM: Artificial Sequence
```

<220> FEATURE:
<223> OTHER INFORMATION: TbetaRI-TbetaRII-ED trimer T2-T2-T1

<400> SEQUENCE: 67

```
Ile Pro Pro His Val Gln Lys Ser Val Asn Asn Asp Met Ile Val Thr
1               5                   10                  15

Asp Asn Asn Gly Ala Val Lys Phe Pro Gln Leu Cys Lys Phe Cys Asp
            20                  25                  30

Val Arg Phe Ser Thr Cys Asp Asn Gln Lys Ser Cys Met Ser Asn Cys
        35                  40                  45

Ser Ile Thr Ser Ile Cys Glu Lys Pro Gln Glu Val Cys Val Ala Val
    50                  55                  60

Trp Arg Lys Asn Asp Glu Asn Ile Thr Leu Glu Thr Val Cys His Asp
65                  70                  75                  80

Pro Lys Leu Pro Tyr His Asp Phe Ile Leu Glu Asp Ala Ala Ser Pro
                85                  90                  95

Lys Cys Ile Met Lys Glu Lys Lys Pro Gly Glu Thr Phe Phe Met
            100                 105                 110

Cys Ser Cys Ser Ser Asp Glu Cys Asn Asp Asn Ile Ile Phe Ser Glu
        115                 120                 125

Glu Tyr Asn Thr Ser Asn Pro Asp Ile Pro Pro His Val Gln Lys Ser
    130                 135                 140

Val Asn Asn Asp Met Ile Val Thr Asp Asn Asn Gly Ala Val Lys Phe
145                 150                 155                 160

Pro Gln Leu Cys Lys Phe Cys Asp Val Arg Phe Ser Thr Cys Asp Asn
                165                 170                 175

Gln Lys Ser Cys Met Ser Asn Cys Ser Ile Thr Ser Ile Cys Glu Lys
            180                 185                 190

Pro Gln Glu Val Cys Val Ala Val Trp Arg Lys Asn Asp Glu Asn Ile
        195                 200                 205

Thr Leu Glu Thr Val Cys His Asp Pro Lys Leu Pro Tyr His Asp Phe
    210                 215                 220

Ile Leu Glu Asp Ala Ala Ser Pro Lys Cys Ile Met Lys Glu Lys Lys
225                 230                 235                 240

Lys Pro Gly Glu Thr Phe Phe Met Cys Ser Cys Ser Ser Asp Glu Cys
                245                 250                 255

Asn Asp Asn Ile Ile Phe Ser Glu Glu Tyr Asn Thr Ser Asn Pro Asp
            260                 265                 270

Ala Ala Leu Leu Pro Gly Ala Thr Ala Leu Gln Cys Phe Cys His Leu
        275                 280                 285

Cys Thr Lys Asp Asn Phe Thr Cys Val Thr Asp Gly Leu Cys Phe Val
    290                 295                 300

Ser Val Thr Glu Thr Thr Asp Lys Val Ile His Asn Ser Met Cys Ile
305                 310                 315                 320

Ala Glu Ile Asp Leu Ile Pro Arg Asp Arg Pro Phe Val Cys Ala Pro
                325                 330                 335

Ser Ser Lys Thr Gly Ser Val Thr Thr Thr Tyr Cys Cys Asn Gln Asp
            340                 345                 350

His Cys Asn Lys Ile Glu Leu Pro Thr Thr Val Lys Ser Ser Pro Gly
        355                 360                 365

Leu Gly Pro Val Glu
    370
```

<210> SEQ ID NO 68

```
<211> LENGTH: 398
<212> TYPE: PRT
<213> ORGANISM: Artificial Sequence
<220> FEATURE:
<223> OTHER INFORMATION: TbetaRI-TbetaRII-ED trimer T2-T2bAA-T1

<400> SEQUENCE: 68
```

Ile Pro Pro His Val Gln Lys Ser Val Asn Asn Asp Met Ile Val Thr
1               5                   10                  15

Asp Asn Asn Gly Ala Val Lys Phe Pro Gln Leu Cys Lys Phe Cys Asp
            20                  25                  30

Val Arg Phe Ser Thr Cys Asp Asn Gln Lys Ser Cys Met Ser Asn Cys
        35                  40                  45

Ser Ile Thr Ser Ile Cys Glu Lys Pro Gln Gl

```
Pro Thr Thr Val Lys Ser Ser Pro Gly Leu Gly Pro Val Glu
385                 390                 395
```

<210> SEQ ID NO 69
<211> LENGTH: 85
<212> TYPE: PRT
<213> ORGANISM: Artificial Sequence
<220> FEATURE:
<223> OTHER INFORMATION: BMPRIa-ED structured domain

<400> SEQUENCE: 69

```
Thr Leu Pro Phe Leu Lys Cys Tyr Cys Ser Gly His Cys Pro Asp Asp
1               5                   10                  15

Ala Ile Asn Asn Thr Cys Ile Thr Asn Gly His Cys Phe Ala Ile Ile
            20                  25                  30

Glu Glu Asp Asp Gln Gly Glu Thr Thr Leu Ala Ser Gly Cys Met Lys
        35                  40                  45

Tyr Glu Gly Ser Asp Phe Gln Cys Lys Asp Ser Pro Lys Ala Gln Leu
    50                  55                  60

Arg Arg Thr Ile Glu Cys Cys Arg Thr Asn Leu Cys Asn Gln Tyr Leu
65                  70                  75                  80

Gln Pro Thr Leu Pro
                85
```

<210> SEQ ID NO 70
<211> LENGTH: 31
<212> TYPE: PRT
<213> ORGANISM: Artificial Sequence
<220> FEATURE:
<223> OTHER INFORMATION: BMPRIa-ED N-term unstructured region and
      natural linker

<400> SEQUENCE: 70

```
Gln Asn Leu Asp Ser Met Leu His Gly Thr Gly Met Lys Ser Asp Ser
1               5                   10                  15

Asp Gln Lys Lys Ser Glu Asn Gly Val Thr Leu Ala Pro Glu Asp
            20                  25                  30
```

<210> SEQ ID NO 71
<211> LENGTH: 13
<212> TYPE: PRT
<213> ORGANISM: Artificial Sequence
<220> FEATURE:
<223> OTHER INFORMATION: BMPRIa-ED C-term unstructured region and
      natural linker

<400> SEQUENCE: 71

```
Pro Val Val Ile Gly Pro Phe Phe Asp Gly Ser Ile Arg
1               5                   10
```

<210> SEQ ID NO 72
<211> LENGTH: 44
<212> TYPE: PRT
<213> ORGANISM: Artificial Sequence
<220> FEATURE:
<223> OTHER INFORMATION: BMPRIa-ED natural linker

<400> SEQUENCE: 72

```
Pro Val Val Ile Gly Pro Phe Phe Asp Gly Ser Ile Arg Gln Asn Leu
1               5                   10                  15

Asp Ser Met Leu His Gly Thr Gly Met Lys Ser Asp Ser Asp Gln Lys
            20                  25                  30
```

```
Lys Ser Glu Asn Gly Val Thr Leu Ala Pro Glu Asp
            35                  40

<210> SEQ ID NO 73
<211> LENGTH: 129
<212> TYPE: PRT
<213> ORGANISM: Artificial Sequence
<220> FEATURE:
<223> OTHER INFORMATION: BMPRIa-ED monomer

<400> SEQUENCE: 73

Gln Asn Leu Asp Ser Met Leu His Gly Thr Gly Met Lys Ser Asp Ser
1               5                   10                  15

Asp Gln Lys Lys Ser Glu Asn Gly Val Thr Leu Ala Pro Glu Asp Thr
            20                  25                  30

Leu Pro Phe Leu Lys Cys Tyr Cys Ser Gly His Cys Pro Asp Asp Ala
        35                  40                  45

Ile Asn Asn Thr Cys Ile Thr Asn Gly His Cys Phe Ala Ile Ile Glu
    50                  55                  60

Glu Asp Asp Gln Gly Glu Thr Thr Leu Ala Ser Gly Cys Met Lys Tyr
65                  70                  75                  80

Glu Gly Ser Asp Phe Gln Cys Lys Asp Ser Pro Lys Ala Gln Leu Arg
                85                  90                  95

Arg Thr Ile Glu Cys Cys Arg Thr Asn Leu Cys Asn Gln Tyr Leu Gln
            100                 105                 110

Pro Thr Leu Pro Pro Val Val Ile Gly Pro Phe Phe Asp Gly Ser Ile
        115                 120                 125

Arg

<210> SEQ ID NO 74
<211> LENGTH: 258
<212> TYPE: PRT
<213> ORGANISM: Artificial Sequence
<220> FEATURE:
<223> OTHER INFORMATION: BMPRIa-ED dimer

<400> SEQUENCE: 74

Gln Asn Leu Asp Ser Met Leu His Gly Thr Gly Met Lys Ser Asp Ser
1               5                   10                  15

Asp Gln Lys Lys Ser Glu Asn Gly Val Thr Leu Ala Pro Glu Asp Thr
            20                  25                  30

Leu Pro Phe Leu Lys Cys Tyr Cys Ser Gly His Cys Pro Asp Asp Ala
        35                  40                  45

Ile Asn Asn Thr Cys Ile Thr Asn Gly His Cys Phe Ala Ile Ile Glu
    50                  55                  60

Glu Asp Asp Gln Gly Glu Thr Thr Leu Ala Ser Gly Cys Met Lys Tyr
65                  70                  75                  80

Glu Gly Ser Asp Phe Gln Cys Lys Asp Ser Pro Lys Ala Gln Leu Arg
                85                  90                  95

Arg Thr Ile Glu Cys Cys Arg Thr Asn Leu Cys Asn Gln Tyr Leu Gln
            100                 105                 110

Pro Thr Leu Pro Pro Val Val Ile Gly Pro Phe Phe Asp Gly Ser Ile
        115                 120                 125

Arg Gln Asn Leu Asp Ser Met Leu His Gly Thr Gly Met Lys Ser Asp
        130                 135                 140

Ser Asp Gln Lys Lys Ser Glu Asn Gly Val Thr Leu Ala Pro Glu Asp
145                 150                 155                 160
```

Thr Leu Pro Phe Leu Lys Cys Tyr Cys Ser Gly His Cys Pro Asp Asp
                165                 170                 175

Ala Ile Asn Asn Thr Cys Ile Thr Asn Gly His Cys Phe Ala Ile Ile
            180                 185                 190

Glu Glu Asp Asp Gln Gly Glu Thr Thr Leu Ala Ser Gly Cys Met Lys
        195                 200                 205

Tyr Glu Gly Ser Asp Phe Gln Cys Lys Asp Ser Pro Lys Ala Gln Leu
    210                 215                 220

Arg Arg Thr Ile Glu Cys Cys Arg Thr Asn Leu Cys Asn Gln Tyr Leu
225                 230                 235                 240

Gln Pro Thr Leu Pro Pro Val Val Ile Gly Pro Phe Phe Asp Gly Ser
                245                 250                 255

Ile Arg

<210> SEQ ID NO 75
<211> LENGTH: 92
<212> TYPE: PRT
<213> ORGANISM: Artificial Sequence
<220> FEATURE:
<223> OTHER INFORMATION: ActRIIa-ED structured domain

<400> SEQUENCE: 75

Thr Gln Glu Cys Leu Phe Phe Asn Ala Asn Trp Glu Lys Asp Arg Thr
1               5                   10                  15

Asn Gln Thr Gly Val Glu Pro Cys Tyr Gly Asp Lys Asp Lys Arg Arg
            20                  25                  30

His Cys Phe Ala Thr Trp Lys Asn Ile Ser Gly Ser Ile Glu Ile Val
        35                  40                  45

Lys Gln Gly Cys Trp Leu Asp Asp Ile Asn Cys Tyr Asp Arg Thr Asp
    50                  55                  60

Cys Val Glu Lys Lys Asp Ser Pro Glu Val Tyr Phe Cys Cys Cys Glu
65                  70                  75                  80

Gly Asn Met Cys Asn Glu Lys Phe Ser Tyr Phe Pro
                85                  90

<210> SEQ ID NO 76
<211> LENGTH: 7
<212> TYPE: PRT
<213> ORGANISM: Artificial Sequence
<220> FEATURE:
<223> OTHER INFORMATION: ActRIIa-ED N-term unstructured region and
      natural linker

<400> SEQUENCE: 76

Ala Ile Leu Gly Arg Ser Glu
1               5

<210> SEQ ID NO 77
<211> LENGTH: 21
<212> TYPE: PRT
<213> ORGANISM: Artificial Sequence
<220> FEATURE:
<223> OTHER INFORMATION: ActRIIa-ED C-term unstructured region and
      natural linker

<400> SEQUENCE: 77

Glu Met Glu Val Thr Gln Pro Thr Ser Asn Pro Val Thr Pro Lys Pro
1               5                   10                  15

Pro Tyr Tyr Asn Ile
            20

<210> SEQ ID NO 78
<211> LENGTH: 28
<212> TYPE: PRT
<213> ORGANISM: Artificial Sequence
<220> FEATURE:
<223> OTHER INFORMATION: ActRIIa-ED natural linker

<400> SEQUENCE: 78

Glu Met Glu Val Thr Gln Pro Thr Ser Asn Pro Val Thr Pro Lys Pro
1               5                   10                  15

Pro Tyr Tyr Asn Ile Ala Ile Leu Gly Arg Ser Glu
            20                  25

<210> SEQ ID NO 79
<211> LENGTH: 120
<212> TYPE: PRT
<213> ORGANISM: Artificial Sequence
<220> FEATURE:
<223> OTHER INFORMATION: ActRIIa-ED monomer

<400> SEQUENCE: 79

Ala Ile Leu Gly Arg Ser Glu Thr Gln Glu Cys Leu Phe Phe Asn Ala
1               5                   10                  15

Asn Trp Glu Lys Asp Arg Thr Asn Gln Thr Gly Val Glu Pro Cys Tyr
            20                  25                  30

Gly Asp Lys Asp Lys Arg Arg His Cys Phe Ala Thr Trp Lys Asn Ile
        35                  40                  45

Ser Gly Ser Ile Glu Ile Val Lys Gln Gly Cys Trp Leu Asp Asp Ile
    50                  55                  60

Asn Cys Tyr Asp Arg Thr Asp Cys Val Glu Lys Lys Asp Ser Pro Glu
65                  70                  75                  80

Val Tyr Phe Cys Cys Cys Glu Gly Asn Met Cys Asn Glu Lys Phe Ser
                85                  90                  95

Tyr Phe Pro Glu Met Glu Val Thr Gln Pro Thr Ser Asn Pro Val Thr
            100                 105                 110

Pro Lys Pro Pro Tyr Tyr Asn Ile
        115                 120

<210> SEQ ID NO 80
<211> LENGTH: 240
<212> TYPE: PRT
<213> ORGANISM: Artificial Sequence
<220> FEATURE:
<223> OTHER INFORMATION: ActRIIa-ED dimer

<400> SEQUENCE: 80

Ala Ile Leu Gly Arg Ser Glu Thr Gln Glu Cys Leu Phe Phe Asn Ala
1               5                   10                  15

Asn Trp Glu Lys Asp Arg Thr Asn Gln Thr Gly Val Glu Pro Cys Tyr
            20                  25                  30

Gly Asp Lys Asp Lys Arg Arg His Cys Phe Ala Thr Trp Lys Asn Ile
        35                  40                  45

Ser Gly Ser Ile Glu Ile Val Lys Gln Gly Cys Trp Leu Asp Asp Ile
    50                  55                  60

Asn Cys Tyr Asp Arg Thr Asp Cys Val Glu Lys Lys Asp Ser Pro Glu
65                  70                  75                  80

Val Tyr Phe Cys Cys Cys Glu Gly Asn Met Cys Asn Glu Lys Phe Ser
                85                  90                  95

Tyr Phe Pro Glu Met Glu Val Thr Gln Pro Thr Ser Asn Pro Val Thr

```
                    100                 105                 110
Pro Lys Pro Pro Tyr Tyr Asn Ile Ala Ile Leu Gly Arg Ser Glu Thr
            115                 120                 125

Gln Glu Cys Leu Phe Phe Asn Ala Asn Trp Glu Lys Asp Arg Thr Asn
        130                 135                 140

Gln Thr Gly Val Glu Pro Cys Tyr Gly Asp Lys Asp Lys Arg Arg His
145                 150                 155                 160

Cys Phe Ala Thr Trp Lys Asn Ile Ser Gly Ser Ile Glu Ile Val Lys
                165                 170                 175

Gln Gly Cys Trp Leu Asp Asp Ile Asn Cys Tyr Asp Arg Thr Asp Cys
            180                 185                 190

Val Glu Lys Lys Asp Ser Pro Glu Val Tyr Phe Cys Cys Cys Glu Gly
        195                 200                 205

Asn Met Cys Asn Glu Lys Phe Ser Tyr Phe Pro Glu Met Glu Val Thr
    210                 215                 220

Gln Pro Thr Ser Asn Pro Val Thr Pro Lys Pro Pro Tyr Tyr Asn Ile
225                 230                 235                 240

<210> SEQ ID NO 81
<211> LENGTH: 91
<212> TYPE: PRT
<213> ORGANISM: Artificial Sequence
<220> FEATURE:
<223> OTHER INFORMATION: ActRIIb-ED structured domain

<400> SEQUENCE: 81

Arg Glu Cys Ile Tyr Tyr Asn Ala Asn Trp Glu Leu Glu Arg Thr Asn
1               5                   10                  15

Gln Ser Gly Leu Glu Arg Cys Glu Gly Glu Gln Asp Lys Arg Leu His
            20                  25                  30

Cys Tyr Ala Ser Trp Arg Asn Ser Ser Gly Thr Ile Glu Leu Val Lys
        35                  40                  45

Lys Gly Cys Trp Leu Asp Asp Phe Asn Cys Tyr Asp Arg Gln Glu Cys
    50                  55                  60

Val Ala Thr Glu Glu Asn Pro Gln Val Tyr Phe Cys Cys Cys Glu Gly
65                  70                  75                  80

Asn Phe Cys Asn Glu Arg Phe Thr His Leu Pro
                85                  90

<210> SEQ ID NO 82
<211> LENGTH: 8
<212> TYPE: PRT
<213> ORGANISM: Artificial Sequence
<220> FEATURE:
<223> OTHER INFORMATION: ActRIIb-ED N-term unstructured region and
      natural linker

<400> SEQUENCE: 82

Ser Gly Arg Gly Glu Ala Glu Thr
1               5

<210> SEQ ID NO 83
<211> LENGTH: 17
<212> TYPE: PRT
<213> ORGANISM: Artificial Sequence
<220> FEATURE:
<223> OTHER INFORMATION: ActRIIb-ED C-term unstructured region and
      natural linker

<400> SEQUENCE: 83
```

```
Glu Ala Gly Gly Pro Glu Val Thr Tyr Glu Pro Pro Thr Ala Pro
1               5                   10                  15

Thr
```

<210> SEQ ID NO 84
<211> LENGTH: 25
<212> TYPE: PRT
<213> ORGANISM: Artificial Sequence
<220> FEATURE:
<223> OTHER INFORMATION: ActRIIb-ED natural linker

<400> SEQUENCE: 84

```
Glu Ala Gly Gly Pro Glu Val Thr Tyr Glu Pro Pro Thr Ala Pro
1               5                   10                  15

Thr Ser Gly Arg Gly Glu Ala Glu Thr
            20                  25
```

<210> SEQ ID NO 85
<211> LENGTH: 116
<212> TYPE: PRT
<213> ORGANISM: Artificial Sequence
<220> FEATURE:
<223> OTHER INFORMATION: ActRIIb-ED monomer

<400> SEQUENCE: 85

```
Ser Gly Arg Gly Glu Ala Glu Thr Arg Glu Cys Ile Tyr Tyr Asn Ala
1               5                   10                  15

Asn Trp Glu Leu Glu Arg Thr Asn Gln Ser Gly Leu Glu Arg Cys Glu
                20                  25                  30

Gly Glu Gln Asp Lys Arg Leu His Cys Tyr Ala Ser Trp Arg Asn Ser
            35                  40                  45

Ser Gly Thr Ile Glu Leu Val Lys Lys Gly Cys Trp Leu Asp Asp Phe
        50                  55                  60

Asn Cys Tyr Asp Arg Gln Glu Cys Val Ala Thr Glu Glu Asn Pro Gln
65                  70                  75                  80

Val Tyr Phe Cys Cys Cys Glu Gly Asn Phe Cys Asn Glu Arg Phe Thr
                85                  90                  95

His Leu Pro Glu Ala Gly Gly Pro Glu Val Thr Tyr Glu Pro Pro
            100                 105                 110

Thr Ala Pro Thr
        115
```

<210> SEQ ID NO 86
<211> LENGTH: 232
<212> TYPE: PRT
<213> ORGANISM: Artificial Sequence
<220> FEATURE:
<223> OTHER INFORMATION: ActRIIb-ED dimer

<400> SEQUENCE: 86

```
Ser Gly Arg Gly Glu Ala Glu Thr Arg Glu Cys Ile Tyr Tyr Asn Ala
1               5                   10                  15

Asn Trp Glu Leu Glu Arg Thr Asn Gln Ser Gly Leu Glu Arg Cys Glu
                20                  25                  30

Gly Glu Gln Asp Lys Arg Leu His Cys Tyr Ala Ser Trp Arg Asn Ser
            35                  40                  45

Ser Gly Thr Ile Glu Leu Val Lys Lys Gly Cys Trp Leu Asp Asp Phe
        50                  55                  60

Asn Cys Tyr Asp Arg Gln Glu Cys Val Ala Thr Glu Glu Asn Pro Gln
65                  70                  75                  80
```

```
Val Tyr Phe Cys Cys Cys Glu Gly Asn Phe Cys Asn Glu Arg Phe Thr
                    85                  90                  95

His Leu Pro Glu Ala Gly Gly Pro Glu Val Thr Tyr Glu Pro Pro Pro
            100                 105                 110

Thr Ala Pro Thr Ser Gly Arg Gly Glu Ala Glu Thr Arg Glu Cys Ile
            115                 120                 125

Tyr Tyr Asn Ala Asn Trp Glu Leu Glu Arg Thr Asn Gln Ser Gly Leu
    130                 135                 140

Glu Arg Cys Glu Gly Glu Gln Asp Lys Arg Leu His Cys Tyr Ala Ser
145                 150                 155                 160

Trp Arg Asn Ser Ser Gly Thr Ile Glu Leu Val Lys Lys Gly Cys Trp
                165                 170                 175

Leu Asp Asp Phe Asn Cys Tyr Asp Arg Gln Glu Cys Val Ala Thr Glu
                180                 185                 190

Glu Asn Pro Gln Val Tyr Phe Cys Cys Cys Glu Gly Asn Phe Cys Asn
            195                 200                 205

Glu Arg Phe Thr His Leu Pro Glu Ala Gly Gly Pro Glu Val Thr Tyr
    210                 215                 220

Glu Pro Pro Pro Thr Ala Pro Thr
225                 230

<210> SEQ ID NO 87
<211> LENGTH: 52
<212> TYPE: PRT
<213> ORGANISM: Artificial Sequence
<220> FEATURE:
<223> OTHER INFORMATION: ActRIIa-BMPRIa-ED natural linker

<400> SEQUENCE: 87

Glu Met Glu Val Thr Gln Pro Thr Ser Asn Pro Val Thr Pro Lys Pro
1               5                   10                  15

Pro Tyr Tyr Asn Ile Gln Asn Leu Asp Ser Met Leu His Gly Thr Gly
            20                  25                  30

Met Lys Ser Asp Ser Asp Gln Lys Lys Ser Glu Asn Gly Val Thr Leu
        35                  40                  45

Ala Pro Glu Asp
    50

<210> SEQ ID NO 88
<211> LENGTH: 249
<212> TYPE: PRT
<213> ORGANISM: Artificial Sequence
<220> FEATURE:
<223> OTHER INFORMATION: ActRIIa-BMPRIa-ED dimer

<400> SEQUENCE: 88

Ala Ile Leu Gly Arg Ser Glu Thr Gln Glu Cys Leu Phe Phe Asn Ala
1               5                   10                  15

Asn Trp Glu Lys Asp Arg Thr Asn Gln Thr Gly Val Glu Pro Cys Tyr
            20                  25                  30

Gly Asp Lys Asp Lys Arg Arg His Cys Phe Ala Thr Trp Lys Asn Ile
        35                  40                  45

Ser Gly Ser Ile Glu Ile Val Lys Gln Gly Cys Trp Leu Asp Asp Ile
    50                  55                  60

Asn Cys Tyr Asp Arg Thr Asp Cys Val Glu Lys Lys Asp Ser Pro Glu
65                  70                  75                  80

Val Tyr Phe Cys Cys Cys Glu Gly Asn Met Cys Asn Glu Lys Phe Ser
```

```
                    85                  90                  95

Tyr Phe Pro Glu Met Glu Val Thr Gln Pro Thr Ser Asn Pro Val Thr
                100                 105                 110

Pro Lys Pro Pro Tyr Tyr Asn Ile Gln Asn Leu Asp Ser Met Leu His
            115                 120                 125

Gly Thr Gly Met Lys Ser Asp Ser Asp Gln Lys Lys Ser Glu Asn Gly
        130                 135                 140

Val Thr Leu Ala Pro Glu Asp Thr Leu Pro Phe Leu Lys Cys Tyr Cys
145                 150                 155                 160

Ser Gly His Cys Pro Asp Asp Ala Ile Asn Asn Thr Cys Ile Thr Asn
                165                 170                 175

Gly His Cys Phe Ala Ile Ile Glu Glu Asp Asp Gln Gly Glu Thr Thr
            180                 185                 190

Leu Ala Ser Gly Cys Met Lys Tyr Glu Gly Ser Asp Phe Gln Cys Lys
        195                 200                 205

Asp Ser Pro Lys Ala Gln Leu Arg Arg Thr Ile Glu Cys Cys Arg Thr
210                 215                 220

Asn Leu Cys Asn Gln Tyr Leu Gln Pro Thr Leu Pro Pro Val Val Ile
225                 230                 235                 240

Gly Pro Phe Phe Asp Gly Ser Ile Arg
                245

<210> SEQ ID NO 89
<211> LENGTH: 19
<212> TYPE: PRT
<213> ORGANISM: Artificial Sequence
<220> FEATURE:
<223> OTHER INFORMATION: Signal peptide

<400> SEQUENCE: 89

Met Asp Trp Thr Trp Arg Ile Leu Phe Leu Val Ala Ala Thr Gly
1               5                   10                  15

Thr His Ala

<210> SEQ ID NO 90
<211> LENGTH: 20
<212> TYPE: PRT
<213> ORGANISM: Artificial Sequence
<220> FEATURE:
<223> OTHER INFORMATION: Signal peptide

<400> SEQUENCE: 90

Met Val Leu Gln Thr Gln Val Phe Ile Ser Leu Leu Leu Trp Ile Ser
1               5                   10                  15

Gly Ala Tyr Gly
            20

<210> SEQ ID NO 91
<211> LENGTH: 352
<212> TYPE: PRT
<213> ORGANISM: Artificial Sequence
<220> FEATURE:
<223> OTHER INFORMATION: hIgG1FcdeltaK-deltaC-T2m fusion

<400> SEQUENCE: 91

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30
```

Val Val Asp Val Ser His Glu Asp Pro Glu Val Lys Phe Asn Trp Tyr
            35                  40                  45

Val Asp Gly Val Glu Val His Asn Ala Lys Thr Lys Pro Arg Glu Glu
50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Asp Glu Leu
        115                 120                 125

Thr Lys Asn Gln Val Ser Leu Thr Cys Leu Val Lys Gly Phe Tyr Pro
130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Tyr Ser Lys Leu Thr Val Asp Lys Ser Arg Trp Gln Gln Gly Asn Val
            180                 185                 190

Phe Ser Cys Ser Val Met His Glu Ala Leu His Asn His Tyr Thr Gln
        195                 200                 205

Lys Ser Leu Ser Leu Ser Pro Gly Ile Pro Pro His Val Gln Lys Ser
210                 215                 220

Val Asn Asn Asp Met Ile Val Thr Asp Asn Gly Ala Val Lys Phe
225                 230                 235                 240

Pro Gln Leu Cys Lys Phe Cys Asp Val Arg Phe Ser Thr Cys Asp Asn
                245                 250                 255

Gln Lys Ser Cys Met Ser Asn Cys Ser Ile Thr Ser Ile Cys Glu Lys
            260                 265                 270

Pro Gln Glu Val Cys Val Ala Val Trp Arg Lys Asn Asp Glu Asn Ile
        275                 280                 285

Thr Leu Glu Thr Val Cys His Asp Pro Lys Leu Pro Tyr His Asp Phe
290                 295                 300

Ile Leu Glu Asp Ala Ala Ser Pro Lys Cys Ile Met Lys Glu Lys Lys
305                 310                 315                 320

Lys Pro Gly Glu Thr Phe Phe Met Cys Ser Cys Ser Ser Asp Glu Cys
                325                 330                 335

Asn Asp Asn Ile Ile Phe Ser Glu Glu Tyr Asn Thr Ser Asn Pro Asp
            340                 345                 350

<210> SEQ ID NO 92
<211> LENGTH: 356
<212> TYPE: PRT
<213> ORGANISM: Artificial Sequence
<220> FEATURE:
<223> OTHER INFORMATION: hIgG1FcdeltaK-C-T2m fusion

<400> SEQUENCE: 92

Pro Pro Cys Pro Ala Pro Glu Leu Leu Gly Gly Pro Ser Val Phe Leu
1               5                   10                  15

Phe Pro Pro Lys Pro Lys Asp Thr Leu Met Ile Ser Arg Thr Pro Glu
            20                  25                  30

Val Thr Cys Val Val Val Asp Val Ser His Glu Asp Pro Glu Val Lys
        35                  40                  45

```
Phe Asn Trp Tyr Val Asp Gly Val Glu Val His Asn Ala Lys Thr Lys
 50                  55                  60

Pro Arg Glu Glu Gln Tyr Asn Ser Thr Tyr Arg Val Val Ser Val Leu
 65                  70                  75                  80

Thr Val Leu His Gln Asp Trp Leu Asn Gly Lys Glu Tyr Lys Cys Lys
                 85                  90                  95

Val Ser Asn Lys Ala Leu Pro Ala Pro Ile Glu Lys Thr Ile Ser Lys
            100                 105                 110

Ala Lys Gly Gln Pro Arg Glu Pro Gln Val Tyr Thr Leu Pro Pro Ser
        115                 120                 125

Arg Asp Glu Leu Thr Lys Asn Gln Val Ser Leu Thr Cys Leu Val Lys
130                 135                 140

Gly Phe Tyr Pro Ser Asp Ile Ala Val Glu Trp Glu Ser Asn Gly Gln
145                 150                 155                 160

Pro Glu Asn Asn Tyr Lys Thr Thr Pro Pro Val Leu Asp Ser Asp Gly
                165                 170                 175

Ser Phe Phe Leu Tyr Ser Lys Leu Thr Val Asp Lys Ser Arg Trp Gln
            180                 185                 190

Gln Gly Asn Val Phe Ser Cys Ser Val Met His Glu Ala Leu His Asn
        195                 200                 205

His Tyr Thr Gln Lys Ser Leu Ser Leu Ser Pro Gly Ile Pro Pro His
210                 215                 220

Val Gln Lys Ser Val Asn Asn Asp Met Ile Val Thr Asp Asn Asn Gly
225                 230                 235                 240

Ala Val Lys Phe Pro Gln Leu Cys Lys Phe Cys Asp Val Arg Phe Ser
                245                 250                 255

Thr Cys Asp Asn Gln Lys Ser Cys Met Ser Asn Cys Ser Ile Thr Ser
            260                 265                 270

Ile Cys Glu Lys Pro Gln Glu Val Cys Val Ala Val Trp Arg Lys Asn
        275                 280                 285

Asp Glu Asn Ile Thr Leu Glu Thr Val Cys His Asp Pro Lys Leu Pro
290                 295                 300

Tyr His Asp Phe Ile Leu Glu Asp Ala Ala Ser Pro Lys Cys Ile Met
305                 310                 315                 320

Lys Glu Lys Lys Lys Pro Gly Glu Thr Phe Phe Met Cys Ser Cys Ser
                325                 330                 335

Ser Asp Glu Cys Asn Asp Asn Ile Ile Phe Ser Glu Glu Tyr Asn Thr
            340                 345                 350

Ser Asn Pro Asp
        355

<210> SEQ ID NO 93
<211> LENGTH: 362
<212> TYPE: PRT
<213> ORGANISM: Artificial Sequence
<220> FEATURE:
<223> OTHER INFORMATION: hIgG1FcdeltaK-CC-T2m fusion

<400> SEQUENCE: 93

Asp Lys Thr His Thr Cys Pro Pro Cys Pro Ala Pro Glu Leu Leu Gly
 1               5                  10                  15

Gly Pro Ser Val Phe Leu Phe Pro Pro Lys Pro Lys Asp Thr Leu Met
                 20                  25                  30

Ile Ser Arg Thr Pro Glu Val Thr Cys Val Val Val Asp Val Ser His
             35                  40                  45
```

Glu Asp Pro Glu Val Lys Phe Asn Trp Tyr Val Asp Gly Val Glu Val
        50                  55                  60

His Asn Ala Lys Thr Lys Pro Arg Glu Gln Tyr Asn Ser Thr Tyr
 65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
            115                 120                 125

Tyr Thr Leu Pro Pro Ser Arg Asp Glu Leu Thr Lys Asn Gln Val Ser
130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
            195                 200                 205

His Glu Ala Leu His Asn His Tyr Thr Gln Lys Ser Leu Ser Leu Ser
210                 215                 220

Pro Gly Ile Pro Pro His Val Gln Lys Ser Val Asn Asn Asp Met Ile
225                 230                 235                 240

Val Thr Asp Asn Asn Gly Ala Val Lys Phe Pro Gln Leu Cys Lys Phe
                245                 250                 255

Cys Asp Val Arg Phe Ser Thr Cys Asp Asn Gln Lys Ser Cys Met Ser
            260                 265                 270

Asn Cys Ser Ile Thr Ser Ile Cys Glu Lys Pro Gln Glu Val Cys Val
            275                 280                 285

Ala Val Trp Arg Lys Asn Asp Glu Asn Ile Thr Leu Glu Thr Val Cys
290                 295                 300

His Asp Pro Lys Leu Pro Tyr His Asp Phe Ile Leu Glu Asp Ala Ala
305                 310                 315                 320

Ser Pro Lys Cys Ile Met Lys Glu Lys Lys Pro Gly Glu Thr Phe
                325                 330                 335

Phe Met Cys Ser Cys Ser Ser Asp Glu Cys Asn Asp Asn Ile Ile Phe
            340                 345                 350

Ser Glu Glu Tyr Asn Thr Ser Asn Pro Asp
            355                 360

<210> SEQ ID NO 94
<211> LENGTH: 351
<212> TYPE: PRT
<213> ORGANISM: Artificial Sequence
<220> FEATURE:
<223> OTHER INFORMATION: hIgG2FcdeltaK-deltaC-T2m fusion

<400> SEQUENCE: 94

Ala Pro Pro Val Ala Gly Pro Ser Val Phe Leu Phe Pro Pro Lys Pro
 1               5                  10                  15

Lys Asp Thr Leu Met Ile Ser Arg Thr Pro Glu Val Thr Cys Val Val
                20                  25                  30

Val Asp Val Ser His Glu Asp Pro Glu Val Gln Phe Asn Trp Tyr Val
            35                  40                  45

```
Asp Gly Val Glu Val His Asn Ala Lys Thr Lys Pro Arg Glu Glu Gln
    50                  55                  60

Phe Asn Ser Thr Phe Arg Val Val Ser Val Leu Thr Val His Gln
65                  70                  75                  80

Asp Trp Leu Asn Gly Lys Glu Tyr Lys Cys Lys Val Ser Asn Lys Gly
                85                  90                  95

Leu Pro Ala Pro Ile Glu Lys Thr Ile Ser Lys Thr Lys Gly Gln Pro
            100                 105                 110

Arg Glu Pro Gln Val Tyr Thr Leu Pro Pro Ser Arg Glu Glu Met Thr
            115                 120                 125

Lys Asn Gln Val Ser Leu Thr Cys Leu Val Lys Gly Phe Tyr Pro Ser
130                 135                 140

Asp Ile Ser Val Glu Trp Glu Ser Asn Gly Gln Pro Glu Asn Asn Tyr
145                 150                 155                 160

Lys Thr Thr Pro Pro Met Leu Asp Ser Asp Gly Ser Phe Phe Leu Tyr
                165                 170                 175

Ser Lys Leu Thr Val Asp Lys Ser Arg Trp Gln Gln Gly Asn Val Phe
            180                 185                 190

Ser Cys Ser Val Met His Glu Ala Leu His Asn His Tyr Thr Gln Lys
            195                 200                 205

Ser Leu Ser Leu Ser Pro Gly Ile Pro Pro His Val Gln Lys Ser Val
210                 215                 220

Asn Asn Asp Met Ile Val Thr Asp Asn Asn Gly Ala Val Lys Phe Pro
225                 230                 235                 240

Gln Leu Cys Lys Phe Cys Asp Val Arg Phe Ser Thr Cys Asp Asn Gln
                245                 250                 255

Lys Ser Cys Met Ser Asn Cys Ser Ile Thr Ser Ile Cys Glu Lys Pro
            260                 265                 270

Gln Glu Val Cys Val Ala Val Trp Arg Lys Asn Asp Glu Asn Ile Thr
            275                 280                 285

Leu Glu Thr Val Cys His Asp Pro Lys Leu Pro Tyr His Asp Phe Ile
290                 295                 300

Leu Glu Asp Ala Ala Ser Pro Lys Cys Ile Met Lys Glu Lys Lys Lys
305                 310                 315                 320

Pro Gly Glu Thr Phe Phe Met Cys Ser Cys Ser Ser Asp Glu Cys Asn
                325                 330                 335

Asp Asn Ile Ile Phe Ser Glu Glu Tyr Asn Thr Ser Asn Pro Asp
            340                 345                 350
```

<210> SEQ ID NO 95
<211> LENGTH: 355
<212> TYPE: PRT
<213> ORGANISM: Artificial Sequence
<220> FEATURE:
<223> OTHER INFORMATION: hIgG2FcdeltaK-C-T2m fusion

<400> SEQUENCE: 95

```
Pro Pro Cys Pro Ala Pro Pro Val Ala Gly Pro Ser Val Phe Leu Phe
1               5                   10                  15

Pro Pro Lys Pro Lys Asp Thr Leu Met Ile Ser Arg Thr Pro Glu Val
            20                  25                  30

Thr Cys Val Val Val Asp Val Ser His Glu Asp Pro Glu Val Gln Phe
            35                  40                  45

Asn Trp Tyr Val Asp Gly Val Glu Val His Asn Ala Lys Thr Lys Pro
50                  55                  60
```

-continued

Arg Glu Glu Gln Phe Asn Ser Thr Phe Arg Val Ser Val Leu Thr
 65                  70                  75                  80

Val Val His Gln Asp Trp Leu Asn Gly Lys Glu Tyr Lys Cys Lys Val
                 85                  90                  95

Ser Asn Lys Gly Leu Pro Ala Pro Ile Glu Lys Thr Ile Ser Lys Thr
            100                 105                 110

Lys Gly Gln Pro Arg Glu Pro Gln Val Tyr Thr Leu Pro Pro Ser Arg
        115                 120                 125

Glu Glu Met Thr Lys Asn Gln Val Ser Leu Thr Cys Leu Val Lys Gly
    130                 135                 140

Phe Tyr Pro Ser Asp Ile Ser Val Glu Trp Glu Ser Asn Gly Gln Pro
145                 150                 155                 160

Glu Asn Asn Tyr Lys Thr Thr Pro Pro Met Leu Asp Ser Asp Gly Ser
                165                 170                 175

Phe Phe Leu Tyr Ser Lys Leu Thr Val Asp Lys Ser Arg Trp Gln Gln
            180                 185                 190

Gly Asn Val Phe Ser Cys Ser Val Met His Glu Ala Leu His Asn His
        195                 200                 205

Tyr Thr Gln Lys Ser Leu Ser Leu Ser Pro Gly Ile Pro Pro His Val
    210                 215                 220

Gln Lys Ser Val Asn Asn Asp Met Ile Val Thr Asp Asn Asn Gly Ala
225                 230                 235                 240

Val Lys Phe Pro Gln Leu Cys Lys Phe Cys Asp Val Arg Phe Ser Thr
                245                 250                 255

Cys Asp Asn Gln Lys Ser Cys Met Ser Asn Cys Ser Ile Thr Ser Ile
            260                 265                 270

Cys Glu Lys Pro Gln Glu Val Cys Val Ala Val Trp Arg Lys Asn Asp
        275                 280                 285

Glu Asn Ile Thr Leu Glu Thr Val Cys His Asp Pro Lys Leu Pro Tyr
    290                 295                 300

His Asp Phe Ile Leu Glu Asp Ala Ala Ser Pro Lys Cys Ile Met Lys
305                 310                 315                 320

Glu Lys Lys Lys Pro Gly Glu Thr Phe Phe Met Cys Ser Cys Ser Ser
                325                 330                 335

Asp Glu Cys Asn Asp Asn Ile Ile Phe Ser Glu Glu Tyr Asn Thr Ser
            340                 345                 350

Asn Pro Asp
        355

<210> SEQ ID NO 96
<211> LENGTH: 351
<212> TYPE: PRT
<213> ORGANISM: Artificial Sequence
<220> FEATURE:
<223> OTHER INFORMATION: hIgG2FcdeltaK-CC-T2m fusion

<400> SEQUENCE: 96

Ala Pro Pro Val Ala Gly Pro Ser Val Phe Leu Phe Pro Pro Lys Pro
  1                   5                  10                  15

Lys Asp Thr Leu Met Ile Ser Arg Thr Pro Glu Val Thr Cys Val Val
                 20                  25                  30

Val Asp Val Ser His Glu Asp Pro Glu Val Gln Phe Asn Trp Tyr Val
             35                  40                  45

Asp Gly Val Glu Val His Asn Ala Lys Thr Lys Pro Arg Glu Glu Gln
         50                  55                  60

Phe Asn Ser Thr Phe Arg Val Val Ser Val Leu Thr Val Val His Gln
65                  70                  75                  80

Asp Trp Leu Asn Gly Lys Glu Tyr Lys Cys Lys Val Ser Asn Lys Gly
                85                  90                  95

Leu Pro Ala Pro Ile Glu Lys Thr Ile Ser Lys Thr Lys Gly Gln Pro
            100                 105                 110

Arg Glu Pro Gln Val Tyr Thr Leu Pro Pro Ser Arg Glu Glu Met Thr
        115                 120                 125

Lys Asn Gln Val Ser Leu Thr Cys Leu Val Lys Gly Phe Tyr Pro Ser
130                 135                 140

Asp Ile Ser Val Glu Trp Glu Ser Asn Gly Gln Pro Glu Asn Asn Tyr
145                 150                 155                 160

Lys Thr Thr Pro Pro Met Leu Asp Ser Asp Gly Ser Phe Phe Leu Tyr
                165                 170                 175

Ser Lys Leu Thr Val Asp Lys Ser Arg Trp Gln Gln Gly Asn Val Phe
            180                 185                 190

Ser Cys Ser Val Met His Glu Ala Leu His Asn His Tyr Thr Gln Lys
        195                 200                 205

Ser Leu Ser Leu Ser Pro Gly Ile Pro Pro His Val Gln Lys Ser Val
210                 215                 220

Asn Asn Asp Met Ile Val Thr Asp Asn Asn Gly Ala Val Lys Phe Pro
225                 230                 235                 240

Gln Leu Cys Lys Phe Cys Asp Val Arg Phe Ser Thr Cys Asp Asn Gln
                245                 250                 255

Lys Ser Cys Met Ser Asn Cys Ser Ile Thr Ser Ile Cys Glu Lys Pro
            260                 265                 270

Gln Glu Val Cys Val Ala Val Trp Arg Lys Asn Asp Glu Asn Ile Thr
        275                 280                 285

Leu Glu Thr Val Cys His Asp Pro Lys Leu Pro Tyr His Asp Phe Ile
290                 295                 300

Leu Glu Asp Ala Ala Ser Pro Lys Cys Ile Met Lys Glu Lys Lys Lys
305                 310                 315                 320

Pro Gly Glu Thr Phe Phe Met Cys Ser Cys Ser Ser Asp Glu Cys Asn
                325                 330                 335

Asp Asn Ile Ile Phe Ser Glu Glu Tyr Asn Thr Ser Asn Pro Asp
            340                 345                 350

<210> SEQ ID NO 97
<211> LENGTH: 383
<212> TYPE: PRT
<213> ORGANISM: Artificial Sequence
<220> FEATURE:
<223> OTHER INFORMATION: hIgG2Fc-CCCC-T2 fusion, also termed Fc-T2m

<400> SEQUENCE: 97

Met Asp Trp Thr Trp Arg Ile Leu Phe Leu Val Ala Ala Ala Thr Gly
1               5                   10                  15

Thr His Ala Glu Arg Lys Cys Cys Val Glu Cys Pro Pro Cys Pro Ala
            20                  25                  30

Pro Pro Val Ala Gly Pro Ser Val Phe Leu Phe Pro Pro Lys Pro Lys
        35                  40                  45

Asp Thr Leu Met Ile Ser Arg Thr Pro Glu Val Thr Cys Val Val Val
    50                  55                  60

Asp Val Ser His Glu Asp Pro Glu Val Gln Phe Asn Trp Tyr Val Asp
65                  70                  75                  80

```
Gly Val Glu Val His Asn Ala Lys Thr Lys Pro Arg Glu Glu Gln Phe
                85                  90                  95
Asn Ser Thr Phe Arg Val Val Ser Val Leu Thr Val Val His Gln Asp
            100                 105                 110
Trp Leu Asn Gly Lys Glu Tyr Lys Cys Lys Val Ser Asn Lys Gly Leu
        115                 120                 125
Pro Ala Pro Ile Glu Lys Thr Ile Ser Lys Thr Lys Gly Gln Pro Arg
    130                 135                 140
Glu Pro Gln Val Tyr Thr Leu Pro Pro Ser Arg Glu Glu Met Thr Lys
145                 150                 155                 160
Asn Gln Val Ser Leu Thr Cys Leu Val Lys Gly Phe Tyr Pro Ser Asp
                165                 170                 175
Ile Ser Val Glu Trp Glu Ser Asn Gly Gln Pro Glu Asn Asn Tyr Lys
            180                 185                 190
Thr Thr Pro Pro Met Leu Asp Ser Asp Gly Ser Phe Phe Leu Tyr Ser
        195                 200                 205
Lys Leu Thr Val Asp Lys Ser Arg Trp Gln Gln Gly Asn Val Phe Ser
    210                 215                 220
Cys Ser Val Met His Glu Ala Leu His Asn His Tyr Thr Gln Lys Ser
225                 230                 235                 240
Leu Ser Leu Ser Pro Gly Lys Ile Pro Pro His Val Gln Lys Ser Val
                245                 250                 255
Asn Asn Asp Met Ile Val Thr Asp Asn Asn Gly Ala Val Lys Phe Pro
            260                 265                 270
Gln Leu Cys Lys Phe Cys Asp Val Arg Phe Ser Thr Cys Asp Asn Gln
        275                 280                 285
Lys Ser Cys Met Ser Asn Cys Ser Ile Thr Ser Ile Cys Glu Lys Pro
    290                 295                 300
Gln Glu Val Cys Val Ala Val Trp Arg Lys Asn Asp Glu Asn Ile Thr
305                 310                 315                 320
Leu Glu Thr Val Cys His Asp Pro Lys Leu Pro Tyr His Asp Phe Ile
                325                 330                 335
Leu Glu Asp Ala Ala Ser Pro Lys Cys Ile Met Lys Glu Lys Lys Lys
            340                 345                 350
Pro Gly Glu Thr Phe Phe Met Cys Ser Cys Ser Ser Asp Glu Cys Asn
        355                 360                 365
Asp Asn Ile Ile Phe Ser Glu Glu Tyr Asn Thr Ser Asn Pro Asp
    370                 375                 380

<210> SEQ ID NO 98
<211> LENGTH: 364
<212> TYPE: PRT
<213> ORGANISM: Artificial Sequence
<220> FEATURE:
<223> OTHER INFORMATION: hIgG4Fc K-CC-228P-T2m fusion

<400> SEQUENCE: 98

Glu Ser Lys Tyr Gly Pro Pro Cys Pro Pro Cys Pro Ala Pro Glu Phe
1               5                   10                  15
Leu Gly Gly Pro Ser Val Phe Leu Phe Pro Pro Lys Pro Lys Asp Thr
            20                  25                  30
Leu Met Ile Ser Arg Thr Pro Glu Val Thr Cys Val Val Val Asp Val
        35                  40                  45
Ser Gln Glu Asp Pro Glu Val Gln Phe Asn Trp Tyr Val Asp Gly Val
    50                  55                  60
```

```
Glu Val His Asn Ala Lys Thr Lys Pro Arg Glu Gln Phe Asn Ser
65                  70                  75                  80

Thr Tyr Arg Val Val Ser Val Leu Thr Val Leu His Gln Asp Trp Leu
            85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
            115                 120                 125

Gln Val Tyr Thr Leu Pro Pro Ser Gln Glu Glu Met Thr Lys Asn Gln
            130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
            165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
            195                 200                 205

Val Met His Glu Ala Leu His Asn His Tyr Thr Gln Lys Ser Leu Ser
210                 215                 220

Leu Ser Leu Gly Ile Pro Pro His Val Gln Lys Ser Val Asn Asn Asp
225                 230                 235                 240

Met Ile Val Thr Asp Asn Gly Ala Val Lys Phe Pro Gln Leu Cys
            245                 250                 255

Lys Phe Cys Asp Val Arg Phe Ser Thr Cys Asp Asn Gln Lys Ser Cys
            260                 265                 270

Met Ser Asn Cys Ser Ile Thr Ser Ile Cys Glu Lys Pro Gln Glu Val
            275                 280                 285

Cys Val Ala Val Trp Arg Lys Asn Asp Glu Asn Ile Thr Leu Glu Thr
            290                 295                 300

Val Cys His Asp Pro Lys Leu Pro Tyr His Asp Phe Ile Leu Glu Asp
305                 310                 315                 320

Ala Ala Ser Pro Lys Cys Ile Met Lys Glu Lys Lys Pro Gly Glu
            325                 330                 335

Thr Phe Phe Met Cys Ser Cys Ser Ser Asp Glu Cys Asn Asp Asn Ile
            340                 345                 350

Ile Phe Ser Glu Glu Tyr Asn Thr Ser Asn Pro Asp
            355                 360

<210> SEQ ID NO 99
<211> LENGTH: 364
<212> TYPE: PRT
<213> ORGANISM: Artificial Sequence
<220> FEATURE:
<223> OTHER INFORMATION: hIgG4FcdeltaK-CC-228P-409K-T2m fusion

<400> SEQUENCE: 99

Glu Ser Lys Tyr Gly Pro Pro Cys Pro Pro Cys Pro Ala Pro Glu Phe
1               5                   10                  15

Leu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
            35                  40                  45

Ser Gln Glu Asp Pro Glu Val Gln Phe Asn Trp Tyr Val Asp Gly Val
50                  55                  60
```

```
Glu Val His Asn Ala Lys Thr Lys Pro Arg Glu Gln Phe Asn Ser
 65                  70                  75                  80

Thr Tyr Arg Val Val Ser Val Leu Thr Val Leu His Gln Asp Trp Leu
                 85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
        115                 120                 125

Gln Val Tyr Thr Leu Pro Pro Ser Gln Glu Glu Met Thr Lys Asn Gln
    130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Lys Leu
            180                 185                 190

Thr Val Asp Lys Ser Arg Trp Gln Gln Gly Asn Val Phe Ser Cys Ser
        195                 200                 205

Val Met His Glu Ala Leu His Asn His Tyr Thr Gln Lys Ser Leu Ser
    210                 215                 220

Leu Ser Leu Gly Ile Pro Pro His Val Gln Lys Ser Val Asn Asn Asp
225                 230                 235                 240

Met Ile Val Thr Asp Asn Gly Ala Val Lys Phe Pro Gln Leu Cys
                245                 250                 255

Lys Phe Cys Asp Val Arg Phe Ser Thr Cys Asp Asn Gln Lys Ser Cys
            260                 265                 270

Met Ser Asn Cys Ser Ile Thr Ser Ile Cys Glu Lys Pro Gln Glu Val
        275                 280                 285

Cys Val Ala Val Trp Arg Lys Asn Asp Glu Asn Ile Thr Leu Glu Thr
    290                 295                 300

Val Cys His Asp Pro Lys Leu Pro Tyr His Asp Phe Ile Leu Glu Asp
305                 310                 315                 320

Ala Ala Ser Pro Lys Cys Ile Met Lys Glu Lys Lys Pro Gly Glu
                325                 330                 335

Thr Phe Phe Met Cys Ser Cys Ser Ser Asp Glu Cys Asn Asp Asn Ile
            340                 345                 350

Ile Phe Ser Glu Glu Tyr Asn Thr Ser Asn Pro Asp
        355                 360

<210> SEQ ID NO 100
<211> LENGTH: 492
<212> TYPE: PRT
<213> ORGANISM: Artificial Sequence
<220> FEATURE:
<223> OTHER INFORMATION: hIgG1FcdeltaK-C-T22d35 fusion

<400> SEQUENCE: 100

Pro Pro Cys Pro Ala Pro Glu Leu Leu Gly Gly Pro Ser Val Phe Leu
1               5                   10                  15

Phe Pro Pro Lys Pro Lys Asp Thr Leu Met Ile Ser Arg Thr Pro Glu
                20                  25                  30

Val Thr Cys Val Val Val Asp Val Ser His Glu Asp Pro Glu Val Lys
            35                  40                  45

Phe Asn Trp Tyr Val Asp Gly Val Glu Val His Asn Ala Lys Thr Lys
        50                  55                  60
```

```
Pro Arg Glu Glu Gln Tyr Asn Ser Thr Tyr Arg Val Ser Val Leu
 65                  70                  75                  80

Thr Val Leu His Gln Asp Trp Leu Asn Gly Lys Glu Tyr Lys Cys Lys
                 85                  90                  95

Val Ser Asn Lys Ala Leu Pro Ala Pro Ile Glu Lys Thr Ile Ser Lys
            100                 105                 110

Ala Lys Gly Gln Pro Arg Glu Pro Gln Val Tyr Thr Leu Pro Pro Ser
        115                 120                 125

Arg Asp Glu Leu Thr Lys Asn Gln Val Ser Leu Thr Cys Leu Val Lys
    130                 135                 140

Gly Phe Tyr Pro Ser Asp Ile Ala Val Glu Trp Glu Ser Asn Gly Gln
145                 150                 155                 160

Pro Glu Asn Asn Tyr Lys Thr Thr Pro Pro Val Leu Asp Ser Asp Gly
                165                 170                 175

Ser Phe Phe Leu Tyr Ser Lys Leu Thr Val Asp Lys Ser Arg Trp Gln
            180                 185                 190

Gln Gly Asn Val Phe Ser Cys Ser Val Met His Glu Ala Leu His Asn
        195                 200                 205

His Tyr Thr Gln Lys Ser Leu Ser Leu Ser Pro Gly Ile Pro Pro His
    210                 215                 220

Val Gln Lys Ser Val Asn Asn Asp Met Ile Val Thr Asp Asn Asn Gly
225                 230                 235                 240

Ala Val Lys Phe Pro Gln Leu Cys Lys Phe Cys Asp Val Arg Phe Ser
                245                 250                 255

Thr Cys Asp Asn Gln Lys Ser Cys Met Ser Asn Cys Ser Ile Thr Ser
            260                 265                 270

Ile Cys Glu Lys Pro Gln Glu Val Cys Val Ala Val Trp Arg Lys Asn
        275                 280                 285

Asp Glu Asn Ile Thr Leu Glu Thr Val Cys His Asp Pro Lys Leu Pro
    290                 295                 300

Tyr His Asp Phe Ile Leu Glu Asp Ala Ala Ser Pro Lys Cys Ile Met
305                 310                 315                 320

Lys Glu Lys Lys Lys Pro Gly Glu Thr Phe Phe Met Cys Ser Cys Ser
                325                 330                 335

Ser Asp Glu Cys Asn Asp Asn Ile Ile Phe Ser Glu Glu Tyr Asn Thr
            340                 345                 350

Ser Asn Pro Asp Ile Pro Pro His Val Gln Lys Ser Val Asn Asn Asp
        355                 360                 365

Met Ile Val Thr Asp Asn Asn Gly Ala Val Lys Phe Pro Gln Leu Cys
    370                 375                 380

Lys Phe Cys Asp Val Arg Phe Ser Thr Cys Asp Asn Gln Lys Ser Cys
385                 390                 395                 400

Met Ser Asn Cys Ser Ile Thr Ser Ile Cys Glu Lys Pro Gln Glu Val
                405                 410                 415

Cys Val Ala Val Trp Arg Lys Asn Asp Glu Asn Ile Thr Leu Glu Thr
            420                 425                 430

Val Cys His Asp Pro Lys Leu Pro Tyr His Asp Phe Ile Leu Glu Asp
        435                 440                 445

Ala Ala Ser Pro Lys Cys Ile Met Lys Glu Lys Lys Lys Pro Gly Glu
    450                 455                 460

Thr Phe Phe Met Cys Ser Cys Ser Ser Asp Glu Cys Asn Asp Asn Ile
465                 470                 475                 480

Ile Phe Ser Glu Glu Tyr Asn Thr Ser Asn Pro Asp
```

-continued

```
                485                 490

<210> SEQ ID NO 101
<211> LENGTH: 498
<212> TYPE: PRT
<213> ORGANISM: Artificial Sequence
<220> FEATURE:
<223> OTHER INFORMATION: hIgG1FcdeltaK-CC-T22d35 fusion

<400> SEQUENCE: 101

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Asp Glu Leu Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Ile Pro Pro His Val Gln Lys Ser Val Asn Asn Asp Met Ile
225                 230                 235                 240

Val Thr Asp Asn Asn Gly Ala Val Lys Phe Pro Gln Leu Cys Lys Phe
                245                 250                 255

Cys Asp Val Arg Phe Ser Thr Cys Asp Asn Gln Lys Ser Cys Met Ser
            260                 265                 270

Asn Cys Ser Ile Thr Ser Ile Cys Glu Lys Pro Gln Glu Val Cys Val
        275                 280                 285

Ala Val Trp Arg Lys Asn Asp Glu Asn Ile Thr Leu Glu Thr Val Cys
    290                 295                 300

His Asp Pro Lys Leu Pro Tyr His Asp Phe Ile Leu Glu Asp Ala Ala
305                 310                 315                 320

Ser Pro Lys Cys Ile Met Lys Glu Lys Lys Pro Gly Glu Thr Phe
                325                 330                 335

Phe Met Cys Ser Cys Ser Ser Asp Glu Cys Asn Asp Asn Ile Ile Phe
            340                 345                 350

Ser Glu Glu Tyr Asn Thr Ser Asn Pro Asp Ile Pro Pro His Val Gln
```

```
                355                 360                 365
Lys Ser Val Asn Asn Asp Met Ile Val Thr Asp Asn Gly Ala Val
370                 375                 380

Lys Phe Pro Gln Leu Cys Lys Phe Cys Asp Val Arg Phe Ser Thr Cys
385                 390                 395                 400

Asp Asn Gln Lys Ser Cys Met Ser Asn Cys Ser Ile Thr Ser Ile Cys
                405                 410                 415

Glu Lys Pro Gln Glu Val Cys Val Ala Val Trp Arg Lys Asn Asp Glu
                420                 425                 430

Asn Ile Thr Leu Glu Thr Val Cys His Asp Pro Lys Leu Pro Tyr His
                435                 440                 445

Asp Phe Ile Leu Glu Asp Ala Ala Ser Pro Lys Cys Ile Met Lys Glu
                450                 455                 460

Lys Lys Lys Pro Gly Glu Thr Phe Phe Met Cys Ser Cys Ser Ser Asp
465                 470                 475                 480

Glu Cys Asn Asp Asn Ile Ile Phe Ser Glu Glu Tyr Asn Thr Ser Asn
                485                 490                 495

Pro Asp

<210> SEQ ID NO 102
<211> LENGTH: 494
<212> TYPE: PRT
<213> ORGANISM: Artificial Sequence
<220> FEATURE:
<223> OTHER INFORMATION: hIgG2FcdeltaK-CC-T22d35 fusion

<400> SEQUENCE: 102

Val Glu Cys Pro Pro Cys Pro Ala Pro Pro Val Ala Gly Pro Ser Val
1               5                   10                  15

Phe Leu Phe Pro Pro Lys Pro Lys Asp Thr Leu Met Ile Ser Arg Thr
                20                  25                  30

Pro Glu Val Thr Cys Val Val Val Asp Val Ser His Glu Asp Pro Glu
            35                  40                  45

Val Gln Phe Asn Trp Tyr Val Asp Gly Val Glu Val His Asn Ala Lys
        50                  55                  60

Thr Lys Pro Arg Glu Glu Gln Phe Asn Ser Thr Phe Arg Val Val Ser
65                  70                  75                  80

Val Leu Thr Val Val His Gln Asp Trp Leu Asn Gly Lys Glu Tyr Lys
                85                  90                  95

Cys Lys Val Ser Asn Lys Gly Leu Pro Ala Pro Ile Glu Lys Thr Ile
                100                 105                 110

Ser Lys Thr Lys Gly Gln Pro Arg Glu Pro Gln Val Tyr Thr Leu Pro
            115                 120                 125

Pro Ser Arg Glu Glu Met Thr Lys Asn Gln Val Ser Leu Thr Cys Leu
        130                 135                 140

Val Lys Gly Phe Tyr Pro Ser Asp Ile Ser Val Glu Trp Glu Ser Asn
145                 150                 155                 160

Gly Gln Pro Glu Asn Asn Tyr Lys Thr Thr Pro Pro Met Leu Asp Ser
                165                 170                 175

Asp Gly Ser Phe Phe Leu Tyr Ser Lys Leu Thr Val Asp Lys Ser Arg
                180                 185                 190

Trp Gln Gln Gly Asn Val Phe Ser Cys Ser Val Met His Glu Ala Leu
            195                 200                 205

His Asn His Tyr Thr Gln Lys Ser Leu Ser Leu Ser Pro Gly Ile Pro
        210                 215                 220
```

```
Pro His Val Gln Lys Ser Val Asn Asn Asp Met Ile Val Thr Asp Asn
225                 230                 235                 240

Asn Gly Ala Val Lys Phe Pro Gln Leu Cys Lys Phe Cys Asp Val Arg
            245                 250                 255

Phe Ser Thr Cys Asp Asn Gln Lys Ser Cys Met Ser Asn Cys Ser Ile
        260                 265                 270

Thr Ser Ile Cys Glu Lys Pro Gln Glu Val Cys Val Ala Val Trp Arg
    275                 280                 285

Lys Asn Asp Glu Asn Ile Thr Leu Glu Thr Val Cys His Asp Pro Lys
290                 295                 300

Leu Pro Tyr His Asp Phe Ile Leu Glu Asp Ala Ala Ser Pro Lys Cys
305                 310                 315                 320

Ile Met Lys Glu Lys Lys Pro Gly Glu Thr Phe Phe Met Cys Ser
            325                 330                 335

Cys Ser Ser Asp Glu Cys Asn Asp Asn Ile Ile Phe Ser Glu Glu Tyr
        340                 345                 350

Asn Thr Ser Asn Pro Asp Ile Pro Pro His Val Gln Lys Ser Val Asn
    355                 360                 365

Asn Asp Met Ile Val Thr Asp Asn Asn Gly Ala Val Lys Phe Pro Gln
370                 375                 380

Leu Cys Lys Phe Cys Asp Val Arg Phe Ser Thr Cys Asp Asn Gln Lys
385                 390                 395                 400

Ser Cys Met Ser Asn Cys Ser Ile Thr Ser Ile Cys Glu Lys Pro Gln
            405                 410                 415

Glu Val Cys Val Ala Val Trp Arg Lys Asn Asp Glu Asn Ile Thr Leu
        420                 425                 430

Glu Thr Val Cys His Asp Pro Lys Leu Pro Tyr His Asp Phe Ile Leu
    435                 440                 445

Glu Asp Ala Ala Ser Pro Lys Cys Ile Met Lys Glu Lys Lys Pro
450                 455                 460

Gly Glu Thr Phe Phe Met Cys Ser Cys Ser Ser Asp Glu Cys Asn Asp
465                 470                 475                 480

Asn Ile Ile Phe Ser Glu Glu Tyr Asn Thr Ser Asn Pro Asp
            485                 490

<210> SEQ ID NO 103
<211> LENGTH: 500
<212> TYPE: PRT
<213> ORGANISM: Artificial Sequence
<220> FEATURE:
<223> OTHER INFORMATION: hIgG4FcdeltaK-CC-228P-T22d35 fusion

<400> SEQUENCE: 103

Glu Ser Lys Tyr Gly Pro Pro Cys Pro Pro Cys Pro Ala Pro Glu Phe
1               5                   10                  15

Leu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Glu Gln Phe Asn Ser
65                  70                  75                  80

Thr Tyr Arg Val Val Ser Val Leu Thr Val Leu His Gln Asp Trp Leu
            85                  90                  95
```

```
Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
            115                 120                 125

Gln Val Tyr Thr Leu Pro Pro Ser Gln Glu Met Thr Lys Asn Gln
            130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
            165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
            195                 200                 205

Val Met His Glu Ala Leu His Asn His Tyr Thr Gln Lys Ser Leu Ser
            210                 215                 220

Leu Ser Leu Gly Ile Pro Pro His Val Gln Lys Ser Val Asn Asn Asp
225                 230                 235                 240

Met Ile Val Thr Asp Asn Asn Gly Ala Val Lys Phe Pro Gln Leu Cys
            245                 250                 255

Lys Phe Cys Asp Val Arg Phe Ser Thr Cys Asp Asn Gln Lys Ser Cys
            260                 265                 270

Met Ser Asn Cys Ser Ile Thr Ser Ile Cys Glu Lys Pro Gln Glu Val
            275                 280                 285

Cys Val Ala Val Trp Arg Lys Asn Asp Glu Asn Ile Thr Leu Glu Thr
            290                 295                 300

Val Cys His Asp Pro Lys Leu Pro Tyr His Asp Phe Ile Leu Glu Asp
305                 310                 315                 320

Ala Ala Ser Pro Lys Cys Ile Met Lys Glu Lys Lys Pro Gly Glu
            325                 330                 335

Thr Phe Phe Met Cys Ser Cys Ser Ser Asp Glu Cys Asn Asp Asn Ile
            340                 345                 350

Ile Phe Ser Glu Glu Tyr Asn Thr Ser Asn Pro Asp Ile Pro Pro His
            355                 360                 365

Val Gln Lys Ser Val Asn Asn Asp Met Ile Val Thr Asp Asn Asn Gly
            370                 375                 380

Ala Val Lys Phe Pro Gln Leu Cys Lys Phe Cys Asp Val Arg Phe Ser
385                 390                 395                 400

Thr Cys Asp Asn Gln Lys Ser Cys Met Ser Asn Cys Ser Ile Thr Ser
            405                 410                 415

Ile Cys Glu Lys Pro Gln Glu Val Cys Val Ala Val Trp Arg Lys Asn
            420                 425                 430

Asp Glu Asn Ile Thr Leu Glu Thr Val Cys His Asp Pro Lys Leu Pro
            435                 440                 445

Tyr His Asp Phe Ile Leu Glu Asp Ala Ala Ser Pro Lys Cys Ile Met
            450                 455                 460

Lys Glu Lys Lys Lys Pro Gly Glu Thr Phe Phe Met Cys Ser Cys Ser
465                 470                 475                 480

Ser Asp Glu Cys Asn Asp Asn Ile Ile Phe Ser Glu Glu Tyr Asn Thr
            485                 490                 495

Ser Asn Pro Asp
            500
```

<210> SEQ ID NO 104
<211> LENGTH: 500
<212> TYPE: PRT
<213> ORGANISM: Artificial Sequence
<220> FEATURE:
<223> OTHER INFORMATION: hIgG4FcdeltaK-CC-228P-409K-T22d35 fusion

<400> SEQUENCE: 104

```
Glu Ser Lys Tyr Gly Pro Pro Cys Pro Pro Cys Pro Ala Pro Glu Phe
1               5                   10                  15

Leu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
        115                 120                 125

Gln Val Tyr Thr Leu Pro Pro Ser Gln Glu Glu Met Thr Lys Asn Gln
    130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Lys Leu
            180                 185                 190

Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
    210                 215                 220

Leu Ser Leu Gly Ile Pro Pro His Val Gln Lys Ser Val Asn Asn Asp
225                 230                 235                 240

Met Ile Val Thr Asp Asn Asn Gly Ala Val Lys Phe Pro Gln Leu Cys
                245                 250                 255

Lys Phe Cys Asp Val Arg Phe Ser Thr Cys Asp Asn Gln Lys Ser Cys
            260                 265                 270

Met Ser Asn Cys Ser Ile Thr Ser Ile Cys Glu Lys Pro Gln Glu Val
        275                 280                 285

Cys Val Ala Val Trp Arg Lys Asn Asp Glu Asn Ile Thr Leu Glu Thr
    290                 295                 300

Val Cys His Asp Pro Lys Leu Pro Tyr His Asp Phe Ile Leu Glu Asp
305                 310                 315                 320

Ala Ala Ser Pro Lys Cys Ile Met Lys Glu Lys Lys Pro Gly Glu
                325                 330                 335

Thr Phe Phe Met Cys Ser Cys Ser Ser Asp Glu Cys Asn Asp Asn Ile
            340                 345                 350

Ile Phe Ser Glu Glu Tyr Asn Thr Ser Asn Pro Asp Ile Pro Pro His
        355                 360                 365
```

-continued

```
Val Gln Lys Ser Val Asn Asn Asp Met Ile Val Thr Asp Asn Asn Gly
    370                 375                 380

Ala Val Lys Phe Pro Gln Leu Cys Lys Phe Cys Asp Val Arg Phe Ser
385                 390                 395                 400

Thr Cys Asp Asn Gln Lys Ser Cys Met Ser Asn Cys Ser Ile Thr Ser
                405                 410                 415

Ile Cys Glu Lys Pro Gln Glu Val Cys Val Ala Val Trp Arg Lys Asn
                420                 425                 430

Asp Glu Asn Ile Thr Leu Glu Thr Val Cys His Asp Pro Lys Leu Pro
                435                 440                 445

Tyr His Asp Phe Ile Leu Glu Asp Ala Ala Ser Pro Lys Cys Ile Met
    450                 455                 460

Lys Glu Lys Lys Pro Gly Glu Thr Phe Phe Met Cys Ser Cys Ser
465                 470                 475                 480

Ser Asp Glu Cys Asn Asp Asn Ile Ile Phe Ser Glu Glu Tyr Asn Thr
                485                 490                 495

Ser Asn Pro Asp
                500

<210> SEQ ID NO 105
<211> LENGTH: 519
<212> TYPE: PRT
<213> ORGANISM: Artificial Sequence
<220> FEATURE:
<223> OTHER INFORMATION: hIgG2Fc-CCCC-T22d35 fusion, also termed
      Fc-T22d35

<400> SEQUENCE: 105

Met Asp Trp Thr Trp Arg Ile Leu Phe Leu Val Ala Ala Ala Thr Gly
1               5                   10                  15

Thr His Ala Glu Arg Lys Cys Cys Val Glu Cys Pro Pro Cys Pro Ala
                20                  25                  30

Pro Pro Val Ala Gly Pro Ser Val Phe Leu Phe Pro Pro Lys Pro Lys
                35                  40                  45

Asp Thr Leu Met Ile Ser Arg Thr Pro Glu Val Thr Cys Val Val Val
    50                  55                  60

Asp Val Ser His Glu Asp Pro Glu Val Gln Phe Asn Trp Tyr Val Asp
65                  70                  75                  80

Gly Val Glu Val His Asn Ala Lys Thr Lys Pro Arg Glu Glu Gln Phe
                85                  90                  95

Asn Ser Thr Phe Arg Val Val Ser Val Leu Thr Val Val His Gln Asp
                100                 105                 110

Trp Leu Asn Gly Lys Glu Tyr Lys Cys Lys Val Ser Asn Lys Gly Leu
                115                 120                 125

Pro Ala Pro Ile Glu Lys Thr Ile Ser Lys Thr Lys Gly Gln Pro Arg
    130                 135                 140

Glu Pro Gln Val Tyr Thr Leu Pro Pro Ser Arg Glu Glu Met Thr Lys
145                 150                 155                 160

Asn Gln Val Ser Leu Thr Cys Leu Val Lys Gly Phe Tyr Pro Ser Asp
                165                 170                 175

Ile Ser Val Glu Trp Glu Ser Asn Gly Gln Pro Glu Asn Asn Tyr Lys
                180                 185                 190

Thr Thr Pro Pro Met Leu Asp Ser Asp Gly Ser Phe Phe Leu Tyr Ser
                195                 200                 205

Lys Leu Thr Val Asp Lys Ser Arg Trp Gln Gln Gly Asn Val Phe Ser
    210                 215                 220
```

```
Cys Ser Val Met His Glu Ala Leu His Asn His Tyr Thr Gln Lys Ser
225                 230                 235                 240

Leu Ser Leu Ser Pro Gly Lys Ile Pro Pro His Val Gln Lys Ser Val
            245                 250                 255

Asn Asn Asp Met Ile Val Thr Asp Asn Asn Gly Ala Val Lys Phe Pro
        260                 265                 270

Gln Leu Cys Lys Phe Cys Asp Val Arg Phe Ser Thr Cys Asp Asn Gln
    275                 280                 285

Lys Ser Cys Met Ser Asn Cys Ser Ile Thr Ser Ile Cys Glu Lys Pro
290                 295                 300

Gln Glu Val Cys Val Ala Val Trp Arg Lys Asn Asp Glu Asn Ile Thr
305                 310                 315                 320

Leu Glu Thr Val Cys His Asp Pro Lys Leu Pro Tyr His Asp Phe Ile
            325                 330                 335

Leu Glu Asp Ala Ala Ser Pro Lys Cys Ile Met Lys Glu Lys Lys
        340                 345                 350

Pro Gly Glu Thr Phe Phe Met Cys Ser Cys Ser Ser Asp Glu Cys Asn
    355                 360                 365

Asp Asn Ile Ile Phe Ser Glu Glu Tyr Asn Thr Ser Asn Pro Asp Ile
370                 375                 380

Pro Pro His Val Gln Lys Ser Val Asn Asn Asp Met Ile Val Thr Asp
385                 390                 395                 400

Asn Asn Gly Ala Val Lys Phe Pro Gln Leu Cys Lys Phe Cys Asp Val
            405                 410                 415

Arg Phe Ser Thr Cys Asp Asn Gln Lys Ser Cys Met Ser Asn Cys Ser
        420                 425                 430

Ile Thr Ser Ile Cys Glu Lys Pro Gln Glu Val Cys Val Ala Val Trp
    435                 440                 445

Arg Lys Asn Asp Glu Asn Ile Thr Leu Glu Thr Val Cys His Asp Pro
450                 455                 460

Lys Leu Pro Tyr His Asp Phe Ile Leu Glu Asp Ala Ala Ser Pro Lys
465                 470                 475                 480

Cys Ile Met Lys Glu Lys Lys Pro Gly Glu Thr Phe Phe Met Cys
            485                 490                 495

Ser Cys Ser Ser Asp Glu Cys Asn Asp Asn Ile Ile Phe Ser Glu Glu
        500                 505                 510

Tyr Asn Thr Ser Asn Pro Asp
        515

<210> SEQ ID NO 106
<211> LENGTH: 517
<212> TYPE: PRT
<213> ORGANISM: Artificial Sequence
<220> FEATURE:
<223> OTHER INFORMATION: hIgG1FcdeltaK-C-T2-T2bAA fusion

<400> SEQUENCE: 106

Pro Pro Cys Pro Ala Pro Glu Leu Leu Gly Gly Pro Ser Val Phe Leu
1               5                   10                  15

Phe Pro Pro Lys Pro Lys Asp Thr Leu Met Ile Ser Arg Thr Pro Glu
            20                  25                  30

Val Thr Cys Val Val Val Asp Val Ser His Glu Asp Pro Glu Val Lys
        35                  40                  45

Phe Asn Trp Tyr Val Asp Gly Val Glu Val His Asn Ala Lys Thr Lys
    50                  55                  60
```

```
Pro Arg Glu Glu Gln Tyr Asn Ser Thr Tyr Arg Val Val Ser Val Leu
 65                  70                  75                  80

Thr Val Leu His Gln Asp Trp Leu Asn Gly Lys Glu Tyr Lys Cys Lys
                 85                  90                  95

Val Ser Asn Lys Ala Leu Pro Ala Pro Ile Glu Lys Thr Ile Ser Lys
                100                 105                 110

Ala Lys Gly Gln Pro Arg Glu Pro Gln Val Tyr Thr Leu Pro Pro Ser
                115                 120                 125

Arg Asp Glu Leu Thr Lys Asn Gln Val Ser Leu Thr Cys Leu Val Lys
                130                 135                 140

Gly Phe Tyr Pro Ser Asp Ile Ala Val Glu Trp Glu Ser Asn Gly Gln
145                 150                 155                 160

Pro Glu Asn Asn Tyr Lys Thr Thr Pro Pro Val Leu Asp Ser Asp Gly
                165                 170                 175

Ser Phe Phe Leu Tyr Ser Lys Leu Thr Val Asp Lys Ser Arg Trp Gln
                180                 185                 190

Gln Gly Asn Val Phe Ser Cys Ser Val Met His Glu Ala Leu His Asn
                195                 200                 205

His Tyr Thr Gln Lys Ser Leu Ser Leu Ser Pro Gly Ile Pro Pro His
                210                 215                 220

Val Gln Lys Ser Val Asn Asn Asp Met Ile Val Thr Asp Asn Asn Gly
225                 230                 235                 240

Ala Val Lys Phe Pro Gln Leu Cys Lys Phe Cys Asp Val Arg Phe Ser
                245                 250                 255

Thr Cys Asp Asn Gln Lys Ser Cys Met Ser Asn Cys Ser Ile Thr Ser
                260                 265                 270

Ile Cys Glu Lys Pro Gln Glu Val Cys Val Ala Val Trp Arg Lys Asn
                275                 280                 285

Asp Glu Asn Ile Thr Leu Glu Thr Val Cys His Asp Pro Lys Leu Pro
                290                 295                 300

Tyr His Asp Phe Ile Leu Glu Asp Ala Ala Ser Pro Lys Cys Ile Met
305                 310                 315                 320

Lys Glu Lys Lys Lys Pro Gly Glu Thr Phe Phe Met Cys Ser Cys Ser
                325                 330                 335

Ser Asp Glu Cys Asn Asp Asn Ile Ile Phe Ser Glu Glu Tyr Asn Thr
                340                 345                 350

Ser Asn Pro Asp Ile Pro Pro His Val Gln Lys Ser Asp Val Glu Met
                355                 360                 365

Glu Ala Gln Lys Asp Glu Ile Ile Ala Pro Ser Ala Asn Arg Thr Ala
                370                 375                 380

His Pro Leu Arg His Ile Asn Asn Asp Met Ile Val Thr Asp Asn Asn
385                 390                 395                 400

Gly Ala Val Lys Phe Pro Gln Leu Cys Lys Phe Cys Asp Val Arg Phe
                405                 410                 415

Ser Thr Cys Asp Asn Gln Lys Ser Cys Met Ser Asn Cys Ser Ile Thr
                420                 425                 430

Ser Ile Cys Glu Lys Pro Gln Glu Val Cys Val Ala Val Trp Arg Lys
                435                 440                 445

Asn Asp Glu Asn Ile Thr Leu Glu Thr Val Cys His Asp Pro Lys Leu
                450                 455                 460

Pro Tyr His Asp Phe Ile Leu Glu Asp Ala Ala Ser Pro Lys Cys Ile
465                 470                 475                 480
```

```
Met Lys Glu Lys Lys Lys Pro Gly Glu Thr Phe Phe Met Cys Ser Cys
                    485                 490                 495
Ser Ser Asp Glu Cys Asn Asp Asn Ile Ile Phe Ser Glu Tyr Asn
                500                 505                 510
Thr Ser Asn Pro Asp
        515

<210> SEQ ID NO 107
<211> LENGTH: 523
<212> TYPE: PRT
<213> ORGANISM: Artificial Sequence
<220> FEATURE:
<223> OTHER INFORMATION: hIgG1FcdeltaK-CC-T2-T2bAA fusion

<400> SEQUENCE: 107

Asp Lys Thr His Thr Cys Pro Pro Cys Pro Ala Pro Glu Leu Leu Gly
1               5                   10                  15
Gly Pro Ser Val Phe Leu Phe Pro Pro Lys Pro Lys Asp Thr Leu Met
                20                  25                  30
Ile Ser Arg Thr Pro Glu Val Thr Cys Val Val Val Asp Val Ser His
            35                  40                  45
Glu Asp Pro Glu Val Lys Phe Asn Trp Tyr Val Asp Gly Val Glu Val
    50                  55                  60
His Asn Ala Lys Thr Lys Pro Arg Glu Glu Gln Tyr Asn Ser Thr Tyr
65                  70                  75                  80
Arg Val Val Ser Val Leu Thr Val Leu His Gln Asp Trp Leu Asn Gly
                85                  90                  95
Lys Glu Tyr Lys Cys Lys Val Ser Asn Lys Ala Leu Pro Ala Pro Ile
            100                 105                 110
Glu Lys Thr Ile Ser Lys Ala Lys Gly Gln Pro Arg Glu Pro Gln Val
        115                 120                 125
Tyr Thr Leu Pro Pro Ser Arg Asp Glu Leu Thr Lys Asn Gln Val Ser
    130                 135                 140
Leu Thr Cys Leu Val Lys Gly Phe Tyr Pro Ser Asp Ile Ala Val Glu
145                 150                 155                 160
Trp Glu Ser Asn Gly Gln Pro Glu Asn Asn Tyr Lys Thr Thr Pro Pro
                165                 170                 175
Val Leu Asp Ser Asp Gly Ser Phe Phe Leu Tyr Ser Lys Leu Thr Val
            180                 185                 190
Asp Lys Ser Arg Trp Gln Gln Gly Asn Val Phe Ser Cys Ser Val Met
        195                 200                 205
His Glu Ala Leu His Asn His Tyr Thr Gln Lys Ser Leu Ser Leu Ser
    210                 215                 220
Pro Gly Ile Pro Pro His Val Gln Lys Ser Val Asn Asn Asp Met Ile
225                 230                 235                 240
Val Thr Asp Asn Asn Gly Ala Val Lys Phe Pro Gln Leu Cys Lys Phe
                245                 250                 255
Cys Asp Val Arg Phe Ser Thr Cys Asp Asn Gln Lys Ser Cys Met Ser
            260                 265                 270
Asn Cys Ser Ile Thr Ser Ile Cys Glu Lys Pro Gln Glu Val Cys Val
        275                 280                 285
Ala Val Trp Arg Lys Asn Asp Glu Asn Ile Thr Leu Glu Thr Val Cys
    290                 295                 300
His Asp Pro Lys Leu Pro Tyr His Asp Phe Ile Leu Glu Asp Ala Ala
305                 310                 315                 320
```

```
Ser Pro Lys Cys Ile Met Lys Glu Lys Lys Pro Gly Glu Thr Phe
            325                 330                 335

Phe Met Cys Ser Cys Ser Ser Asp Glu Cys Asn Asp Asn Ile Ile Phe
            340                 345                 350

Ser Glu Glu Tyr Asn Thr Ser Asn Pro Asp Ile Pro Pro His Val Gln
            355                 360                 365

Lys Ser Asp Val Glu Met Glu Ala Gln Lys Asp Glu Ile Ile Ala Pro
370                 375                 380

Ser Ala Asn Arg Thr Ala His Pro Leu Arg His Ile Asn Asn Asp Met
385                 390                 395                 400

Ile Val Thr Asp Asn Asn Gly Ala Val Lys Phe Pro Gln Leu Cys Lys
            405                 410                 415

Phe Cys Asp Val Arg Phe Ser Thr Cys Asp Asn Gln Lys Ser Cys Met
            420                 425                 430

Ser Asn Cys Ser Ile Thr Ser Ile Cys Glu Lys Pro Gln Glu Val Cys
            435                 440                 445

Val Ala Val Trp Arg Lys Asn Asp Glu Asn Ile Thr Leu Glu Thr Val
450                 455                 460

Cys His Asp Pro Lys Leu Pro Tyr His Asp Phe Ile Leu Glu Asp Ala
465                 470                 475                 480

Ala Ser Pro Lys Cys Ile Met Lys Glu Lys Lys Pro Gly Glu Thr
            485                 490                 495

Phe Phe Met Cys Ser Cys Ser Ser Asp Glu Cys Asn Asp Asn Ile Ile
            500                 505                 510

Phe Ser Glu Glu Tyr Asn Thr Ser Asn Pro Asp
            515                 520
```

<210> SEQ ID NO 108
<211> LENGTH: 519
<212> TYPE: PRT
<213> ORGANISM: Artificial Sequence
<220> FEATURE:
<223> OTHER INFORMATION: hIgG2FcdeltaK-CC-T2-T2bAA fusion

<400> SEQUENCE: 108

```
Val Glu Cys Pro Pro Cys Pro Ala Pro Pro Val Ala Gly Pro Ser Val
1               5                   10                  15

Phe Leu Phe Pro Pro Lys Pro Lys Asp Thr Leu Met Ile Ser Arg Thr
            20                  25                  30

Pro Glu Val Thr Cys Val Val Val Asp Val Ser His Glu Asp Pro Glu
            35                  40                  45

Val Gln Phe Asn Trp Tyr Val Asp Gly Val Glu Val His Asn Ala Lys
50                  55                  60

Thr Lys Pro Arg Glu Glu Gln Phe Asn Ser Thr Phe Arg Val Val Ser
65                  70                  75                  80

Val Leu Thr Val Val His Gln Asp Trp Leu Asn Gly Lys Glu Tyr Lys
            85                  90                  95

Cys Lys Val Ser Asn Lys Gly Leu Pro Ala Pro Ile Glu Lys Thr Ile
            100                 105                 110

Ser Lys Thr Lys Gly Gln Pro Arg Glu Pro Gln Val Tyr Thr Leu Pro
            115                 120                 125

Pro Ser Arg Glu Glu Met Thr Lys Asn Gln Val Ser Leu Thr Cys Leu
            130                 135                 140

Val Lys Gly Phe Tyr Pro Ser Asp Ile Ser Val Glu Trp Glu Ser Asn
145                 150                 155                 160
```

Gly Gln Pro Glu Asn Asn Tyr Lys Thr Thr Pro Pro Met Leu Asp Ser
            165                 170                 175

Asp Gly Ser Phe Phe Leu Tyr Ser Lys Leu Thr Val Asp Lys Ser Arg
        180                 185                 190

Trp Gln Gln Gly Asn Val Phe Ser Cys Ser Val Met His Glu Ala Leu
            195                 200                 205

His Asn His Tyr Thr Gln Lys Ser Leu Ser Leu Ser Pro Gly Ile Pro
    210                 215                 220

Pro His Val Gln Lys Ser Val Asn Asn Asp Met Ile Val Thr Asp Asn
225                 230                 235                 240

Asn Gly Ala Val Lys Phe Pro Gln Leu Cys Lys Phe Cys Asp Val Arg
                245                 250                 255

Phe Ser Thr Cys Asp Asn Gln Lys Ser Cys Met Ser Asn Cys Ser Ile
            260                 265                 270

Thr Ser Ile Cys Glu Lys Pro Gln Glu Val Cys Val Ala Val Trp Arg
        275                 280                 285

Lys Asn Asp Glu Asn Ile Thr Leu Glu Thr Val Cys His Asp Pro Lys
    290                 295                 300

Leu Pro Tyr His Asp Phe Ile Leu Glu Asp Ala Ala Ser Pro Lys Cys
305                 310                 315                 320

Ile Met Lys Glu Lys Lys Pro Gly Glu Thr Phe Phe Met Cys Ser
                325                 330                 335

Cys Ser Ser Asp Glu Cys Asn Asp Asn Ile Ile Phe Ser Glu Tyr
            340                 345                 350

Asn Thr Ser Asn Pro Asp Ile Pro Pro His Val Gln Lys Ser Asp Val
            355                 360                 365

Glu Met Glu Ala Gln Lys Asp Glu Ile Ile Ala Pro Ser Ala Asn Arg
    370                 375                 380

Thr Ala His Pro Leu Arg His Ile Asn Asn Asp Met Ile Val Thr Asp
385                 390                 395                 400

Asn Asn Gly Ala Val Lys Phe Pro Gln Leu Cys Lys Phe Cys Asp Val
                405                 410                 415

Arg Phe Ser Thr Cys Asp Asn Gln Lys Ser Cys Met Ser Asn Cys Ser
            420                 425                 430

Ile Thr Ser Ile Cys Glu Lys Pro Gln Glu Val Cys Val Ala Val Trp
        435                 440                 445

Arg Lys Asn Asp Glu Asn Ile Thr Leu Glu Thr Val Cys His Asp Pro
    450                 455                 460

Lys Leu Pro Tyr His Asp Phe Ile Leu Glu Asp Ala Ala Ser Pro Lys
465                 470                 475                 480

Cys Ile Met Lys Glu Lys Lys Pro Gly Glu Thr Phe Phe Met Cys
                485                 490                 495

Ser Cys Ser Ser Asp Glu Cys Asn Asp Asn Ile Ile Phe Ser Glu Glu
            500                 505                 510

Tyr Asn Thr Ser Asn Pro Asp
        515

<210> SEQ ID NO 109
<211> LENGTH: 525
<212> TYPE: PRT
<213> ORGANISM: Artificial Sequence
<220> FEATURE:
<223> OTHER INFORMATION: hIgG4FcdeltaK-CC-228P-T2-T2bAA fusion

<400> SEQUENCE: 109

-continued

```
Glu Ser Lys Tyr Gly Pro Pro Cys Pro Pro Cys Pro Ala Pro Glu Phe
1               5                   10                  15

Leu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
            35                  40                  45

Ser Gln Glu Asp Pro Glu Val Gln Phe Asn Trp Tyr Val Asp Gly Val
50                  55                  60

Glu Val His Asn Ala Lys Thr Lys Pro Arg Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
            115                 120                 125

Gln Val Tyr Thr Leu Pro Pro Ser Gln Glu Glu Met Thr Lys Asn Gln
    130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
            195                 200                 205

Val Met His Glu Ala Leu His Asn His Tyr Thr Gln Lys Ser Leu Ser
    210                 215                 220

Leu Ser Leu Gly Ile Pro Pro His Val Gln Lys Ser Val Asn Asn Asp
225                 230                 235                 240

Met Ile Val Thr Asp Asn Asn Gly Ala Val Lys Phe Pro Gln Leu Cys
                245                 250                 255

Lys Phe Cys Asp Val Arg Phe Ser Thr Cys Asp Asn Gln Lys Ser Cys
            260                 265                 270

Met Ser Asn Cys Ser Ile Thr Ser Ile Cys Glu Lys Pro Gln Glu Val
            275                 280                 285

Cys Val Ala Val Trp Arg Lys Asn Asp Glu Asn Ile Thr Leu Glu Thr
    290                 295                 300

Val Cys His Asp Pro Lys Leu Pro Tyr His Asp Phe Ile Leu Glu Asp
305                 310                 315                 320

Ala Ala Ser Pro Lys Cys Ile Met Lys Glu Lys Lys Pro Gly Glu
                325                 330                 335

Thr Phe Phe Met Cys Ser Cys Ser Ser Asp Glu Cys Asn Asp Asn Ile
            340                 345                 350

Ile Phe Ser Glu Glu Tyr Asn Thr Ser Asn Pro Asp Ile Pro Pro His
            355                 360                 365

Val Gln Lys Ser Asp Val Glu Met Glu Ala Gln Lys Asp Glu Ile Ile
    370                 375                 380

Ala Pro Ser Ala Asn Arg Thr Ala His Pro Leu Arg His Ile Asn Asn
385                 390                 395                 400

Asp Met Ile Val Thr Asp Asn Asn Gly Ala Val Lys Phe Pro Gln Leu
                405                 410                 415

Cys Lys Phe Cys Asp Val Arg Phe Ser Thr Cys Asp Asn Gln Lys Ser
```

```
              420                 425                 430
Cys Met Ser Asn Cys Ser Ile Thr Ser Ile Cys Glu Lys Pro Gln Glu
        435                 440                 445

Val Cys Val Ala Val Trp Arg Lys Asn Asp Glu Asn Ile Thr Leu Glu
    450                 455                 460

Thr Val Cys His Asp Pro Lys Leu Pro Tyr His Asp Phe Ile Leu Glu
465                 470                 475                 480

Asp Ala Ala Ser Pro Lys Cys Ile Met Lys Glu Lys Lys Pro Gly
                485                 490                 495

Glu Thr Phe Phe Met Cys Ser Cys Ser Ser Asp Glu Cys Asn Asp Asn
            500                 505                 510

Ile Ile Phe Ser Glu Glu Tyr Asn Thr Ser Asn Pro Asp
        515                 520                 525

<210> SEQ ID NO 110
<211> LENGTH: 525
<212> TYPE: PRT
<213> ORGANISM: Artificial Sequence
<220> FEATURE:
<223> OTHER INFORMATION: hIgG4FcdeltaK-CC-228P-409K-T2-T2bAA fusion

<400> SEQUENCE: 110

Glu Ser Lys Tyr Gly Pro Pro Cys Pro Pro Cys Pro Ala Pro Glu Phe
1               5                   10                  15

Leu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
        115                 120                 125

Gln Val Tyr Thr Leu Pro Pro Ser Gln Glu Glu Met Thr Lys Asn Gln
    130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Lys Leu
            180                 185                 190

Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
    210                 215                 220

Leu Ser Leu Gly Ile Pro Pro His Val Gln Lys Ser Val Asn Asn Asp
225                 230                 235                 240

Met Ile Val Thr Asp Asn Asn Gly Ala Val Lys Phe Pro Gln Leu Cys
                245                 250                 255

Lys Phe Cys Asp Val Arg Phe Ser Thr Cys Asp Asn Gln Lys Ser Cys
```

```
                260              265              270
Met Ser Asn Cys Ser Ile Thr Ser Ile Cys Glu Lys Pro Gln Glu Val
            275              280              285

Cys Val Ala Val Trp Arg Lys Asn Asp Glu Asn Ile Thr Leu Glu Thr
            290              295              300

Val Cys His Asp Pro Lys Leu Pro Tyr His Asp Phe Ile Leu Glu Asp
305              310              315              320

Ala Ala Ser Pro Lys Cys Ile Met Lys Glu Lys Lys Pro Gly Glu
                325              330              335

Thr Phe Phe Met Cys Ser Cys Ser Ser Asp Glu Cys Asn Asp Asn Ile
            340              345              350

Ile Phe Ser Glu Glu Tyr Asn Thr Ser Asn Pro Asp Ile Pro Pro His
            355              360              365

Val Gln Lys Ser Asp Val Glu Met Glu Ala Gln Lys Asp Glu Ile Ile
            370              375              380

Ala Pro Ser Ala Asn Arg Thr Ala His Pro Leu Arg His Ile Asn Asn
385              390              395              400

Asp Met Ile Val Thr Asp Asn Asn Gly Ala Val Lys Phe Pro Gln Leu
            405              410              415

Cys Lys Phe Cys Asp Val Arg Phe Ser Thr Cys Asp Asn Gln Lys Ser
            420              425              430

Cys Met Ser Asn Cys Ser Ile Thr Ser Ile Cys Glu Lys Pro Gln Glu
            435              440              445

Val Cys Val Ala Val Trp Arg Lys Asn Asp Glu Asn Ile Thr Leu Glu
            450              455              460

Thr Val Cys His Asp Pro Lys Leu Pro Tyr His Asp Phe Ile Leu Glu
465              470              475              480

Asp Ala Ala Ser Pro Lys Cys Ile Met Lys Glu Lys Lys Pro Gly
                485              490              495

Glu Thr Phe Phe Met Cys Ser Cys Ser Ser Asp Glu Cys Asn Asp Asn
            500              505              510

Ile Ile Phe Ser Glu Glu Tyr Asn Thr Ser Asn Pro Asp
            515              520              525

<210> SEQ ID NO 111
<211> LENGTH: 628
<212> TYPE: PRT
<213> ORGANISM: Artificial Sequence
<220> FEATURE:
<223> OTHER INFORMATION: hIgG1FcdeltaK-C-T2-T2-T2 fusion

<400> SEQUENCE: 111

Pro Pro Cys Pro Ala Pro Glu Leu Leu Gly Gly Pro Ser Val Phe Leu
1               5                   10                  15

Phe Pro Pro Lys Pro Lys Asp Thr Leu Met Ile Ser Arg Thr Pro Glu
            20                  25                  30

Val Thr Cys Val Val Asp Val Ser His Glu Asp Pro Glu Val Lys
            35                  40                  45

Phe Asn Trp Tyr Val Asp Gly Val Glu Val His Asn Ala Lys Thr Lys
        50                  55                  60

Pro Arg Glu Glu Gln Tyr Asn Ser Thr Tyr Arg Val Val Ser Val Leu
65                  70                  75                  80

Thr Val Leu His Gln Asp Trp Leu Asn Gly Lys Glu Tyr Lys Cys Lys
                85                  90                  95

Val Ser Asn Lys Ala Leu Pro Ala Pro Ile Glu Lys Thr Ile Ser Lys
```

```
                100                 105                 110
Ala Lys Gly Gln Pro Arg Glu Pro Gln Val Tyr Thr Leu Pro Pro Ser
            115                 120                 125

Arg Asp Glu Leu Thr Lys Asn Gln Val Ser Leu Thr Cys Leu Val Lys
130                 135                 140

Gly Phe Tyr Pro Ser Asp Ile Ala Val Glu Trp Glu Ser Asn Gly Gln
145                 150                 155                 160

Pro Glu Asn Asn Tyr Lys Thr Thr Pro Pro Val Leu Asp Ser Asp Gly
                165                 170                 175

Ser Phe Phe Leu Tyr Ser Lys Leu Thr Val Asp Lys Ser Arg Trp Gln
            180                 185                 190

Gln Gly Asn Val Phe Ser Cys Ser Val Met His Glu Ala Leu His Asn
        195                 200                 205

His Tyr Thr Gln Lys Ser Leu Ser Leu Ser Pro Gly Ile Pro Pro His
    210                 215                 220

Val Gln Lys Ser Val Asn Asn Asp Met Ile Val Thr Asp Asn Asn Gly
225                 230                 235                 240

Ala Val Lys Phe Pro Gln Leu Cys Lys Phe Cys Asp Val Arg Phe Ser
                245                 250                 255

Thr Cys Asp Asn Gln Lys Ser Cys Met Ser Asn Cys Ser Ile Thr Ser
            260                 265                 270

Ile Cys Glu Lys Pro Gln Glu Val Cys Val Ala Val Trp Arg Lys Asn
        275                 280                 285

Asp Glu Asn Ile Thr Leu Glu Thr Val Cys His Asp Pro Lys Leu Pro
    290                 295                 300

Tyr His Asp Phe Ile Leu Glu Asp Ala Ala Ser Pro Lys Cys Ile Met
305                 310                 315                 320

Lys Glu Lys Lys Lys Pro Gly Glu Thr Phe Phe Met Cys Ser Cys Ser
                325                 330                 335

Ser Asp Glu Cys Asn Asp Asn Ile Ile Phe Ser Glu Glu Tyr Asn Thr
            340                 345                 350

Ser Asn Pro Asp Ile Pro Pro His Val Gln Lys Ser Val Asn Asn Asp
        355                 360                 365

Met Ile Val Thr Asp Asn Asn Gly Ala Val Lys Phe Pro Gln Leu Cys
    370                 375                 380

Lys Phe Cys Asp Val Arg Phe Ser Thr Cys Asp Asn Gln Lys Ser Cys
385                 390                 395                 400

Met Ser Asn Cys Ser Ile Thr Ser Ile Cys Glu Lys Pro Gln Glu Val
                405                 410                 415

Cys Val Ala Val Trp Arg Lys Asn Asp Glu Asn Ile Thr Leu Glu Thr
            420                 425                 430

Val Cys His Asp Pro Lys Leu Pro Tyr His Asp Phe Ile Leu Glu Asp
        435                 440                 445

Ala Ala Ser Pro Lys Cys Ile Met Lys Glu Lys Lys Lys Pro Gly Glu
    450                 455                 460

Thr Phe Phe Met Cys Ser Cys Ser Ser Asp Glu Cys Asn Asp Asn Ile
465                 470                 475                 480

Ile Phe Ser Glu Glu Tyr Asn Thr Ser Asn Pro Asp Ile Pro Pro His
                485                 490                 495

Val Gln Lys Ser Val Asn Asn Asp Met Ile Val Thr Asp Asn Asn Gly
            500                 505                 510

Ala Val Lys Phe Pro Gln Leu Cys Lys Phe Cys Asp Val Arg Phe Ser
        515                 520                 525
```

```
Thr Cys Asp Asn Gln Lys Ser Cys Met Ser Asn Cys Ser Ile Thr Ser
    530                 535                 540

Ile Cys Glu Lys Pro Gln Glu Val Cys Val Ala Val Trp Arg Lys Asn
545                 550                 555                 560

Asp Glu Asn Ile Thr Leu Glu Thr Val Cys His Asp Pro Lys Leu Pro
            565                 570                 575

Tyr His Asp Phe Ile Leu Glu Asp Ala Ala Ser Pro Lys Cys Ile Met
            580                 585                 590

Lys Glu Lys Lys Pro Gly Glu Thr Phe Phe Met Cys Ser Cys Ser
            595                 600                 605

Ser Asp Glu Cys Asn Asp Asn Ile Ile Phe Ser Glu Glu Tyr Asn Thr
    610                 615                 620

Ser Asn Pro Asp
625

<210> SEQ ID NO 112
<211> LENGTH: 634
<212> TYPE: PRT
<213> ORGANISM: Artificial Sequence
<220> FEATURE:
<223> OTHER INFORMATION: hIgG1FcdeltaK-CC-T2-T2-T2 fusion

<400> SEQUENCE: 112

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Asp Glu Leu Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Ile Pro Pro His Val Gln Lys Ser Val Asn Asn Asp Met Ile
225                 230                 235                 240

Val Thr Asp Asn Asn Gly Ala Val Lys Phe Pro Gln Leu Cys Lys Phe
                245                 250                 255
```

Cys Asp Val Arg Phe Ser Thr Cys Asp Asn Gln Lys Ser Cys Met Ser
            260                 265                 270

Asn Cys Ser Ile Thr Ser Ile Cys Glu Lys Pro Gln Glu Val Cys Val
            275                 280                 285

Ala Val Trp Arg Lys Asn Asp Glu Asn Ile Thr Leu Glu Thr Val Cys
            290                 295                 300

His Asp Pro Lys Leu Pro Tyr His Asp Phe Ile Leu Glu Asp Ala Ala
305                 310                 315                 320

Ser Pro Lys Cys Ile Met Lys Glu Lys Lys Pro Gly Glu Thr Phe
            325                 330                 335

Phe Met Cys Ser Cys Ser Ser Asp Glu Cys Asn Asp Asn Ile Ile Phe
            340                 345                 350

Ser Glu Glu Tyr Asn Thr Ser Asn Pro Asp Ile Pro Pro His Val Gln
            355                 360                 365

Lys Ser Val Asn Asn Asp Met Ile Val Thr Asp Asn Asn Gly Ala Val
            370                 375                 380

Lys Phe Pro Gln Leu Cys Lys Phe Cys Asp Val Arg Phe Ser Thr Cys
385                 390                 395                 400

Asp Asn Gln Lys Ser Cys Met Ser Asn Cys Ser Ile Thr Ser Ile Cys
            405                 410                 415

Glu Lys Pro Gln Glu Val Cys Val Ala Val Trp Arg Lys Asn Asp Glu
            420                 425                 430

Asn Ile Thr Leu Glu Thr Val Cys His Asp Pro Lys Leu Pro Tyr His
            435                 440                 445

Asp Phe Ile Leu Glu Asp Ala Ala Ser Pro Lys Cys Ile Met Lys Glu
            450                 455                 460

Lys Lys Pro Gly Glu Thr Phe Phe Met Cys Ser Cys Ser Ser Asp
465                 470                 475                 480

Glu Cys Asn Asp Asn Ile Ile Phe Ser Glu Glu Tyr Asn Thr Ser Asn
            485                 490                 495

Pro Asp Ile Pro Pro His Val Gln Lys Ser Val Asn Asn Asp Met Ile
            500                 505                 510

Val Thr Asp Asn Asn Gly Ala Val Lys Phe Pro Gln Leu Cys Lys Phe
            515                 520                 525

Cys Asp Val Arg Phe Ser Thr Cys Asp Asn Gln Lys Ser Cys Met Ser
            530                 535                 540

Asn Cys Ser Ile Thr Ser Ile Cys Glu Lys Pro Gln Glu Val Cys Val
545                 550                 555                 560

Ala Val Trp Arg Lys Asn Asp Glu Asn Ile Thr Leu Glu Thr Val Cys
            565                 570                 575

His Asp Pro Lys Leu Pro Tyr His Asp Phe Ile Leu Glu Asp Ala Ala
            580                 585                 590

Ser Pro Lys Cys Ile Met Lys Glu Lys Lys Pro Gly Glu Thr Phe
            595                 600                 605

Phe Met Cys Ser Cys Ser Ser Asp Glu Cys Asn Asp Asn Ile Ile Phe
            610                 615                 620

Ser Glu Glu Tyr Asn Thr Ser Asn Pro Asp
625                 630

<210> SEQ ID NO 113
<211> LENGTH: 630
<212> TYPE: PRT
<213> ORGANISM: Artificial Sequence
<220> FEATURE:

<223> OTHER INFORMATION: hIgG2FcdeltaK-CC-T2-T2-T2 fusion

<400> SEQUENCE: 113

| | | | | | | | | | | | | | | |
|---|---|---|---|---|---|---|---|---|---|---|---|---|---|---|
| Val | Glu | Cys | Pro | Pro | Cys | Pro | Ala | Pro | Val | Ala | Gly | Pro | Ser | Val |
| 1 | | | | 5 | | | | | 10 | | | | | 15 |
| Phe | Leu | Phe | Pro | Pro | Lys | Pro | Lys | Asp | Thr | Leu | Met | Ile | Ser | Arg | Thr |
| | | | | 20 | | | | | 25 | | | | | 30 |
| Pro | Glu | Val | Thr | Cys | Val | Val | Val | Asp | Val | Ser | His | Glu | Asp | Pro | Glu |
| | | | | 35 | | | | | 40 | | | | | 45 |
| Val | Gln | Phe | Asn | Trp | Tyr | Val | Asp | Gly | Val | Glu | Val | His | Asn | Ala | Lys |
| | | | 50 | | | | | 55 | | | | | 60 | |
| Thr | Lys | Pro | Arg | Glu | Glu | Gln | Phe | Asn | Ser | Thr | Phe | Arg | Val | Val | Ser |
| 65 | | | | | 70 | | | | | 75 | | | | | 80 |
| Val | Leu | Thr | Val | Val | His | Gln | Asp | Trp | Leu | Asn | Gly | Lys | Glu | Tyr | Lys |
| | | | | 85 | | | | | 90 | | | | | 95 | |
| Cys | Lys | Val | Ser | Asn | Lys | Gly | Leu | Pro | Ala | Pro | Ile | Glu | Lys | Thr | Ile |
| | | | 100 | | | | | 105 | | | | | 110 | |
| Ser | Lys | Thr | Lys | Gly | Gln | Pro | Arg | Glu | Pro | Gln | Val | Tyr | Thr | Leu | Pro |
| | | | 115 | | | | | 120 | | | | | 125 | |
| Pro | Ser | Arg | Glu | Glu | Met | Thr | Lys | Asn | Gln | Val | Ser | Leu | Thr | Cys | Leu |
| | 130 | | | | | 135 | | | | | 140 | | | | |
| Val | Lys | Gly | Phe | Tyr | Pro | Ser | Asp | Ile | Ser | Val | Glu | Trp | Glu | Ser | Asn |
| 145 | | | | | 150 | | | | | 155 | | | | | 160 |
| Gly | Gln | Pro | Glu | Asn | Asn | Tyr | Lys | Thr | Thr | Pro | Pro | Met | Leu | Asp | Ser |
| | | | | 165 | | | | | 170 | | | | | 175 | |
| Asp | Gly | Ser | Phe | Phe | Leu | Tyr | Ser | Lys | Leu | Thr | Val | Asp | Lys | Ser | Arg |
| | | | 180 | | | | | 185 | | | | | 190 | |
| Trp | Gln | Gln | Gly | Asn | Val | Phe | Ser | Cys | Ser | Val | Met | His | Glu | Ala | Leu |
| | | | 195 | | | | | 200 | | | | | 205 | |
| His | Asn | His | Tyr | Thr | Gln | Lys | Ser | Leu | Ser | Leu | Ser | Pro | Gly | Ile | Pro |
| | 210 | | | | | 215 | | | | | 220 | | | | |
| Pro | His | Val | Gln | Lys | Ser | Val | Asn | Asn | Asp | Met | Ile | Val | Thr | Asp | Asn |
| 225 | | | | | 230 | | | | | 235 | | | | | 240 |
| Asn | Gly | Ala | Val | Lys | Phe | Pro | Gln | Leu | Cys | Lys | Phe | Cys | Asp | Val | Arg |
| | | | 245 | | | | | 250 | | | | | 255 | |
| Phe | Ser | Thr | Cys | Asp | Asn | Gln | Lys | Ser | Cys | Met | Ser | Asn | Cys | Ser | Ile |
| | | | 260 | | | | | 265 | | | | | 270 | |
| Thr | Ser | Ile | Cys | Glu | Lys | Pro | Gln | Glu | Val | Cys | Val | Ala | Val | Trp | Arg |
| | | 275 | | | | | 280 | | | | | 285 | | | |
| Lys | Asn | Asp | Glu | Asn | Ile | Thr | Leu | Glu | Thr | Val | Cys | His | Asp | Pro | Lys |
| | 290 | | | | | 295 | | | | | 300 | | | | |
| Leu | Pro | Tyr | His | Asp | Phe | Ile | Leu | Glu | Asp | Ala | Ala | Ser | Pro | Lys | Cys |
| 305 | | | | | 310 | | | | | 315 | | | | | 320 |
| Ile | Met | Lys | Glu | Lys | Lys | Lys | Pro | Gly | Glu | Thr | Phe | Phe | Met | Cys | Ser |
| | | | | 325 | | | | | 330 | | | | | 335 | |
| Cys | Ser | Ser | Asp | Glu | Cys | Asn | Asp | Asn | Ile | Ile | Phe | Ser | Glu | Glu | Tyr |
| | | | 340 | | | | | 345 | | | | | 350 | |
| Asn | Thr | Ser | Asn | Pro | Asp | Ile | Pro | Pro | His | Val | Gln | Lys | Ser | Val | Asn |
| | | | 355 | | | | | 360 | | | | | 365 | |
| Asn | Asp | Met | Ile | Val | Thr | Asp | Asn | Asn | Gly | Ala | Val | Lys | Phe | Pro | Gln |
| | | 370 | | | | | 375 | | | | | 380 | | | |
| Leu | Cys | Lys | Phe | Cys | Asp | Val | Arg | Phe | Ser | Thr | Cys | Asp | Asn | Gln | Lys |
| 385 | | | | | 390 | | | | | 395 | | | | | 400 |

```
Ser Cys Met Ser Asn Cys Ser Ile Thr Ser Ile Cys Glu Lys Pro Gln
            405                 410                 415

Glu Val Cys Val Ala Val Trp Arg Lys Asn Asp Glu Asn Ile Thr Leu
            420                 425                 430

Glu Thr Val Cys His Asp Pro Lys Leu Pro Tyr His Asp Phe Ile Leu
            435                 440                 445

Glu Asp Ala Ala Ser Pro Lys Cys Ile Met Lys Glu Lys Lys Lys Pro
450                 455                 460

Gly Glu Thr Phe Phe Met Cys Ser Cys Ser Ser Asp Glu Cys Asn Asp
465                 470                 475                 480

Asn Ile Ile Phe Ser Glu Glu Tyr Asn Thr Ser Asn Pro Asp Ile Pro
                485                 490                 495

Pro His Val Gln Lys Ser Val Asn Asn Asp Met Ile Val Thr Asp Asn
                500                 505                 510

Asn Gly Ala Val Lys Phe Pro Gln Leu Cys Lys Phe Cys Asp Val Arg
                515                 520                 525

Phe Ser Thr Cys Asp Asn Gln Lys Ser Cys Met Ser Asn Cys Ser Ile
        530                 535                 540

Thr Ser Ile Cys Glu Lys Pro Gln Glu Val Cys Val Ala Val Trp Arg
545                 550                 555                 560

Lys Asn Asp Glu Asn Ile Thr Leu Glu Thr Val Cys His Asp Pro Lys
                565                 570                 575

Leu Pro Tyr His Asp Phe Ile Leu Glu Asp Ala Ala Ser Pro Lys Cys
                580                 585                 590

Ile Met Lys Glu Lys Lys Lys Pro Gly Glu Thr Phe Phe Met Cys Ser
                595                 600                 605

Cys Ser Ser Asp Glu Cys Asn Asp Asn Ile Ile Phe Ser Glu Glu Tyr
        610                 615                 620

Asn Thr Ser Asn Pro Asp
625                 630

<210> SEQ ID NO 114
<211> LENGTH: 636
<212> TYPE: PRT
<213> ORGANISM: Artificial Sequence
<220> FEATURE:
<223> OTHER INFORMATION: hIgG4FcdeltaK-CC-228P-T2-T2-T2 fusion

<400> SEQUENCE: 114

Glu Ser Lys Tyr Gly Pro Pro Cys Pro Pro Cys Pro Ala Pro Glu Phe
1               5                   10                  15

Leu Gly Gly Pro Ser Val Phe Leu Phe Pro Pro Lys Pro Lys Asp Thr
                20                  25                  30

Leu Met Ile Ser Arg Thr Pro Glu Val Thr Cys Val Val Val Asp Val
            35                  40                  45

Ser Gln Glu Asp Pro Glu Val Gln Phe Asn Trp Tyr Val Asp Gly Val
        50                  55                  60

Glu Val His Asn Ala Lys Thr Lys Pro Arg Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
                100                 105                 110

Ser Ile Glu Lys Thr Ile Ser Lys Ala Lys Gly Gln Pro Arg Glu Pro
            115                 120                 125
```

```
Gln Val Tyr Thr Leu Pro Pro Ser Gln Glu Glu Met Thr Lys Asn Gln
    130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
210                 215                 220

Leu Ser Leu Gly Ile Pro Pro His Val Gln Lys Ser Val Asn Asn Asp
225                 230                 235                 240

Met Ile Val Thr Asp Asn Asn Gly Ala Val Lys Phe Pro Gln Leu Cys
                245                 250                 255

Lys Phe Cys Asp Val Arg Phe Ser Thr Cys Asp Asn Gln Lys Ser Cys
            260                 265                 270

Met Ser Asn Cys Ser Ile Thr Ser Ile Cys Glu Lys Pro Gln Glu Val
        275                 280                 285

Cys Val Ala Val Trp Arg Lys Asn Asp Glu Asn Ile Thr Leu Glu Thr
290                 295                 300

Val Cys His Asp Pro Lys Leu Pro Tyr His Asp Phe Ile Leu Glu Asp
305                 310                 315                 320

Ala Ala Ser Pro Lys Cys Ile Met Lys Glu Lys Lys Pro Gly Glu
                325                 330                 335

Thr Phe Phe Met Cys Ser Cys Ser Ser Asp Glu Cys Asn Asp Asn Ile
            340                 345                 350

Ile Phe Ser Glu Glu Tyr Asn Thr Ser Asn Pro Asp Ile Pro Pro His
        355                 360                 365

Val Gln Lys Ser Val Asn Asn Asp Met Ile Val Thr Asp Asn Asn Gly
370                 375                 380

Ala Val Lys Phe Pro Gln Leu Cys Lys Phe Cys Asp Val Arg Phe Ser
385                 390                 395                 400

Thr Cys Asp Asn Gln Lys Ser Cys Met Ser Asn Cys Ser Ile Thr Ser
                405                 410                 415

Ile Cys Glu Lys Pro Gln Glu Val Cys Val Ala Val Trp Arg Lys Asn
            420                 425                 430

Asp Glu Asn Ile Thr Leu Glu Thr Val Cys His Asp Pro Lys Leu Pro
        435                 440                 445

Tyr His Asp Phe Ile Leu Glu Asp Ala Ala Ser Pro Lys Cys Ile Met
450                 455                 460

Lys Glu Lys Lys Pro Gly Glu Thr Phe Phe Met Cys Ser Cys Ser
465                 470                 475                 480

Ser Asp Glu Cys Asn Asp Asn Ile Ile Phe Ser Glu Glu Tyr Asn Thr
                485                 490                 495

Ser Asn Pro Asp Ile Pro Pro His Val Gln Lys Ser Val Asn Asn Asp
            500                 505                 510

Met Ile Val Thr Asp Asn Asn Gly Ala Val Lys Phe Pro Gln Leu Cys
        515                 520                 525

Lys Phe Cys Asp Val Arg Phe Ser Thr Cys Asp Asn Gln Lys Ser Cys
530                 535                 540

Met Ser Asn Cys Ser Ile Thr Ser Ile Cys Glu Lys Pro Gln Glu Val
```

```
                545                 550                 555                 560
Cys Val Ala Val Trp Arg Lys Asn Asp Glu Asn Ile Thr Leu Glu Thr
                    565                 570                 575

Val Cys His Asp Pro Lys Leu Pro Tyr His Asp Phe Ile Leu Glu Asp
            580                 585                 590

Ala Ala Ser Pro Lys Cys Ile Met Lys Glu Lys Lys Pro Gly Glu
        595                 600                 605

Thr Phe Phe Met Cys Ser Cys Ser Ser Asp Cys Asn Asp Asn Ile
    610                 615                 620

Ile Phe Ser Glu Glu Tyr Asn Thr Ser Asn Pro Asp
625                 630                 635

<210> SEQ ID NO 115
<211> LENGTH: 636
<212> TYPE: PRT
<213> ORGANISM: Artificial Sequence
<220> FEATURE:
<223> OTHER INFORMATION: hIgG4FcdeltaK-CC-228P-409K-T2-T2-T2 fusion

<400> SEQUENCE: 115

Glu Ser Lys Tyr Gly Pro Pro Cys Pro Pro Cys Pro Ala Pro Glu Phe
1               5                   10                  15

Leu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Asp Val
        35                  40                  45

Ser Gln Glu Asp Pro Glu Val Gln Phe Asn Trp Tyr Val Asp Gly Val
50                  55                  60

Glu Val His Asn Ala Lys Thr Lys Pro Arg Glu Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
        115                 120                 125

Gln Val Tyr Thr Leu Pro Pro Ser Gln Glu Glu Met Thr Lys Asn Gln
    130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Lys Leu
            180                 185                 190

Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
    210                 215                 220

Leu Ser Leu Gly Ile Pro Pro His Val Gln Lys Ser Val Asn Asn Asp
225                 230                 235                 240

Met Ile Val Thr Asp Asn Asn Gly Ala Val Lys Phe Pro Gln Leu Cys
                245                 250                 255

Lys Phe Cys Asp Val Arg Phe Ser Thr Cys Asp Asn Gln Lys Ser Cys
            260                 265                 270

Met Ser Asn Cys Ser Ile Thr Ser Ile Cys Glu Lys Pro Gln Glu Val
```

```
            275                 280                 285
Cys Val Ala Val Trp Arg Lys Asn Asp Glu Asn Ile Thr Leu Glu Thr
290                 295                 300

Val Cys His Asp Pro Lys Leu Pro Tyr His Asp Phe Ile Leu Glu Asp
305                 310                 315                 320

Ala Ala Ser Pro Lys Cys Ile Met Lys Glu Lys Lys Pro Gly Glu
            325                 330                 335

Thr Phe Phe Met Cys Ser Cys Ser Ser Asp Glu Cys Asn Asp Asn Ile
            340                 345                 350

Ile Phe Ser Glu Glu Tyr Asn Thr Ser Asn Pro Asp Ile Pro Pro His
            355                 360                 365

Val Gln Lys Ser Val Asn Asn Asp Met Ile Val Thr Asp Asn Asn Gly
370                 375                 380

Ala Val Lys Phe Pro Gln Leu Cys Lys Phe Cys Asp Val Arg Phe Ser
385                 390                 395                 400

Thr Cys Asp Asn Gln Lys Ser Cys Met Ser Asn Cys Ser Ile Thr Ser
            405                 410                 415

Ile Cys Glu Lys Pro Gln Glu Val Cys Val Ala Val Trp Arg Lys Asn
            420                 425                 430

Asp Glu Asn Ile Thr Leu Glu Thr Val Cys His Asp Pro Lys Leu Pro
            435                 440                 445

Tyr His Asp Phe Ile Leu Glu Asp Ala Ala Ser Pro Lys Cys Ile Met
450                 455                 460

Lys Glu Lys Lys Lys Pro Gly Glu Thr Phe Phe Met Cys Ser Cys Ser
465                 470                 475                 480

Ser Asp Glu Cys Asn Asp Asn Ile Ile Phe Ser Glu Glu Tyr Asn Thr
            485                 490                 495

Ser Asn Pro Asp Ile Pro Pro His Val Gln Lys Ser Val Asn Asn Asp
            500                 505                 510

Met Ile Val Thr Asp Asn Asn Gly Ala Val Lys Phe Pro Gln Leu Cys
            515                 520                 525

Lys Phe Cys Asp Val Arg Phe Ser Thr Cys Asp Asn Gln Lys Ser Cys
530                 535                 540

Met Ser Asn Cys Ser Ile Thr Ser Ile Cys Glu Lys Pro Gln Glu Val
545                 550                 555                 560

Cys Val Ala Val Trp Arg Lys Asn Asp Glu Asn Ile Thr Leu Glu Thr
            565                 570                 575

Val Cys His Asp Pro Lys Leu Pro Tyr His Asp Phe Ile Leu Glu Asp
            580                 585                 590

Ala Ala Ser Pro Lys Cys Ile Met Lys Glu Lys Lys Pro Gly Glu
            595                 600                 605

Thr Phe Phe Met Cys Ser Cys Ser Ser Asp Glu Cys Asn Asp Asn Ile
            610                 615                 620

Ile Phe Ser Glu Glu Tyr Asn Thr Ser Asn Pro Asp
            625                 630                 635

<210> SEQ ID NO 116
<211> LENGTH: 678
<212> TYPE: PRT
<213> ORGANISM: Artificial Sequence
<220> FEATURE:
<223> OTHER INFORMATION: hIgG1FcdeltaK-C-T2-T2bAA-T2bAA fusion

<400> SEQUENCE: 116

Pro Pro Cys Pro Ala Pro Glu Leu Leu Gly Gly Pro Ser Val Phe Leu
```

```
1               5                   10                  15
Phe Pro Pro Lys Pro Lys Asp Thr Leu Met Ile Ser Arg Thr Pro Glu
                20                  25                  30
Val Thr Cys Val Val Asp Val Ser His Glu Asp Pro Glu Val Lys
            35                  40                  45
Phe Asn Trp Tyr Val Asp Gly Val Glu Val His Asn Ala Lys Thr Lys
        50                  55                  60
Pro Arg Glu Glu Gln Tyr Asn Ser Thr Tyr Arg Val Val Ser Val Leu
65                  70                  75                  80
Thr Val Leu His Gln Asp Trp Leu Asn Gly Lys Glu Tyr Lys Cys Lys
                85                  90                  95
Val Ser Asn Lys Ala Leu Pro Ala Pro Ile Glu Lys Thr Ile Ser Lys
                100                 105                 110
Ala Lys Gly Gln Pro Arg Glu Pro Gln Val Tyr Thr Leu Pro Pro Ser
            115                 120                 125
Arg Asp Glu Leu Thr Lys Asn Gln Val Ser Leu Thr Cys Leu Val Lys
    130                 135                 140
Gly Phe Tyr Pro Ser Asp Ile Ala Val Glu Trp Glu Ser Asn Gly Gln
145                 150                 155                 160
Pro Glu Asn Asn Tyr Lys Thr Thr Pro Pro Val Leu Asp Ser Asp Gly
                165                 170                 175
Ser Phe Phe Leu Tyr Ser Lys Leu Thr Val Asp Lys Ser Arg Trp Gln
                180                 185                 190
Gln Gly Asn Val Phe Ser Cys Ser Val Met His Glu Ala Leu His Asn
            195                 200                 205
His Tyr Thr Gln Lys Ser Leu Ser Leu Ser Pro Gly Ile Pro Pro His
    210                 215                 220
Val Gln Lys Ser Val Asn Asn Asp Met Ile Val Thr Asp Asn Asn Gly
225                 230                 235                 240
Ala Val Lys Phe Pro Gln Leu Cys Lys Phe Cys Asp Val Arg Phe Ser
                245                 250                 255
Thr Cys Asp Asn Gln Lys Ser Cys Met Ser Asn Cys Ser Ile Thr Ser
            260                 265                 270
Ile Cys Glu Lys Pro Gln Glu Val Cys Val Ala Val Trp Arg Lys Asn
    275                 280                 285
Asp Glu Asn Ile Thr Leu Glu Thr Val Cys His Asp Pro Lys Leu Pro
290                 295                 300
Tyr His Asp Phe Ile Leu Glu Asp Ala Ala Ser Pro Lys Cys Ile Met
305                 310                 315                 320
Lys Glu Lys Lys Lys Pro Gly Glu Thr Phe Phe Met Cys Ser Cys Ser
                325                 330                 335
Ser Asp Glu Cys Asn Asp Asn Ile Ile Phe Ser Glu Glu Tyr Asn Thr
            340                 345                 350
Ser Asn Pro Asp Ile Pro Pro His Val Gln Lys Ser Asp Val Glu Met
            355                 360                 365
Glu Ala Gln Lys Asp Glu Ile Ile Ala Pro Ser Ala Asn Arg Thr Ala
370                 375                 380
His Pro Leu Arg His Ile Asn Asn Asp Met Ile Val Thr Asp Asn Asn
385                 390                 395                 400
Gly Ala Val Lys Phe Pro Gln Leu Cys Lys Phe Cys Asp Val Arg Phe
            405                 410                 415
Ser Thr Cys Asp Asn Gln Lys Ser Cys Met Ser Asn Cys Ser Ile Thr
            420                 425                 430
```

-continued

```
Ser Ile Cys Glu Lys Pro Gln Glu Val Cys Val Ala Val Trp Arg Lys
        435                 440                 445

Asn Asp Glu Asn Ile Thr Leu Glu Thr Val Cys His Asp Pro Lys Leu
450                 455                 460

Pro Tyr His Asp Phe Ile Leu Glu Asp Ala Ala Ser Pro Lys Cys Ile
465                 470                 475                 480

Met Lys Glu Lys Lys Pro Gly Glu Thr Phe Phe Met Cys Ser Cys
            485                 490                 495

Ser Ser Asp Glu Cys Asn Asp Asn Ile Ile Phe Ser Glu Glu Tyr Asn
            500                 505                 510

Thr Ser Asn Pro Asp Ile Pro Pro His Val Gln Lys Ser Asp Val Glu
            515                 520                 525

Met Glu Ala Gln Lys Asp Glu Ile Ile Ala Pro Ser Ala Asn Arg Thr
        530                 535                 540

Ala His Pro Leu Arg His Ile Asn Asn Asp Met Ile Val Thr Asp Asn
545                 550                 555                 560

Asn Gly Ala Val Lys Phe Pro Gln Leu Cys Lys Phe Cys Asp Val Arg
                565                 570                 575

Phe Ser Thr Cys Asp Asn Gln Lys Ser Cys Met Ser Asn Cys Ser Ile
            580                 585                 590

Thr Ser Ile Cys Glu Lys Pro Gln Glu Val Cys Val Ala Val Trp Arg
            595                 600                 605

Lys Asn Asp Glu Asn Ile Thr Leu Glu Thr Val Cys His Asp Pro Lys
        610                 615                 620

Leu Pro Tyr His Asp Phe Ile Leu Glu Asp Ala Ala Ser Pro Lys Cys
625                 630                 635                 640

Ile Met Lys Glu Lys Lys Pro Gly Glu Thr Phe Phe Met Cys Ser
                645                 650                 655

Cys Ser Ser Asp Glu Cys Asn Asp Asn Ile Ile Phe Ser Glu Glu Tyr
            660                 665                 670

Asn Thr Ser Asn Pro Asp
            675
```

<210> SEQ ID NO 117
<211> LENGTH: 684
<212> TYPE: PRT
<213> ORGANISM: Artificial Sequence
<220> FEATURE:
<223> OTHER INFORMATION: hIgG1FcdeltaK-CC-T2-T2bAA-T2bAA fusion

<400> SEQUENCE: 117

```
Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110
```

```
Glu Lys Thr Ile Ser Lys Ala Lys Gly Gln Pro Arg Glu Pro Gln Val
        115                 120                 125
Tyr Thr Leu Pro Pro Ser Arg Asp Glu Leu Thr Lys Asn Gln Val Ser
    130                 135                 140
Leu Thr Cys Leu Val Lys Gly Phe Tyr Pro Ser Asp Ile Ala Val Glu
145                 150                 155                 160
Trp Glu Ser Asn Gly Gln Pro Glu Asn Asn Tyr Lys Thr Thr Pro Pro
                165                 170                 175
Val Leu Asp Ser Asp Gly Ser Phe Phe Leu Tyr Ser Lys Leu Thr Val
                180                 185                 190
Asp Lys Ser Arg Trp Gln Gln Gly Asn Val Phe Ser Cys Ser Val Met
        195                 200                 205
His Glu Ala Leu His Asn His Tyr Thr Gln Lys Ser Leu Ser Leu Ser
    210                 215                 220
Pro Gly Ile Pro Pro His Val Gln Lys Ser Val Asn Asn Asp Met Ile
225                 230                 235                 240
Val Thr Asp Asn Asn Gly Ala Val Lys Phe Pro Gln Leu Cys Lys Phe
                245                 250                 255
Cys Asp Val Arg Phe Ser Thr Cys Asp Asn Gln Lys Ser Cys Met Ser
                260                 265                 270
Asn Cys Ser Ile Thr Ser Ile Cys Glu Lys Pro Gln Glu Val Cys Val
        275                 280                 285
Ala Val Trp Arg Lys Asn Asp Glu Asn Ile Thr Leu Glu Thr Val Cys
        290                 295                 300
His Asp Pro Lys Leu Pro Tyr His Asp Phe Ile Leu Glu Asp Ala Ala
305                 310                 315                 320
Ser Pro Lys Cys Ile Met Lys Glu Lys Lys Pro Gly Glu Thr Phe
                325                 330                 335
Phe Met Cys Ser Cys Ser Ser Asp Glu Cys Asn Asp Asn Ile Ile Phe
                340                 345                 350
Ser Glu Glu Tyr Asn Thr Ser Asn Pro Asp Ile Pro Pro His Val Gln
        355                 360                 365
Lys Ser Asp Val Glu Met Glu Ala Gln Lys Asp Glu Ile Ile Ala Pro
    370                 375                 380
Ser Ala Asn Arg Thr Ala His Pro Leu Arg His Ile Asn Asn Asp Met
385                 390                 395                 400
Ile Val Thr Asp Asn Asn Gly Ala Val Lys Phe Pro Gln Leu Cys Lys
                405                 410                 415
Phe Cys Asp Val Arg Phe Ser Thr Cys Asp Asn Gln Lys Ser Cys Met
                420                 425                 430
Ser Asn Cys Ser Ile Thr Ser Ile Cys Glu Lys Pro Gln Glu Val Cys
        435                 440                 445
Val Ala Val Trp Arg Lys Asn Asp Glu Asn Ile Thr Leu Glu Thr Val
    450                 455                 460
Cys His Asp Pro Lys Leu Pro Tyr His Asp Phe Ile Leu Glu Asp Ala
465                 470                 475                 480
Ala Ser Pro Lys Cys Ile Met Lys Glu Lys Lys Pro Gly Glu Thr
                485                 490                 495
Phe Phe Met Cys Ser Cys Ser Ser Asp Glu Cys Asn Asp Asn Ile Ile
                500                 505                 510
Phe Ser Glu Glu Tyr Asn Thr Ser Asn Pro Asp Ile Pro Pro His Val
        515                 520                 525
```

```
Gln Lys Ser Asp Val Glu Met Glu Ala Gln Lys Asp Glu Ile Ile Ala
        530                 535                 540

Pro Ser Ala Asn Arg Thr Ala His Pro Leu Arg His Ile Asn Asn Asp
545                 550                 555                 560

Met Ile Val Thr Asp Asn Asn Gly Ala Val Lys Phe Pro Gln Leu Cys
                565                 570                 575

Lys Phe Cys Asp Val Arg Phe Ser Thr Cys Asp Asn Gln Lys Ser Cys
                580                 585                 590

Met Ser Asn Cys Ser Ile Thr Ser Ile Cys Glu Lys Pro Gln Glu Val
            595                 600                 605

Cys Val Ala Val Trp Arg Lys Asn Asp Glu Asn Ile Thr Leu Glu Thr
610                 615                 620

Val Cys His Asp Pro Lys Leu Pro Tyr His Asp Phe Ile Leu Glu Asp
625                 630                 635                 640

Ala Ala Ser Pro Lys Cys Ile Met Lys Glu Lys Lys Pro Gly Glu
                645                 650                 655

Thr Phe Phe Met Cys Ser Cys Ser Asp Glu Cys Asn Asp Asn Ile
            660                 665                 670

Ile Phe Ser Glu Glu Tyr Asn Thr Ser Asn Pro Asp
        675                 680

<210> SEQ ID NO 118
<211> LENGTH: 680
<212> TYPE: PRT
<213> ORGANISM: Artificial Sequence
<220> FEATURE:
<223> OTHER INFORMATION: hIgG2FcdeltaK-CC-T2-T2bAA-T2bAA fusion

<400> SEQUENCE: 118

Val Glu Cys Pro Pro Cys Pro Ala Pro Val Ala Gly Pro Ser Val
1               5                   10                  15

Phe Leu Phe Pro Pro Lys Pro Lys Asp Thr Leu Met Ile Ser Arg Thr
                20                  25                  30

Pro Glu Val Thr Cys Val Val Asp Val Ser His Glu Asp Pro Glu
                35                  40                  45

Val Gln Phe Asn Trp Tyr Val Asp Gly Val Glu Val His Asn Ala Lys
        50                  55                  60

Thr Lys Pro Arg Glu Glu Gln Phe Asn Ser Thr Phe Arg Val Val Ser
65                  70                  75                  80

Val Leu Thr Val Val His Gln Asp Trp Leu Asn Gly Lys Glu Tyr Lys
                85                  90                  95

Cys Lys Val Ser Asn Lys Gly Leu Pro Ala Pro Ile Glu Lys Thr Ile
                100                 105                 110

Ser Lys Thr Lys Gly Gln Pro Arg Glu Pro Gln Val Tyr Thr Leu Pro
            115                 120                 125

Pro Ser Arg Glu Glu Met Thr Lys Asn Gln Val Ser Leu Thr Cys Leu
130                 135                 140

Val Lys Gly Phe Tyr Pro Ser Asp Ile Ser Val Glu Trp Glu Ser Asn
145                 150                 155                 160

Gly Gln Pro Glu Asn Asn Tyr Lys Thr Thr Pro Pro Met Leu Asp Ser
                165                 170                 175

Asp Gly Ser Phe Phe Leu Tyr Ser Lys Leu Thr Val Asp Lys Ser Arg
            180                 185                 190

Trp Gln Gln Gly Asn Val Phe Ser Cys Ser Val Met His Glu Ala Leu
        195                 200                 205
```

```
His Asn His Tyr Thr Gln Lys Ser Leu Ser Leu Ser Pro Gly Ile Pro
    210                 215                 220

Pro His Val Gln Lys Ser Val Asn Asn Asp Met Ile Val Thr Asp Asn
225                 230                 235                 240

Asn Gly Ala Val Lys Phe Pro Gln Leu Cys Lys Phe Cys Asp Val Arg
                245                 250                 255

Phe Ser Thr Cys Asp Asn Gln Lys Ser Cys Met Ser Asn Cys Ser Ile
                260                 265                 270

Thr Ser Ile Cys Glu Lys Pro Gln Glu Val Cys Val Ala Val Trp Arg
            275                 280                 285

Lys Asn Asp Glu Asn Ile Thr Leu Glu Thr Val Cys His Asp Pro Lys
290                 295                 300

Leu Pro Tyr His Asp Phe Ile Leu Glu Asp Ala Ala Ser Pro Lys Cys
305                 310                 315                 320

Ile Met Lys Glu Lys Lys Pro Gly Glu Thr Phe Phe Met Cys Ser
                325                 330                 335

Cys Ser Ser Asp Glu Cys Asn Asp Asn Ile Ile Phe Ser Glu Glu Tyr
            340                 345                 350

Asn Thr Ser Asn Pro Asp Ile Pro Pro His Val Gln Lys Ser Asp Val
            355                 360                 365

Glu Met Glu Ala Gln Lys Asp Glu Ile Ile Ala Pro Ser Ala Asn Arg
370                 375                 380

Thr Ala His Pro Leu Arg His Ile Asn Asn Asp Met Ile Val Thr Asp
385                 390                 395                 400

Asn Asn Gly Ala Val Lys Phe Pro Gln Leu Cys Lys Phe Cys Asp Val
                405                 410                 415

Arg Phe Ser Thr Cys Asp Asn Gln Lys Ser Cys Met Ser Asn Cys Ser
                420                 425                 430

Ile Thr Ser Ile Cys Glu Lys Pro Gln Glu Val Cys Val Ala Val Trp
            435                 440                 445

Arg Lys Asn Asp Glu Asn Ile Thr Leu Glu Thr Val Cys His Asp Pro
    450                 455                 460

Lys Leu Pro Tyr His Asp Phe Ile Leu Glu Asp Ala Ala Ser Pro Lys
465                 470                 475                 480

Cys Ile Met Lys Glu Lys Lys Pro Gly Glu Thr Phe Phe Met Cys
                485                 490                 495

Ser Cys Ser Ser Asp Glu Cys Asn Asp Asn Ile Ile Phe Ser Glu Glu
            500                 505                 510

Tyr Asn Thr Ser Asn Pro Asp Ile Pro Pro His Val Gln Lys Ser Asp
            515                 520                 525

Val Glu Met Glu Ala Gln Lys Asp Glu Ile Ile Ala Pro Ser Ala Asn
    530                 535                 540

Arg Thr Ala His Pro Leu Arg His Ile Asn Asn Asp Met Ile Val Thr
545                 550                 555                 560

Asp Asn Asn Gly Ala Val Lys Phe Pro Gln Leu Cys Lys Phe Cys Asp
                565                 570                 575

Val Arg Phe Ser Thr Cys Asp Asn Gln Lys Ser Cys Met Ser Asn Cys
                580                 585                 590

Ser Ile Thr Ser Ile Cys Glu Lys Pro Gln Glu Val Cys Val Ala Val
            595                 600                 605

Trp Arg Lys Asn Asp Glu Asn Ile Thr Leu Glu Thr Val Cys His Asp
    610                 615                 620

Pro Lys Leu Pro Tyr His Asp Phe Ile Leu Glu Asp Ala Ala Ser Pro
```

```
                   625                 630                 635                 640
Lys Cys Ile Met Lys Glu Lys Lys Pro Gly Glu Thr Phe Phe Met
                645                 650                 655
Cys Ser Cys Ser Ser Asp Glu Cys Asn Asp Asn Ile Ile Phe Ser Glu
            660                 665                 670
Glu Tyr Asn Thr Ser Asn Pro Asp
            675                 680

<210> SEQ ID NO 119
<211> LENGTH: 686
<212> TYPE: PRT
<213> ORGANISM: Artificial Sequence
<220> FEATURE:
<223> OTHER INFORMATION: hIgG4FcdeltaK-CC-228P-T2-T2bAA-T2bAA fusion

<400> SEQUENCE: 119

Glu Ser Lys Tyr Gly Pro Pro Cys Pro Pro Cys Pro Ala Pro Glu Phe
1               5                   10                  15
Leu Gly Gly Pro Ser Val Phe Leu Phe Pro Pro Lys Pro Lys Asp Thr
            20                  25                  30
Leu Met Ile Ser Arg Thr Pro Glu Val Thr Cys Val Val Val Asp Val
        35                  40                  45
Ser Gln Glu Asp Pro Glu Val Gln Phe Asn Trp Tyr Val Asp Gly Val
    50                  55                  60
Glu Val His Asn Ala Lys Thr Lys Pro Arg Glu Glu Gln Phe Asn Ser
65                  70                  75                  80
Thr Tyr Arg Val Val Ser Val Leu Thr Val Leu His Gln Asp Trp Leu
                85                  90                  95
Asn Gly Lys Glu Tyr Lys Cys Lys Val Ser Asn Lys Gly Leu Pro Ser
            100                 105                 110
Ser Ile Glu Lys Thr Ile Ser Lys Ala Lys Gly Gln Pro Arg Glu Pro
        115                 120                 125
Gln Val Tyr Thr Leu Pro Pro Ser Gln Glu Glu Met Thr Lys Asn Gln
    130                 135                 140
Val Ser Leu Thr Cys Leu Val Lys Gly Phe Tyr Pro Ser Asp Ile Ala
145                 150                 155                 160
Val Glu Trp Glu Ser Asn Gly Gln Pro Glu Asn Asn Tyr Lys Thr Thr
                165                 170                 175
Pro Pro Val Leu Asp Ser Asp Gly Ser Phe Phe Leu Tyr Ser Arg Leu
            180                 185                 190
Thr Val Asp Lys Ser Arg Trp Gln Glu Gly Asn Val Phe Ser Cys Ser
        195                 200                 205
Val Met His Glu Ala Leu His Asn His Tyr Thr Gln Lys Ser Leu Ser
    210                 215                 220
Leu Ser Leu Gly Ile Pro Pro His Val Gln Lys Ser Val Asn Asn Asp
225                 230                 235                 240
Met Ile Val Thr Asp Asn Asn Gly Ala Val Lys Phe Pro Gln Leu Cys
                245                 250                 255
Lys Phe Cys Asp Val Arg Phe Ser Thr Cys Asp Asn Gln Lys Ser Cys
            260                 265                 270
Met Ser Asn Cys Ser Ile Thr Ser Ile Cys Glu Lys Pro Gln Glu Val
        275                 280                 285
Cys Val Ala Val Trp Arg Lys Asn Asp Glu Asn Ile Thr Leu Glu Thr
    290                 295                 300
Val Cys His Asp Pro Lys Leu Pro Tyr His Asp Phe Ile Leu Glu Asp
```

```
                    305              310              315              320
Ala Ala Ser Pro Lys Cys Ile Met Lys Glu Lys Lys Pro Gly Glu
                325              330              335

Thr Phe Phe Met Cys Ser Cys Ser Ser Asp Glu Cys Asn Asp Asn Ile
                340              345              350

Ile Phe Ser Glu Glu Tyr Asn Thr Ser Asn Pro Asp Ile Pro Pro His
                355              360              365

Val Gln Lys Ser Asp Val Glu Met Glu Ala Gln Lys Asp Glu Ile Ile
    370              375              380

Ala Pro Ser Ala Asn Arg Thr Ala His Pro Leu Arg His Ile Asn Asn
385              390              395              400

Asp Met Ile Val Thr Asp Asn Asn Gly Ala Val Lys Phe Pro Gln Leu
                405              410              415

Cys Lys Phe Cys Asp Val Arg Phe Ser Thr Cys Asp Asn Gln Lys Ser
            420              425              430

Cys Met Ser Asn Cys Ser Ile Thr Ser Ile Cys Glu Lys Pro Gln Glu
            435              440              445

Val Cys Val Ala Val Trp Arg Lys Asn Asp Glu Asn Ile Thr Leu Glu
450              455              460

Thr Val Cys His Asp Pro Lys Leu Pro Tyr His Asp Phe Ile Leu Glu
465              470              475              480

Asp Ala Ala Ser Pro Lys Cys Ile Met Lys Glu Lys Lys Pro Gly
                485              490              495

Glu Thr Phe Phe Met Cys Ser Cys Ser Ser Asp Glu Cys Asn Asp Asn
            500              505              510

Ile Ile Phe Ser Glu Glu Tyr Asn Thr Ser Asn Pro Asp Ile Pro Pro
            515              520              525

His Val Gln Lys Ser Asp Val Glu Met Glu Ala Gln Lys Asp Glu Ile
        530              535              540

Ile Ala Pro Ser Ala Asn Arg Thr Ala His Pro Leu Arg His Ile Asn
545              550              555              560

Asn Asp Met Ile Val Thr Asp Asn Asn Gly Ala Val Lys Phe Pro Gln
                565              570              575

Leu Cys Lys Phe Cys Asp Val Arg Phe Ser Thr Cys Asp Asn Gln Lys
                580              585              590

Ser Cys Met Ser Asn Cys Ser Ile Thr Ser Ile Cys Glu Lys Pro Gln
            595              600              605

Glu Val Cys Val Ala Val Trp Arg Lys Asn Asp Glu Asn Ile Thr Leu
            610              615              620

Glu Thr Val Cys His Asp Pro Lys Leu Pro Tyr His Asp Phe Ile Leu
625              630              635              640

Glu Asp Ala Ala Ser Pro Lys Cys Ile Met Lys Glu Lys Lys Lys Pro
                645              650              655

Gly Glu Thr Phe Phe Met Cys Ser Cys Ser Ser Asp Glu Cys Asn Asp
                660              665              670

Asn Ile Ile Phe Ser Glu Glu Tyr Asn Thr Ser Asn Pro Asp
            675              680              685

<210> SEQ ID NO 120
<211> LENGTH: 686
<212> TYPE: PRT
<213> ORGANISM: Artificial Sequence
<220> FEATURE:
<223> OTHER INFORMATION: hIgG4FcdeltaK-CC-228P-409K-T2-T2bAA-T2bAA
      fusion
```

<400> SEQUENCE: 120

Glu Ser Lys Tyr Gly Pro Pro Cys Pro Pro Cys Pro Ala Pro Glu Phe
1               5                   10                  15

Leu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
        115                 120                 125

Gln Val Tyr Thr Leu Pro Pro Ser Gln Glu Glu Met Thr Lys Asn Gln
    130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Lys Leu
            180                 185                 190

Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
210                 215                 220

Leu Ser Leu Gly Ile Pro Pro His Val Gln Lys Ser Val Asn Asn Asp
225                 230                 235                 240

Met Ile Val Thr Asp Asn Asn Gly Ala Val Lys Phe Pro Gln Leu Cys
                245                 250                 255

Lys Phe Cys Asp Val Arg Phe Ser Thr Cys Asp Asn Gln Lys Ser Cys
            260                 265                 270

Met Ser Asn Cys Ser Ile Thr Ser Ile Cys Glu Lys Pro Gln Glu Val
        275                 280                 285

Cys Val Ala Val Trp Arg Lys Asn Asp Glu Asn Ile Thr Leu Glu Thr
290                 295                 300

Val Cys His Asp Pro Lys Leu Pro Tyr His Asp Phe Ile Leu Glu Asp
305                 310                 315                 320

Ala Ala Ser Pro Lys Cys Ile Met Lys Glu Lys Lys Pro Gly Glu
                325                 330                 335

Thr Phe Phe Met Cys Ser Cys Ser Asp Glu Cys Asn Asp Asn Ile
            340                 345                 350

Ile Phe Ser Glu Glu Tyr Asn Thr Ser Asn Pro Asp Ile Pro Pro His
        355                 360                 365

Val Gln Lys Ser Asp Val Glu Met Glu Ala Gln Lys Asp Glu Ile Ile
    370                 375                 380

Ala Pro Ser Ala Asn Arg Thr Ala His Pro Leu Arg His Ile Asn Asn
385                 390                 395                 400

Asp Met Ile Val Thr Asp Asn Asn Gly Ala Val Lys Phe Pro Gln Leu

```
            405                 410                 415
Cys Lys Phe Cys Asp Val Arg Phe Ser Thr Cys Asp Asn Gln Lys Ser
        420                 425                 430

Cys Met Ser Asn Cys Ser Ile Thr Ser Ile Cys Glu Lys Pro Gln Glu
        435                 440                 445

Val Cys Val Ala Val Trp Arg Lys Asn Asp Glu Asn Ile Thr Leu Glu
        450                 455                 460

Thr Val Cys His Asp Pro Lys Leu Pro Tyr His Asp Phe Ile Leu Glu
465                 470                 475                 480

Asp Ala Ala Ser Pro Lys Cys Ile Met Lys Glu Lys Lys Pro Gly
        485                 490                 495

Glu Thr Phe Phe Met Cys Ser Cys Ser Ser Asp Glu Cys Asn Asp Asn
        500                 505                 510

Ile Ile Phe Ser Glu Glu Tyr Asn Thr Ser Asn Pro Asp Ile Pro Pro
        515                 520                 525

His Val Gln Lys Ser Asp Val Glu Met Glu Ala Gln Lys Asp Glu Ile
        530                 535                 540

Ile Ala Pro Ser Ala Asn Arg Thr Ala His Pro Leu Arg His Ile Asn
545                 550                 555                 560

Asn Asp Met Ile Val Thr Asp Asn Asn Gly Ala Val Lys Phe Pro Gln
                565                 570                 575

Leu Cys Lys Phe Cys Asp Val Arg Phe Ser Thr Cys Asp Asn Gln Lys
                580                 585                 590

Ser Cys Met Ser Asn Cys Ser Ile Thr Ser Ile Cys Glu Lys Pro Gln
                595                 600                 605

Glu Val Cys Val Ala Val Trp Arg Lys Asn Asp Glu Asn Ile Thr Leu
        610                 615                 620

Glu Thr Val Cys His Asp Pro Lys Leu Pro Tyr His Asp Phe Ile Leu
625                 630                 635                 640

Glu Asp Ala Ala Ser Pro Lys Cys Ile Met Lys Glu Lys Lys Pro
                645                 650                 655

Gly Glu Thr Phe Phe Met Cys Ser Cys Ser Ser Asp Glu Cys Asn Asp
                660                 665                 670

Asn Ile Ile Phe Ser Glu Glu Tyr Asn Thr Ser Asn Pro Asp
        675                 680                 685

<210> SEQ ID NO 121
<211> LENGTH: 214
<212> TYPE: PRT
<213> ORGANISM: Artificial Sequence
<220> FEATURE:
<223> OTHER INFORMATION: Cetuximab LC

<400> SEQUENCE: 121

Asp Ile Leu Leu Thr Gln Ser Pro Val Ile Leu Ser Val Ser Pro Gly
1               5                   10                  15

Glu Arg Val Ser Phe Ser Cys Arg Ala Ser Gln Ser Ile Gly Thr Asn
            20                  25                  30

Ile His Trp Tyr Gln Gln Arg Thr Asn Gly Ser Pro Arg Leu Leu Ile
        35                  40                  45

Lys Tyr Ala Ser Glu Ser Ile Ser Gly Ile Pro Ser Arg Phe Ser Gly
    50                  55                  60

Ser Gly Ser Gly Thr Asp Phe Thr Leu Ser Ile Asn Ser Val Glu Ser
65                  70                  75                  80

Glu Asp Ile Ala Asp Tyr Tyr Cys Gln Gln Asn Asn Asn Trp Pro Thr
```

```
                85                  90                  95
Thr Phe Gly Ala Gly Thr Lys Leu Glu Leu Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 122
<211> LENGTH: 721
<212> TYPE: PRT
<213> ORGANISM: Artificial Sequence
<220> FEATURE:
<223> OTHER INFORMATION: Cetuximab HC-T22d35

<400> SEQUENCE: 122

Gln Val Gln Leu Lys Gln Ser Gly Pro Gly Leu Val Gln Pro Ser Gln
1               5                   10                  15

Ser Leu Ser Ile Thr Cys Thr Val Ser Gly Phe Ser Leu Thr Asn Tyr
            20                  25                  30

Gly Val His Trp Val Arg Gln Ser Pro Gly Lys Gly Leu Glu Trp Leu
        35                  40                  45

Gly Val Ile Trp Ser Gly Gly Asn Thr Asp Tyr Asn Thr Pro Phe Thr
    50                  55                  60

Ser Arg Leu Ser Ile Asn Lys Asp Asn Ser Lys Ser Gln Val Phe Phe
65                  70                  75                  80

Lys Met Asn Ser Leu Gln Ser Asn Asp Thr Ala Ile Tyr Tyr Cys Ala
                85                  90                  95

Arg Ala Leu Thr Tyr Tyr Asp Tyr Glu Phe Ala Tyr Trp Gly Gln Gly
            100                 105                 110

Thr Leu Val Thr Val Ser Ala Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Arg Val Glu Pro Lys Ser Cys Asp Lys
    210                 215                 220

Thr His Thr Cys Pro Pro Cys Pro Ala Pro Glu Leu Leu Gly Gly Pro
```

```
            225                 230                 235                 240
Ser Val Phe Leu Phe Pro Pro Lys Pro Lys Asp Thr Leu Met Ile Ser
                    245                 250                 255

Arg Thr Pro Glu Val Thr Cys Val Val Val Asp Val Ser His Glu Asp
                    260                 265                 270

Pro Glu Val Lys Phe Asn Trp Tyr Val Asp Gly Val Glu Val His Asn
                    275                 280                 285

Ala Lys Thr Lys Pro Arg Glu Glu Gln Tyr Asn Ser Thr Tyr Arg Val
        290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                    325                 330                 335

Thr Ile Ser Lys Ala Lys Gly Gln Pro Arg Glu Pro Gln Val Tyr Thr
                    340                 345                 350

Leu Pro Pro Ser Arg Asp Glu Leu Thr Lys Asn Gln Val Ser Leu Thr
                    355                 360                 365

Cys Leu Val Lys Gly Phe Tyr Pro Ser Asp Ile Ala Val Glu Trp Glu
        370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                    405                 410                 415

Ser Arg Trp Gln Gln Gly Asn Val Phe Ser Cys Ser Val Met His Glu
                    420                 425                 430

Ala Leu His Asn His Tyr Thr Gln Lys Ser Leu Ser Leu Ser Pro Gly
                    435                 440                 445

Lys Ile Pro Pro His Val Gln Lys Ser Val Asn Asn Asp Met Ile Val
        450                 455                 460

Thr Asp Asn Asn Gly Ala Val Lys Phe Pro Gln Leu Cys Lys Phe Cys
465                 470                 475                 480

Asp Val Arg Phe Ser Thr Cys Asp Asn Gln Lys Ser Cys Met Ser Asn
                    485                 490                 495

Cys Ser Ile Thr Ser Ile Cys Glu Lys Pro Gln Glu Val Cys Val Ala
                    500                 505                 510

Val Trp Arg Lys Asn Asp Glu Asn Ile Thr Leu Glu Thr Val Cys His
                    515                 520                 525

Asp Pro Lys Leu Pro Tyr His Asp Phe Ile Leu Glu Asp Ala Ala Ser
        530                 535                 540

Pro Lys Cys Ile Met Lys Glu Lys Lys Pro Gly Glu Thr Phe Phe
545                 550                 555                 560

Met Cys Ser Cys Ser Ser Asp Glu Cys Asn Asp Asn Ile Ile Phe Ser
                    565                 570                 575

Glu Glu Tyr Asn Thr Ser Asn Pro Asp Ile Pro Pro His Val Gln Lys
                    580                 585                 590

Ser Val Asn Asn Asp Met Ile Val Thr Asp Asn Asn Gly Ala Val Lys
                    595                 600                 605

Phe Pro Gln Leu Cys Lys Phe Cys Asp Val Arg Phe Ser Thr Cys Asp
        610                 615                 620

Asn Gln Lys Ser Cys Met Ser Asn Cys Ser Ile Thr Ser Ile Cys Glu
625                 630                 635                 640

Lys Pro Gln Glu Val Cys Val Ala Val Trp Arg Lys Asn Asp Glu Asn
                    645                 650                 655
```

```
Ile Thr Leu Glu Thr Val Cys His Asp Pro Lys Leu Pro Tyr His Asp
            660                 665                 670

Phe Ile Leu Glu Asp Ala Ala Ser Pro Lys Cys Ile Met Lys Glu Lys
            675                 680                 685

Lys Lys Pro Gly Glu Thr Phe Phe Met Cys Ser Cys Ser Ser Asp Glu
            690                 695                 700

Cys Asn Asp Asn Ile Ile Phe Ser Glu Glu Tyr Asn Thr Ser Asn Pro
705                 710                 715                 720

Asp

<210> SEQ ID NO 123
<211> LENGTH: 585
<212> TYPE: PRT
<213> ORGANISM: Artificial Sequence
<220> FEATURE:
<223> OTHER INFORMATION: Cetuximab HC-T2m

<400> SEQUENCE: 123

Gln Val Gln Leu Lys Gln Ser Gly Pro Gly Leu Val Gln Pro Ser Gln
1               5                   10                  15

Ser Leu Ser Ile Thr Cys Thr Val Ser Gly Phe Ser Leu Thr Asn Tyr
            20                  25                  30

Gly Val His Trp Val Arg Gln Ser Pro Gly Lys Gly Leu Glu Trp Leu
        35                  40                  45

Gly Val Ile Trp Ser Gly Gly Asn Thr Asp Tyr Asn Thr Pro Phe Thr
    50                  55                  60

Ser Arg Leu Ser Ile Asn Lys Asp Asn Ser Lys Ser Gln Val Phe Phe
65                  70                  75                  80

Lys Met Asn Ser Leu Gln Ser Asn Asp Thr Ala Ile Tyr Tyr Cys Ala
                85                  90                  95

Arg Ala Leu Thr Tyr Tyr Asp Tyr Glu Phe Ala Tyr Trp Gly Gln Gly
            100                 105                 110

Thr Leu Val Thr Val Ser Ala Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Arg Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285
```

```
Ala Lys Thr Lys Pro Arg Glu Glu Gln Tyr Asn Ser Thr Tyr Arg Val
    290                 295                 300
Val Ser Val Leu Thr Val Leu His Gln Asp Trp Leu Asn Gly Lys Glu
305                 310                 315                 320
Tyr Lys Cys Lys Val Ser Asn Lys Ala Leu Pro Ala Pro Ile Glu Lys
                325                 330                 335
Thr Ile Ser Lys Ala Lys Gly Gln Pro Arg Glu Pro Gln Val Tyr Thr
            340                 345                 350
Leu Pro Pro Ser Arg Asp Glu Leu Thr Lys Asn Gln Val Ser Leu Thr
            355                 360                 365
Cys Leu Val Lys Gly Phe Tyr Pro Ser Asp Ile Ala Val Glu Trp Glu
370                 375                 380
Ser Asn Gly Gln Pro Glu Asn Asn Tyr Lys Thr Thr Pro Pro Val Leu
385                 390                 395                 400
Asp Ser Asp Gly Ser Phe Phe Leu Tyr Ser Lys Leu Thr Val Asp Lys
                405                 410                 415
Ser Arg Trp Gln Gln Gly Asn Val Phe Ser Cys Ser Val Met His Glu
                420                 425                 430
Ala Leu His Asn His Tyr Thr Gln Lys Ser Leu Ser Leu Ser Pro Gly
            435                 440                 445
Lys Ile Pro Pro His Val Gln Lys Ser Val Asn Asn Asp Met Ile Val
450                 455                 460
Thr Asp Asn Asn Gly Ala Val Lys Phe Pro Gln Leu Cys Lys Phe Cys
465                 470                 475                 480
Asp Val Arg Phe Ser Thr Cys Asp Asn Gln Lys Ser Cys Met Ser Asn
                485                 490                 495
Cys Ser Ile Thr Ser Ile Cys Glu Lys Pro Gln Glu Val Cys Val Ala
                500                 505                 510
Val Trp Arg Lys Asn Asp Glu Asn Ile Thr Leu Glu Thr Val Cys His
            515                 520                 525
Asp Pro Lys Leu Pro Tyr His Asp Phe Ile Leu Glu Asp Ala Ala Ser
            530                 535                 540
Pro Lys Cys Ile Met Lys Glu Lys Lys Lys Pro Gly Glu Thr Phe Phe
545                 550                 555                 560
Met Cys Ser Cys Ser Ser Asp Glu Cys Asn Asp Asn Ile Ile Phe Ser
                565                 570                 575
Glu Glu Tyr Asn Thr Ser Asn Pro Asp
            580                 585

<210> SEQ ID NO 124
<211> LENGTH: 214
<212> TYPE: PRT
<213> ORGANISM: Artificial Sequence
<220> FEATURE:
<223> OTHER INFORMATION: Herceptin LC

<400> SEQUENCE: 124

Asp Ile Gln Met Thr Gln Ser Pro Ser Ser Leu Ser Ala Ser Val Gly
1               5                   10                  15
Asp Arg Val Thr Ile Thr Cys Arg Ala Ser Gln Asp Val Asn Thr Ala
            20                  25                  30
Val Ala Trp Tyr Gln Gln Lys Pro Gly Lys Ala Pro Lys Leu Leu Ile
        35                  40                  45
Tyr Ser Ala Ser Phe Leu Tyr Ser Gly Val Pro Ser Arg Phe Ser Gly
    50                  55                  60
```

```
Ser Arg Ser Gly Thr Asp Phe Thr Leu Thr Ile Ser Ser Leu Gln Pro
 65                  70                  75                  80

Glu Asp Phe Ala Thr Tyr Tyr Cys Gln Gln His Tyr Thr Thr Pro Pro
                 85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 125
<211> LENGTH: 722
<212> TYPE: PRT
<213> ORGANISM: Artificial Sequence
<220> FEATURE:
<223> OTHER INFORMATION: Herceptin HC-T22d35

<400> SEQUENCE: 125

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Asn Ile Lys Asp Thr
             20                  25                  30

Tyr Ile His Trp Val Arg Gln Ala Pro Gly Lys Gly Leu Glu Trp Val
         35                  40                  45

Ala Arg Ile Tyr Pro Thr Asn Gly Tyr Thr Arg Tyr Ala Asp Ser Val
     50                  55                  60

Lys Gly Arg Phe Thr Ile Ser Ala Asp Thr Ser Lys Asn Thr Ala Tyr
 65                  70                  75                  80

Leu Gln Met Asn Ser Leu Arg Ala Glu Asp Thr Ala Val Tyr Tyr Cys
                 85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205
```

```
Pro Ser Asn Thr Lys Val Asp Lys Lys Val Glu Pro Lys Ser Cys Asp
210                 215                 220
Lys Thr His Thr Cys Pro Pro Cys Pro Ala Pro Glu Leu Leu Gly Gly
225                 230                 235                 240
Pro Ser Val Phe Leu Phe Pro Pro Lys Pro Lys Asp Thr Leu Met Ile
            245                 250                 255
Ser Arg Thr Pro Glu Val Thr Cys Val Val Val Asp Val Ser His Glu
                260                 265                 270
Asp Pro Glu Val Lys Phe Asn Trp Tyr Val Asp Gly Val Glu Val His
                275                 280                 285
Asn Ala Lys Thr Lys Pro Arg Glu Glu Gln Tyr Asn Ser Thr Tyr Arg
290                 295                 300
Val Val Ser Val Leu Thr Val Leu His Gln Asp Trp Leu Asn Gly Lys
305                 310                 315                 320
Glu Tyr Lys Cys Lys Val Ser Asn Lys Ala Leu Pro Ala Pro Ile Glu
                325                 330                 335
Lys Thr Ile Ser Lys Ala Lys Gly Gln Pro Arg Glu Pro Gln Val Tyr
                340                 345                 350
Thr Leu Pro Pro Ser Arg Asp Glu Leu Thr Lys Asn Gln Val Ser Leu
                355                 360                 365
Thr Cys Leu Val Lys Gly Phe Tyr Pro Ser Asp Ile Ala Val Glu Trp
370                 375                 380
Glu Ser Asn Gly Gln Pro Glu Asn Asn Tyr Lys Thr Thr Pro Pro Val
385                 390                 395                 400
Leu Asp Ser Asp Gly Ser Phe Phe Leu Tyr Ser Lys Leu Thr Val Asp
                405                 410                 415
Lys Ser Arg Trp Gln Gln Gly Asn Val Phe Ser Cys Ser Val Met His
                420                 425                 430
Glu Ala Leu His Asn His Tyr Thr Gln Lys Ser Leu Ser Leu Ser Pro
            435                 440                 445
Gly Lys Ile Pro Pro His Val Gln Lys Ser Val Asn Asn Asp Met Ile
450                 455                 460
Val Thr Asp Asn Asn Gly Ala Val Lys Phe Pro Gln Leu Cys Lys Phe
465                 470                 475                 480
Cys Asp Val Arg Phe Ser Thr Cys Asp Asn Gln Lys Ser Cys Met Ser
            485                 490                 495
Asn Cys Ser Ile Thr Ser Ile Cys Glu Lys Pro Gln Glu Val Cys Val
                500                 505                 510
Ala Val Trp Arg Lys Asn Asp Glu Asn Ile Thr Leu Glu Thr Val Cys
            515                 520                 525
His Asp Pro Lys Leu Pro Tyr His Asp Phe Ile Leu Glu Asp Ala Ala
530                 535                 540
Ser Pro Lys Cys Ile Met Lys Glu Lys Lys Lys Pro Gly Glu Thr Phe
545                 550                 555                 560
Phe Met Cys Ser Cys Ser Ser Asp Glu Cys Asn Asp Asn Ile Ile Phe
            565                 570                 575
Ser Glu Glu Tyr Asn Thr Ser Asn Pro Asp Ile Pro Pro His Val Gln
                580                 585                 590
Lys Ser Val Asn Asn Asp Met Ile Val Thr Asp Asn Asn Gly Ala Val
                595                 600                 605
Lys Phe Pro Gln Leu Cys Lys Phe Cys Asp Val Arg Phe Ser Thr Cys
            610                 615                 620
Asp Asn Gln Lys Ser Cys Met Ser Asn Cys Ser Ile Thr Ser Ile Cys
```

```
                625                 630                 635                 640
Glu Lys Pro Gln Glu Val Cys Val Ala Val Trp Arg Lys Asn Asp Glu
                    645                 650                 655

Asn Ile Thr Leu Glu Thr Val Cys His Asp Pro Lys Leu Pro Tyr His
                660                 665                 670

Asp Phe Ile Leu Glu Asp Ala Ala Ser Pro Lys Cys Ile Met Lys Glu
            675                 680                 685

Lys Lys Lys Pro Gly Glu Thr Phe Phe Met Cys Ser Cys Ser Ser Asp
690                 695                 700

Glu Cys Asn Asp Asn Ile Ile Phe Ser Glu Gly Tyr Asn Thr Ser Asn
705                 710                 715                 720

Pro Asp

<210> SEQ ID NO 126
<211> LENGTH: 214
<212> TYPE: PRT
<213> ORGANISM: Artificial Sequence
<220> FEATURE:
<223> OTHER INFORMATION: Avastin LC

<400> SEQUENCE: 126

Asp Ile Gln Met Thr Gln Ser Pro Ser Ser Leu Ser Ala Ser Val Gly
1               5                   10                  15

Asp Arg Val Thr Ile Thr Cys Ser Ala Ser Gln Asp Ile Ser Asn Tyr
            20                  25                  30

Leu Asn Trp Tyr Gln Gln Lys Pro Gly Lys Ala Pro Lys Val Leu Ile
        35                  40                  45

Tyr Phe Thr Ser Ser Leu His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Thr Val Pro Trp
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 127
<211> LENGTH: 725
<212> TYPE: PRT
<213> ORGANISM: Artificial Sequence
<220> FEATURE:
<223> OTHER INFORMATION: Avastin HC-T22d35
```

```
<400> SEQUENCE: 127

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Asn Tyr
            20                  25                  30

Gly Met Asn Trp Val Arg Gln Ala Pro Gly Lys Gly Leu Glu Trp Val
        35                  40                  45

Gly Trp Ile Asn Thr Tyr Thr Gly Glu Pro Thr Tyr Ala Ala Asp Phe
    50                  55                  60

Lys Arg Arg Phe Thr Phe Ser Leu Asp Thr Ser Lys Ser Thr Ala Tyr
65                  70                  75                  80

Leu Gln Met Asn Ser Leu Arg Ala Glu Asp Thr Ala Val Tyr Tyr Cys
                85                  90                  95

Ala Lys Tyr Pro His Tyr Gly Ser Ser His Trp Tyr Phe Asp Val
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Val Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Asp Glu Leu Thr Lys Asn Gln
        355                 360                 365

Val Ser Leu Thr Cys Leu Val Lys Gly Phe Tyr Pro Ser Asp Ile Ala
    370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415
```

```
Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
            435                 440                 445

Leu Ser Pro Gly Lys Ile Pro Pro His Val Gln Lys Ser Val Asn Asn
450                 455                 460

Asp Met Ile Val Thr Asp Asn Asn Gly Ala Val Lys Phe Pro Gln Leu
465                 470                 475                 480

Cys Lys Phe Cys Asp Val Arg Phe Ser Thr Cys Asp Asn Gln Lys Ser
                485                 490                 495

Cys Met Ser Asn Cys Ser Ile Thr Ser Ile Cys Glu Lys Pro Gln Glu
                500                 505                 510

Val Cys Val Ala Val Trp Arg Lys Asn Asp Glu Asn Ile Thr Leu Glu
            515                 520                 525

Thr Val Cys His Asp Pro Lys Leu Pro Tyr His Asp Phe Ile Leu Glu
        530                 535                 540

Asp Ala Ala Ser Pro Lys Cys Ile Met Lys Glu Lys Lys Pro Gly
545                 550                 555                 560

Glu Thr Phe Phe Met Cys Ser Cys Ser Ser Asp Glu Cys Asn Asp Asn
                565                 570                 575

Ile Ile Phe Ser Glu Glu Tyr Asn Thr Ser Asn Pro Asp Ile Pro Pro
            580                 585                 590

His Val Gln Lys Ser Val Asn Asn Asp Met Ile Val Thr Asp Asn Asn
        595                 600                 605

Gly Ala Val Lys Phe Pro Gln Leu Cys Lys Phe Cys Asp Val Arg Phe
    610                 615                 620

Ser Thr Cys Asp Asn Gln Lys Ser Cys Met Ser Asn Cys Ser Ile Thr
625                 630                 635                 640

Ser Ile Cys Glu Lys Pro Gln Glu Val Cys Val Ala Val Trp Arg Lys
                645                 650                 655

Asn Asp Glu Asn Ile Thr Leu Glu Thr Val Cys His Asp Pro Lys Leu
            660                 665                 670

Pro Tyr His Asp Phe Ile Leu Glu Asp Ala Ala Ser Pro Lys Cys Ile
        675                 680                 685

Met Lys Glu Lys Lys Lys Pro Gly Glu Thr Phe Phe Met Cys Ser Cys
    690                 695                 700

Ser Ser Asp Glu Cys Asn Asp Asn Ile Ile Phe Ser Glu Glu Tyr Asn
705                 710                 715                 720

Thr Ser Asn Pro Asp
                725
```

<210> SEQ ID NO 128
<211> LENGTH: 213
<212> TYPE: PRT
<213> ORGANISM: Artificial Sequence
<220> FEATURE:
<223> OTHER INFORMATION: Synagis LC

<400> SEQUENCE: 128

```
Asp Ile Gln Met Thr Gln Ser Pro Ser Thr Leu Ser Ala Ser Val Gly
1               5                   10                  15

Asp Arg Val Thr Ile Thr Cys Lys Cys Gln Leu Ser Val Gly Tyr Met
            20                  25                  30

His Trp Tyr Gln Gln Lys Pro Gly Lys Ala Pro Lys Leu Leu Ile Tyr
        35                  40                  45
```

```
Asp Thr Ser Lys Leu Ala Ser Gly Val Pro Ser Arg Phe Ser Gly Ser
        50                  55                  60
Gly Ser Gly Thr Glu Phe Thr Leu Thr Ile Ser Ser Leu Gln Pro Asp
 65                  70                  75                  80
Asp Phe Ala Thr Tyr Tyr Cys Phe Gln Gly Ser Gly Tyr Pro Phe Thr
                85                  90                  95
Phe Gly Gly Gly Thr Lys Leu Glu Ile Lys Arg Thr Val Ala Ala Pro
            100                 105                 110
Ser Val Phe Ile Phe Pro Pro Ser Asp Glu Gln Leu Lys Ser Gly Thr
                115                 120                 125
Ala Ser Val Val Cys Leu Leu Asn Asn Phe Tyr Pro Arg Glu Ala Lys
        130                 135                 140
Val Gln Trp Lys Val Asp Asn Ala Leu Gln Ser Gly Asn Ser Gln Glu
145                 150                 155                 160
Ser Val Thr Glu Gln Asp Ser Lys Asp Ser Thr Tyr Ser Leu Ser Ser
                165                 170                 175
Thr Leu Thr Leu Ser Lys Ala Asp Tyr Glu Lys His Lys Val Tyr Ala
            180                 185                 190
Cys Glu Val Thr His Gln Gly Leu Ser Ser Pro Val Thr Lys Ser Phe
        195                 200                 205
Asn Arg Gly Glu Cys
    210

<210> SEQ ID NO 129
<211> LENGTH: 721
<212> TYPE: PRT
<213> ORGANISM: Artificial Sequence
<220> FEATURE:
<223> OTHER INFORMATION: Synagis HC-T22d35

<400> SEQUENCE: 129

Gln Val Thr Leu Arg Glu Ser Gly Pro Ala Leu Val Lys Pro Thr Gln
 1               5                  10                  15
Thr Leu Thr Leu Thr Cys Thr Phe Ser Gly Phe Ser Leu Ser Thr Ser
                20                  25                  30
Gly Met Ser Val Gly Trp Ile Arg Gln Pro Pro Gly Lys Ala Leu Glu
            35                  40                  45
Trp Leu Ala Asp Ile Trp Trp Asp Asp Lys Lys Asp Tyr Asn Pro Ser
        50                  55                  60
Leu Lys Ser Arg Leu Thr Ile Ser Lys Asp Thr Ser Lys Asn Gln Val
 65                  70                  75                  80
Val Leu Lys Val Thr Asn Met Asp Pro Ala Asp Thr Ala Thr Tyr Tyr
                85                  90                  95
Cys Ala Arg Ser Met Ile Thr Asn Trp Tyr Phe Asp Val Trp Gly Ala
            100                 105                 110
Gly Thr Thr Val Thr Val Ser Ser Ala Ser Thr Lys Gly Pro Ser Val
                115                 120                 125
Phe Pro Leu Ala Pro Ser Ser Ala Ala Ala Gly Gly Thr Ala Ala
        130                 135                 140
Leu Gly Cys Leu Val Lys Asp Tyr Phe Pro Glu Pro Val Thr Val Ser
145                 150                 155                 160
Trp Asn Ser Gly Ala Leu Thr Ser Gly Val His Thr Phe Pro Ala Val
                165                 170                 175
Leu Gln Ser Ser Gly Leu Tyr Ser Leu Ser Ser Val Val Thr Val Pro
            180                 185                 190
```

-continued

```
Ser Ser Ser Leu Gly Thr Gln Thr Tyr Ile Cys Asn Val Asn His Lys
        195                 200                 205

Pro Ser Asn Thr Lys Val Asp Lys Arg Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
                260                 265                 270

Asp Pro Glu Val Lys Phe Asn Trp Tyr Val Asp Gly Val Glu Val His
            275                 280                 285

Asn Ala Lys Thr Lys Pro Arg Glu Glu Gln Tyr Asn Ser Thr Tyr Arg
        290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Ile Pro Pro His Val Gln Lys Ser Val Asn Asp Met Ile Val
    450                 455                 460

Thr Asp Asn Asn Gly Ala Val Lys Phe Pro Gln Leu Cys Lys Phe Cys
465                 470                 475                 480

Asp Val Arg Phe Ser Thr Cys Asp Asn Gln Lys Ser Cys Met Ser Asn
                485                 490                 495

Cys Ser Ile Thr Ser Ile Cys Glu Lys Pro Gln Glu Val Cys Val Ala
            500                 505                 510

Val Trp Arg Lys Asn Asp Glu Asn Ile Thr Leu Glu Thr Val Cys His
        515                 520                 525

Asp Pro Lys Leu Pro Tyr His Asp Phe Ile Leu Glu Asp Ala Ala Ser
    530                 535                 540

Pro Lys Cys Ile Met Lys Glu Lys Lys Pro Gly Glu Thr Phe Phe
545                 550                 555                 560

Met Cys Ser Cys Ser Ser Asp Glu Cys Asn Asp Asn Ile Ile Phe Ser
                565                 570                 575

Glu Glu Tyr Asn Thr Ser Asn Pro Asp Ile Pro Pro His Val Gln Lys
            580                 585                 590

Ser Val Asn Asn Asp Met Ile Val Thr Asp Asn Asn Gly Ala Val Lys
        595                 600                 605
```

```
Phe Pro Gln Leu Cys Lys Phe Cys Asp Val Arg Phe Ser Thr Cys Asp
    610                 615                 620

Asn Gln Lys Ser Cys Met Ser Asn Cys Ser Ile Thr Ser Ile Cys Glu
625                 630                 635                 640

Lys Pro Gln Glu Val Cys Val Ala Val Trp Arg Lys Asn Asp Glu Asn
                645                 650                 655

Ile Thr Leu Glu Thr Val Cys His Asp Pro Lys Leu Pro Tyr His Asp
                660                 665                 670

Phe Ile Leu Glu Asp Ala Ala Ser Pro Lys Cys Ile Met Lys Glu Lys
                675                 680                 685

Lys Lys Pro Gly Glu Thr Phe Phe Met Cys Ser Cys Ser Ser Asp Glu
690                 695                 700

Cys Asn Asp Asn Ile Ile Phe Ser Glu Glu Tyr Asn Thr Ser Asn Pro
705                 710                 715                 720

Asp

<210> SEQ ID NO 130
<211> LENGTH: 630
<212> TYPE: PRT
<213> ORGANISM: Artificial Sequence
<220> FEATURE:
<223> OTHER INFORMATION: FC5-Fc-T22d35

<400> SEQUENCE: 130

Glu Val Gln Leu Gln Ala Ser Gly Gly Gly Leu Val Gln Ala Gly Gly
1               5                   10                  15

Ser Leu Arg Leu Ser Cys Ala Ala Ser Gly Phe Lys Ile Thr His Tyr
            20                  25                  30

Thr Met Gly Trp Phe Arg Gln Ala Pro Gly Lys Glu Arg Glu Phe Val
        35                  40                  45

Ser Arg Ile Thr Trp Gly Gly Asp Asn Thr Phe Tyr Ser Asn Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Asp Tyr Tyr Cys
                85                  90                  95

Ala Ala Gly Ser Thr Ser Thr Ala Thr Pro Leu Arg Val Asp Tyr Trp
            100                 105                 110

Gly Lys Gly Thr Gln Val Thr Val Ser Ser Ala Ser Glu Pro Arg Gly
            115                 120                 125

Pro Thr Ile Lys Pro Cys Pro Pro Cys Lys Cys Pro Ala Pro Asn Leu
        130                 135                 140

Leu Gly Gly Pro Ser Val Phe Ile Phe Pro Pro Lys Ile Lys Asp Val
145                 150                 155                 160

Leu Met Ile Ser Leu Ser Pro Ile Val Thr Cys Val Val Val Asp Val
                165                 170                 175

Ser Glu Asp Asp Pro Asp Val Gln Ile Ser Trp Phe Val Asn Asn Val
            180                 185                 190

Glu Val His Thr Ala Gln Thr Gln Thr His Arg Glu Asp Tyr Asn Ser
        195                 200                 205

Thr Leu Arg Val Val Ser Ala Leu Pro Ile Gln His Gln Asp Trp Met
    210                 215                 220

Ser Gly Lys Glu Phe Lys Cys Lys Val Asn Asn Lys Asp Leu Pro Ala
225                 230                 235                 240

Pro Ile Glu Arg Thr Ile Ser Lys Pro Lys Gly Ser Val Arg Ala Pro
```

```
                    245                 250                 255
Gln Val Tyr Val Leu Pro Pro Glu Glu Met Thr Lys Lys Gln
            260                 265                 270
Val Thr Leu Thr Cys Met Val Thr Asp Phe Met Pro Glu Asp Ile Tyr
            275                 280                 285
Val Glu Trp Thr Asn Asn Gly Lys Thr Glu Leu Asn Tyr Lys Asn Thr
        290                 295                 300
Glu Pro Val Leu Asp Ser Asp Gly Ser Tyr Phe Met Tyr Ser Lys Leu
305                 310                 315                 320
Arg Val Glu Lys Lys Asn Trp Val Arg Asn Ser Tyr Ser Cys Ser
                325                 330                 335
Val Val His Glu Gly Leu His Asn His His Thr Thr Lys Ser Phe Ser
            340                 345                 350
Arg Thr Pro Gly Thr Gly Ile Pro Pro His Val Gln Lys Ser Val Asn
            355                 360                 365
Asn Asp Met Ile Val Thr Asp Asn Asn Gly Ala Val Lys Phe Pro Gln
        370                 375                 380
Leu Cys Lys Phe Cys Asp Val Arg Phe Ser Thr Cys Asp Asn Gln Lys
385                 390                 395                 400
Ser Cys Met Ser Asn Cys Ser Ile Thr Ser Ile Cys Glu Lys Pro Gln
                405                 410                 415
Glu Val Cys Val Ala Val Trp Arg Lys Asn Asp Glu Asn Ile Thr Leu
            420                 425                 430
Glu Thr Val Cys His Asp Pro Lys Leu Pro Tyr His Asp Phe Ile Leu
            435                 440                 445
Glu Asp Ala Ala Ser Pro Lys Cys Ile Met Lys Glu Lys Lys Pro
        450                 455                 460
Gly Glu Thr Phe Phe Met Cys Ser Cys Ser Ser Asp Glu Cys Asn Asp
465                 470                 475                 480
Asn Ile Ile Phe Ser Glu Glu Tyr Asn Thr Ser Asn Pro Asp Ile Pro
                485                 490                 495
Pro His Val Gln Lys Ser Val Asn Asn Asp Met Ile Val Thr Asp Asn
            500                 505                 510
Asn Gly Ala Val Lys Phe Pro Gln Leu Cys Lys Phe Cys Asp Val Arg
        515                 520                 525
Phe Ser Thr Cys Asp Asn Gln Lys Ser Cys Met Ser Asn Cys Ser Ile
    530                 535                 540
Thr Ser Ile Cys Glu Lys Pro Gln Glu Val Cys Val Ala Val Trp Arg
545                 550                 555                 560
Lys Asn Asp Glu Asn Ile Thr Leu Glu Thr Val Cys His Asp Pro Lys
                565                 570                 575
Leu Pro Tyr His Asp Phe Ile Leu Glu Asp Ala Ala Ser Pro Lys Cys
            580                 585                 590
Ile Met Lys Glu Lys Lys Pro Gly Glu Thr Phe Phe Met Cys Ser
                595                 600                 605
Cys Ser Ser Asp Glu Cys Asn Asp Asn Ile Ile Phe Ser Glu Glu Tyr
        610                 615                 620
Asn Thr Ser Asn Pro Asp
625                 630

<210> SEQ ID NO 131
<211> LENGTH: 494
<212> TYPE: PRT
<213> ORGANISM: Artificial Sequence
```

<220> FEATURE:
<223> OTHER INFORMATION: FC5-Fc-T2m

<400> SEQUENCE: 131

```
Glu Val Gln Leu Gln Ala Ser Gly Gly Gly Leu Val Gln Ala Gly
1               5                   10                  15

Ser Leu Arg Leu Ser Cys Ala Ala Ser Gly Phe Lys Ile Thr His Tyr
            20                  25                  30

Thr Met Gly Trp Phe Arg Gln Ala Pro Gly Lys Glu Arg Glu Phe Val
        35                  40                  45

Ser Arg Ile Thr Trp Gly Gly Asp Asn Thr Phe Tyr Ser Asn Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Asp Tyr Tyr Cys
                85                  90                  95

Ala Ala Gly Ser Thr Ser Thr Ala Thr Pro Leu Arg Val Asp Tyr Trp
            100                 105                 110

Gly Lys Gly Thr Gln Val Thr Val Ser Ser Ala Ser Glu Pro Arg Gly
        115                 120                 125

Pro Thr Ile Lys Pro Cys Pro Pro Cys Lys Cys Pro Ala Pro Asn Leu
    130                 135                 140

Leu Gly Gly Pro Ser Val Phe Ile Phe Pro Pro Lys Ile Lys Asp Val
145                 150                 155                 160

Leu Met Ile Ser Leu Ser Pro Ile Val Thr Cys Val Val Asp Val
                165                 170                 175

Ser Glu Asp Asp Pro Asp Val Gln Ile Ser Trp Phe Val Asn Asn Val
            180                 185                 190

Glu Val His Thr Ala Gln Thr Gln Thr His Arg Glu Asp Tyr Asn Ser
        195                 200                 205

Thr Leu Arg Val Val Ser Ala Leu Pro Ile Gln His Gln Asp Trp Met
    210                 215                 220

Ser Gly Lys Glu Phe Lys Cys Lys Val Asn Asn Lys Asp Leu Pro Ala
225                 230                 235                 240

Pro Ile Glu Arg Thr Ile Ser Lys Pro Lys Gly Ser Val Arg Ala Pro
                245                 250                 255

Gln Val Tyr Val Leu Pro Pro Pro Glu Glu Glu Met Thr Lys Lys Gln
            260                 265                 270

Val Thr Leu Thr Cys Met Val Thr Asp Phe Met Pro Glu Asp Ile Tyr
        275                 280                 285

Val Glu Trp Thr Asn Asn Gly Lys Thr Glu Leu Asn Tyr Lys Asn Thr
    290                 295                 300

Glu Pro Val Leu Asp Ser Asp Gly Ser Tyr Phe Met Tyr Ser Lys Leu
305                 310                 315                 320

Arg Val Glu Lys Lys Asn Trp Val Glu Arg Asn Ser Tyr Ser Cys Ser
                325                 330                 335

Val Val His Glu Gly Leu His Asn His His Thr Thr Lys Ser Phe Ser
            340                 345                 350

Arg Thr Pro Gly Thr Gly Ile Pro Pro His Val Gln Lys Ser Val Asn
        355                 360                 365

Asn Asp Met Ile Val Thr Asp Asn Asn Gly Ala Val Lys Phe Pro Gln
    370                 375                 380

Leu Cys Lys Phe Cys Asp Val Arg Phe Ser Thr Cys Asn Gln Lys
385                 390                 395                 400
```

```
Ser Cys Met Ser Asn Cys Ser Ile Thr Ser Ile Cys Glu Lys Pro Gln
            405                 410                 415

Glu Val Cys Val Ala Val Trp Arg Lys Asn Asp Glu Asn Ile Thr Leu
        420                 425                 430

Glu Thr Val Cys His Asp Pro Lys Leu Pro Tyr His Asp Phe Ile Leu
        435                 440                 445

Glu Asp Ala Ala Ser Pro Lys Cys Ile Met Lys Glu Lys Lys Pro
450                 455                 460

Gly Glu Thr Phe Phe Met Cys Ser Cys Ser Ser Asp Glu Cys Asn Asp
465                 470                 475                 480

Asn Ile Ile Phe Ser Glu Glu Tyr Asn Thr Ser Asn Pro Asp
            485                 490

<210> SEQ ID NO 132
<211> LENGTH: 392
<212> TYPE: PRT
<213> ORGANISM: Artificial Sequence
<220> FEATURE:
<223> OTHER INFORMATION: T2-hIgG1Fc fusion from R&D, also termed T2m-Fc
      (R&D)

<400> SEQUENCE: 132

Met Gly Arg Gly Leu Arg Gly Leu Trp Pro Leu His Ile Val Leu
1               5                   10                  15

Trp Thr Arg Ile Ala Ser Thr Ile Pro Pro His Val Gln Lys Ser Val
            20                  25                  30

Asn Asn Asp Met Ile Val Thr Asp Asn Asn Gly Ala Val Lys Phe Pro
        35                  40                  45

Gln Leu Cys Lys Phe Cys Asp Val Arg Phe Ser Thr Cys Asp Asn Gln
    50                  55                  60

Lys Ser Cys Met Ser Asn Cys Ser Ile Thr Ser Ile Cys Glu Lys Pro
65              70                  75                  80

Gln Glu Val Cys Val Ala Val Trp Arg Lys Asn Asp Glu Asn Ile Thr
                85                  90                  95

Leu Glu Thr Val Cys His Asp Pro Lys Leu Pro Tyr His Asp Phe Ile
            100                 105                 110

Leu Glu Asp Ala Ala Ser Pro Lys Cys Ile Met Lys Glu Lys Lys Lys
        115                 120                 125

Pro Gly Glu Thr Phe Phe Met Cys Ser Cys Ser Ser Asp Glu Cys Asn
    130                 135                 140

Asp Asn Ile Ile Phe Ser Glu Glu Tyr Asn Thr Ser Asn Pro Asp Met
145                 150                 155                 160

Asp Pro Lys Ser Cys Asp Lys Thr His Thr Cys Pro Pro Cys Pro Ala
                165                 170                 175

Pro Glu Leu Leu Gly Gly Pro Ser Val Phe Leu Phe Pro Pro Lys Pro
            180                 185                 190

Lys Asp Thr Leu Met Ile Ser Arg Thr Pro Glu Val Thr Cys Val Val
        195                 200                 205

Val Asp Val Ser His Glu Asp Pro Glu Val Lys Phe Asn Trp Tyr Val
    210                 215                 220

Asp Gly Val Glu Val His Asn Ala Lys Thr Lys Pro Arg Glu Glu Gln
225                 230                 235                 240

Tyr Asn Ser Thr Tyr Arg Val Val Ser Val Leu Thr Val Leu His Gln
                245                 250                 255

Asp Trp Leu Asn Gly Lys Glu Tyr Lys Cys Lys Val Ser Asn Lys Ala
```

```
                    260                 265                 270
Leu Pro Ala Pro Ile Glu Lys Thr Ile Ser Lys Ala Lys Gly Gln Pro
            275                 280                 285

Arg Glu Pro Gln Val Tyr Thr Leu Pro Pro Ser Arg Asp Glu Leu Thr
        290                 295                 300

Lys Asn Gln Val Ser Leu Thr Cys Leu Val Lys Gly Phe Tyr Pro Ser
305                 310                 315                 320

Asp Ile Ala Val Glu Trp Glu Ser Asn Gly Gln Pro Glu Asn Asn Tyr
                325                 330                 335

Lys Thr Thr Pro Pro Val Leu Asp Ser Asp Gly Ser Phe Phe Leu Tyr
            340                 345                 350

Ser Lys Leu Thr Val Asp Lys Ser Arg Trp Gln Gln Gly Asn Val Phe
        355                 360                 365

Ser Cys Ser Val Met His Glu Ala Leu His Asn His Tyr Thr Gln Lys
    370                 375                 380

Ser Leu Ser Leu Ser Pro Gly Lys
385                 390

<210> SEQ ID NO 133
<211> LENGTH: 382
<212> TYPE: PRT
<213> ORGANISM: Artificial Sequence
<220> FEATURE:
<223> OTHER INFORMATION: T2-hIgG2Fc-CCCC fusion, also termed T2m-Fc

<400> SEQUENCE: 133

Met Asp Trp Thr Trp Arg Ile Leu Phe Leu Val Ala Ala Thr Gly
1               5                   10                  15

Thr His Ala Ile Pro Pro His Val Gln Lys Ser Val Asn Asn Asp Met
            20                  25                  30

Ile Val Thr Asp Asn Asn Gly Ala Val Lys Phe Pro Gln Leu Cys Lys
        35                  40                  45

Phe Cys Asp Val Arg Phe Ser Thr Cys Asp Asn Gln Lys Ser Cys Met
    50                  55                  60

Ser Asn Cys Ser Ile Thr Ser Ile Cys Glu Lys Pro Gln Glu Val Cys
65                  70                  75                  80

Val Ala Val Trp Arg Lys Asn Asp Glu Asn Ile Thr Leu Glu Thr Val
                85                  90                  95

Cys His Asp Pro Lys Leu Pro Tyr His Asp Phe Ile Leu Glu Asp Ala
            100                 105                 110

Ala Ser Pro Lys Cys Ile Met Lys Glu Lys Lys Pro Gly Glu Thr
        115                 120                 125

Phe Phe Met Cys Ser Cys Ser Ser Asp Glu Cys Asn Asp Asn Ile Ile
    130                 135                 140

Phe Ser Glu Glu Tyr Asn Thr Ser Asn Pro Asp Glu Arg Lys Cys Cys
145                 150                 155                 160

Val Glu Cys Pro Pro Cys Pro Ala Pro Pro Val Ala Gly Pro Ser Val
                165                 170                 175

Phe Leu Phe Pro Pro Lys Pro Lys Asp Thr Leu Met Ile Ser Arg Thr
            180                 185                 190

Pro Glu Val Thr Cys Val Val Asp Val Ser His Glu Asp Pro Glu
        195                 200                 205

Val Gln Phe Asn Trp Tyr Val Asp Gly Val Glu Val His Asn Ala Lys
    210                 215                 220

Thr Lys Pro Arg Glu Glu Gln Phe Asn Ser Thr Phe Arg Val Val Ser
```

```
                225                 230                 235                 240
Val Leu Thr Val His Gln Asp Trp Leu Asn Gly Lys Glu Tyr Lys
                    245                 250                 255

Cys Lys Val Ser Asn Lys Gly Leu Pro Ala Pro Ile Glu Lys Thr Ile
                260                 265                 270

Ser Lys Thr Lys Gly Gln Pro Arg Glu Pro Gln Val Tyr Thr Leu Pro
                275                 280                 285

Pro Ser Arg Glu Glu Met Thr Lys Asn Gln Val Ser Leu Thr Cys Leu
            290                 295                 300

Val Lys Gly Phe Tyr Pro Ser Asp Ile Ser Val Glu Trp Glu Ser Asn
305                 310                 315                 320

Gly Gln Pro Glu Asn Asn Tyr Lys Thr Thr Pro Pro Met Leu Asp Ser
                325                 330                 335

Asp Gly Ser Phe Phe Leu Tyr Ser Lys Leu Thr Val Asp Lys Ser Arg
            340                 345                 350

Trp Gln Gln Gly Asn Val Phe Ser Cys Ser Val Met His Glu Ala Leu
            355                 360                 365

His Asn His Tyr Thr Gln Lys Ser Leu Ser Leu Ser Pro Gly
            370                 375                 380

<210> SEQ ID NO 134
<211> LENGTH: 15
<212> TYPE: PRT
<213> ORGANISM: Artificial Sequence
<220> FEATURE:
<223> OTHER INFORMATION: Isotope-labelled peptide for T22d35

<400> SEQUENCE: 134

Leu Pro Tyr His Asp Phe Ile Leu Glu Asp Ala Ala Ser Pro Lys
1               5                   10                  15

<210> SEQ ID NO 135
<211> LENGTH: 8
<212> TYPE: PRT
<213> ORGANISM: Artificial Sequence
<220> FEATURE:
<223> OTHER INFORMATION: Isotope-labelled peptide for Cetuximab

<400> SEQUENCE: 135

Ala Leu Pro Ala Pro Ile Glu Lys
1               5

<210> SEQ ID NO 136
<211> LENGTH: 372
<212> TYPE: PRT
<213> ORGANISM: Artificial Sequence
<220> FEATURE:
<223> OTHER INFORMATION: D10-hIgG1FcdeltaK-CC-T2m fusion

<400> SEQUENCE: 136

Asp Asp Asp Asp Asp Asp Asp Asp Asp Asp Lys Thr His Thr Cys
1               5                   10                  15

Pro Pro Cys Pro Ala Pro Glu Leu Leu Gly Gly Pro Ser Val Phe Leu
                20                  25                  30

Phe Pro Pro Lys Pro Lys Asp Thr Leu Met Ile Ser Arg Thr Pro Glu
            35                  40                  45

Val Thr Cys Val Val Val Asp Val Ser His Glu Asp Pro Glu Val Lys
        50                  55                  60

Phe Asn Trp Tyr Val Asp Gly Val Glu Val His Asn Ala Lys Thr Lys
65                  70                  75                  80
```

Pro Arg Glu Glu Gln Tyr Asn Ser Thr Tyr Arg Val Val Ser Val Leu
            85                  90                  95

Thr Val Leu His Gln Asp Trp Leu Asn Gly Lys Glu Tyr Lys Cys Lys
            100                 105                 110

Val Ser Asn Lys Ala Leu Pro Ala Pro Ile Glu Lys Thr Ile Ser Lys
            115                 120                 125

Ala Lys Gly Gln Pro Arg Glu Pro Gln Val Tyr Thr Leu Pro Pro Ser
130                 135                 140

Arg Asp Glu Leu Thr Lys Asn Gln Val Ser Leu Thr Cys Leu Val Lys
145                 150                 155                 160

Gly Phe Tyr Pro Ser Asp Ile Ala Val Glu Trp Glu Ser Asn Gly Gln
            165                 170                 175

Pro Glu Asn Asn Tyr Lys Thr Thr Pro Pro Val Leu Asp Ser Asp Gly
            180                 185                 190

Ser Phe Phe Leu Tyr Ser Lys Leu Thr Val Asp Lys Ser Arg Trp Gln
            195                 200                 205

Gln Gly Asn Val Phe Ser Cys Ser Val Met His Glu Ala Leu His Asn
            210                 215                 220

His Tyr Thr Gln Lys Ser Leu Ser Leu Ser Pro Gly Ile Pro Pro His
225                 230                 235                 240

Val Gln Lys Ser Val Asn Asn Asp Met Ile Val Thr Asp Asn Asn Gly
            245                 250                 255

Ala Val Lys Phe Pro Gln Leu Cys Lys Phe Cys Asp Val Arg Phe Ser
            260                 265                 270

Thr Cys Asp Asn Gln Lys Ser Cys Met Ser Asn Cys Ser Ile Thr Ser
            275                 280                 285

Ile Cys Glu Lys Pro Gln Glu Val Cys Val Ala Val Trp Arg Lys Asn
            290                 295                 300

Asp Glu Asn Ile Thr Leu Glu Thr Val Cys His Asp Pro Lys Leu Pro
305                 310                 315                 320

Tyr His Asp Phe Ile Leu Glu Asp Ala Ala Ser Pro Lys Cys Ile Met
            325                 330                 335

Lys Glu Lys Lys Lys Pro Gly Glu Thr Phe Phe Met Cys Ser Cys Ser
            340                 345                 350

Ser Asp Glu Cys Asn Asp Asn Ile Ile Phe Ser Glu Glu Tyr Asn Thr
            355                 360                 365

Ser Asn Pro Asp
    370

<210> SEQ ID NO 137
<211> LENGTH: 376
<212> TYPE: PRT
<213> ORGANISM: Artificial Sequence
<220> FEATURE:
<223> OTHER INFORMATION: D10-G3S-hIgG1FcdeltaK-CC-T2m fusion

<400> SEQUENCE: 137

Asp Asp Asp Asp Asp Asp Asp Asp Asp Gly Gly Gly Ser Asp Lys
1               5                   10                  15

Thr His Thr Cys Pro Pro Cys Pro Ala Pro Glu Leu Leu Gly Gly Pro
            20                  25                  30

Ser Val Phe Leu Phe Pro Pro Lys Pro Lys Asp Thr Leu Met Ile Ser
            35                  40                  45

Arg Thr Pro Glu Val Thr Cys Val Val Val Asp Val Ser His Glu Asp
50                  55                  60

```
Pro Glu Val Lys Phe Asn Trp Tyr Val Asp Gly Val Glu Val His Asn
 65                  70                  75                  80

Ala Lys Thr Lys Pro Arg Glu Glu Gln Tyr Asn Ser Thr Tyr Arg Val
                 85                  90                  95

Val Ser Val Leu Thr Val Leu His Gln Asp Trp Leu Asn Gly Lys Glu
            100                 105                 110

Tyr Lys Cys Lys Val Ser Asn Lys Ala Leu Pro Ala Pro Ile Glu Lys
        115                 120                 125

Thr Ile Ser Lys Ala Lys Gly Gln Pro Arg Glu Pro Gln Val Tyr Thr
130                 135                 140

Leu Pro Pro Ser Arg Asp Glu Leu Thr Lys Asn Gln Val Ser Leu Thr
145                 150                 155                 160

Cys Leu Val Lys Gly Phe Tyr Pro Ser Asp Ile Ala Val Glu Trp Glu
                165                 170                 175

Ser Asn Gly Gln Pro Glu Asn Asn Tyr Lys Thr Thr Pro Pro Val Leu
            180                 185                 190

Asp Ser Asp Gly Ser Phe Phe Leu Tyr Ser Lys Leu Thr Val Asp Lys
        195                 200                 205

Ser Arg Trp Gln Gln Gly Asn Val Phe Ser Cys Ser Val Met His Glu
210                 215                 220

Ala Leu His Asn His Tyr Thr Gln Lys Ser Leu Ser Leu Ser Pro Gly
225                 230                 235                 240

Ile Pro Pro His Val Gln Lys Ser Val Asn Asn Asp Met Ile Val Thr
                245                 250                 255

Asp Asn Asn Gly Ala Val Lys Phe Pro Gln Leu Cys Lys Phe Cys Asp
            260                 265                 270

Val Arg Phe Ser Thr Cys Asp Asn Gln Lys Ser Cys Met Ser Asn Cys
        275                 280                 285

Ser Ile Thr Ser Ile Cys Glu Lys Pro Gln Glu Val Cys Val Ala Val
290                 295                 300

Trp Arg Lys Asn Asp Glu Asn Ile Thr Leu Glu Thr Val Cys His Asp
305                 310                 315                 320

Pro Lys Leu Pro Tyr His Asp Phe Ile Leu Glu Asp Ala Ala Ser Pro
                325                 330                 335

Lys Cys Ile Met Lys Glu Lys Lys Pro Gly Glu Thr Phe Phe Met
            340                 345                 350

Cys Ser Cys Ser Ser Asp Glu Cys Asn Asp Asn Ile Ile Phe Ser Glu
        355                 360                 365

Glu Tyr Asn Thr Ser Asn Pro Asp
            370                 375

<210> SEQ ID NO 138
<211> LENGTH: 366
<212> TYPE: PRT
<213> ORGANISM: Artificial Sequence
<220> FEATURE:
<223> OTHER INFORMATION: D10-hIgG1FcdeltaK-C-T2m fusion

<400> SEQUENCE: 138

Asp Asp Asp Asp Asp Asp Asp Asp Pro Pro Cys Pro Ala Pro
  1               5                  10                  15

Glu Leu Leu Gly Gly Pro Ser Val Phe Leu Phe Pro Pro Lys Pro Lys
                 20                  25                  30

Asp Thr Leu Met Ile Ser Arg Thr Pro Glu Val Thr Cys Val Val Val
             35                  40                  45
```

```
Asp Val Ser His Glu Asp Pro Glu Val Lys Phe Asn Trp Tyr Val Asp
    50                  55                  60

Gly Val Glu Val His Asn Ala Lys Thr Lys Pro Arg Glu Glu Gln Tyr
65                  70                  75                  80

Asn Ser Thr Tyr Arg Val Val Ser Val Leu Thr Val Leu His Gln Asp
                85                  90                  95

Trp Leu Asn Gly Lys Glu Tyr Lys Cys Lys Val Ser Asn Lys Ala Leu
            100                 105                 110

Pro Ala Pro Ile Glu Lys Thr Ile Ser Lys Ala Lys Gly Gln Pro Arg
        115                 120                 125

Glu Pro Gln Val Tyr Thr Leu Pro Pro Ser Arg Asp Glu Leu Thr Lys
    130                 135                 140

Asn Gln Val Ser Leu Thr Cys Leu Val Lys Gly Phe Tyr Pro Ser Asp
145                 150                 155                 160

Ile Ala Val Glu Trp Glu Ser Asn Gly Gln Pro Glu Asn Asn Tyr Lys
                165                 170                 175

Thr Thr Pro Pro Val Leu Asp Ser Asp Gly Ser Phe Phe Leu Tyr Ser
            180                 185                 190

Lys Leu Thr Val Asp Lys Ser Arg Trp Gln Gln Gly Asn Val Phe Ser
        195                 200                 205

Cys Ser Val Met His Glu Ala Leu His Asn His Tyr Thr Gln Lys Ser
    210                 215                 220

Leu Ser Leu Ser Pro Gly Ile Pro Pro His Val Gln Lys Ser Val Asn
225                 230                 235                 240

Asn Asp Met Ile Val Thr Asp Asn Asn Gly Ala Val Lys Phe Pro Gln
                245                 250                 255

Leu Cys Lys Phe Cys Asp Val Arg Phe Ser Thr Cys Asp Asn Gln Lys
            260                 265                 270

Ser Cys Met Ser Asn Cys Ser Ile Thr Ser Ile Cys Glu Lys Pro Gln
        275                 280                 285

Glu Val Cys Val Ala Val Trp Arg Lys Asn Asp Glu Asn Ile Thr Leu
    290                 295                 300

Glu Thr Val Cys His Asp Pro Lys Leu Pro Tyr His Asp Phe Ile Leu
305                 310                 315                 320

Glu Asp Ala Ala Ser Pro Lys Cys Ile Met Lys Glu Lys Lys Lys Pro
                325                 330                 335

Gly Glu Thr Phe Phe Met Cys Ser Cys Ser Ser Asp Glu Cys Asn Asp
            340                 345                 350

Asn Ile Ile Phe Ser Glu Glu Tyr Asn Thr Ser Asn Pro Asp
        355                 360                 365

<210> SEQ ID NO 139
<211> LENGTH: 374
<212> TYPE: PRT
<213> ORGANISM: Artificial Sequence
<220> FEATURE:
<223> OTHER INFORMATION: D10-(G3S)2-hIgG1FcdeltaK-C-T2m fusion

<400> SEQUENCE: 139

Asp Asp Asp Asp Asp Asp Asp Asp Gly Gly Gly Ser Gly Gly
1               5                   10                  15

Gly Ser Pro Pro Cys Pro Ala Pro Glu Leu Leu Gly Gly Pro Ser Val
            20                  25                  30

Phe Leu Phe Pro Pro Lys Pro Lys Asp Thr Leu Met Ile Ser Arg Thr
        35                  40                  45
```

```
Pro Glu Val Thr Cys Val Val Asp Val Ser His Glu Asp Pro Glu
    50              55              60
Val Lys Phe Asn Trp Tyr Val Asp Gly Val Glu Val His Asn Ala Lys
65              70              75              80
Thr Lys Pro Arg Glu Glu Gln Tyr Asn Ser Thr Tyr Arg Val Val Ser
                85              90              95
Val Leu Thr Val Leu His Gln Asp Trp Leu Asn Gly Lys Glu Tyr Lys
            100             105             110
Cys Lys Val Ser Asn Lys Ala Leu Pro Ala Pro Ile Glu Lys Thr Ile
        115             120             125
Ser Lys Ala Lys Gly Gln Pro Arg Glu Pro Gln Val Tyr Thr Leu Pro
130             135             140
Pro Ser Arg Asp Glu Leu Thr Lys Asn Gln Val Ser Leu Thr Cys Leu
145             150             155             160
Val Lys Gly Phe Tyr Pro Ser Asp Ile Ala Val Glu Trp Glu Ser Asn
                165             170             175
Gly Gln Pro Glu Asn Asn Tyr Lys Thr Thr Pro Pro Val Leu Asp Ser
            180             185             190
Asp Gly Ser Phe Phe Leu Tyr Ser Lys Leu Thr Val Asp Lys Ser Arg
        195             200             205
Trp Gln Gln Gly Asn Val Phe Ser Cys Ser Val Met His Glu Ala Leu
210             215             220
His Asn His Tyr Thr Gln Lys Ser Leu Ser Leu Ser Pro Gly Ile Pro
225             230             235             240
Pro His Val Gln Lys Ser Val Asn Asn Asp Met Ile Val Thr Asp Asn
                245             250             255
Asn Gly Ala Val Lys Phe Pro Gln Leu Cys Lys Phe Cys Asp Val Arg
            260             265             270
Phe Ser Thr Cys Asp Asn Gln Lys Ser Cys Met Ser Asn Cys Ser Ile
        275             280             285
Thr Ser Ile Cys Glu Lys Pro Gln Glu Val Cys Val Ala Val Trp Arg
290             295             300
Lys Asn Asp Glu Asn Ile Thr Leu Glu Thr Val Cys His Asp Pro Lys
305             310             315             320
Leu Pro Tyr His Asp Phe Ile Leu Glu Asp Ala Ala Ser Pro Lys Cys
                325             330             335
Ile Met Lys Glu Lys Lys Pro Gly Glu Thr Phe Phe Met Cys Ser
            340             345             350
Cys Ser Ser Asp Glu Cys Asn Asp Asn Ile Ile Phe Ser Glu Glu Tyr
        355             360             365
Asn Thr Ser Asn Pro Asp
    370

<210> SEQ ID NO 140
<211> LENGTH: 368
<212> TYPE: PRT
<213> ORGANISM: Artificial Sequence
<220> FEATURE:
<223> OTHER INFORMATION: D10-hIgG2FcdeltaK-CC-T2m fusion

<400> SEQUENCE: 140

Asp Asp Asp Asp Asp Asp Asp Asp Val Glu Cys Pro Cys
1               5               10              15

Pro Ala Pro Pro Val Ala Gly Pro Ser Val Phe Leu Phe Pro Pro Lys
                20              25              30
```

```
Pro Lys Asp Thr Leu Met Ile Ser Arg Thr Pro Glu Val Thr Cys Val
        35                  40                  45

Val Val Asp Val Ser His Glu Asp Pro Glu Val Gln Phe Asn Trp Tyr
50                  55                  60

Val Asp Gly Val Glu Val His Asn Ala Lys Thr Lys Pro Arg Glu Glu
65                  70                  75                  80

Gln Phe Asn Ser Thr Phe Arg Val Val Ser Val Leu Thr Val His
                85                  90                  95

Gln Asp Trp Leu Asn Gly Lys Glu Tyr Lys Cys Lys Val Ser Asn Lys
            100                 105                 110

Gly Leu Pro Ala Pro Ile Glu Lys Thr Ile Ser Lys Thr Lys Gly Gln
        115                 120                 125

Pro Arg Glu Pro Gln Val Tyr Thr Leu Pro Pro Ser Arg Glu Glu Met
    130                 135                 140

Thr Lys Asn Gln Val Ser Leu Thr Cys Leu Val Lys Gly Phe Tyr Pro
145                 150                 155                 160

Ser Asp Ile Ser Val Glu Trp Glu Ser Asn Gly Gln Pro Glu Asn Asn
                165                 170                 175

Tyr Lys Thr Thr Pro Pro Met Leu Asp Ser Asp Gly Ser Phe Phe Leu
            180                 185                 190

Tyr Ser Lys Leu Thr Val Asp Lys Ser Arg Trp Gln Gln Gly Asn Val
        195                 200                 205

Phe Ser Cys Ser Val Met His Glu Ala Leu His Asn His Tyr Thr Gln
    210                 215                 220

Lys Ser Leu Ser Leu Ser Pro Gly Ile Pro Pro His Val Gln Lys Ser
225                 230                 235                 240

Val Asn Asn Asp Met Ile Val Thr Asp Asn Asn Gly Ala Val Lys Phe
                245                 250                 255

Pro Gln Leu Cys Lys Phe Cys Asp Val Arg Phe Ser Thr Cys Asp Asn
            260                 265                 270

Gln Lys Ser Cys Met Ser Asn Cys Ser Ile Thr Ser Ile Cys Glu Lys
        275                 280                 285

Pro Gln Glu Val Cys Val Ala Val Trp Arg Lys Asn Asp Glu Asn Ile
    290                 295                 300

Thr Leu Glu Thr Val Cys His Asp Pro Lys Leu Pro Tyr His Asp Phe
305                 310                 315                 320

Ile Leu Glu Asp Ala Ala Ser Pro Lys Cys Ile Met Lys Glu Lys Lys
                325                 330                 335

Lys Pro Gly Glu Thr Phe Phe Met Cys Ser Cys Ser Ser Asp Glu Cys
            340                 345                 350

Asn Asp Asn Ile Ile Phe Ser Glu Glu Tyr Asn Thr Ser Asn Pro Asp
        355                 360                 365

<210> SEQ ID NO 141
<211> LENGTH: 374
<212> TYPE: PRT
<213> ORGANISM: Artificial Sequence
<220> FEATURE:
<223> OTHER INFORMATION: D10-hIgG4FcdeltaK-CC-228P-T2m fusion

<400> SEQUENCE: 141

Asp Asp Asp Asp Asp Asp Asp Asp Glu Ser Lys Tyr Gly Pro
1               5                   10                  15

Pro Cys Pro Pro Cys Pro Ala Pro Glu Phe Leu Gly Gly Pro Ser Val
            20                  25                  30
```

```
Phe Leu Phe Pro Pro Lys Pro Lys Asp Thr Leu Met Ile Ser Arg Thr
        35                  40                  45

Pro Glu Val Thr Cys Val Val Val Asp Val Ser Gln Glu Asp Pro Glu
 50                  55                  60

Val Gln Phe Asn Trp Tyr Val Asp Gly Val Glu Val His Asn Ala Lys
 65                  70                  75                  80

Thr Lys Pro Arg Glu Glu Gln Phe Asn Ser Thr Tyr Arg Val Val Ser
                 85                  90                  95

Val Leu Thr Val Leu His Gln Asp Trp Leu Asn Gly Lys Glu Tyr Lys
                100                 105                 110

Cys Lys Val Ser Asn Lys Gly Leu Pro Ser Ser Ile Glu Lys Thr Ile
                115                 120                 125

Ser Lys Ala Lys Gly Gln Pro Arg Glu Pro Gln Val Tyr Thr Leu Pro
    130                 135                 140

Pro Ser Gln Glu Glu Met Thr Lys Asn Gln Val Ser Leu Thr Cys Leu
145                 150                 155                 160

Val Lys Gly Phe Tyr Pro Ser Asp Ile Ala Val Glu Trp Glu Ser Asn
                165                 170                 175

Gly Gln Pro Glu Asn Asn Tyr Lys Thr Thr Pro Pro Val Leu Asp Ser
            180                 185                 190

Asp Gly Ser Phe Phe Leu Tyr Ser Arg Leu Thr Val Asp Lys Ser Arg
            195                 200                 205

Trp Gln Glu Gly Asn Val Phe Ser Cys Ser Val Met His Glu Ala Leu
    210                 215                 220

His Asn His Tyr Thr Gln Lys Ser Leu Ser Leu Ser Leu Gly Ile Pro
225                 230                 235                 240

Pro His Val Gln Lys Ser Val Asn Asn Asp Met Ile Val Thr Asp Asn
                245                 250                 255

Asn Gly Ala Val Lys Phe Pro Gln Leu Cys Lys Phe Cys Asp Val Arg
                260                 265                 270

Phe Ser Thr Cys Asp Asn Gln Lys Ser Cys Met Ser Asn Cys Ser Ile
    275                 280                 285

Thr Ser Ile Cys Glu Lys Pro Gln Glu Val Cys Val Ala Val Trp Arg
290                 295                 300

Lys Asn Asp Glu Asn Ile Thr Leu Glu Thr Val Cys His Asp Pro Lys
305                 310                 315                 320

Leu Pro Tyr His Asp Phe Ile Leu Glu Asp Ala Ala Ser Pro Lys Cys
                325                 330                 335

Ile Met Lys Glu Lys Lys Pro Gly Glu Thr Phe Phe Met Cys Ser
                340                 345                 350

Cys Ser Ser Asp Glu Cys Asn Asp Asn Ile Ile Phe Ser Glu Glu Tyr
    355                 360                 365

Asn Thr Ser Asn Pro Asp
    370

<210> SEQ ID NO 142
<211> LENGTH: 374
<212> TYPE: PRT
<213> ORGANISM: Artificial Sequence
<220> FEATURE:
<223> OTHER INFORMATION: D10-hIgG4FcdeltaK-CC-228P-409K-T2m fusion

<400> SEQUENCE: 142

Asp Asp Asp Asp Asp Asp Asp Asp Asp Glu Ser Lys Tyr Gly Pro
 1               5                  10                  15
```

```
Pro Cys Pro Pro Cys Pro Ala Pro Glu Phe Leu Gly Gly Pro Ser Val
            20                  25                  30

Phe Leu Phe Pro Pro Lys Pro Lys Asp Thr Leu Met Ile Ser Arg Thr
        35                  40                  45

Pro Glu Val Thr Cys Val Val Val Asp Val Ser Gln Glu Asp Pro Glu
    50                  55                  60

Val Gln Phe Asn Trp Tyr Val Asp Gly Val Glu Val His Asn Ala Lys
65              70                  75                  80

Thr Lys Pro Arg Glu Glu Gln Phe Asn Ser Thr Tyr Arg Val Val Ser
                85                  90                  95

Val Leu Thr Val Leu His Gln Asp Trp Leu Asn Gly Lys Glu Tyr Lys
                100                 105                 110

Cys Lys Val Ser Asn Lys Gly Leu Pro Ser Ser Ile Glu Lys Thr Ile
            115                 120                 125

Ser Lys Ala Lys Gly Gln Pro Arg Glu Pro Gln Val Tyr Thr Leu Pro
    130                 135                 140

Pro Ser Gln Glu Glu Met Thr Lys Asn Gln Val Ser Leu Thr Cys Leu
145                 150                 155                 160

Val Lys Gly Phe Tyr Pro Ser Asp Ile Ala Val Glu Trp Glu Ser Asn
                165                 170                 175

Gly Gln Pro Glu Asn Asn Tyr Lys Thr Thr Pro Pro Val Leu Asp Ser
                180                 185                 190

Asp Gly Ser Phe Phe Leu Tyr Ser Lys Leu Thr Val Asp Lys Ser Arg
            195                 200                 205

Trp Gln Glu Gly Asn Val Phe Ser Cys Ser Val Met His Glu Ala Leu
    210                 215                 220

His Asn His Tyr Thr Gln Lys Ser Leu Ser Leu Ser Leu Gly Ile Pro
225                 230                 235                 240

Pro His Val Gln Lys Ser Val Asn Asn Asp Met Ile Val Thr Asp Asn
                245                 250                 255

Asn Gly Ala Val Lys Phe Pro Gln Leu Cys Lys Phe Cys Asp Val Arg
                260                 265                 270

Phe Ser Thr Cys Asp Asn Gln Lys Ser Cys Met Ser Asn Cys Ser Ile
            275                 280                 285

Thr Ser Ile Cys Glu Lys Pro Gln Glu Val Cys Val Ala Val Trp Arg
    290                 295                 300

Lys Asn Asp Glu Asn Ile Thr Leu Glu Thr Val Cys His Asp Pro Lys
305                 310                 315                 320

Leu Pro Tyr His Asp Phe Ile Leu Glu Asp Ala Ala Ser Pro Lys Cys
                325                 330                 335

Ile Met Lys Glu Lys Lys Lys Pro Gly Glu Thr Phe Phe Met Cys Ser
                340                 345                 350

Cys Ser Ser Asp Glu Cys Asn Asp Asn Ile Ile Phe Ser Glu Glu Tyr
            355                 360                 365

Asn Thr Ser Asn Pro Asp
    370
```

<210> SEQ ID NO 143
<211> LENGTH: 508
<212> TYPE: PRT
<213> ORGANISM: Artificial Sequence
<220> FEATURE:
<223> OTHER INFORMATION: D10-hIgG1FcdeltaK-CC-T22d35 fusion

<400> SEQUENCE: 143

```
Asp Asp Asp Asp Asp Asp Asp Asp Asp Lys Thr His Thr Cys
1               5                   10              15

Pro Pro Cys Pro Ala Pro Glu Leu Leu Gly Gly Pro Ser Val Phe Leu
            20              25              30

Phe Pro Pro Lys Pro Lys Asp Thr Leu Met Ile Ser Arg Thr Pro Glu
        35              40              45

Val Thr Cys Val Val Val Asp Val Ser His Glu Asp Pro Glu Val Lys
    50              55              60

Phe Asn Trp Tyr Val Asp Gly Val Glu Val His Asn Ala Lys Thr Lys
65              70              75              80

Pro Arg Glu Glu Gln Tyr Asn Ser Thr Tyr Arg Val Val Ser Val Leu
                85              90              95

Thr Val Leu His Gln Asp Trp Leu Asn Gly Lys Glu Tyr Lys Cys Lys
            100             105             110

Val Ser Asn Lys Ala Leu Pro Ala Pro Ile Glu Lys Thr Ile Ser Lys
        115             120             125

Ala Lys Gly Gln Pro Arg Glu Pro Gln Val Tyr Thr Leu Pro Pro Ser
130             135                 140

Arg Asp Glu Leu Thr Lys Asn Gln Val Ser Leu Thr Cys Leu Val Lys
145             150             155             160

Gly Phe Tyr Pro Ser Asp Ile Ala Val Glu Trp Glu Ser Asn Gly Gln
                165             170             175

Pro Glu Asn Asn Tyr Lys Thr Thr Pro Pro Val Leu Asp Ser Asp Gly
            180             185             190

Ser Phe Phe Leu Tyr Ser Lys Leu Thr Val Asp Lys Ser Arg Trp Gln
        195             200             205

Gln Gly Asn Val Phe Ser Cys Ser Val Met His Glu Ala Leu His Asn
    210             215             220

His Tyr Thr Gln Lys Ser Leu Ser Leu Ser Pro Gly Ile Pro Pro His
225             230             235             240

Val Gln Lys Ser Val Asn Asn Asp Met Ile Val Thr Asp Asn Asn Gly
                245             250             255

Ala Val Lys Phe Pro Gln Leu Cys Lys Phe Cys Asp Val Arg Phe Ser
            260             265             270

Thr Cys Asp Asn Gln Lys Ser Cys Met Ser Asn Cys Ser Ile Thr Ser
        275             280             285

Ile Cys Glu Lys Pro Gln Glu Val Cys Val Ala Val Trp Arg Lys Asn
    290             295             300

Asp Glu Asn Ile Thr Leu Glu Thr Val Cys His Asp Pro Lys Leu Pro
305             310             315             320

Tyr His Asp Phe Ile Leu Glu Asp Ala Ala Ser Pro Lys Cys Ile Met
                325             330             335

Lys Glu Lys Lys Lys Pro Gly Glu Thr Phe Phe Met Cys Ser Cys Ser
            340             345             350

Ser Asp Glu Cys Asn Asp Asn Ile Ile Phe Ser Glu Glu Tyr Asn Thr
        355             360             365

Ser Asn Pro Asp Ile Pro Pro His Val Gln Lys Ser Val Asn Asn Asp
    370             375             380

Met Ile Val Thr Asp Asn Asn Gly Ala Val Lys Phe Pro Gln Leu Cys
385             390             395             400

Lys Phe Cys Asp Val Arg Phe Ser Thr Cys Asp Asn Gln Lys Ser Cys
                405             410             415
```

Met Ser Asn Cys Ser Ile Thr Ser Ile Cys Glu Lys Pro Gln Glu Val
             420                 425                 430

Cys Val Ala Val Trp Arg Lys Asn Asp Glu Asn Ile Thr Leu Glu Thr
             435                 440                 445

Val Cys His Asp Pro Lys Leu Pro Tyr His Asp Phe Ile Leu Glu Asp
        450                 455                 460

Ala Ala Ser Pro Lys Cys Ile Met Lys Glu Lys Lys Pro Gly Glu
465             470                 475                 480

Thr Phe Phe Met Cys Ser Cys Ser Asp Glu Cys Asn Asp Asn Ile
                485                 490                 495

Ile Phe Ser Glu Glu Tyr Asn Thr Ser Asn Pro Asp
             500                 505

<210> SEQ ID NO 144
<211> LENGTH: 504
<212> TYPE: PRT
<213> ORGANISM: Artificial Sequence
<220> FEATURE:
<223> OTHER INFORMATION: D10-hIgG2FcdeltaK-CC-T22d35 fusion

<400> SEQUENCE: 144

Asp Asp Asp Asp Asp Asp Asp Asp Val Glu Cys Pro Cys
1               5                   10                  15

Pro Ala Pro Pro Val Ala Gly Pro Ser Val Phe Leu Phe Pro Pro Lys
             20                  25                  30

Pro Lys Asp Thr Leu Met Ile Ser Arg Thr Pro Glu Val Thr Cys Val
         35                  40                  45

Val Val Asp Val Ser His Glu Asp Pro Glu Val Gln Phe Asn Trp Tyr
    50                  55                  60

Val Asp Gly Val Glu Val His Asn Ala Lys Thr Lys Pro Arg Glu Glu
65                  70                  75                  80

Gln Phe Asn Ser Thr Phe Arg Val Val Ser Val Leu Thr Val Val His
                 85                  90                  95

Gln Asp Trp Leu Asn Gly Lys Glu Tyr Lys Cys Lys Val Ser Asn Lys
            100                 105                 110

Gly Leu Pro Ala Pro Ile Glu Lys Thr Ile Ser Lys Thr Lys Gly Gln
        115                 120                 125

Pro Arg Glu Pro Gln Val Tyr Thr Leu Pro Pro Ser Arg Glu Glu Met
    130                 135                 140

Thr Lys Asn Gln Val Ser Leu Thr Cys Leu Val Lys Gly Phe Tyr Pro
145                 150                 155                 160

Ser Asp Ile Ser Val Glu Trp Glu Ser Asn Gly Gln Pro Glu Asn Asn
                165                 170                 175

Tyr Lys Thr Thr Pro Pro Met Leu Asp Ser Asp Gly Ser Phe Phe Leu
            180                 185                 190

Tyr Ser Lys Leu Thr Val Asp Lys Ser Arg Trp Gln Gln Gly Asn Val
        195                 200                 205

Phe Ser Cys Ser Val Met His Glu Ala Leu His Asn His Tyr Thr Gln
    210                 215                 220

Lys Ser Leu Ser Leu Ser Pro Gly Ile Pro Pro His Val Gln Lys Ser
225                 230                 235                 240

Val Asn Asn Asp Met Ile Val Thr Asp Asn Asn Gly Ala Val Lys Phe
                245                 250                 255

Pro Gln Leu Cys Lys Phe Cys Asp Val Arg Phe Ser Thr Cys Asp Asn
            260                 265                 270

```
Gln Lys Ser Cys Met Ser Asn Cys Ser Ile Thr Ser Ile Cys Glu Lys
            275                 280                 285

Pro Gln Glu Val Cys Val Ala Val Trp Arg Lys Asn Asp Glu Asn Ile
290                 295                 300

Thr Leu Glu Thr Val Cys His Asp Pro Lys Leu Pro Tyr His Asp Phe
305                 310                 315                 320

Ile Leu Glu Asp Ala Ala Ser Pro Lys Cys Ile Met Lys Lys Lys
                325                 330                 335

Lys Pro Gly Glu Thr Phe Phe Met Cys Ser Cys Ser Ser Asp Glu Cys
            340                 345                 350

Asn Asp Asn Ile Ile Phe Ser Glu Gly Tyr Asn Thr Ser Asn Pro Asp
            355                 360                 365

Ile Pro Pro His Val Gln Lys Ser Val Asn Asn Asp Met Ile Val Thr
370                 375                 380

Asp Asn Asn Gly Ala Val Lys Phe Pro Gln Leu Cys Lys Phe Cys Asp
385                 390                 395                 400

Val Arg Phe Ser Thr Cys Asp Asn Gln Lys Ser Cys Met Ser Asn Cys
                405                 410                 415

Ser Ile Thr Ser Ile Cys Glu Lys Pro Gln Glu Val Cys Val Ala Val
            420                 425                 430

Trp Arg Lys Asn Asp Glu Asn Ile Thr Leu Glu Thr Val Cys His Asp
            435                 440                 445

Pro Lys Leu Pro Tyr His Asp Phe Ile Leu Glu Asp Ala Ala Ser Pro
            450                 455                 460

Lys Cys Ile Met Lys Lys Lys Lys Pro Gly Glu Thr Phe Phe Met
465                 470                 475                 480

Cys Ser Cys Ser Ser Asp Glu Cys Asn Asp Asn Ile Ile Phe Ser Glu
                485                 490                 495

Glu Tyr Asn Thr Ser Asn Pro Asp
            500

<210> SEQ ID NO 145
<211> LENGTH: 510
<212> TYPE: PRT
<213> ORGANISM: Artificial Sequence
<220> FEATURE:
<223> OTHER INFORMATION: D10-hIgG4FcdeltaK-CC-228P-T22d35 fusion

<400> SEQUENCE: 145

Asp Asp Asp Asp Asp Asp Asp Asp Glu Ser Lys Tyr Gly Pro
1               5                   10                  15

Pro Cys Pro Pro Cys Pro Ala Pro Glu Phe Leu Gly Gly Pro Ser Val
                20                  25                  30

Phe Leu Phe Pro Pro Lys Pro Lys Asp Thr Leu Met Ile Ser Arg Thr
            35                  40                  45

Pro Glu Val Thr Cys Val Val Val Asp Val Ser Gln Glu Asp Pro Glu
50                  55                  60

Val Gln Phe Asn Trp Tyr Val Asp Gly Val Glu Val His Asn Ala Lys
65                  70                  75                  80

Thr Lys Pro Arg Glu Glu Gln Phe Asn Ser Thr Tyr Arg Val Val Ser
                85                  90                  95

Val Leu Thr Val Leu His Gln Asp Trp Leu Asn Gly Lys Glu Tyr Lys
            100                 105                 110

Cys Lys Val Ser Asn Lys Gly Leu Pro Ser Ser Ile Glu Lys Thr Ile
            115                 120                 125
```

```
Ser Lys Ala Lys Gly Gln Pro Arg Glu Pro Gln Val Tyr Thr Leu Pro
130                 135                 140

Pro Ser Gln Glu Glu Met Thr Lys Asn Gln Val Ser Leu Thr Cys Leu
145                 150                 155                 160

Val Lys Gly Phe Tyr Pro Ser Asp Ile Ala Val Glu Trp Glu Ser Asn
                165                 170                 175

Gly Gln Pro Glu Asn Asn Tyr Lys Thr Thr Pro Pro Val Leu Asp Ser
            180                 185                 190

Asp Gly Ser Phe Phe Leu Tyr Ser Arg Leu Thr Val Asp Lys Ser Arg
        195                 200                 205

Trp Gln Glu Gly Asn Val Phe Ser Cys Ser Val Met His Glu Ala Leu
    210                 215                 220

His Asn His Tyr Thr Gln Lys Ser Leu Ser Leu Ser Leu Gly Ile Pro
225                 230                 235                 240

Pro His Val Gln Lys Ser Val Asn Asn Asp Met Ile Val Thr Asp Asn
                245                 250                 255

Asn Gly Ala Val Lys Phe Pro Gln Leu Cys Lys Phe Cys Asp Val Arg
                260                 265                 270

Phe Ser Thr Cys Asp Asn Gln Lys Ser Cys Met Ser Asn Cys Ser Ile
            275                 280                 285

Thr Ser Ile Cys Glu Lys Pro Gln Glu Val Cys Val Ala Val Trp Arg
        290                 295                 300

Lys Asn Asp Glu Asn Ile Thr Leu Glu Thr Val Cys His Asp Pro Lys
305                 310                 315                 320

Leu Pro Tyr His Asp Phe Ile Leu Glu Asp Ala Ala Ser Pro Lys Cys
                325                 330                 335

Ile Met Lys Glu Lys Lys Pro Gly Glu Thr Phe Phe Met Cys Ser
                340                 345                 350

Cys Ser Ser Asp Glu Cys Asn Asp Asn Ile Ile Phe Ser Glu Glu Tyr
            355                 360                 365

Asn Thr Ser Asn Pro Asp Ile Pro Pro His Val Gln Lys Ser Val Asn
        370                 375                 380

Asn Asp Met Ile Val Thr Asp Asn Asn Gly Ala Val Lys Phe Pro Gln
385                 390                 395                 400

Leu Cys Lys Phe Cys Asp Val Arg Phe Ser Thr Cys Asp Asn Gln Lys
                405                 410                 415

Ser Cys Met Ser Asn Cys Ser Ile Thr Ser Ile Cys Glu Lys Pro Gln
            420                 425                 430

Glu Val Cys Val Ala Val Trp Arg Lys Asn Asp Glu Asn Ile Thr Leu
        435                 440                 445

Glu Thr Val Cys His Asp Pro Lys Leu Pro Tyr His Asp Phe Ile Leu
    450                 455                 460

Glu Asp Ala Ala Ser Pro Lys Cys Ile Met Lys Glu Lys Lys Lys Pro
465                 470                 475                 480

Gly Glu Thr Phe Phe Met Cys Ser Cys Ser Ser Asp Glu Cys Asn Asp
                485                 490                 495

Asn Ile Ile Phe Ser Glu Glu Tyr Asn Thr Ser Asn Pro Asp
            500                 505                 510

<210> SEQ ID NO 146
<211> LENGTH: 510
<212> TYPE: PRT
<213> ORGANISM: Artificial Sequence
<220> FEATURE:
<223> OTHER INFORMATION: D10-hIgG4FcdeltaK-CC-228P-409K-T22d35 fusion
```

<400> SEQUENCE: 146

Asp Asp Asp Asp Asp Asp Asp Asp Glu Ser Lys Tyr Gly Pro
1               5                   10                  15

Pro Cys Pro Pro Cys Pro Ala Pro Glu Phe Leu Gly Gly Pro Ser Val
            20                  25                  30

Phe Leu Phe Pro Pro Lys Pro Lys Asp Thr Leu Met Ile Ser Arg Thr
        35                  40                  45

Pro Glu Val Thr Cys Val Val Val Asp Val Ser Gln Glu Asp Pro Glu
    50                  55                  60

Val Gln Phe Asn Trp Tyr Val Asp Gly Val Glu Val His Asn Ala Lys
65              70                  75                  80

Thr Lys Pro Arg Glu Glu Gln Phe Asn Ser Thr Tyr Arg Val Val Ser
                85                  90                  95

Val Leu Thr Val Leu His Gln Asp Trp Leu Asn Gly Lys Glu Tyr Lys
            100                 105                 110

Cys Lys Val Ser Asn Lys Gly Leu Pro Ser Ser Ile Glu Lys Thr Ile
        115                 120                 125

Ser Lys Ala Lys Gly Gln Pro Arg Glu Pro Gln Val Tyr Thr Leu Pro
130                 135                 140

Pro Ser Gln Glu Glu Met Thr Lys Asn Gln Val Ser Leu Thr Cys Leu
145                 150                 155                 160

Val Lys Gly Phe Tyr Pro Ser Asp Ile Ala Val Glu Trp Glu Ser Asn
                165                 170                 175

Gly Gln Pro Glu Asn Asn Tyr Lys Thr Thr Pro Pro Val Leu Asp Ser
            180                 185                 190

Asp Gly Ser Phe Phe Leu Tyr Ser Lys Leu Thr Val Asp Lys Ser Arg
        195                 200                 205

Trp Gln Glu Gly Asn Val Phe Ser Cys Ser Val Met His Glu Ala Leu
210                 215                 220

His Asn His Tyr Thr Gln Lys Ser Leu Ser Leu Ser Leu Gly Ile Pro
225                 230                 235                 240

Pro His Val Gln Lys Ser Val Asn Asn Asp Met Ile Val Thr Asp Asn
                245                 250                 255

Asn Gly Ala Val Lys Phe Pro Gln Leu Cys Lys Phe Cys Asp Val Arg
            260                 265                 270

Phe Ser Thr Cys Asp Asn Gln Lys Ser Cys Met Ser Asn Cys Ser Ile
        275                 280                 285

Thr Ser Ile Cys Glu Lys Pro Gln Glu Val Cys Val Ala Val Trp Arg
290                 295                 300

Lys Asn Asp Glu Asn Ile Thr Leu Glu Thr Val Cys His Asp Pro Lys
305                 310                 315                 320

Leu Pro Tyr His Asp Phe Ile Leu Glu Asp Ala Ala Ser Pro Lys Cys
                325                 330                 335

Ile Met Lys Glu Lys Lys Pro Gly Glu Thr Phe Phe Met Cys Ser
            340                 345                 350

Cys Ser Ser Asp Glu Cys Asn Asp Asn Ile Ile Phe Ser Glu Glu Tyr
        355                 360                 365

Asn Thr Ser Asn Pro Asp Ile Pro Pro His Val Gln Lys Ser Val Asn
370                 375                 380

Asn Asp Met Ile Val Thr Asp Asn Asn Gly Ala Val Lys Phe Pro Gln
385                 390                 395                 400

Leu Cys Lys Phe Cys Asp Val Arg Phe Ser Thr Cys Asp Asn Gln Lys

```
                    405                 410                 415
Ser Cys Met Ser Asn Cys Ser Ile Thr Ser Ile Cys Glu Lys Pro Gln
                420                 425                 430

Glu Val Cys Val Ala Val Trp Arg Lys Asn Asp Glu Asn Ile Thr Leu
                435                 440                 445

Glu Thr Val Cys His Asp Pro Lys Leu Pro Tyr His Asp Phe Ile Leu
                450                 455                 460

Glu Asp Ala Ala Ser Pro Lys Cys Ile Met Lys Glu Lys Lys Pro
465                 470                 475                 480

Gly Glu Thr Phe Phe Met Cys Ser Cys Ser Ser Asp Glu Cys Asn Asp
                485                 490                 495

Asn Ile Ile Phe Ser Glu Glu Tyr Asn Thr Ser Asn Pro Asp
                500                 505                 510

<210> SEQ ID NO 147
<211> LENGTH: 644
<212> TYPE: PRT
<213> ORGANISM: Artificial Sequence
<220> FEATURE:
<223> OTHER INFORMATION: D10-hIgG1FcdeltaK-CC-T2-T2-T2 fusion

<400> SEQUENCE: 147

Asp Asp Asp Asp Asp Asp Asp Asp Asp Asp Lys Thr His Thr Cys
1               5                   10                  15

Pro Pro Cys Pro Ala Pro Glu Leu Leu Gly Gly Pro Ser Val Phe Leu
                20                  25                  30

Phe Pro Pro Lys Pro Lys Asp Thr Leu Met Ile Ser Arg Thr Pro Glu
                35                  40                  45

Val Thr Cys Val Val Val Asp Val Ser His Glu Asp Pro Glu Val Lys
                50                  55                  60

Phe Asn Trp Tyr Val Asp Gly Val Glu Val His Asn Ala Lys Thr Lys
65                  70                  75                  80

Pro Arg Glu Glu Gln Tyr Asn Ser Thr Tyr Arg Val Val Ser Val Leu
                85                  90                  95

Thr Val Leu His Gln Asp Trp Leu Asn Gly Lys Glu Tyr Lys Cys Lys
                100                 105                 110

Val Ser Asn Lys Ala Leu Pro Ala Pro Ile Glu Lys Thr Ile Ser Lys
                115                 120                 125

Ala Lys Gly Gln Pro Arg Glu Pro Gln Val Tyr Thr Leu Pro Pro Ser
                130                 135                 140

Arg Asp Glu Leu Thr Lys Asn Gln Val Ser Leu Thr Cys Leu Val Lys
145                 150                 155                 160

Gly Phe Tyr Pro Ser Asp Ile Ala Val Glu Trp Glu Ser Asn Gly Gln
                165                 170                 175

Pro Glu Asn Asn Tyr Lys Thr Thr Pro Pro Val Leu Asp Ser Asp Gly
                180                 185                 190

Ser Phe Phe Leu Tyr Ser Lys Leu Thr Val Asp Lys Ser Arg Trp Gln
                195                 200                 205

Gln Gly Asn Val Phe Ser Cys Ser Val Met His Glu Ala Leu His Asn
                210                 215                 220

His Tyr Thr Gln Lys Ser Leu Ser Leu Ser Pro Gly Ile Pro Pro His
225                 230                 235                 240

Val Gln Lys Ser Val Asn Asn Asp Met Ile Val Thr Asp Asn Asn Gly
                245                 250                 255

Ala Val Lys Phe Pro Gln Leu Cys Lys Phe Cys Asp Val Arg Phe Ser
```

```
                260                 265                 270
Thr Cys Asp Asn Gln Lys Ser Cys Met Ser Asn Cys Ser Ile Thr Ser
            275                 280                 285
Ile Cys Glu Lys Pro Gln Glu Val Cys Val Ala Val Trp Arg Lys Asn
        290                 295                 300
Asp Glu Asn Ile Thr Leu Glu Thr Val Cys His Asp Pro Lys Leu Pro
305                 310                 315                 320
Tyr His Asp Phe Ile Leu Glu Asp Ala Ala Ser Pro Lys Cys Ile Met
                325                 330                 335
Lys Glu Lys Lys Lys Pro Gly Glu Thr Phe Phe Met Cys Ser Cys Ser
            340                 345                 350
Ser Asp Glu Cys Asn Asp Asn Ile Ile Phe Ser Glu Glu Tyr Asn Thr
        355                 360                 365
Ser Asn Pro Asp Ile Pro Pro His Val Gln Lys Ser Val Asn Asn Asp
    370                 375                 380
Met Ile Val Thr Asp Asn Asn Gly Ala Val Lys Phe Pro Gln Leu Cys
385                 390                 395                 400
Lys Phe Cys Asp Val Arg Phe Ser Thr Cys Asp Asn Gln Lys Ser Cys
                405                 410                 415
Met Ser Asn Cys Ser Ile Thr Ser Ile Cys Glu Lys Pro Gln Glu Val
            420                 425                 430
Cys Val Ala Val Trp Arg Lys Asn Asp Glu Asn Ile Thr Leu Glu Thr
        435                 440                 445
Val Cys His Asp Pro Lys Leu Pro Tyr His Asp Phe Ile Leu Glu Asp
    450                 455                 460
Ala Ala Ser Pro Lys Cys Ile Met Lys Glu Lys Lys Lys Pro Gly Glu
465                 470                 475                 480
Thr Phe Phe Met Cys Ser Cys Ser Ser Asp Glu Cys Asn Asp Asn Ile
                485                 490                 495
Ile Phe Ser Glu Glu Tyr Asn Thr Ser Asn Pro Asp Ile Pro Pro His
            500                 505                 510
Val Gln Lys Ser Val Asn Asn Asp Met Ile Val Thr Asp Asn Asn Gly
        515                 520                 525
Ala Val Lys Phe Pro Gln Leu Cys Lys Phe Cys Asp Val Arg Phe Ser
    530                 535                 540
Thr Cys Asp Asn Gln Lys Ser Cys Met Ser Asn Cys Ser Ile Thr Ser
545                 550                 555                 560
Ile Cys Glu Lys Pro Gln Glu Val Cys Val Ala Val Trp Arg Lys Asn
                565                 570                 575
Asp Glu Asn Ile Thr Leu Glu Thr Val Cys His Asp Pro Lys Leu Pro
            580                 585                 590
Tyr His Asp Phe Ile Leu Glu Asp Ala Ala Ser Pro Lys Cys Ile Met
        595                 600                 605
Lys Glu Lys Lys Lys Pro Gly Glu Thr Phe Phe Met Cys Ser Cys Ser
    610                 615                 620
Ser Asp Glu Cys Asn Asp Asn Ile Ile Phe Ser Glu Glu Tyr Asn Thr
625                 630                 635                 640

Ser Asn Pro Asp

<210> SEQ ID NO 148
<211> LENGTH: 640
<212> TYPE: PRT
<213> ORGANISM: Artificial Sequence
<220> FEATURE:
```

-continued

<223> OTHER INFORMATION: D10-hIgG2FcdeltaK-CC-T2-T2-T2 fusion

<400> SEQUENCE: 148

```
Asp Asp Asp Asp Asp Asp Asp Asp Val Glu Cys Pro Pro Cys
1               5                   10                  15

Pro Ala Pro Pro Val Ala Gly Pro Ser Val Phe Leu Phe Pro Pro Lys
            20                  25                  30

Pro Lys Asp Thr Leu Met Ile Ser Arg Thr Pro Glu Val Thr Cys Val
        35                  40                  45

Val Val Asp Val Ser His Glu Asp Pro Glu Val Gln Phe Asn Trp Tyr
    50                  55                  60

Val Asp Gly Val Glu Val His Asn Ala Lys Thr Lys Pro Arg Glu Glu
65                  70                  75                  80

Gln Phe Asn Ser Thr Phe Arg Val Val Ser Val Leu Thr Val Val His
                85                  90                  95

Gln Asp Trp Leu Asn Gly Lys Glu Tyr Lys Cys Lys Val Ser Asn Lys
            100                 105                 110

Gly Leu Pro Ala Pro Ile Glu Lys Thr Ile Ser Lys Thr Lys Gly Gln
        115                 120                 125

Pro Arg Glu Pro Gln Val Tyr Thr Leu Pro Pro Ser Arg Glu Glu Met
130                 135                 140

Thr Lys Asn Gln Val Ser Leu Thr Cys Leu Val Lys Gly Phe Tyr Pro
145                 150                 155                 160

Ser Asp Ile Ser Val Glu Trp Glu Ser Asn Gly Gln Pro Glu Asn Asn
                165                 170                 175

Tyr Lys Thr Thr Pro Pro Met Leu Asp Ser Asp Gly Ser Phe Phe Leu
            180                 185                 190

Tyr Ser Lys Leu Thr Val Asp Lys Ser Arg Trp Gln Gln Gly Asn Val
        195                 200                 205

Phe Ser Cys Ser Val Met His Glu Ala Leu His Asn His Tyr Thr Gln
210                 215                 220

Lys Ser Leu Ser Leu Ser Pro Gly Ile Pro Pro His Val Gln Lys Ser
225                 230                 235                 240

Val Asn Asn Asp Met Ile Val Thr Asp Asn Gly Ala Val Lys Phe
                245                 250                 255

Pro Gln Leu Cys Lys Phe Cys Asp Val Arg Phe Ser Thr Cys Asp Asn
            260                 265                 270

Gln Lys Ser Cys Met Ser Asn Cys Ser Ile Thr Ser Ile Cys Glu Lys
        275                 280                 285

Pro Gln Glu Val Cys Val Ala Val Trp Arg Lys Asn Asp Glu Asn Ile
290                 295                 300

Thr Leu Glu Thr Val Cys His Asp Pro Lys Leu Pro Tyr His Asp Phe
305                 310                 315                 320

Ile Leu Glu Asp Ala Ala Ser Pro Lys Cys Ile Met Lys Glu Lys Lys
                325                 330                 335

Lys Pro Gly Glu Thr Phe Phe Met Cys Ser Cys Ser Ser Asp Glu Cys
            340                 345                 350

Asn Asp Asn Ile Ile Phe Ser Glu Glu Tyr Asn Thr Ser Asn Pro Asp
        355                 360                 365

Ile Pro Pro His Val Gln Lys Ser Val Asn Asn Asp Met Ile Val Thr
370                 375                 380

Asp Asn Asn Gly Ala Val Lys Phe Pro Gln Leu Cys Lys Phe Cys Asp
385                 390                 395                 400
```

Val Arg Phe Ser Thr Cys Asp Asn Gln Lys Ser Cys Met Ser Asn Cys
            405                 410                 415

Ser Ile Thr Ser Ile Cys Glu Lys Pro Gln Glu Val Cys Val Ala Val
            420                 425                 430

Trp Arg Lys Asn Asp Glu Asn Ile Thr Leu Glu Thr Val Cys His Asp
            435                 440                 445

Pro Lys Leu Pro Tyr His Asp Phe Ile Leu Glu Asp Ala Ala Ser Pro
            450                 455                 460

Lys Cys Ile Met Lys Glu Lys Lys Pro Gly Glu Thr Phe Phe Met
465                 470                 475                 480

Cys Ser Cys Ser Ser Asp Glu Cys Asn Asp Asn Ile Ile Phe Ser Glu
            485                 490                 495

Glu Tyr Asn Thr Ser Asn Pro Asp Ile Pro Pro His Val Gln Lys Ser
            500                 505                 510

Val Asn Asn Asp Met Ile Val Thr Asp Asn Asn Gly Ala Val Lys Phe
            515                 520                 525

Pro Gln Leu Cys Lys Phe Cys Asp Val Arg Phe Ser Thr Cys Asp Asn
            530                 535                 540

Gln Lys Ser Cys Met Ser Asn Cys Ser Ile Thr Ser Ile Cys Glu Lys
545                 550                 555                 560

Pro Gln Glu Val Cys Val Ala Val Trp Arg Lys Asn Asp Glu Asn Ile
                565                 570                 575

Thr Leu Glu Thr Val Cys His Asp Pro Lys Leu Pro Tyr His Asp Phe
            580                 585                 590

Ile Leu Glu Asp Ala Ala Ser Pro Lys Cys Ile Met Lys Glu Lys Lys
            595                 600                 605

Lys Pro Gly Glu Thr Phe Phe Met Cys Ser Cys Ser Ser Asp Glu Cys
            610                 615                 620

Asn Asp Asn Ile Ile Phe Ser Glu Glu Tyr Asn Thr Ser Asn Pro Asp
625                 630                 635                 640

<210> SEQ ID NO 149
<211> LENGTH: 646
<212> TYPE: PRT
<213> ORGANISM: Artificial Sequence
<220> FEATURE:
<223> OTHER INFORMATION: D10-hIgG4FcdeltaK-CC-228P-T2-T2-T2 fusion

<400> SEQUENCE: 149

Asp Asp Asp Asp Asp Asp Asp Asp Glu Ser Lys Tyr Gly Pro
1               5                   10                  15

Pro Cys Pro Pro Cys Pro Ala Pro Glu Phe Leu Gly Gly Pro Ser Val
            20                  25                  30

Phe Leu Phe Pro Pro Lys Pro Lys Asp Thr Leu Met Ile Ser Arg Thr
            35                  40                  45

Pro Glu Val Thr Cys Val Val Val Asp Val Ser Gln Glu Asp Pro Glu
        50                  55                  60

Val Gln Phe Asn Trp Tyr Val Asp Gly Val Glu Val His Asn Ala Lys
65                  70                  75                  80

Thr Lys Pro Arg Glu Glu Gln Phe Asn Ser Thr Tyr Arg Val Val Ser
            85                  90                  95

Val Leu Thr Val Leu His Gln Asp Trp Leu Asn Gly Lys Glu Tyr Lys
            100                 105                 110

Cys Lys Val Ser Asn Lys Gly Leu Pro Ser Ser Ile Glu Lys Thr Ile
            115                 120                 125

```
Ser Lys Ala Lys Gly Gln Pro Arg Glu Pro Gln Val Tyr Thr Leu Pro
130                 135                 140

Pro Ser Gln Glu Glu Met Thr Lys Asn Gln Val Ser Leu Thr Cys Leu
145                 150                 155                 160

Val Lys Gly Phe Tyr Pro Ser Asp Ile Ala Val Glu Trp Glu Ser Asn
                165                 170                 175

Gly Gln Pro Glu Asn Asn Tyr Lys Thr Thr Pro Pro Val Leu Asp Ser
            180                 185                 190

Asp Gly Ser Phe Phe Leu Tyr Ser Arg Leu Thr Val Asp Lys Ser Arg
        195                 200                 205

Trp Gln Glu Gly Asn Val Phe Ser Cys Ser Val Met His Glu Ala Leu
210                 215                 220

His Asn His Tyr Thr Gln Lys Ser Leu Ser Leu Ser Leu Gly Ile Pro
225                 230                 235                 240

Pro His Val Gln Lys Ser Val Asn Asn Asp Met Ile Val Thr Asp Asn
                245                 250                 255

Asn Gly Ala Val Lys Phe Pro Gln Leu Cys Lys Phe Cys Asp Val Arg
            260                 265                 270

Phe Ser Thr Cys Asp Asn Gln Lys Ser Cys Met Ser Asn Cys Ser Ile
        275                 280                 285

Thr Ser Ile Cys Glu Lys Pro Gln Glu Val Cys Val Ala Val Trp Arg
290                 295                 300

Lys Asn Asp Glu Asn Ile Thr Leu Glu Thr Val Cys His Asp Pro Lys
305                 310                 315                 320

Leu Pro Tyr His Asp Phe Ile Leu Glu Asp Ala Ala Ser Pro Lys Cys
                325                 330                 335

Ile Met Lys Glu Lys Lys Pro Gly Glu Thr Phe Phe Met Cys Ser
            340                 345                 350

Cys Ser Ser Asp Glu Cys Asn Asp Asn Ile Ile Phe Ser Glu Glu Tyr
        355                 360                 365

Asn Thr Ser Asn Pro Asp Ile Pro Pro His Val Gln Lys Ser Val Asn
370                 375                 380

Asn Asp Met Ile Val Thr Asp Asn Asn Gly Ala Val Lys Phe Pro Gln
385                 390                 395                 400

Leu Cys Lys Phe Cys Asp Val Arg Phe Ser Thr Cys Asp Asn Gln Lys
                405                 410                 415

Ser Cys Met Ser Asn Cys Ser Ile Thr Ser Ile Cys Glu Lys Pro Gln
            420                 425                 430

Glu Val Cys Val Ala Val Trp Arg Lys Asn Asp Glu Asn Ile Thr Leu
        435                 440                 445

Glu Thr Val Cys His Asp Pro Lys Leu Pro Tyr His Asp Phe Ile Leu
450                 455                 460

Glu Asp Ala Ala Ser Pro Lys Cys Ile Met Lys Glu Lys Lys Lys Pro
465                 470                 475                 480

Gly Glu Thr Phe Phe Met Cys Ser Cys Ser Ser Asp Glu Cys Asn Asp
                485                 490                 495

Asn Ile Ile Phe Ser Glu Glu Tyr Asn Thr Ser Asn Pro Asp Ile Pro
            500                 505                 510

Pro His Val Gln Lys Ser Val Asn Asn Asp Met Ile Val Thr Asp Asn
        515                 520                 525

Asn Gly Ala Val Lys Phe Pro Gln Leu Cys Lys Phe Cys Asp Val Arg
530                 535                 540

Phe Ser Thr Cys Asp Asn Gln Lys Ser Cys Met Ser Asn Cys Ser Ile
```

```
545                 550                 555                 560
Thr Ser Ile Cys Glu Lys Pro Gln Glu Val Cys Val Ala Val Trp Arg
                565                 570                 575
Lys Asn Asp Glu Asn Ile Thr Leu Glu Thr Val Cys His Asp Pro Lys
                580                 585                 590
Leu Pro Tyr His Asp Phe Ile Leu Glu Asp Ala Ala Ser Pro Lys Cys
                595                 600                 605
Ile Met Lys Glu Lys Lys Pro Gly Glu Thr Phe Phe Met Cys Ser
610                 615                 620
Cys Ser Ser Asp Glu Cys Asn Asp Asn Ile Ile Phe Ser Glu Glu Tyr
625                 630                 635                 640
Asn Thr Ser Asn Pro Asp
                645

<210> SEQ ID NO 150
<211> LENGTH: 649
<212> TYPE: PRT
<213> ORGANISM: Artificial Sequence
<220> FEATURE:
<223> OTHER INFORMATION: D10-hIgG4FcdeltaK-CC-228P-409K-T2-T2-T2 fusion

<400> SEQUENCE: 150

Asp Asp Asp Asp Asp Asp Asp Asp Glu Ser Lys Tyr Gly Pro
1               5                   10                  15
Pro Cys Pro Pro Cys Pro Ala Pro Glu Phe Leu Gly Gly Pro Ser Val
                20                  25                  30
Phe Leu Phe Pro Pro Lys Pro Lys Asp Thr Leu Met Ile Ser Arg Thr
                35                  40                  45
Pro Glu Val Thr Cys Val Val Val Asp Val Ser Gln Glu Asp Pro Glu
            50                  55                  60
Val Gln Phe Asn Trp Tyr Val Asp Gly Val Glu Val His Asn Ala Lys
65                  70                  75                  80
Thr Lys Pro Arg Glu Glu Gln Phe Asn Ser Thr Tyr Arg Val Val Ser
                85                  90                  95
Val Leu Thr Val Leu His Gln Asp Trp Leu Asn Gly Lys Glu Tyr Lys
                100                 105                 110
Cys Lys Val Ser Asn Lys Gly Leu Pro Ser Ser Ile Ser Glu Gln Glu
                115                 120                 125
Lys Thr Ile Ser Lys Ala Lys Gly Gln Pro Arg Glu Pro Gln Val Tyr
            130                 135                 140
Thr Leu Pro Pro Ser Gln Glu Glu Met Thr Lys Asn Gln Val Ser Leu
145                 150                 155                 160
Thr Cys Leu Val Lys Gly Phe Tyr Pro Ser Asp Ile Ala Val Glu Trp
                165                 170                 175
Glu Ser Asn Gly Gln Pro Glu Asn Asn Tyr Lys Thr Thr Pro Pro Val
                180                 185                 190
Leu Asp Ser Asp Gly Ser Phe Phe Leu Tyr Ser Lys Leu Thr Val Asp
                195                 200                 205
Lys Ser Arg Trp Gln Glu Gly Asn Val Phe Ser Cys Ser Val Met His
            210                 215                 220
Glu Ala Leu His Asn His Tyr Thr Gln Lys Ser Leu Ser Leu Ser Leu
225                 230                 235                 240
Gly Ile Pro Pro His Val Gln Lys Ser Val Asn Asn Asp Met Ile Val
                245                 250                 255
Thr Asp Asn Asn Gly Ala Val Lys Phe Pro Gln Leu Cys Lys Phe Cys
```

```
                260             265             270
Asp Val Arg Phe Ser Thr Cys Asp Asn Gln Lys Ser Cys Met Ser Asn
            275             280             285
Cys Ser Ile Thr Ser Ile Cys Glu Lys Pro Gln Glu Val Cys Val Ala
            290             295             300
Val Trp Arg Lys Asn Asp Glu Asn Ile Thr Leu Glu Thr Val Cys His
305             310             315             320
Asp Pro Lys Leu Pro Tyr His Asp Phe Ile Leu Glu Asp Ala Ala Ser
            325             330             335
Pro Lys Cys Ile Met Lys Glu Lys Lys Pro Gly Glu Thr Phe Phe
            340             345             350
Met Cys Ser Cys Ser Ser Asp Glu Cys Asn Asp Asn Ile Ile Phe Ser
            355             360             365
Glu Glu Tyr Asn Thr Ser Asn Pro Asp Ile Pro Pro His Val Gln Lys
            370             375             380
Ser Val Asn Asn Asp Met Ile Val Thr Asp Asn Asn Gly Ala Val Lys
385             390             395             400
Phe Pro Gln Leu Cys Lys Phe Cys Asp Val Arg Phe Ser Thr Cys Asp
            405             410             415
Asn Gln Lys Ser Cys Met Ser Asn Cys Ser Ile Thr Ser Ile Cys Glu
            420             425             430
Lys Pro Gln Glu Val Cys Val Ala Val Trp Arg Lys Asn Asp Glu Asn
            435             440             445
Ile Thr Leu Glu Thr Val Cys His Asp Pro Lys Leu Pro Tyr His Asp
            450             455             460
Phe Ile Leu Glu Asp Ala Ala Ser Pro Lys Cys Ile Met Lys Glu Lys
465             470             475             480
Lys Lys Pro Gly Glu Thr Phe Phe Met Cys Ser Cys Ser Ser Asp Glu
            485             490             495
Cys Asn Asp Asn Ile Ile Phe Ser Glu Glu Tyr Asn Thr Ser Asn Pro
            500             505             510
Asp Ile Pro Pro His Val Gln Lys Ser Val Asn Asn Asp Met Ile Val
            515             520             525
Thr Asp Asn Asn Gly Ala Val Lys Phe Pro Gln Leu Cys Lys Phe Cys
            530             535             540
Asp Val Arg Phe Ser Thr Cys Asp Asn Gln Lys Ser Cys Met Ser Asn
545             550             555             560
Cys Ser Ile Thr Ser Ile Cys Glu Lys Pro Gln Glu Val Cys Val Ala
            565             570             575
Val Trp Arg Lys Asn Asp Glu Asn Ile Thr Leu Glu Thr Val Cys His
            580             585             590
Asp Pro Lys Leu Pro Tyr His Asp Phe Ile Leu Glu Asp Ala Ala Ser
            595             600             605
Pro Lys Cys Ile Met Lys Glu Lys Lys Pro Gly Glu Thr Phe Phe
            610             615             620
Met Cys Ser Cys Ser Ser Asp Glu Cys Asn Asp Asn Ile Ile Phe Ser
625             630             635             640
Glu Glu Tyr Asn Thr Ser Asn Pro Asp
            645
```